(12) United States Patent
Sun et al.

(10) Patent No.: US 9,643,999 B2
(45) Date of Patent: *May 9, 2017

(54) HEPATITIS C VIRUS INHIBITORS

(71) Applicant: Bristol-Myers Squibb Company, Princeton, NJ (US)

(72) Inventors: Li-Qiang Sun, Glastonbury, CT (US); Qian Zhao, Wallingford, CT (US); Kishore V. Renduchintala, Hyderabad (IN); Kandhasamy Sarkunam, Hosur (IN); Pulicharla Nagalakshmi, Bangalore (IN); Eric P. Gillis, Cheshire, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 376 days.

This patent is subject to a terminal disclaimer.

(21) Appl. No.: 14/064,619

(22) Filed: Oct. 28, 2013

(65) Prior Publication Data

US 2014/0127156 A1 May 8, 2014

Related U.S. Application Data

(60) Provisional application No. 61/721,560, filed on Nov. 2, 2012.

(51) Int. Cl.

| C07D 225/02 | (2006.01) |
| C07K 5/087 | (2006.01) |
| A61K 31/13 | (2006.01) |
| A61K 31/7056 | (2006.01) |
| A61K 38/20 | (2006.01) |
| A61K 38/21 | (2006.01) |
| A61K 45/06 | (2006.01) |
| C07K 5/083 | (2006.01) |
| C07K 5/08 | (2006.01) |
| A61K 38/06 | (2006.01) |
| A61K 38/00 | (2006.01) |

(52) U.S. Cl.
CPC .......... *C07K 5/0812* (2013.01); *A61K 31/13* (2013.01); *A61K 31/7056* (2013.01); *A61K 38/06* (2013.01); *A61K 38/204* (2013.01); *A61K 38/208* (2013.01); *A61K 38/2013* (2013.01); *A61K 38/212* (2013.01); *A61K 45/06* (2013.01); *C07K 5/0804* (2013.01); *C07K 5/0827* (2013.01); *A61K 38/00* (2013.01)

(58) Field of Classification Search
None
See application file for complete search history.

(56) References Cited

U.S. PATENT DOCUMENTS

| 5,223,432 A | 6/1993 | Wirz et al. |
| 7,449,479 B2 | 11/2008 | Wang et al. |
| 7,582,605 B2 | 9/2009 | Moore et al. |
| 7,601,709 B2 | 10/2009 | Miao et al. |
| 7,605,126 B2 | 10/2009 | Niu et al. |
| 7,635,683 B2 | 12/2009 | Gai et al. |
| 7,915,291 B2 | 3/2011 | Wang et al. |
| 8,232,246 B2 | 7/2012 | McDaniel et al. |
| 8,268,776 B2 | 9/2012 | Sun et al. |
| 8,299,094 B2 | 10/2012 | Wang et al. |
| 8,309,685 B2 | 11/2012 | Petter et al. |
| 8,338,606 B2 | 12/2012 | Perrone et al. |
| 8,415,374 B2 | 4/2013 | Lemm et al. |
| 8,507,722 B2 | 8/2013 | Wang |
| 8,710,229 B2 | 4/2014 | Wang et al. |
| 2005/0209135 A1 | 9/2005 | Busacca et al. |
| 2006/0199773 A1 | 9/2006 | Sausker et al. |
| 2006/0257980 A1 | 11/2006 | Li |
| 2007/0078081 A1 | 4/2007 | Casarez et al. |
| 2008/0279821 A1 | 11/2008 | Niu et al. |
| 2013/0302414 A1 | 11/2013 | Perrone |

FOREIGN PATENT DOCUMENTS

| WO | WO 98/17679 | 4/1998 |
| WO | WO 99/07733 | 2/1999 |
| WO | WO 99/07734 | 2/1999 |

(Continued)

OTHER PUBLICATIONS

Lauer, G.M. et al., "Hepatitis C Virus Infection", The New England Journal of Medicine, vol. 345, No. 1, pp. 41-52 (2001).

Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).

Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

*Primary Examiner* — Jeffrey S Lundgren
*Assistant Examiner* — Stephanie Springer
(74) *Attorney, Agent, or Firm* — Pamela A. Mingo

(57) ABSTRACT

Hepatitis C virus inhibitors having the general formula (I)

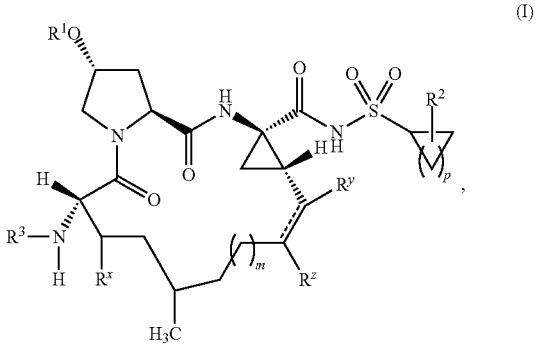

are disclosed. Compositions comprising the compounds and methods for using the compounds to inhibit HCV are also disclosed.

16 Claims, No Drawings

(56) References Cited

FOREIGN PATENT DOCUMENTS

| | | |
|---|---|---|
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/011658 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/030656 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/120595 | 10/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/005565 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/086161 | 7/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106130 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/005676 | 1/2009 |
| WO | WO 2009/005677 | 1/2009 |
| WO | WO 2009/005690 | 1/2009 |
| WO | WO 2009/010804 | 1/2009 |
| WO | WO 2009/014730 | 1/2009 |
| WO | WO 2009/047264 | 4/2009 |
| WO | WO 2009/053828 | 4/2009 |
| WO | WO 2009/055335 | 4/2009 |
| WO | WO 2009/064955 | 5/2009 |
| WO | WO 2009/064975 | 5/2009 |
| WO | WO 2009/070689 | 6/2009 |
| WO | WO 2009/070692 | 6/2009 |
| WO | WO 2009/073713 | 6/2009 |
| WO | WO 2009/073719 | 6/2009 |
| WO | WO 2009/073780 | 6/2009 |
| WO | WO 2009/076166 | 6/2009 |
| WO | WO 2009/076173 | 6/2009 |

| | | | | | | |
|---|---|---|---|---|---|---|
| WO | WO 2009/079352 | 6/2009 | | WO | WO 2011/025849 | 3/2011 |
| WO | WO 2009/079353 | 6/2009 | | WO | WO 2011/034518 | 3/2011 |
| WO | WO 2009/080542 | 7/2009 | | WO | WO 2011/038283 | 3/2011 |
| WO | WO 2009/082697 | 7/2009 | | WO | WO 2011/038293 | 3/2011 |
| WO | WO 2009/082701 | 7/2009 | | WO | WO 2011/041551 | 4/2011 |
| WO | WO 2009/085659 | 7/2009 | | WO | WO 2011/046811 | 4/2011 |
| WO | WO 2009/094438 | 7/2009 | | WO | WO 2011/049908 | 4/2011 |
| WO | WO 2009/094443 | 7/2009 | | WO | WO 2011/063501 | 6/2011 |
| WO | WO 2009/108507 | 9/2009 | | WO | WO 2011/063502 | 6/2011 |
| WO | WO 2009/117594 | 9/2009 | | WO | WO 2011/072370 | 6/2011 |
| WO | WO 2009/129109 | 10/2009 | | WO | WO 2011/091757 | 8/2011 |
| WO | WO 2009/134624 | 11/2009 | | WO | WO 2011/150190 | 12/2011 |
| WO | WO 2009/134987 | 11/2009 | | WO | WO 2011/156337 | 12/2011 |
| WO | WO 2009/139792 | 11/2009 | | WO | WO 2012/018829 | 2/2012 |
| WO | WO 2009/140475 | 11/2009 | | WO | WO 2012/019299 | 2/2012 |
| WO | WO 2009/140500 | 11/2009 | | WO | WO 2012/037259 | 3/2012 |
| WO | WO 2009/142842 | 11/2009 | | WO | WO 2012/040040 | 3/2012 |
| WO | WO 2009/146347 | 12/2009 | | WO | WO 2012/040167 | 3/2012 |
| WO | WO 2010/011566 | 1/2010 | | WO | WO 2012/040242 | 3/2012 |
| WO | WO 2010/015545 | 2/2010 | | WO | WO 2009/148923 | 4/2012 |
| WO | WO 2010/030359 | 3/2010 | | WO | WO 2012/047764 | 4/2012 |
| WO | WO 2010/031829 | 3/2010 | | WO | WO 2012/054874 | 4/2012 |
| WO | WO 2010/031832 | 3/2010 | | WO | WO 2012/082672 | 6/2012 |
| WO | WO 2010/033466 | 3/2010 | | WO | WO 2012/092409 | 7/2012 |
| WO | WO 2010/034105 | 4/2010 | | WO | WO 2012/092411 | 7/2012 |
| WO | WO 2010/036551 | 4/2010 | | WO | WO 2012/151195 | 11/2012 |
| WO | WO 2010/036871 | 4/2010 | | WO | WO 2012/166459 | 12/2012 |
| WO | WO 2010/036896 | 4/2010 | | WO | WO 2012/173983 | 12/2012 |
| WO | WO 2010/059937 | 5/2010 | | WO | WO 2013/028465 | 2/2013 |
| WO | WO 2010/065577 | 6/2010 | | WO | WO 2013/028470 | 2/2013 |
| WO | WO 2010/068760 | 6/2010 | | WO | WO 2013/028471 | 2/2013 |
| WO | WO 2010/068761 | 6/2010 | | WO | WO 2013/040568 | 3/2013 |
| WO | WO 2010/075127 | 7/2010 | | WO | WO 2013/066753 | 5/2013 |
| WO | WO 2010/077783 | 7/2010 | | WO | WO 2013/074386 | 5/2013 |
| WO | WO 2010/080389 | 7/2010 | | WO | WO 2013/106689 | 7/2013 |
| WO | WO 2010/088394 | 8/2010 | | WO | WO 2013/120371 | 8/2013 |
| WO | WO 2010/115981 | 10/2010 | | WO | WO 2014/008285 | 1/2014 |
| WO | WO 2010/116248 | 10/2010 | | WO | WO 2014/019344 | 2/2014 |
| WO | WO 2010/132163 | 11/2010 | | WO | WO 2014/025736 | 2/2014 |
| WO | WO 2010/145523 | 12/2010 | | WO | WO 2014/062196 | 4/2014 |
| WO | WO 2011/002807 | 1/2011 | | WO | WO 2014/070964 | 5/2014 |
| WO | WO 2011/002808 | 1/2011 | | WO | WO 2014/070974 | 5/2014 |
| WO | WO 2011/005646 | 1/2011 | | WO | WO 2014/071007 | 5/2014 |
| WO | WO 2011/014487 | 2/2011 | | | | |

HEPATITIS C VIRUS INHIBITORS

CROSS-REFERENCE TO RELATED APPLICATIONS

This application claims the benefit of U.S. Provisional Application Ser. No. 61/721,560 filed Nov. 2, 2012.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with additional compounds having anti-HCV activity.

In its first aspect the present disclosure provides a compound of formula (I)

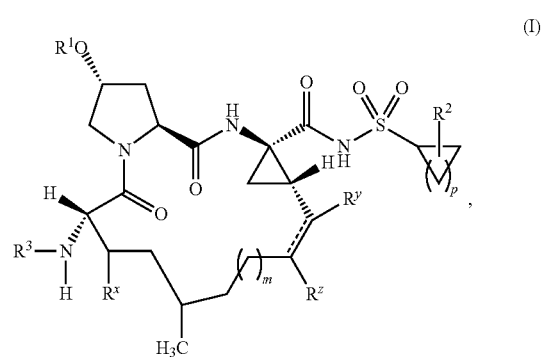

or a pharmaceutically acceptable salt thereof, wherein
i is 1 or 2;
----- is a single or double bond;
$R^1$ is selected from

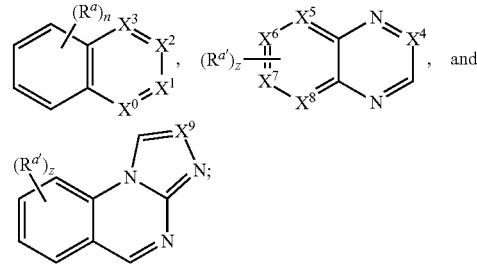

wherein $R^1$ is attached to the parent molecular moiety through any substitutable carbon atom in the group;
m is 0, 1, or 2;
n is 1, 2, 3, 4, 5, or 6;
z is 0, 1, 2, 3, 4, 5, or 6;
$X^0$ is selected from CH and N;
$X^1$ is selected from CH and N;
$X^2$ and $X^3$ are independently selected from CH, C($R^a$) and N; provided that at least one of $X^1$, $X^2$, and $X^3$ is other than N;
$X^4$ is selected from CH and $CR^a$;
one of $X^5$, $X^6$, $X^7$, and $X^8$ is N and the others are selected from CH and $CR^{a'}$;
$X^9$ is selected from $CR^a$, CH, and N;
each $R^a$ and $R^{a'}$ are independently selected from alkoxy, alkoxycarbonyl, alkyl, cycloalkyl, halo, haloalkyl, imidazolyl, oxazolyl, substituted pyrazolyl, thiazolyl, and —$NR^xR^y$, wherein the imidazolyl, the oxazolyl, and the thiazolyl are optionally substituted with one or two groups independently selected from alkoxy, alkyl, halo, and haloalkyl; and wherein the substituted pyrazolyl is substituted with one or two groups independently selected from alkoxy, alkyl, halo, and haloalkyl; and wherein two adjacent $R^a$ groups, together with the carbon atoms to which they are attached, can optionally form a furanyl ring; provided that at least one $R^a$ is other than alkoxy, alkyl, halo, or haloalkyl;

$R^x$ is selected from methyl and ethyl;

$R^y$ and $R^z$ are independently selected from hydrogen and hydroxy; provided that when ----- is a double bond, $R^y$ and $R^z$ are each hydrogen;

$R^2$ is selected from hydrogen, alkyl, halo, haloalkoxy, haloalkyl, and hydroxyalkyl;

$R^3$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl; and one of $R^x$ and $R^y$ is selected from hydrogen and alkyl and the other is selected from alkylcarbonyl and phenylcarbonyl.

In a first embodiment of the first aspect the present disclosure provides a compound of claim 1, or a pharmaceutically acceptable salt thereof, wherein m and p are 1.

In a second embodiment of the first aspect the present disclosure provides a compound of claim 1, or a pharmaceutically acceptable salt thereof, wherein ----- is a double bond.

In a third embodiment of the first aspect the present disclosure provides a compound of claim 1, or a pharmaceutically acceptable salt thereof, wherein $R^y$ and $R^z$ are hydrogen.

In a fourth embodiment of the first aspect the present disclosure provides a compound of claim 1, or a pharmaceutically acceptable salt thereof, $R^2$ is selected from hydrogen and alkyl.

In a fifth embodiment of the first aspect the present disclosure provides a compound of claim 1, or a pharmaceutically acceptable salt thereof, wherein $R^1$ is

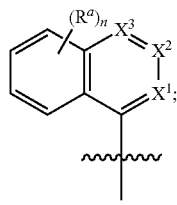

wherein $X^3$ is N;
$X^2$ is $C(R^a)$;
$X^1$ is CH;
n and $R^a$ are as defined in claim 1; and
"⌇" denotes the point of attachment to the parent molecular moiety.

In a sixth embodiment of the first aspect the present disclosure provides a compound of claim 1, or a pharmaceutically acceptable salt thereof, wherein $R^1$ is

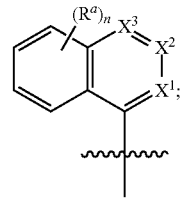

wherein $X^1$ is N;
$X^2$ and $X^3$ are independently selected from CH and $C(R^a)$;
n and $R^a$ are as defined in claim 1; and "⌇" denotes the point of attachment to the parent molecular moiety.

In a seventh embodiment of the first aspect the present disclosure provides a compound of claim 1, or a pharmaceutically acceptable salt thereof, wherein $R^1$ is

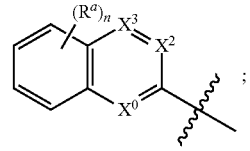

wherein $X^0$ and $X^3$ are N;
$X^2$ is $C(R^a)$;
n and $R^a$ are as defined in claim 1; and
"⌇" denotes the point of attachment to the parent molecular moiety.

In a eighth embodiment of the first aspect the present disclosure provides a compound of claim 1, or a pharmaceutically acceptable salt thereof, wherein $R^1$ is

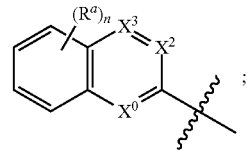

wherein $X^0$ is N;
$X^2$ and $X^3$ are independently selected from CH and $C(R^a)$;
n and $R^a$ are as defined in claim 1; and
"⌇" denotes the point of attachment to the parent molecular moiety.

In a ninth embodiment of the first aspect the present disclosure provides a compound of claim 1, or a pharmaceutically acceptable salt thereof, wherein $R^1$ is

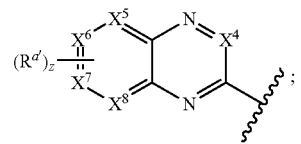

wherein "⌇" denotes the point of attachment to the parent molecular moiety.

In a tenth embodiment of the first aspect the present disclosure provides a compound of claim 1, or a pharmaceutically acceptable salt thereof, wherein $R^1$ is

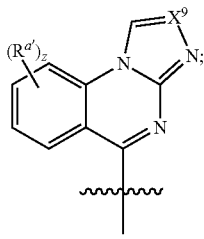

wherein "⌇⌇" denotes the point of attachment to the parent molecular moiety.

In an eleventh embodiment of the first aspect the present disclosure provides a compound of claim 1, or a pharmaceutically acceptable salt thereof, wherein
m and p are 1;
----- is a double bond;
$R^y$ and $R^z$ are hydrogen;
and $R^2$ is selected from hydrogen and alkyl.

In a second aspect the present disclosure provides a composition comprising a compound of formula (I), or a pharmaceutically acceptable salt thereof, and a pharmaceutically acceptable carrier. In a first embodiment of the second aspect the present disclosure provides a composition comprising a compound of formula (I), or a pharmaceutically acceptable salt thereof, at least one additional compound having anti-HCV activity, and a pharmaceutical carrier. In a second embodiment at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the second aspect the present disclosure provides a composition comprising a compound of formula (I), or a pharmaceutically acceptable salt thereof, at least one additional compound having anti-HCV activity, and a pharmaceutical carrier, wherein at least one of the additional compounds is selected from interleukin 2, interleukin 6, interleukin 12, Imiquimod, ribavirin, an inosine 5'-monophospate dehydrogenase inhibitor, amantadine, and rimantadine. In a fifth embodiment of the second aspect the present disclosure provides a composition comprising a compound of formula (I), or a pharmaceutically acceptable salt thereof, at least one additional compound having anti-HCV activity, and a pharmaceutical carrier, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of formula (I), or a pharmaceutically acceptable salt thereof. In a first embodiment of the third aspect the method further comprises administering at least one additional compound having anti-HCV activity prior to, after, or simultaneously with the compound of formula (I), or a pharmaceutically acceptable salt thereof. In a second embodiment of the third aspect at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, Imiquimod, ribavirin, an inosine 5'-monophospate dehydrogenase inhibitor, amantadine, and rimantadine. In a fifth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substitutent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^1$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "alkoxy," as used herein, refers to an alkyl group attached to the parent molecular moiety through an oxygen atom.

The term "alkoxyalkoxy," as used herein, refers to an alkoxyalkyl group attached to the parent molecular moiety through an oxygen atom.

The term "alkoxyalkoxycarbonyl," as used herein, refers to an alkoxyalkoxy group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms. In one embodiment the alkyl group contains from one to six carbon atoms. In another embodiment the alkyl group contains from one to three carbon atoms.

The term "alkylamino," as used herein, refers to —NHR, wherein R is an alkyl group.

The term "alkylaminocarbonyl," as used herein, refers to an alkylamino group attached to the parent molecular moiety through a carbonyl group.

The term "alkylcarbonyl," as used herein, refers to an alkyl group attached to the parent molecular moiety through a carbonyl group.

The term "carbonyl," as used herein, refers to —C(O)—.

The term "cycloalkyl," as used herein, refers to a saturated monocyclic or bicyclic hydrocarbon ring system having three to seven carbon atoms and zero heteroatoms. Representative examples of cycloalkyl groups include, but are not limited to, cyclopropyl, cyclobutyl, and cyclopentyl.

The term "cycloalkylalkoxy," as used herein, refers to a (cycloalkyl)alkyl group attached to the parent molecular moiety through an oxygen atom.

The term "cycloalkylalkoxycarbonyl," as used herein, refers to a cycloalkylalkoxy group attached to the parent molecular moiety through a carbonyl group.

The term "(cycloalkyl)alkyl," as used herein, refers to an alkyl group substituted with one, two, or three cycloalkyl groups.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "deuteroalkoxy," as used herein, refers to an alkoxy group wherein at least one hydrogen atom is replaced by a deuterium atom.

The term "deuteroalkoxycarbonyl," as used herein, refers to a deuteroalkoxy group attached to the parent molecular moiety through a carbonyl group.

The term "deuterohaloalkoxy," as used herein, refers to a haloalkoxy group wherein at least one hydrogen atom is replaced by a deuterium atom.

The term "deuterohaloalkoxycarbonyl," as used herein, refers to a deuterohaloalkoxy group attached to the parent molecular moiety through a carbonyl group.

The term "dialkylamino," as used herein, refers to —NR$^p$R$^q$, wherein R$^p$ and R$^q$ are alkyl groups. The alkyl groups may be the same or different.

The term "dialkylaminocarbonyl," as used herein, refers to a dialkylamino group attached to the parent molecular moiety through a carbonyl group.

The term "dialkylaminocarbonylcarbonyl," as used herein, refers to a dialkylaminocarbonyl group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylamino," as used herein, refers to an alkyl amino group wherein the alkyl is substituted with one, two, three, or four halogen atoms.

The term "haloalkylaminocarbonyl," as used herein, refers to a haloalkylamino group attached to the parent molecular moiety through a carbonyl group.

The term "haloalkylcarbonyl," as used herein, refers to a haloalkyl group attached to the parent molecular moiety through a carbonyl group.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein refers to an alkyl group substituted with one, two, or three hydroxy groups.

The term "phenylcarbonyl," as used herein, refers to a phenyl group attached to the parent molecular moiety through a carbonyl group.

The term "phenyloxy," as used herein, refers to a phenyl group attached to the parent molecular moiety through an oxygen atom.

The term "phenyloxycarbonyl," as used herein, refers to a phenyloxy group attached to the parent molecular moiety through a carbonyl group.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

Asymmetric centers exist in the compounds of the present disclosure. For example, the compounds may include P1 cyclopropyl element of formula

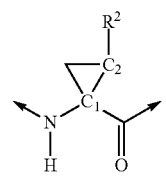

P1 wherein $C_1$ and $C_2$ each represent an asymmetric carbon atom at positions 1 and 2 of the cyclopropyl ring.

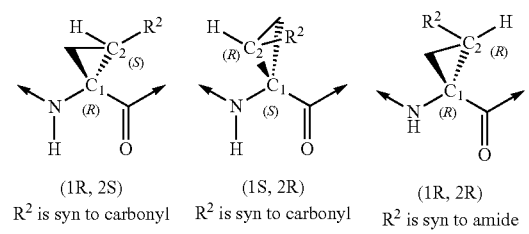

(1R, 2S)  (1S, 2R)  (1R, 2R)
$R^2$ is syn to carbonyl  $R^2$ is syn to carbonyl  $R^2$ is syn to amide

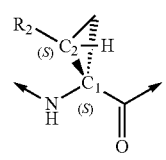

(1S, 2S)
$R^2$ is syn to amide

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Pharmaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |

TABLE 1-continued

| Brand Name | Physiological Class | Type of Inhibitor or Target | Source Company |
|---|---|---|---|
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |

TABLE 1-continued

| Brand Name | Physiological Class | Type of Inhibitor or Target | Source Company |
|---|---|---|---|
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| INX-189 | Antiviral | Nucleotide NS5B Polymerase Inhibitor | Inhibitex |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| daclatasvir | Antiviral | NS5A inhibitor | Bristol-Myers Squibb |
| BMS-791325 | Antiviral | NS5B Polymerase Inhibitor | Bristol-Myers Squibb |
| ACH-3102 | Antiviral | NS5A inhibitor | Bristol-Myers Squibb |
| BMS-984478 | Antiviral | NS5A inhibitor | Bristol-Myers Squibb |
| asunaprevir | Antiviral | serine protease inhibitor | Bristol-Myers Squibb |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: LAH for lithium aluminum hydride; THF for tetrahydrofuran; min for minutes; h or hr or hrs for hours; r.t. or RT or Rt for room temprature or retention time (context will dictate); MS for methanesulfonyl; DCM for dichloromethane; TBME for tert-butyl methyl ether; pet ether or pet-ether for petroleum ether; DMAP for N,N-dimethylaminpyridine; Ph for phenyl; LiHMDS for lithium hexamethyldisilazide; DIPEA or DIEA for diisopropylethylamine; $(BOC)_2O$ for di-tert-butyl dicarbonate; t-BuOK or tert-BuOK for potassium tert-butoxide; DMSO for N,N-dimethylsulfoxide; HATU for O-(7-azabenzotriazol-1-yl)-N,N,N',N'-tetramethyluronium phosphate; TFA for trifluoroacetic acid; EtOAC or EtOAc for ethyl acetate; DBU for 1,8-diazabicyclo(5.4.0)undec-7-ene; DMF for N,N-dimethylformamide; CDI for 1,1'-carbonyldiimidazole; NH$_4$OAc for ammonium acetate; EtOH for ethanol; DDQ for 2,3-dichloro-5,6-dicyano-1,4-benzoquinone; DAST for (diethylamino) sulfur trifluoride; PPh$_3$ for triphenylphoshphine; TMS for trimethylsilane; and DPPA for diphenylphosphoryl azide.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art The preparation of intermediates and Compounds for Formula 1 is described in following three sections: Section 1, Section 2 and Section 3. Compounds were named using ChemDraw.

4-chloro-7-methoxy-2-(3-(trifluoromethyl)-1H-pyrazol-1-yl)quinoline (0.45 g, 1.37 mmol) 54% as white solid. $^1$H NMR (400 MHz, CDCl$_3$): δ ppm 8.60 (d, J=2.51 Hz, 1H) 8.07 (d, J=9.04 Hz, 1H) 8.15 (s, 1H) 8.07 (d, J=9.04 Hz, 1H) 8.15 (s, 1H) 7.26 (s, 2H) 7.16-7.22 (m, 1H) 6.35 (d, J=2.51 Hz, 1H) 3.97-3.99 (m, 4H) MS: MS m/z 330.1 (M$^+$+1).

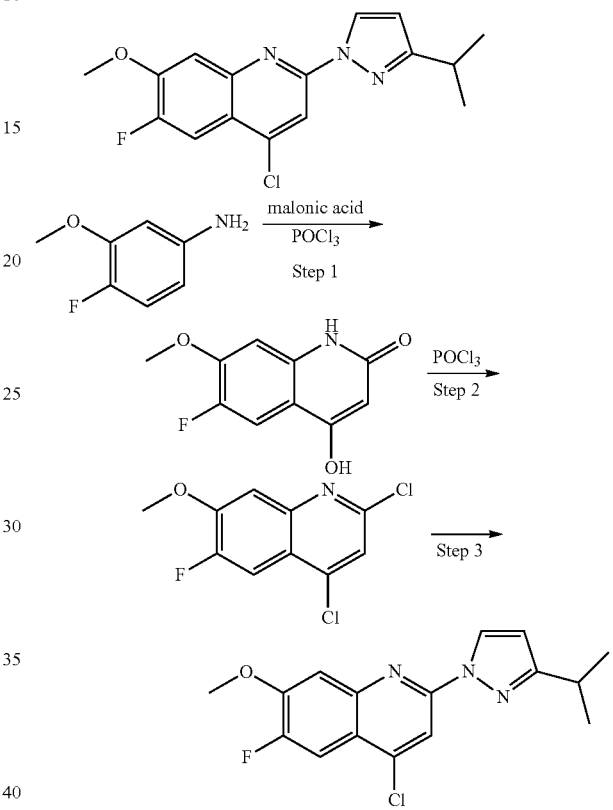

Scheme: Preparation of 4-chloro-6-fluoro-2-(3-isopropyl-1H-pyrazol-1-yl)-7-methoxyquinoline.

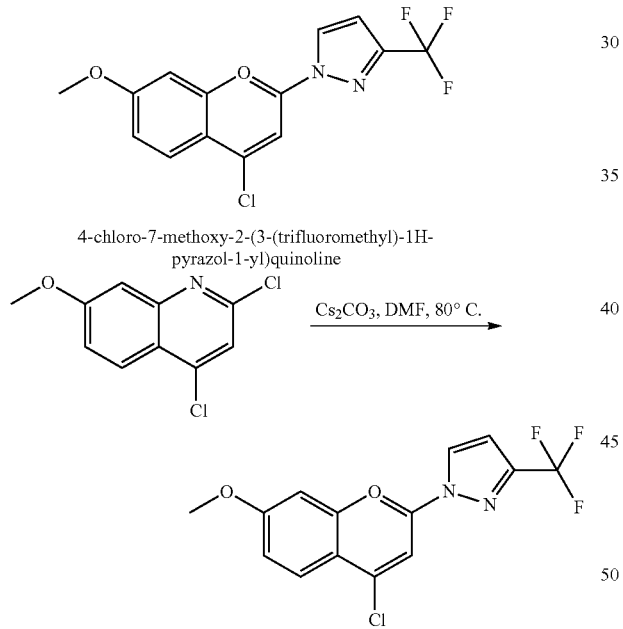

Scheme: Preparation of 4-chloro-7-methoxy-2-(3-(trifluoromethyl)-1H-pyrazol-1-yl)quinoline Step 1: Preparation of 4-chloro-7-methoxy-2-(3-(trifluoromethyl)-1H-pyrazol-1-yl)quinoline To a solution of 2,4-dichloro-7-methoxyisoquinolin (0.5 g, 2.19 mmol) in DMF (5 ml) was added Cs$_2$CO$_3$ (0.3 g, 2.2 mmol) followed by 3-(trifluoromethyl)-1H-pyrazole (0.9 g, 6.58 mmol). The reaction mixture was heated to 80° C. for 18 h. The reaction mass was evaporated under reduced pressure. The residue was diluted with water and extracted with ethyl acetate. The combined organic layers were dried over anhydrous Na$_2$SO$_4$; filtered; then evaporated under reduced pressure to get crude compound. The crude compound was purified by silica gel chromatography to get Step 1: Preparation of 6-fluoro-4-hydroxy-7-methoxyquinolin-2(1H)-one POCl$_3$ (3.96 ml, 42.5 mmol) was added to the mixture of 4-fluoro-3-methoxy aniline (5.0 g, 35.4 mmol) and Malonic acid (3.69 g, 35.46 mmol). The reaction mass was heated to 105° C. for 1 h. The reaction mass was carefully diluted with water (20 ml) and stirred for 30 min. The precipitated solid isolated via filtration and washed with water. The solid was combined with aq NaOH solution (2N, 30 ml) and the mixture was stirred for 18 h. The mixture was filtered. The filtrate was diluted with ethanol (5 ml) adjusted to pH ~2 using aq. conc. HCl. The precipitated solid was isolated via filtration and washed with water. The solid was dried under reduced pressure to afford 6-fluoro-7-methoxyquinoline-2,4-diol (7 g, 33.5 mmol, 94%) as white solid. $^1$H NMR (400 MHz, DMSO-D$_6$): δ ppm 11.09 (b s, 1H), 10.01 (s, 1H), 7.57-7.54 (d, J=12 Hz, 1H), 7.06-7.04 (d, J=12 Hz, 1H), 5.92 (s, 1H), 3.90 (s, 3H). MS: MS m/z 210.55 (M$^+$+1).

Step 2: Preparation of 2,4-dichloro-6-fluoro-7-methoxyquinoline

A solution of 6-fluoro-7-methoxyquinoline-2,4-diol (7.5 g, 35.9 mmol) in POCl$_3$ (3.66 ml, 39.2 mmol) was refluxed for 3 h. The solvent was evaporated under reduced pressure and the residue was diluted with cold water. The aqueous solution was basified by addition of solid sodium carbonate; then was extracted with ethyl acetate. The combined organic layers were dried over anhydrous sodium sulphate; filtered; then concentrated under reduced pressure to get crude compound. The crude compound was purified by silica gel chromatography (20% ethyl acetate in pet ether) to afford 2,4-dichloro-6-fluoro-7-methoxyquinoline (6 g, 24.38 mmol, 68.0%). $^1$H NMR (400 MHz, CDCl$_3$): δ ppm 7.81-7.78 (d, J=12 Hz, 1H), 7.46-7.44 (d, J=8 Hz, 1H) 7.41 (s, 1H), 4.02 (s, 3H). MS: MS m/z 246.44 (M$^+$+1).

Step 3: 4-chloro-6-fluoro-2-(3-isopropyl-1H-pyrazol-1-yl)-7-methoxyquinoline To a stirred solution of 2,4-dichloro-6-fluoro-7-methoxyquinoline (0.2 g, 0.813 mmol) in DMF (5 mL) was added cesium carbonate (0.530 g, 1.626 mmol) followed by 3-isopropyl-1H-pyrazole (0.269 g, 2.438 mmol). The reaction mixture was stirred for 12 h at 80° C. Reaction mixture was poured in water; extracted with ethyl acetate. The combined organic layers were dried over anhydrous sodium sulphate; filtered; then concentrated under reduced pressure. The resulting crude compound was purified by silica gel chromatography (1-2% ethyl acetate in pet ether) to afford 4-chloro-6-fluoro-2-(3-isopropyl-1H-pyrazol-1-yl)-7-methoxyquinoline (0.04 g, 0.13 mmol, 16%). $^1$H NMR (400 MHz, CDCl$_3$): δ ppm 8.56-8.55 (dd, J=2.50, 0.50 Hz, 1H) 8.19 (d, J=0.50 Hz, 1H) 7.82-7.79 (d, J=11.76 Hz, 1H) 7.41-7.39 (d, J=8.00 Hz, 1H) 6.35 (s, 1H) 4.05 (s, 3H) 3.12-3.06 (m, 1H) 1.35-1.33 (d, 6H). MS: MS m/z 320.4 (M$^+$+1).

Scheme: Preparation of Methyl 1-chloro-6-methoxyisoquinoline-4-carboxylate

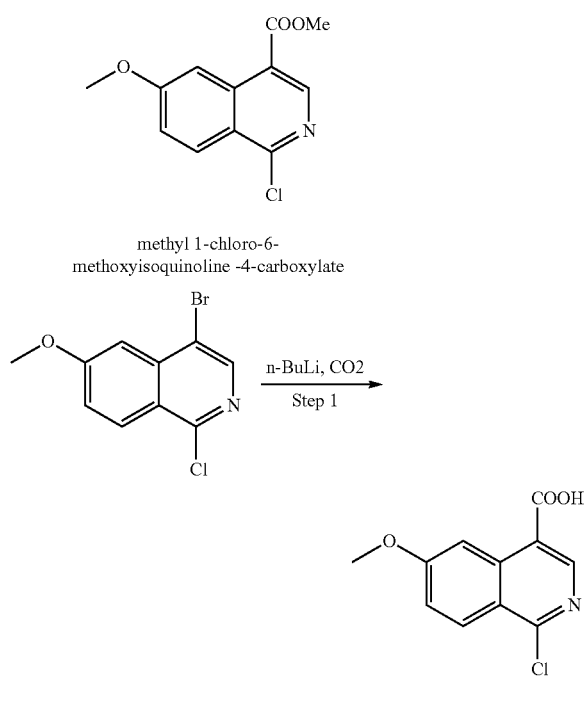

Step 1: Synthesis of 1-chloro-6-methoxyisoquinoline-4-carboxylic acid

A solution of 4-bromo-1-chloro-6-methoxyisoquinoline (340 mg, 1.248 mmol) in THF (10 mL) was cooled to −78° C. To the solution was added t-BuLi in pentane (1.715 mL, 2.74 mmol). The resulting colored solution was stirred at the same temperature for 20 min, then was transferred by syringe onto crushed dry ice (CO2) under nitrogen atmosphere. Once the dry ice had fully sublimed, the resulting solution was transferred to a reparatory funnel and was diluted with water. The pH was adjusted to basic using 10% sodium hydroxide solution. The organic layer was separated and discarded. The aqueous phase was washed with ethyl acetate. The aqueous layer was then adjusted to pH 2.0 with aqueous HCl, then was twice extracted with EtOAc. The combined organic layers were washed with brine solution, dried over Na2SO4, filtered and concentrated in vacuo to afford 1-chloro-6-methoxyisoquinoline-4-carboxylic acid (140 mg, 0.589 mmol, 47.2% yield) as light pink solid $^1$H NMR (400 MHz, CDCl$_3$): δ ppm: 13.60 (bs, 1H), 8.82 (s, 1H) 8.43-8.42 (d, J=2.40 Hz, 1H) 7.54-7.51 (dd, J=12.0, 2.4 Hz, 1H) 3.97 (s, 3H). MS: MS m/z 238.06 (M$^+$+1).

Step 2: Synthesis of Methyl 1-chloro-6-methoxyisoquinoline-4-carboxylate

To a suspension of 1-chloro-6-methoxyisoquinoline-4-carboxylic acid (0.15 g, 0.631 mmol) in THF (7 mL) and MeOH (3 mL) at 5° C. was added TMS-Diazomethane in hexanes (0.316 mL, 0.631 mmol). The solution was allowed to warm to room temperature with stirring overnight. The volatiles were removed under vacuum; the resulting residue was purified by silica gel chromatography eluting with 10% ethyl acetate in pet-ether to afford methyl 1-chloro-6-methoxyisoquinoline-4-carboxylate (0.11 g, 0.437 mmol, 69.2% yield) as white solid. $^1$H NMR (400 MHz, CDCl$_3$): δ ppm 8.91 (s, 1H) 8.46 (d, J=2.51 Hz, 1H) 8.31 (s, 1H) 7.34 (dd, J=9.29, 2.51 Hz, 1H) 4.01 (d, J=0.75 Hz, 6H) MS: MS m/z 252.1 (M$^+$+1).

Preparation of tert-butyl((2R,6S,7R,13aS,14aR,16aS,Z)-7-ethyl-2-hydroxy-9-methyl-14a-(((D3-1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

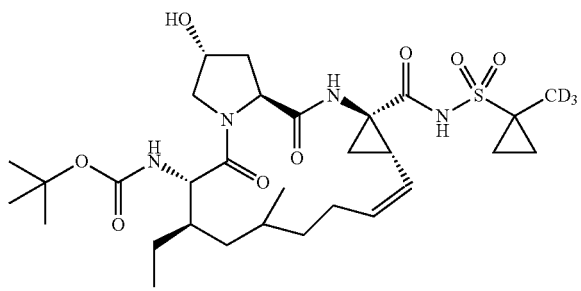 [SMILES: [2H]C([2H])([2H])C1(S(=O)(=O)NC(=O)[C@@]23C[C@H]2/C=C\CCC(C)C[C@@H](CC)[C@H](NC(=O)OC(C)(C)C)C(=O)N2C[C@H](O)C[C@H]2C(=O)N3)CC1]

Tert-butyl((2R,6S,7R,13aS,14aR,16aS,Z)-7-ethyl-2-hydroxy-9-methyl-14a-((((CD3-1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate was synthesized following the procedure reported in synthesis of tert-butyl ((2R,6S,7R,13aS,14aR,16aS,Z)-7-ethyl-2-hydroxy-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. CD$_3$I was used as a reagent instead of MeI. MS: MS m/z 650.43 (M$^+$+23).

Preparation of Compound 4286

Compound 4286

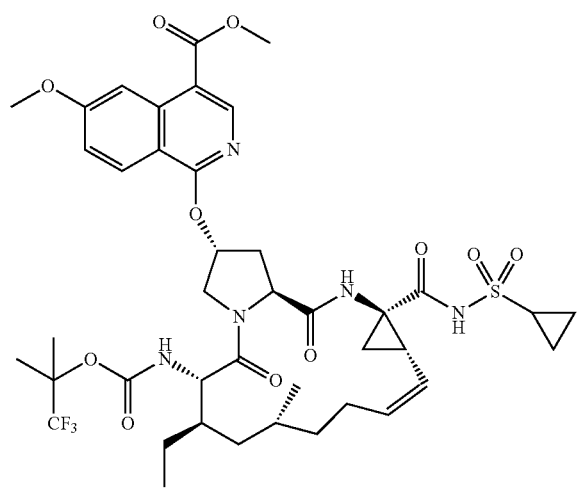

Compound 4286 was prepared using the intermediates described herein and by following the general procedure described for the synthesis of Compound 4303 Compound 4286: methyl 1-(((2R,6S,7R,9R,13aS,14aR,16aS,Z)-14a-((cyclopropylsulfonyl)carbamoyl)-7-ethyl-9-methyl-5,16-dioxo-6-(((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl)oxy)-6-methoxyisoquinoline-4-carboxylate. $^1$H NMR (400 MHz, CD$_3$OD): δ ppm 8.36 (d, J=3.01 Hz, 1H) 7.84 (d, J=8.53 Hz, 1H) 7.72 (d, J=2.51 Hz, 1H) 7.39 (d, J=9.04 Hz, 1H) 7.23-7.31 (m, 2H) 5.64 (td, J=10.29, 6.02 Hz, 1H) 5.39 (br. s., 1H) 5.02 (t, J=10.04 Hz, 1H) 4.71 (d, J=10.04 Hz, 1H) 4.60 (dd, J=10.04, 7.03 Hz, 1H) 4.22 (q, J=7.03 Hz, 2H) 4.01-4.11 (m, 2H) 2.64-2.74 (m, 2H) 2.45 (ddd, J=13.93, 9.91, 4.77 Hz, 2H) 1.91-2.07 (m, 2H) 1.78 (dd, J=8.28, 5.77 Hz, 1H) 1.62-1.69 (m, 1H) 1.58 (dd, J=9.54, 5.52 Hz, 3H) 1.48-1.54 (m, 9H) 1.44 (dd, J=8.78, 5.27 Hz, 1H) 1.34 (s, 3H) 1.19-1.29 (m, 2H) 1.09-1.16 (m, 3H) 1.01 (d, J=6.53 Hz, 3H) 0.87-0.93 (m, 4H) 0.82 (t, J=7.53 Hz, 3H). MS: MS m/z 880.8 (M$^+$+1).

Preparation of Compound 4287

Compound 4287

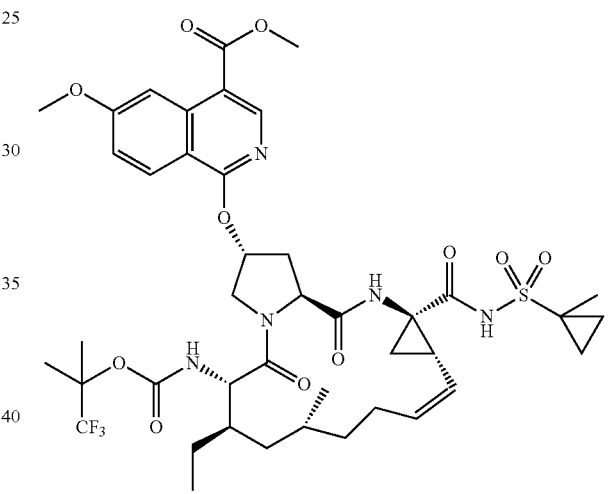

Compound 4287 was prepared using the intermediates described herein and by following the general procedure described for the synthesis of Compound 4303 Compound 4287: methyl 1-(((2R,6S,7R,9R,13aS,14aR,16aS,Z)-7-ethyl-9-methyl-14a-4(1-methylcyclopropyl)sulfonyl)carbamoyl)-5,16-dioxo-6-(4(1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl)oxy)-6-methoxyisoquinoline-4-carboxylate. $^1$H NMR (400 MHz, CD$_3$OD): δ ppm 8.81 (s, 1H) 8.44 (d, J=2.51 Hz, 1H) 8.19 (d, J=9.03 Hz, 1H) 7.20 (dd, J=9.03, 2.51 Hz, 1H) 5.98 (br. s., 1H) 5.60-5.66 (m, 1H) 5.05 (t, J=9.91 Hz, 2H) 4.81 (s, 2H) 4.64-4.69 (m, 1H) 4.02-4.06 (m, 2H) 3.99 (d, J=1.51 Hz, 6H) 2.92-2.98 (m, 1H) 2.71-2.80 (m, 2H) 2.41-2.50 (m, 2H) 1.96-2.03 (m, 2H) 1.80 (s, 1H) 1.50-1.62 (m, 7H) 1.27-1.38 (m, 6H) 1.05-1.19 (m, 3H) 0.94 (s, 4H) 0.83 (t, J=7.53 Hz, 3H). MS: MS m/z 894.3 (M$^+$+1).

Preparation of Compound 4294

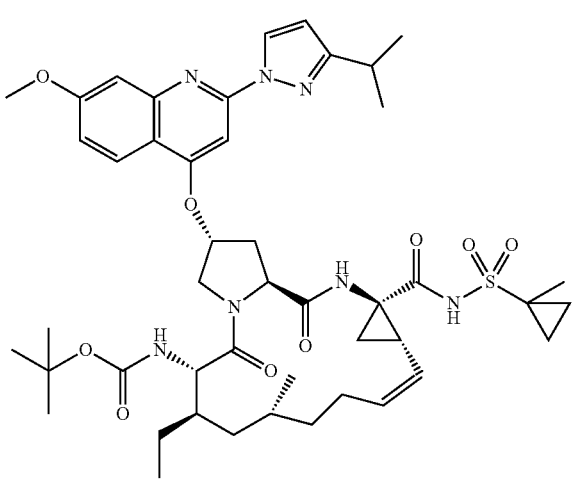

Compound 4294

Compound 4294 was prepared using the intermediates described herein and by following the general procedure described for the synthesis of Compound 4303. Compound 4294: tert-butyl((2R,6S,7R,9R,13aS,14aR,16aS,Z)-7-ethyl-2-(2-(3-isopropyl-1H-pyrazol-1-yl)-7-methoxyquinolin-4-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 9.04 (s, 1H) 8.70 (d, J=2.76 Hz, 1H) 8.08 (d, J=9.29 Hz, 1H) 7.53 (s, 1H) 7.38 (d, J=2.26 Hz, 1H) 7.03-7.13 (m, 1H) 6.54 (d, J=2.51 Hz, 1H) 5.66 (br. s., 2H) 4.97-5.09 (m, 1H) 4.51-4.67 (m, 1H) 4.06-4.19 (m, 2H) 3.97 (s, 3H) 3.10-3.20 (m, 2H) 2.68-2.92 (m, 2H) 2.33-2.61 (m, 2H) 1.93-2.05 (m, 2H) 1.77 (dd, J=8.41, 5.65 Hz, 1H) 1.55-1.72 (m, 4H) 1.52 (s, 4H) 1.35-1.46 (m, 9H) 1.23-1.32 (m, 2H) 1.15-1.23 (m, 9H) 0.98-1.09 (m, 4H) 0.67-0.95 (m, 6H). MS: MS m/z 890.4 (M$^+$+1).

Preparation of Compound 4295

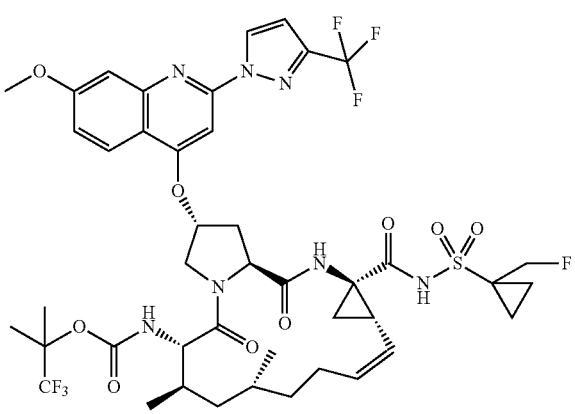

Compound 4295

Compound 4295 was prepared using the intermediates described herein and by following the general procedure described for the synthesis of Compound 4303 Compound 4295: 1,1,1-trifluoro-2-methylpropan-2-yl((2R,6S,7R,9R,13aS,14aR,16aS,Z)-14a-(((1-(fluoromethyl)cyclopropyl)sulfonyl)carbamoyl)-2-((7-methoxy-2-(3-(trifluoromethyl)-1H-pyrazol-1-yl)quinolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.89-8.96 (m, 1H) 8.09 (d, J=9.04 Hz, 1H) 7.57 (s, 1H) 7.38 (d, J=2.51 Hz, 1H) 7.11 (dd, J=9.04, 2.51 Hz, 1H) 6.93 (d, J=2.51 Hz, 1H) 5.67 (br. s., 1H) 4.59-4.70 (m, 2H) 4.11 (dd, J=11.80, 2.76 Hz, 1H) 3.98 (s, 3H) 3.85 (d, J=10.54 Hz, 1H) 3.50 (d, J=1.51 Hz, 1H) 3.16 (t, J=1.51 Hz, 1H) 2.82 (dd, J=14.81, 6.78 Hz, 1H) 2.50-2.62 (m, 2H) 1.72 (dd, J=8.53, 5.52 Hz, 2H) 1.58 (dd, J=9.54, 5.52 Hz, 2H) 1.49 (br. s., 2H) 1.36 (s, 3H) 1.07 (s, 3H) 1.01 (dd, J=13.80, 6.78 Hz, 10H) 0.79-0.92 (m, 3H). MS: MS m/z 974.8 (M$^+$+1).

Preparation of Compound 4297

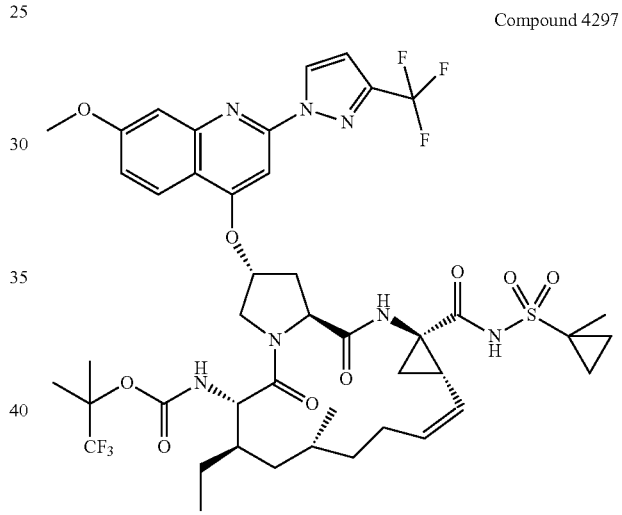

Compound 4297

Compound 4297 was prepared using the intermediates described herein and by following the general procedure described for the synthesis of Compound 4303

Compound 4297: 1,1,1-trifluoro-2-methylpropan-2-yl ((2R,6S,7R,9R,13aS,14aR,16aS,Z)-7-ethyl-2-((7-methoxy-2-(3-(trifluoromethyl)-1H-pyrazol-1-yl)quinolin-4-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.94 (s, 1H) 8.09 (s, 1H) 7.58 (s, 1H) 7.38 (s, 1H) 7.07-7.15 (m, 1H) 6.94 (s, 1H) 5.69 (br. s., 1H) 4.61-4.69 (m, 1H) 4.06-4.14 (m, 7H) 3.98 (s, 3H) 2.84 (d, J=6.02 Hz, 1H) 2.54 (t, J=10.29 Hz, 1H) 1.99 (br. s., 2H) 1.73-1.79 (m, 6H) 1.25-1.65 (m, 12H) 0.80-1.20 (m, 13H). MS: MS m/z 969.9 (M$^+$+1).

Preparation of Compound 4299

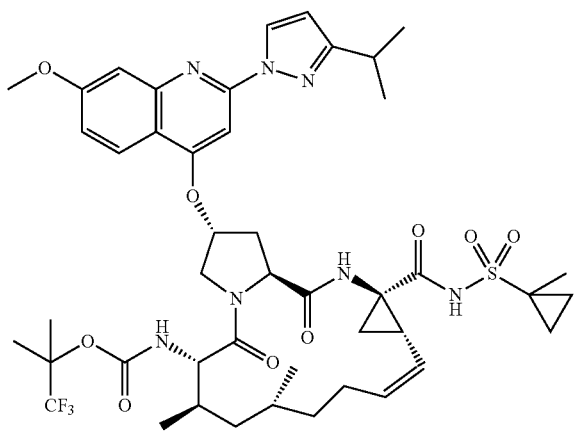

Compound 4299

Compound 4299 was prepared using the intermediates described herein and by following the general procedure described for the synthesis of Compound 4303 Compound 4299: 1,1,1-trifluoro-2-methylpropan-2-yl((2R,6S,7R,9R,13aS,14aR,16aS,Z)-2-(2-(3-isopropyl-1H-pyrazol-1-yl)-7-methoxyquinolin-4-yl)oxy)-7,9-dimethyl-14a-(((1-methyl-cyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, CD₃OD): 8.67 (d, J=3.01 Hz, 1H) 8.06 (s, 1H) 7.50 (s, 1H) 7.31 (d, J=2.51 Hz, 1H) 7.04 (dd, J=9.04, 2.51 Hz, 1H) 6.49 (d, J=2.51 Hz, 1H) 5.62 (br. s., 1H) 5.03 (t, J=9.79 Hz, 1H) 4.66 (dd, J=10.54, 7.03 Hz, 1H) 4.11 (dd, J=11.55, 3.01 Hz, 1H) 3.96 (s, 3H) 3.87 (d, J=10.54 Hz, 1H) 2.82-2.88 (m, 1H) 2.74 (d, J=8.53 Hz, 1H) 2.42-2.58 (m, 1H) 1.77 (dd, J=8.28, 5.77 Hz, 1H) 1.56-1.69 (m, 11H) 1.49-1.54 (m, 9H) 1.33-1.43 (m, 9H) 1.10 (s, 2H) 0.87-1.05 (m, 9H). MS: MS m/z 930.5 (M⁺+1).

Preparation of Compound 4301

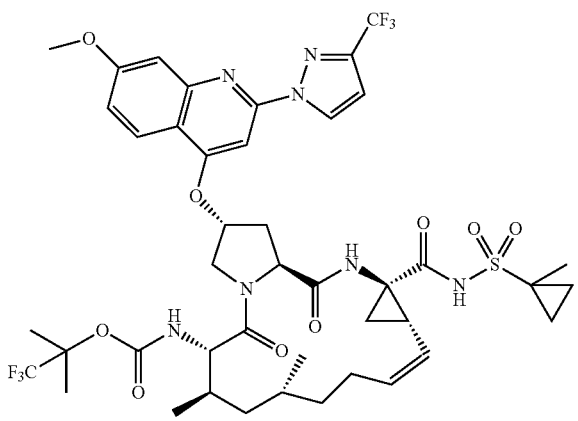

Compound 4301

Compound 4301 was prepared using the intermediates described herein and by following the general procedure described for the synthesis of Compound 4303.

Compound 4301: 1,1,1-trifluoro-2-methylpropan-2-yl ((2R,6S,7R,9R,13aS,14aR,16aS,Z)-2-((7-methoxy-2-(3-(trifluoromethyl)-1H-pyrazol-1-yl)quinolin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, CD₃OD): δ ppm 8.85-9.05 (m, 1H) 8.09 (d, J=9.04 Hz, 1H) 7.57 (s, 1H) 7.38 (d, J=2.51 Hz, 1H) 7.11 (dd, J=9.04, 2.51 Hz, 1H) 6.93 (d, J=2.51 Hz, 1H) 5.43-5.84 (m, 2H) 5.04 (br. s., 1H) 4.66 (dd, J=10.29, 6.78 Hz, 1H) 4.11 (dd, J=12.05, 3.01 Hz, 1H) 3.98 (s, 3H) 3.85 (d, J=11.04 Hz, 1H) 2.68-2.93 (m, 2H) 2.33-2.62 (m, 2H) 1.84-2.08 (m, 2H) 1.73-1.84 (m, 2H) 1.66 (d, J=10.54 Hz, 1H) 1.57-1.63 (m, 1H) 1.53 (s, 5H) 1.39-1.48 (m, 2H) 1.31-1.39 (m, 4H) 1.19-1.30 (m, 1H) 1.06 (s, 3H) 0.93-1.06 (m, 7H) 0.74-0.92 (m, 4H). MS: MS m/z 953.9 (M⁺−1).

Preparation of Compound 4358

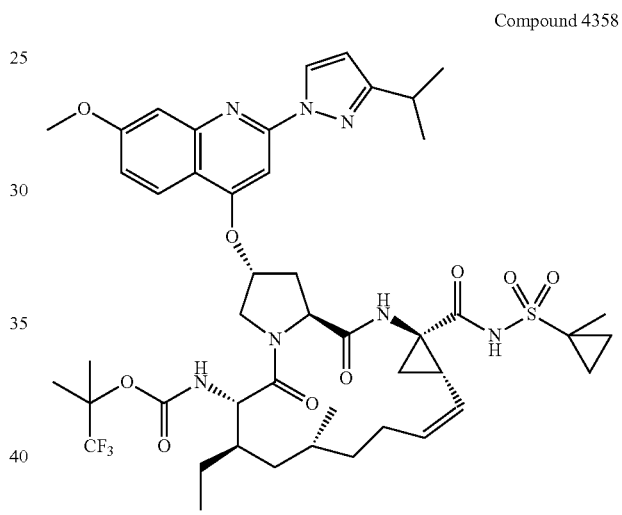

Compound 4358

Compound 4358 was prepared using the intermediates described herein and by following the general procedure described for the synthesis of Compound 4303 Compound 4358: 1,1,1-trifluoro-2-methylpropan-2-yl((2R,6S,7R,9R,13aS,14aR,16aS,Z)-7-ethyl-2-(2-(3-isopropyl-1H-pyrazol-1-yl)-7-methoxyquinolin-4-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, CD₃OD): δ ppm 9.07 (s, 1H) 8.70 (d, J=2.51 Hz, 1H) 8.02-8.07 (m, 1H) 7.52 (s, 1H) 7.35 (d, J=2.51 Hz, 1H) 7.07 (dd, J=9.04, 2.51 Hz, 1H) 6.52 (d, J=3.01 Hz, 1H) 5.61-5.68 (m, 1H) 5.00 (s, 1H) 4.66 (dd, J=10.29, 6.78 Hz, 1H) 4.06-4.14 (m, 1H) 3.98 (s, 3H) 3.12-3.18 (m, 1H) 2.85 (dd, J=13.80, 6.78 Hz, 1H) 2.70-2.76 (m, 1H) 2.50-2.58 (m, 1H) 2.43 (d, J=13.05 Hz, 1H) 2.01 (br. s., 1H) 1.78 (dd, J=8.53, 5.52 Hz, 1H) 1.51-1.69 (m, 8H) 1.37-1.45 (m, 9H) 1.15-1.22 (m, 9H) 1.07-1.13 (m, 8H) 0.81-0.92 (m, 6H). MS: MS m/z 944.0 (M⁺+1).

31
Preparation of Compound 5506 and Compound 5507

32
Preparation of Compound 5508 and Compound 5509

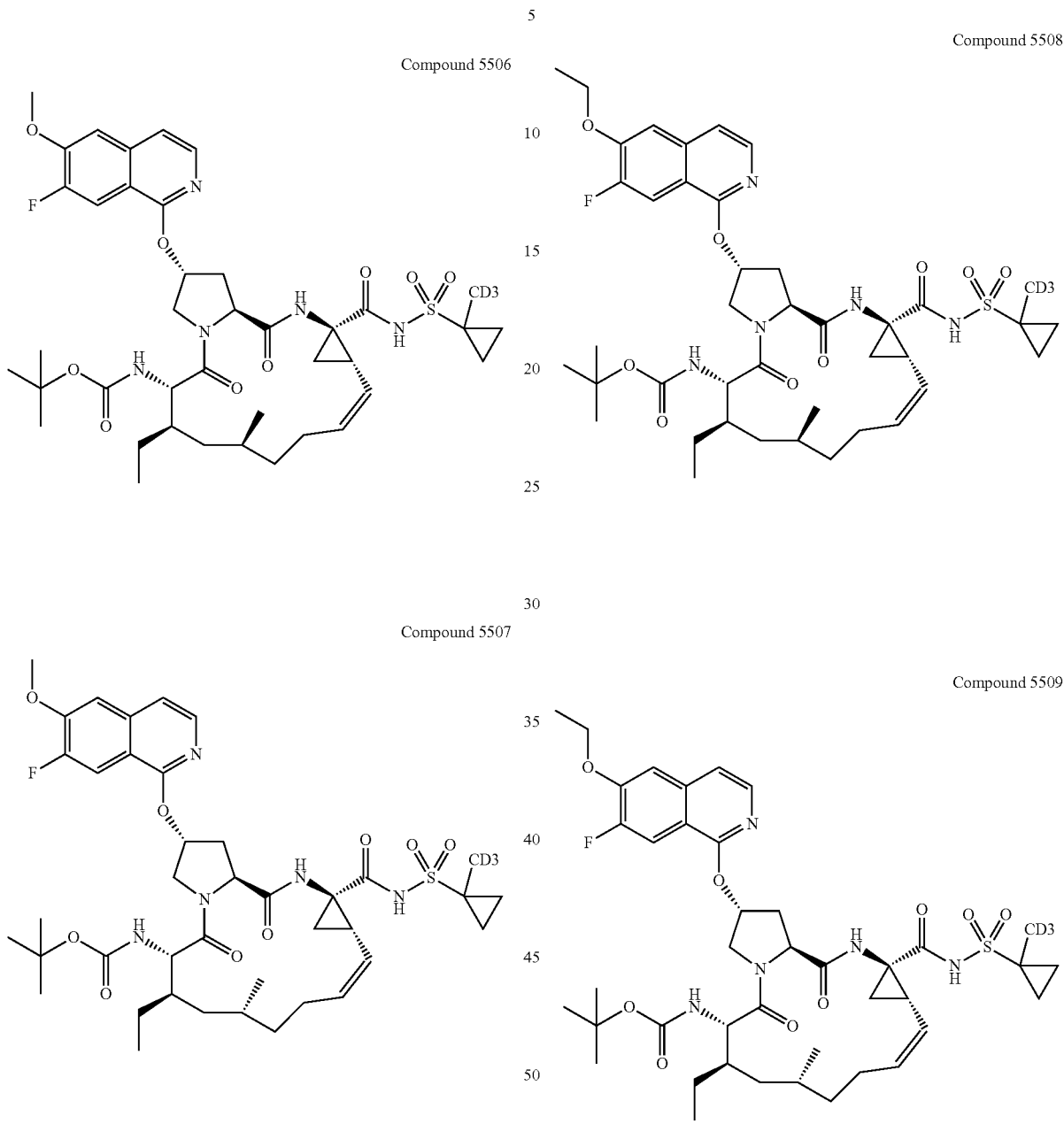

Compounds 5506 and 5507 were prepared using the intermediates described herein and by following the general procedure described for the synthesis of Compound 4303:

Compound 5506: MS: MS m/z 803.7 (M$^+$+1).

Compound 5507: $^1$H NMR (500 MHz, DMSO-d$_6$) δ 7.98 (d, J=5.8 Hz, 1H), 7.69 (d, J=11.6 Hz, 1H), 7.54 (d, J=8.2 Hz, 1H), 7.35 (d, J=5.8 Hz, 1H), 7.17 (d, J=8.2 Hz, 1H), 5.81 (br. s., 1H), 5.50 (br. s., 1H), 4.98 (br. s., 1H), 4.62-4.44 (m, 2H), 3.98 (s, 3H), 3.93-3.86 (m, 2H), 2.71-2.54 (m, 2H), 2.30 (d, J=9.2 Hz, 2H), 1.90 (d, J=11.3 Hz, 2H), 1.63-0.68 (m, 28H). MS: MS m/z 803.8 (M$^+$+1).

Compounds 5508 and 5509 were prepared using the intermediates described herein and by following the general procedure described for the synthesis of Compound 4303:

Compound 5508: MS: MS m/z 817.7 (M$^+$+1).

Compound 5509: MS: MS m/z 817.8 (M$^+$+1).

Preparation of Compound 5510 and Compound 5511

Preparation of Compound 5512 and Compound 5513

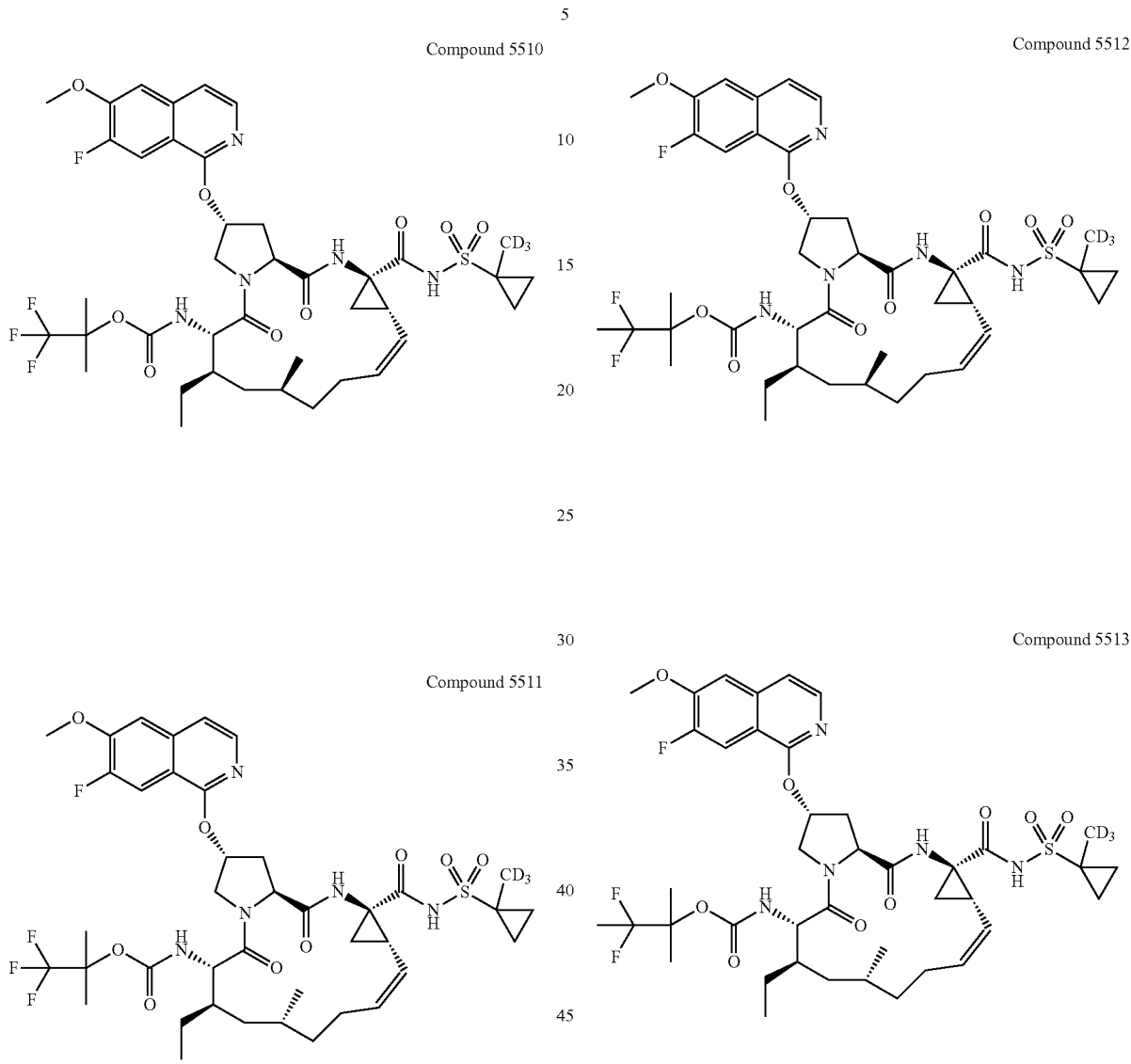

Compound 5510

Compound 5512

Compound 5511

Compound 5513

Compounds 5510 and 5511 were prepared using the intermediates described herein and by following the general procedure described for the synthesis of Compound 4303:

Compound 5510: MS: MS m/z 857.7 (M⁺+1).

Compound 5511: $^1$H NMR (500 MHz, DMSO-d$_6$) δ 7.97 (d, J=5.8 Hz, 1H), 7.82 (d, J=8.2 Hz, 1H), 7.69 (d, J=11.3 Hz, 1H), 7.54 (d, J=8.5 Hz, 1H), 7.35 (d, J=5.5 Hz, 1H), 5.81 (br. s., 1H), 5.51 (d, J=5.2 Hz, 1H), 5.00 (br. s., 1H), 4.50 (d, J=10.1 Hz, 2H), 3.97 (s, 3H), 3.94-3.84 (m, 2H), 2.61 (d, J=7.6 Hz, 2H), 2.29 (d, J=9.5 Hz, 2H), 1.91 (t, J=14.5 Hz, 2H), 1.62-1.07 (m, 16H), 0.99 (t, J=12.8 Hz, 1H), 0.93-0.82 (m, 5H), 0.72 (t, J=7.3 Hz, 3H). MS: MS m/z 857.7 (M⁺+1).

Compounds 5512 and 5513 were prepared using the intermediates described herein and by following the general procedure described for the synthesis of Compound 4303:

Compound 5512: MS: MS m/z 851.6 (M⁺+1).

Compound 5513: $^1$H NMR (500 MHz, DMSO-d$_6$) δ 7.97 (d, J=6.1 Hz, 1H), 7.69 (d, J=11.6 Hz, 1H), 7.60 (d, J=8.9 Hz, 1H), 7.54 (d, J=8.2 Hz, 1H), 7.35 (d, J=5.8 Hz, 1H), 5.81 (br. s., 1H), 5.51 (d, J=6.4 Hz, 1H), 5.00 (br. s., 1H), 4.54-4.47 (m, 2H), 3.97 (s, 3H), 3.94-3.86 (m, 2H), 2.70-2.56 (m, 2H), 2.36-2.23 (m, 2H), 1.90 (d, J=10.4 Hz, 2H), 1.62-1.11 (m, 16H), 1.03-0.81 (m, 9H), 0.72 (t, J=7.3 Hz, 3H). MS: MS m/z 851.6 (M⁺+1).

Preparation of Compound 5514 and Compound 5515

Compound 5514

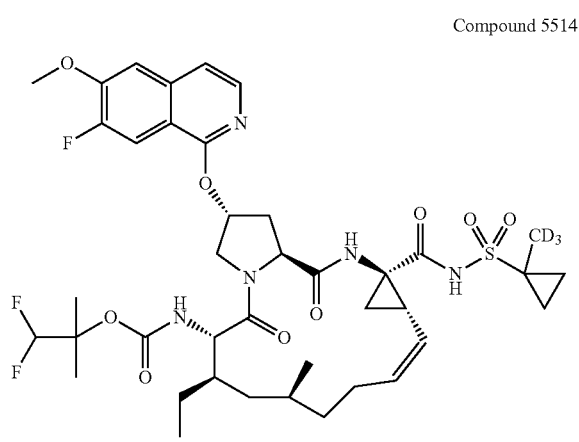

Compound 5515

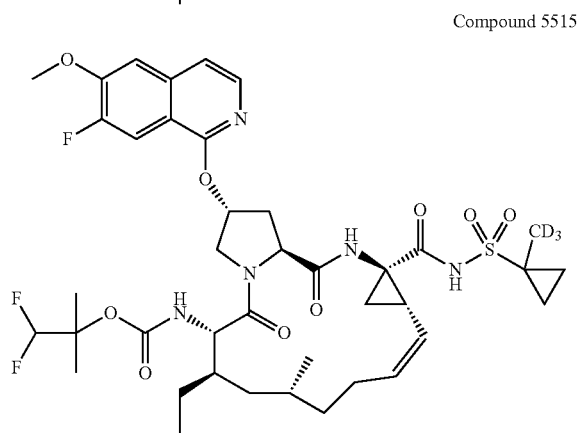

Compounds 5514 and 5515 were prepared using the intermediates described herein and by following the general procedure described for the synthesis of Compound 4303:

Compound 5514: MS: MS m/z 839.8 (M$^+$+1).

Compound 5515: $^1$H NMR (500 MHz, DMSO-d$_6$) δ 8.00-7.93 (m, 1H), 7.71-7.62 (m, 2H), 7.53 (d, J=8.5 Hz, 1H), 7.35 (d, J=6.1 Hz, 1H), 5.84-5.57 (m, 2H), 5.51 (d, J=5.5 Hz, 1H), 5.00 (br. s., 1H), 4.58-4.48 (m, 2H), 3.96 (s, 3H), 3.91-3.80 (m, 2H), 2.61 (d, J=7.0 Hz, 2H), 2.34-2.22 (m, 2H), 1.96-1.82 (m, 2H), 1.63-0.81 (m, 22H), 0.70 (t, J=7.5 Hz, 3H). MS: MS m/z 839.7 (M$^+$+1).

Preparation of Compound 5516 and Compound 5517

Compound 5516

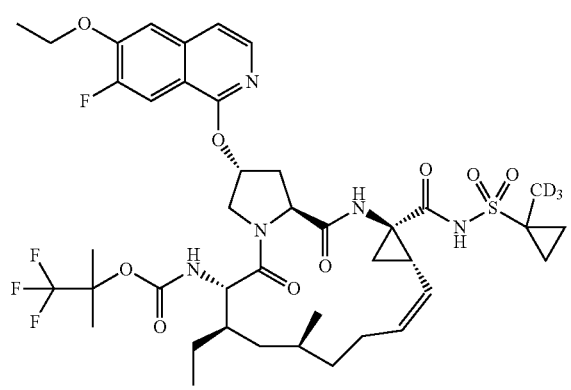

Compound 5517

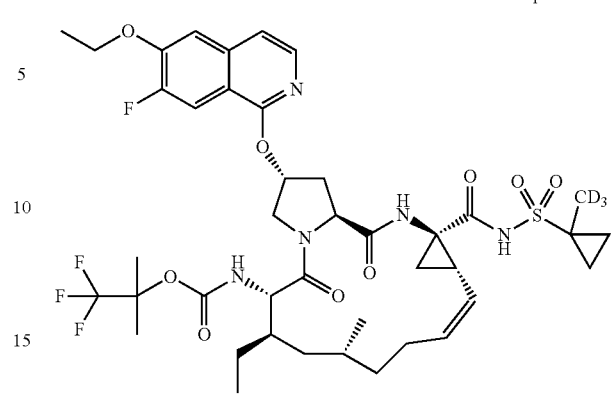

Compounds 5516 and 5517 were prepared using the intermediates described herein and by following the general procedure described for the synthesis of Compound 4303:

Compound 5516: MS: MS m/z 839.8 (M$^+$+1).

Compound 5517: $^1$H NMR (500 MHz, DMSO-d$_6$) δ 7.98-7.92 (m, 1H), 7.81 (d, J=7.9 Hz, 1H), 7.69 (d, J=11.6 Hz, 1H), 7.52 (d, J=8.5 Hz, 1H), 7.33 (d, J=5.8 Hz, 1H), 5.79 (br. s., 1H), 5.51 (d, J=6.4 Hz, 1H), 5.00 (br. s., 1H), 4.50 (d, J=10.4 Hz, 2H), 4.24 (q, J=6.9 Hz, 2H), 3.93-3.84 (m, 2H), 2.61 (d, J=7.3 Hz, 2H), 2.28 (d, J=10.1 Hz, 2H), 1.98-1.82 (m, 2H), 1.61-1.08 (m, 20H), 0.99 (t, J=13.0 Hz, 1H), 0.93-0.82 (m, 5H), 0.71 (t, J=7.3 Hz, 3H). MS: MS m/z 839.7 (M$^+$+1).

Preparation of Compound 5518 and Compound 5519

Compound 5518

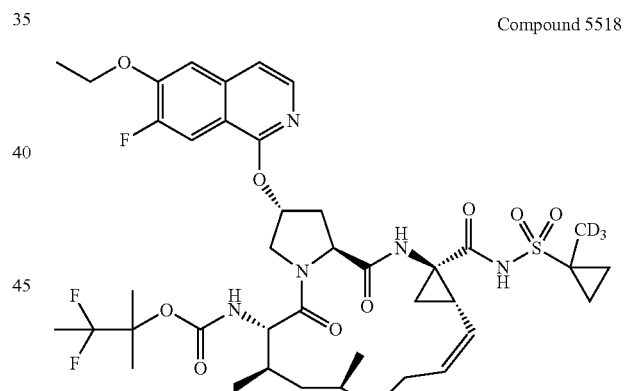

Compound 5519

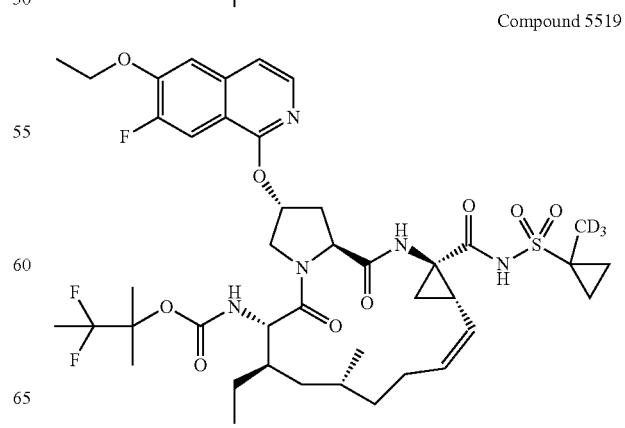

Compounds 5518 and 5519 were prepared using the intermediates described herein and by following the general procedure described for the synthesis of Compound 4303:

Compound 5518: MS: MS m/z 867.8 (M⁺+1).

Compound 5519: ¹H NMR (500 MHz, DMSO-d₆) δ 7.96 (d, J=5.8 Hz, 1H), 7.73-7.63 (m, 2H), 7.52 (d, J=8.2 Hz, 1H), 7.33 (d, J=6.1 Hz, 1H), 5.88-5.61 (m, 2H), 5.50 (d, J=6.1 Hz, 1H), 5.02 (br. s., 1H), 4.58-4.47 (m, 2H), 4.28-4.18 (m, 2H), 3.92-3.80 (m, 2H), 2.60 (d, J=7.3 Hz, 2H), 2.35-2.23 (m, 2H), 1.90 (d, J=9.5 Hz, 2H), 1.62-0.80 (m, 25H), 0.70 (t, J=7.3 Hz, 3H). MS: MS m/z 867.8 (M⁺+1).

Preparation of Compound 5520 and Compound 5521

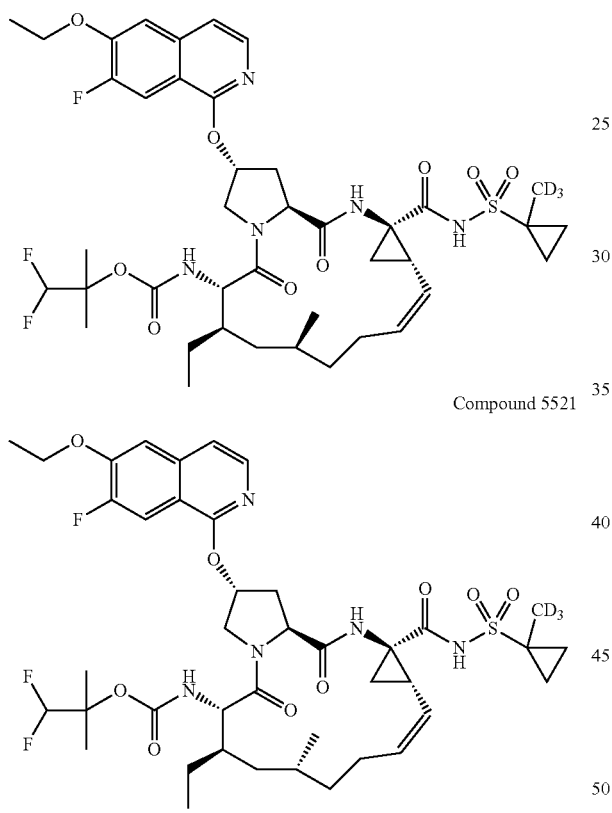

Compound 5520

Compound 5521

Preparation of Compound 5538 and Compound 5539

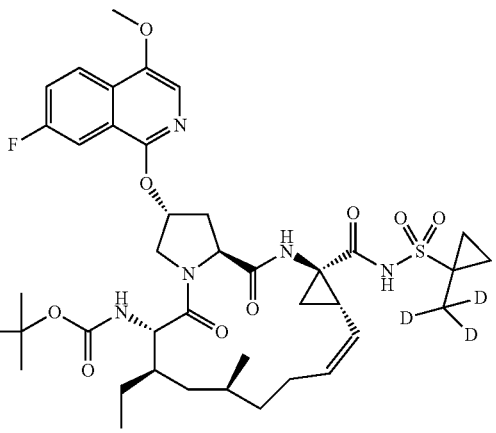

Compound 5538

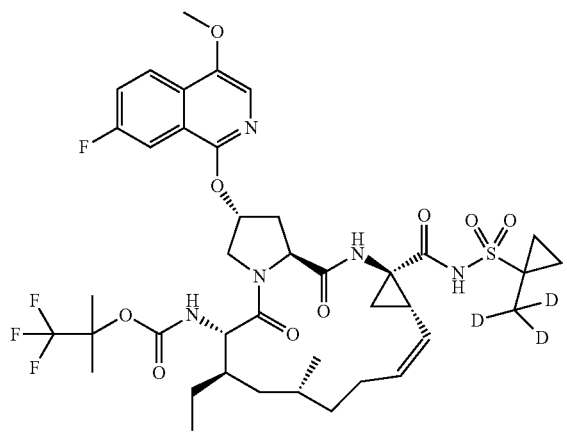

Compound 5539

Compounds 5520 and 5521 were prepared using the intermediates described herein and by following the general procedure described for the synthesis of Compound 4303:

Compound 5520: MS: MS m/z 853.8 (M⁺+1).

Compound 5521: ¹H NMR (500 MHz, DMSO-d₆) δ 7.96 (d, J=5.8 Hz, 1H), 7.72-7.64 (m, 2H), 7.52 (d, J=8.2 Hz, 1H), 7.33 (d, J=6.1 Hz, 1H), 5.87-5.61 (m, 2H), 5.50 (d, J=6.1 Hz, 1H), 5.02 (br. s., 1H), 4.59-4.48 (m, 2H), 4.29-4.18 (m, 2H), 3.92-3.80 (m, 2H), 2.60 (d, J=7.3 Hz, 2H), 2.35-2.23 (m, 2H), 1.95-1.85 (m, 2H), 1.59 (br. s., 1H), 1.54-1.03 (m, 17H), 0.98 (t, J=12.5 Hz, 1H), 0.93-0.80 (m, 5H), 0.70 (t, J=7.3 Hz, 3H). MS: MS m/z 853.9 (M⁺+1).

Compounds 5538 and 5539 were prepared using the intermediates described herein and by following the general procedure described for the synthesis of Compound 4303:

Compound 5538: MS: MS m/z 857.8 (M⁺+1).

Compound 5539: ¹H NMR (500 MHz, DMSO-d₆) δ 8.13 (d, J=5.8 Hz, 1H), 7.79 (d, J=7.9 Hz, 1H), 7.72-7.59 (m, 3H), 5.75 (br. s., 1H), 5.52 (br. s., 1H), 4.96 (br. s., 1H), 4.51 (d, J=9.8 Hz, 2H), 3.95 (s, 3H), 3.92-3.83 (m, 2H), 2.63 (br. s., 2H), 2.28 (d, J=13.4 Hz, 2H), 1.91 (d, J=11.3 Hz, 2H), 1.63-1.09 (m, 12H), 1.05-0.82 (m, 10H), 0.70 (t, J=6.7 Hz, 3H). MS: MS m/z 857.9 (M⁺+1).

Preparation of Compound 5540 and Compound 5541

Preparation of Compound 5542 and Compound 5543

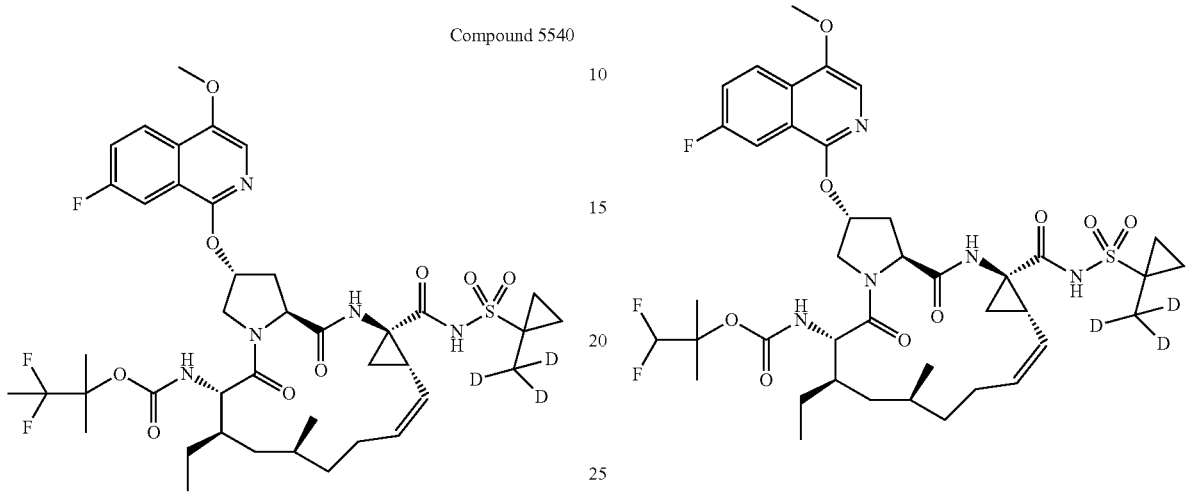

Compound 5540

Compound 5542

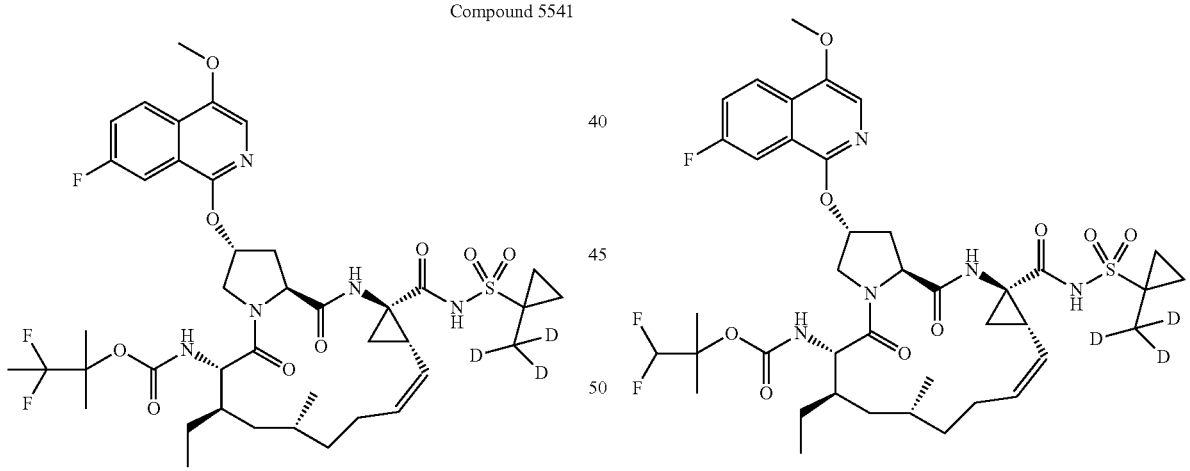

Compound 5541

Compound 5543

Compounds 5540 and 5541 were prepared using the intermediates described herein and by following the general procedure described for the synthesis of Compound 4303:

Compound 5540: MS: MS m/z 853.9 (M⁺+1).

Compound 5541: $^1$H NMR (500 MHz, DMSO-d$_6$) δ 8.13 (dd, J=9.2, 5.5 Hz, 1H), 7.73-7.54 (m, 4H), 5.76 (br. s., 1H), 5.51 (d, J=6.1 Hz, 1H), 4.99 (br. s., 1H), 4.52 (t, J=10.2 Hz, 2H), 3.96 (s, 3H), 3.93-3.84 (m, 2H), 2.71-2.57 (m, 2H), 2.36-2.23 (m, 2H), 1.96-1.83 (m, 2H), 1.64-1.10 (m, 16H), 1.04-0.81 (m, 9H), 0.72 (t, J=7.5 Hz, 3H). MS: MS m/z 853.8 (M⁺+1).

Compounds 5542 and 5543 were prepared using the intermediates described herein and by following the general procedure described for the synthesis of Compound 4303:

Compound 5542: MS: MS m/z 839.8 (M⁺+1).

Compound 5543: $^1$H NMR (500 MHz, DMSO-d$_6$) δ 8.12 (dd, J=9.0, 5.6 Hz, 1H), 7.73-7.60 (m, 4H), 5.88-5.61 (m, 2H), 5.52 (d, J=5.5 Hz, 1H), 4.97 (br. s., 1H), 4.61-4.48 (m, 2H), 3.97 (s, 3H), 3.91-3.80 (m, 2H), 2.69-2.57 (m, 2H), 2.35-2.24 (m, 2H), 1.90 (d, J=7.6 Hz, 2H), 1.61 (br. s., 1H), 1.54-0.95 (m, 15H), 0.94-0.82 (m, 6H), 0.70 (t, J=7.3 Hz, 3H). MS: MS m/z 839.8 (M⁺+1).

41
Preparation of Compound 5544 and Compound 5545

42
Preparation of Compound 5546 and Compound 5547

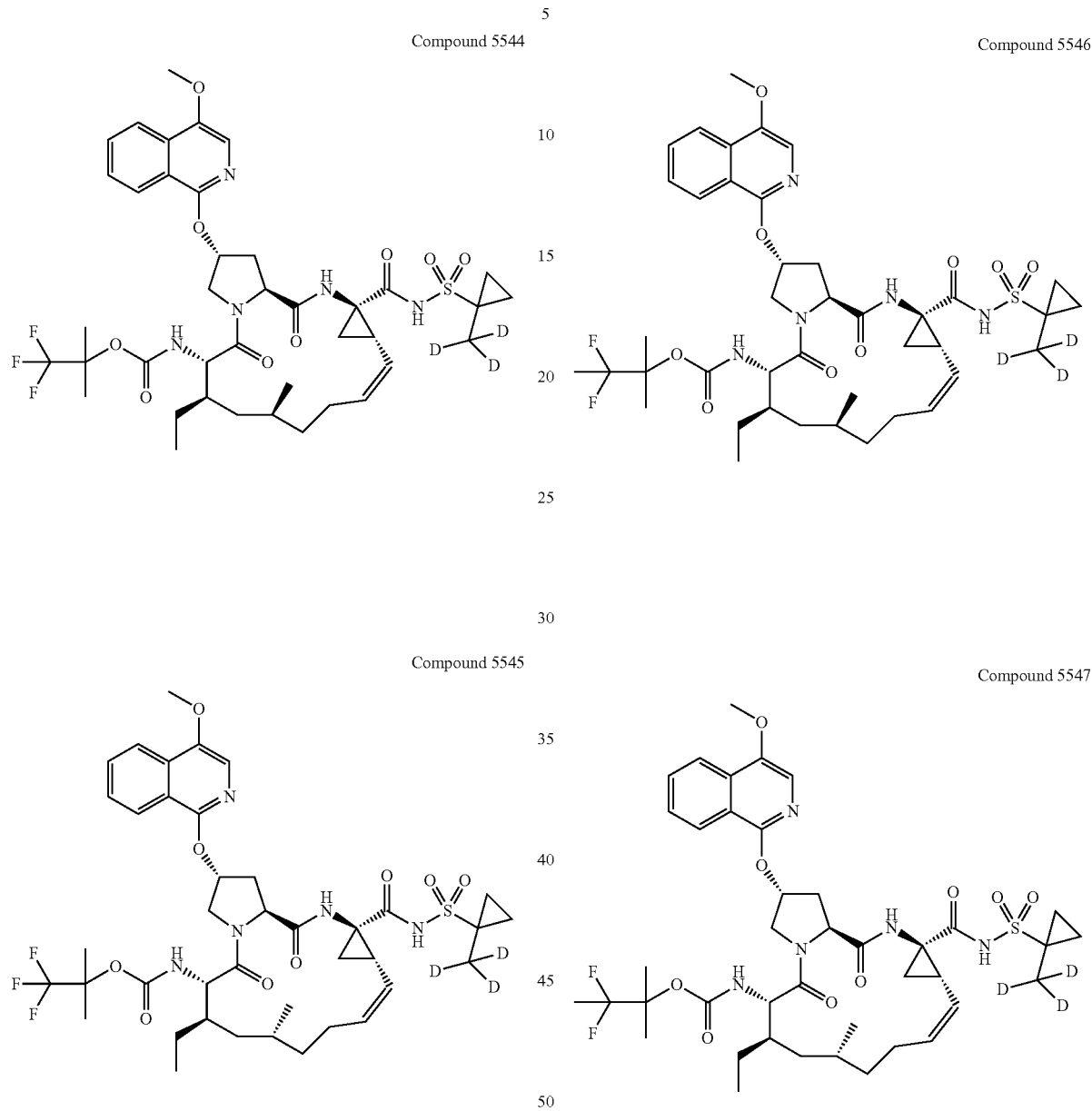

Compounds 5544 and 5545 were prepared using the intermediates described herein and by following the general procedure described for the synthesis of Compound 4303:

Compound 5544: MS: MS m/z 839.9 (M⁺+1).

Compound 5545: $^1$H NMR (500 MHz, DMSO-d$_6$) δ 8.10-8.03 (m, 2H), 7.82-7.75 (m, 2H), 7.66-7.58 (m, 2H), 5.77 (br. s., 1H), 5.52 (d, J=6.1 Hz, 1H), 4.98 (br. s., 1H), 4.52 (t, J=11.7 Hz, 2H), 3.99-3.84 (m, 5H), 2.62 (dd, J=14.2, 7.2 Hz, 2H), 2.35-2.24 (m, 2H), 1.99-1.84 (m, 2H), 1.63-0.81 (m, 22H), 0.71 (t, J=7.5 Hz, 3H). MS: MS m/z 839.9 (M⁺+1).

Compounds 5546 and 5547 were prepared using the intermediates described herein and by following the general procedure described for the synthesis of Compound 4303:

Compound 5546: MS: MS m/z 835.9 (M⁺+1).

Compound 5547: $^1$H NMR (500 MHz, DMSO-d$_6$) δ 8.10-8.02 (m, 2H), 7.78 (t, J=7.6 Hz, 1H), 7.67-7.55 (m, 3H), 5.77 (br. s., 1H), 5.58-5.47 (m, 1H), 4.98 (br. s., 1H), 4.00-3.86 (m, 6H), 2.75-2.57 (m, 2H), 2.39-2.24 (m, 2H), 1.97-1.83 (m, 2H), 1.63-1.09 (m, 17H), 1.00 (t, J=12.1 Hz, 1H), 0.94-0.84 (m, 8H), 0.73 (t, J=7.3 Hz, 3H). MS: MS m/z 835.8 (M⁺+1).

Preparation of Compound 5548 and Compound 5549

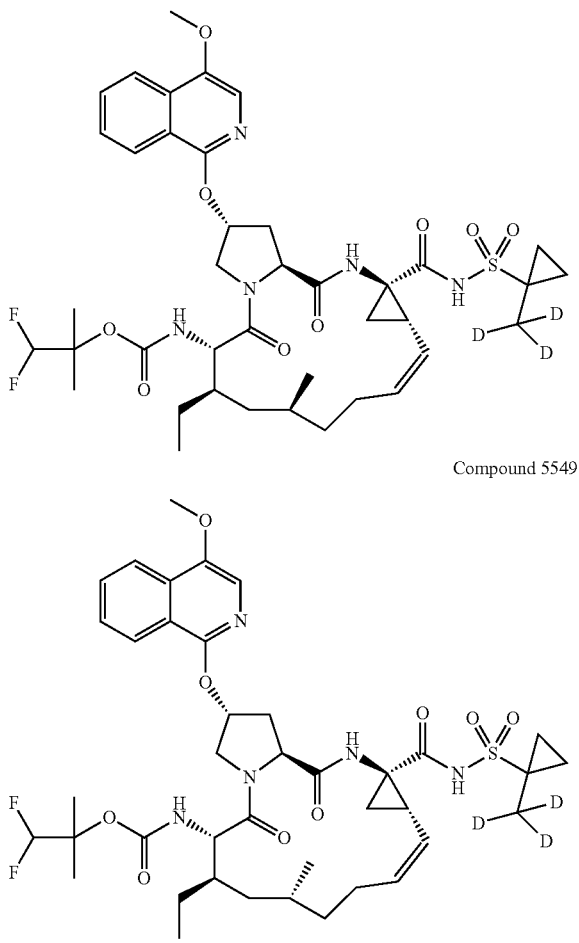

Compound 5548

Compound 5549

Compounds 5548 and 5549 were prepared using the intermediates described herein and by following the general procedure described for the synthesis of Compound 4303:

Compound 5548: MS: MS m/z 821.8 (M$^+$+1).

Compound 5549: MS: $^1$H NMR (500 MHz, DMSO-d$_6$) δ 8.05 (dd, J=7.9, 3.4 Hz, 2H), 7.78 (t, J=7.6 Hz, 1H), 7.69-7.56 (m, 3H), 5.90-5.63 (m, 2H), 5.57-5.46 (m, 1H), 4.97 (br. s., 1H), 4.63-4.47 (m, 2H), 3.96 (s, 3H), 3.93-3.82 (m, 2H), 2.61 (dd, J=13.7, 6.1 Hz, 2H), 2.37-2.23 (m, 2H), 1.92 (d, J=8.2 Hz, 2H), 1.64-1.56 (m, 1H), 1.54-0.81 (m, 21H), 0.70 (t, J=7.5 Hz, 3H). MS m/z 821.8 (M$^+$+1).

Preparation of 6-chloro-2,3-dihydrofuro[2,3-f]isoquinoline

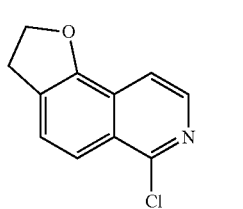

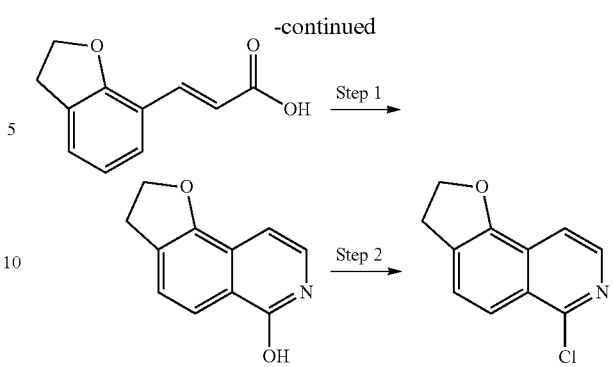

Step 1

(E)-3-(2,3-dihydrobenzofuran-7-yl)acrylic acid (0.19 g, 1.0 mmol), diphenylphosphoryl azide (0.205 mL, 0.949 mmol), and Et$_3$N (0.278 mL, 2.00 mmol) were dissolved in benzene (30 mL) and stirred for 16 h. The solution was concentrated under vacuum and the residue was purified by silica gel chromatography eluting with 20% EtOAc in hexanes to afford (E)-3-(2,3-dihydrobenzofuran-7-yl)acryloyl azide as a yellow solid (0.19 g), which was taken into PhCH$_2$Ph (5 mL). The resulting solution was slowly heated to 80° C. for 1 h and then to reflux for 3 h. After cooling to room temperature, the solid was collected washing with benzene to afford 2,3-dihydrofuro[2,3-f]isoquinolin-6-ol as a solid give (0.1 g). $^1$H NMR (400 MHz, CD$_3$OD) δ ppm 3.37 (t, J=9.05 Hz, 1H), 4.73 (t, J=9.05 Hz, 2H), 6.67 (d, J=7.09 Hz, 1H), 7.10 (d, J=7.09 Hz, 1H), 7.37 (d, J=8.07 Hz, 1H), 7.81 (d, J=8.07 Hz, 1H); MS: (M+H)$^+$ 188.

Step 2

A solution of 2,3-dihydrofuro[2,3-f]isoquinolin-6-ol (0.1 g, 0.534 mmol) in POCl$_3$ (5.0 mL, 54 mmol) was refluxed for 14 h. The solution was concentrated in vacuo and then the residue was taken into the mixture of DCM and aq. NaOH solution (4.0 N). The organic phase was collected and dried over sodium sulfate, filtered, then concentrated under vacuum. The crude material was purified by silica gel chromatography using 20% EtOAc/Hexanes as eluent to give 100 mg of the desired product 6-chloro-2,3-dihydrofuro[2,3-f]isoquinoline. $^1$H NMR (400 Hz, CDCl$_3$) δ ppm 3.43 (t, J=9.05 Hz, 2H), 4.82 (t, J=9.05 Hz, 2H), 7.52 (d, J=8.56 Hz, 1H), 7.66 (d, J=5.62 Hz, 1H), 7.84 (d, J=8.31 Hz, 1H), 8.19 (d, J=5.62 Hz, 1H); MS: MS m/z (M+H)$^+$ 206.

Preparation of 5-chloro-8-methoxy-2-methylimidazo[1,2-a]quinazoline

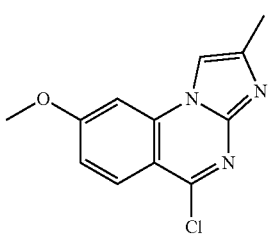

Scheme

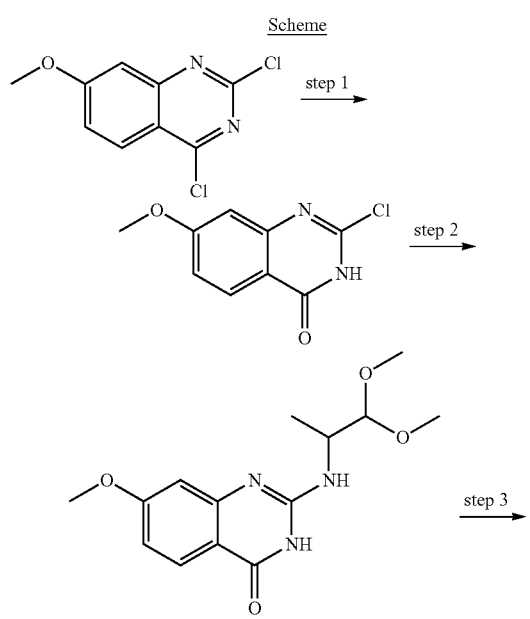

Step 1

2,4-dichloro-7-methoxyquinazoline (500 mg, 2.18 mmol) was suspended in 2% aqueous NaOH (6 mL). THF (1 mL) was added and the reaction was stirred for 4 h. The reaction was diluted with water and the solid that remained was filtered off. The filtrate was diluted with 1 N HCl. The precipitate that formed was isolated via filtration, washed with water and dried to give 2-chloro-7-methoxyquinazolin-4-ol (288 mg, 63% yield). MS: MS m/z 211.1 (M$^+$+1).

Step 2

A mixture of 2-chloro-7-methoxyquinazolin-4(3H)-one (0.88 g, 4.2 mmol) and 1,1-dimethoxypropan-2-amine (2.0 mL, 21 mmol) was heated at 80° C. for 5 h. The reaction was cooled to room temperature. The crude solid was collected and washed with water, filtered and dried to give 2-(1,1-dimethoxypropan-2-ylamino)-7-methoxyquinazolin-4(3H)-one (819 mg, 67%) as a yellow solid. MS: MS m/z 294.2 (M$^+$+1).

Step 3

2-(1,1-dimethoxypropan-2-ylamino)-7-methoxyquinazolin-4(3H)-one (1.23 g, 4.18 mmol) in acetic acid (6.00 mL, 105 mmol) was heated at reflux for 5 days. The mixture was cooled to r.t. Ether was added to the mixture. The precipitate that formed was isolated via filtration, washed with water and dried to give 8-methoxy-2-methylimidazo[1,2-a]quinazolin-5(4H)-one (400 mg, 70% pure, 30% yield). MS: MS m/z 230.1 (M$^+$+1).

Step 4

The solution of 70% pure 8-methoxy-2-methylimidazo[1,2-a]quinazolin-5(4H)-one (400 mg, 1.31 mmol) in phosphoryl trichloride (10 ml, 1.3 mmol) was stirred at 90° C. for 6 h. The solution was cooled to r.t and then concentrated in vacuo. 1N NaOH was added to the mixture to adjust pH=7. The brown solid was collected and washed with water. The crude product 5-chloro-8-methoxy-2-methylimidazo[1,2-a]quinazoline (300 mg) was used directly for the next step reaction. MS: MS m/z 248.2 (M$^+$+1).

Preparation of 5-chloroimidazo[1,2-a]quinazoline

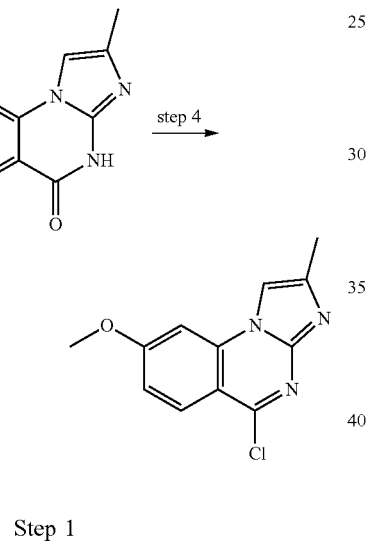

Scheme

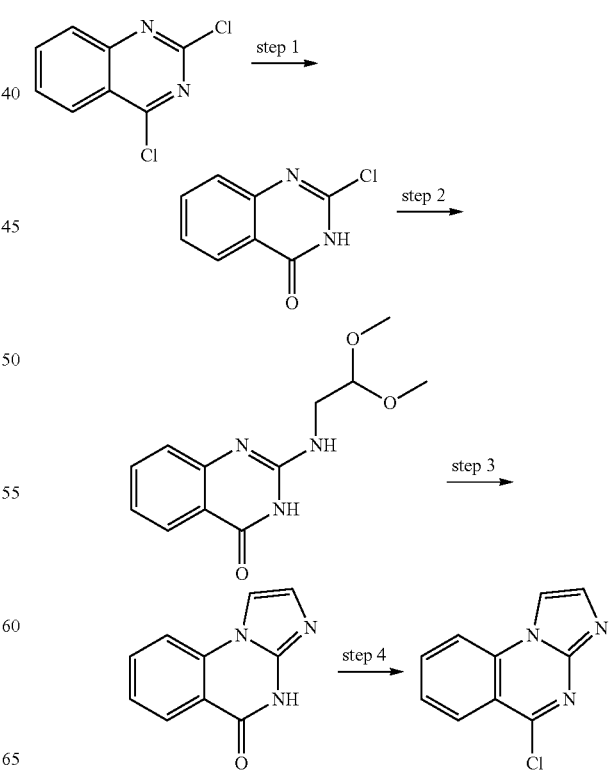

47

Step 1-4

5-chloroimidazo[1,2-a]quinazoline was then prepared using the similar procedure described for synthesizing 5-chloro-8-methoxy-2-methylimidazo[1,2-a]quinazoline. 2,4-dichloroquinazoline in step 1 and 1,1-dimethoxypropan-2-amine in step 2 were used as starting materials instead of 2,4-dichloro-7-methoxyquinazoline and 1-dimethoxypropan-2-amine respectively. MS: MS m/z 205.0 (M$^+$+1).

Preparation of 5,7-dichloroimidazo[1,2-a]quinazoline

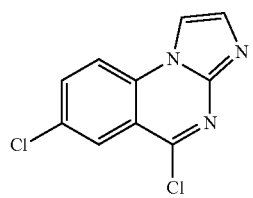 [SMILES: Clc1ccc2c(c1)c(Cl)nc1nccn12]

Scheme

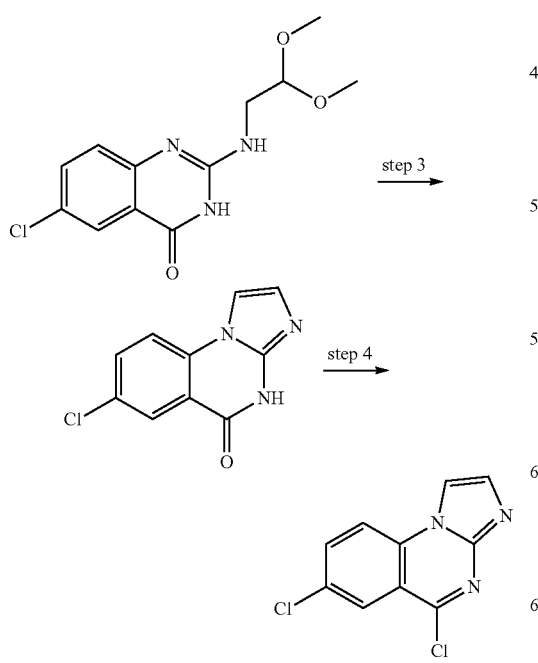

48

Step 1-4

5,7-dichloroimidazo[1,2-a]quinazoline was then prepared using the similar procedure described for synthesizing 5-chloro-8-methoxy-2-methylimidazo[1,2-a]quinazoline. 2,4,6-trichloroquinazoline in step 1 and 1,1-dimethoxypropan-2-amine in step 2 were used as starting materials instead of 2,4-dichloro-7-methoxyquinazoline and 1-dimethoxypropan-2-amine respectively. MS: MS m/z 238.0 (M$^+$+1).

Preparation of 5,7-dichloro-2-methylimidazo[1,2-a]quinazoline

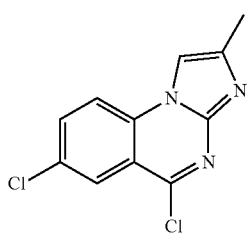 [SMILES: Cc1cn2c(n1)nc(Cl)c1cc(Cl)ccc12]

Scheme

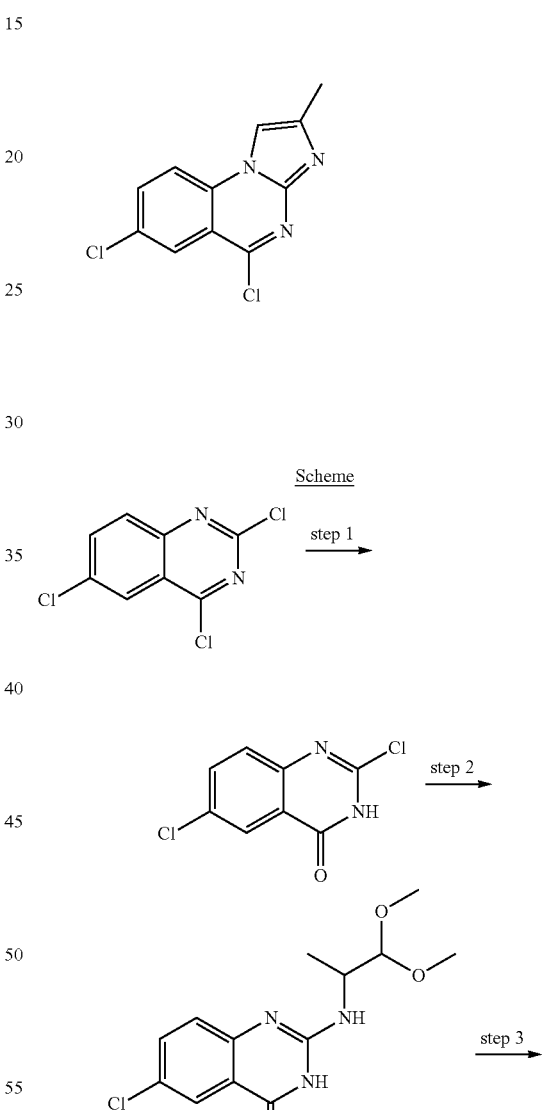

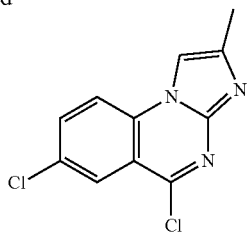

Step 1-4

5,7-dichloro-2-methylimidazo[1,2-a]quinazoline was then prepared using the similar procedure described for synthesizing 5-chloro-8-methoxy-2-methylimidazo[1,2-a]quinazoline. 2,4,6-trichloroquinazoline in step 1 was used as starting materials instead of 2,4-dichloro-7-methoxyquinazoline. MS: MS m/z 251.9 (M$^+$+1).

Preparation of 5-chloro-[1,2,4]-triazolo[4,3-a]quinazoline

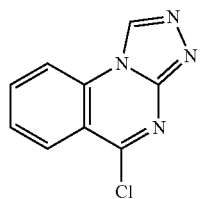 [SMILES: Clc1nc2nncn2c2ccccc12]

Scheme

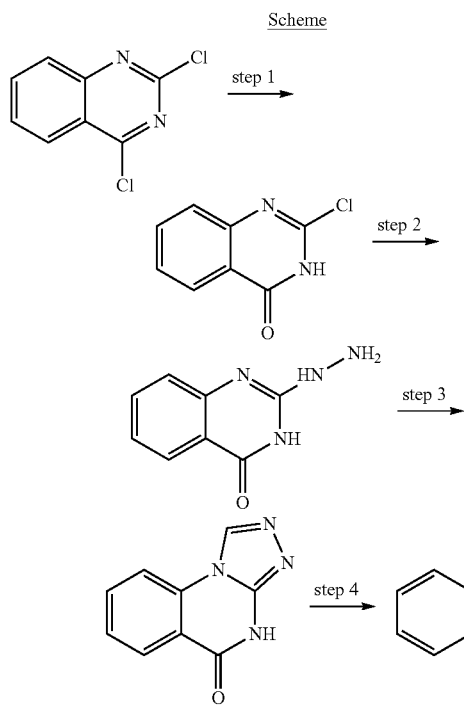

Step 1

A solution of 2,4-dichloroquinazoline (2.7 g, 13.6 mmol) in 20 mL THF and 20 mL of aq. 1N NaOH solution was stirred at r.t for 2 h. The volatiles were removed in vacuo and the aqueous solution containing crude product 2-chloroquinazolin-4(3H)-one was used directly in the next step. MS: MS m/z 181.0 (M$^+$+1).

Step 2

To the solution of 2-chloroquinazolin-4(3H)-one (2.46 g, 13.6 mmol) in water from step 1 was added hydrazine (3 mL). The solution was heated at 95° C. for 3 h. The mixture was cooled to r.t. The reaction was worked up by adding acetic acid into the solution to adjust to pH=7. The precipitated solid was isolated via filtrated and washed with water to afford crude product 2-hydrazinylquinazolin-4(3H)-one (2.11 g, 74%) that was used directly in step 3. MS: MS m/z 177.0 (M$^+$+1).

Step 3

2-hydrazinylquinazolin-4(3H)-one (2.11 g, 12.0 mmol) in formic acid (10 mL) was heated at 100° C. in for 2 h. The reaction was cooled down to r.t and then poured into water to precipitate the product. Sat. aq. NaHCO$_3$ was added to the mixture to neutralize the acid. The resulting solid was isolated via filtration and washed with water. The product [1,2,4]triazolo[4,3-a]quinazolin-5(4H)-one (1.87 g, 81% yield) was dried and used directly in the next step reaction. MS: MS m/z 187.0 (M$^+$+1).

Step 4

A solution of [1,2,4]triazolo[4,3-a]quinazolin-5(4H)-one (1.87 g, 10.04 mmol) in phosphoryl trichloride (10 mL) was stirred at 90° C. for 2 h. The solution was cooled to r.t and then concentrated in vacuo. To the residue was added aq. 1N NaOH to adjust pH=7. The brown solid was collected and washed with water. The crude product 5-chloro-[1,2,4]triazolo[4,3-a]quinazoline (1.57 g, 73%) was used directly without further purification. MS: MS m/z 205.0 (M$^+$+1).

Preparation of (1R,2S)-1-amino-N-((1-(fluoromethyl)cyclopropyl)sulfonyl)-2-vinylcyclopropanecarboxamide hydrochloride

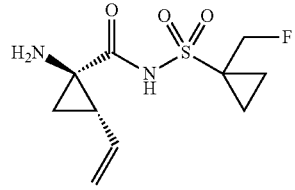 [SMILES: C=C[C@@H]1C[C@]1(N)C(=O)NS(=O)(=O)C1(CF)CC1]

Scheme

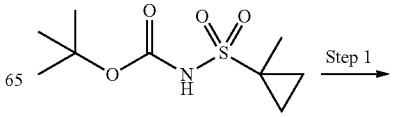

Step 1

Step 1

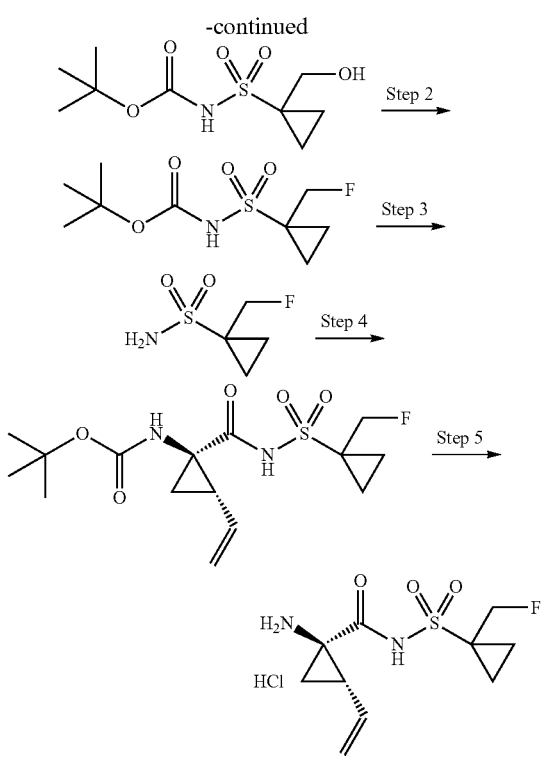

To a solution of tert-butyl cyclopropylsulfonylcarbamate (30 g, 136 mmol) in 750 mL of THF was added dropwise butyllithium (1.6 M in hexane, 212 mL, 339 mmol) over 30 min at −78° C. and the resulting mixture was stirred at −78° C. for 1 h. Formaldehyde gas was generated from paraformaldehyde (by heating at 180° C.) and was purged in to the above reaction mass for 30 min at −30° C. The reaction was stirred at the same temperature for 1 h and then allowed to warm to room temperature. The reaction was quenched with aqueous ammonium chloride solution and diluted with water. The resulting mass was washed with ethyl acetate and the aqueous layer was acidified to pH ~2 and extracted with ethyl acetate. The combined organics were dried over sodium sulfate and evaporated under reduced pressure to get desired compound tert-butyl (1-(hydroxymethyl)cyclopropyl)sulfonylcarbamate (27 g, 79%) as white solid. $^1$H NMR (400 MHz, DMSO-$d_6$): δ ppm 10.90 (sb, 1H), 4.95 (sb, 1H), 3.75 (s, 2H), 1.42 (s, 9H), 1.27 (m, 2H), 1.08 (m, 2H).

Step 2

A solution of tert-butyl 1-hydroxymethylcyclopropylsulfonylcarbamate (26.0 g, 103 mmol) in DCM (300 mL) was cooled to −78° C. To this solution was added diethylaminosulfur trifluoride ("DAST", 41.0 mL, 310 mmol). The reaction mass was stirred at the same temperature for 30 min. The reaction mass was quenched with aqueous 1N NaOH solution. The organic layer was discarded and the aqueous layer was acidified to pH ~2 by using aq. 1.5 N HCl solution. The aqueous solution was extracted with DCM (50 mL×4). The combined organic layers were dried over anhydrous sodium sulfate; filtered; then concentrated to afford desired tert-butyl (1-(fluoromethyl)cyclopropyl)sulfonylcarbamate (19 g, 72%) as gummy solid. $^1$H NMR (400 MHz, DMSO-$d_6$): δ ppm 11.25 (sb, 1H), 4.75 (s, 1H), 4.63 (s, 1H), 1.44 (s, 9H), 1.28 (m, 2H), 1.07 (m, 2H). $^{19}$F NMR: −211.7 (1F).

Step 3

To a solution of tert-butyl 1-fluoromethyl cyclopropylsulfonylcarbamate (19 g, 75 mmol) in dichlomethane (200 mL) at room temperature was added trifluoroacetic acid ("TFA", 50 mL). The reaction mass was stirred at room temperature for 1 h. The solvent was evaporated under reduced pressure and the residue was diluted with hexane. The precipitated solid was isolated via filtration and washed with hexane to afford pure 1-(fluoromethyl)cyclopropane-1-sulfonamide (11 g, 96%) as an off-white solid. $^1$H NMR (400 MHz, DMSO-$d_6$): δ ppm 6.98 (sb, 2H), 4.75 (s, 1H), 4.63 (s, 1H), 1.28 (m, 2H), 1.08 (m, 2H). $^{19}$F NMR: −211.74 (1 F).

Step 4

To a solution of (1R,2S)-1-(tert-butoxycarbonylamino)-2-vinylcyclopropanecarboxylic acid (7.5 g, 33 mmol) in DMF (50 mL) was added 1,1'-carbonyldiimidazole ("CDI", 10.7 g, 66.0 mmol) and the reaction mass was heated at 55° C. for 4 h. To this reaction mass was added 1-fluoromethylcyclopropane-1-sulfonamide (6.5 g, 42.9 mmol) followed by 1,8-diazabicyclo[5.4.0]undec-7-ene ("DBU", 6.0 mL, 43 mmol). The reaction mixture was stirred at 55° C. for 18 h. The solvent was evaporated under reduced pressure and the residue was diluted with water and acidified to pH ~2 by using aq. 1.5 N HCl solution. The precipitated solid was isolated via filtration and washed with water to afford tert-butyl (1R,2S)-1-(1-(fluoromethyl)cyclopropylsulfonylcarbamoyl)-2-vinylcyclopropylcarbamate as off-white solid (11.5 g, 96%). MS: MS m/z 361.4 (M$^+$−1).

Step 5

A solution of tert-butyl (1R,2S)-1-(1-(fluoromethyl)cyclopropylsulfonylcarbamoyl)-2-vinylcyclopropylcarbamate (11.5 g, 31.7 mmol) in 4 N HCl in dioxane (100 mL) was stirred at room temperature for 1 h. The volatiles were removed under reduced pressure and the residue was washed with diethyl ether to afford crude (1R,2S)-1-amino-N-(1-(fluoromethyl)cyclopropylsulfonyl)-2-vinylcyclopropanecarboxamide hydrochloride (6 g, 72%). The crude compound was taken to the next step without further purification. MS: MS m/z 263.14 (M$^+$+1)

Preparation of 3,3-difluoro-2-methylbutan-2-yl pyridin-2-yl carbonate

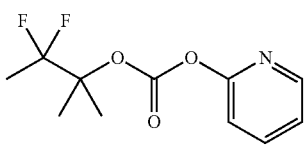 [SMILES: CC(F)(F)C(C)(C)OC(=O)Oc1ccccn1]

Scheme:

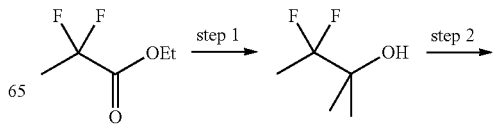

-continued

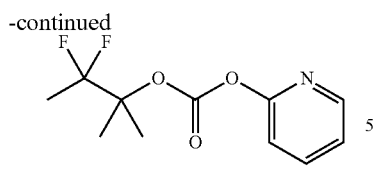

Step 1

Methylmagnesium bromide (24.9 mL, 74.7 mmol) was added dropwise via syringe to a solution of ethyl 2,2-difluoropropanoate (3.44 g, 24.91 mmol) in diethyl ether (50 mL) at −20° C. and stirred at this temp for 1 h before warming up to RT. The reaction was quenched with sat. ammonium chloride and extracted with ether. The organic layer was washed with brine; dried over $MgSO_4$; filtered and concentrated in vacuo to afford the crude 3,3-difluoro-2-methylbutan-2-ol (1.84 g, 59.5% yield) as an oil. $^1$H NMR (500 MHz, $CDCl_3$) δ 1.68-1.58 (m, 3H), 1.31 (t, J=1.2 Hz, 6H).

Step 2

To a suspension of sodium hydride, 60% in mineral oil (0.652 g, 16.31 mmol) in THF (25 mL) was added 3,3-difluoro-2-methylbutan-2-ol (1.84 g, 14.82 mmol) at 0° C. After stirring 30 min, the solution was transferred to a solution of di(pyridin-2-yl) carbonate (3.20 g, 14.82 mmol) in THF (25 mL) through a cannula. The formed slurry was stirred at 0° C. for 30 min. The slurry was warmed to rt and stirred for 2 h. The reaction was diluted with EtOAc, washed with brine, dried over $MgSO_4$, filtered, concentrated to give a residue that was purified by silica gel chromatography eluting with 10-50% EtOAc in hexanes to 3,3-difluoro-2-methylbutan-2-yl pyridin-2-yl carbonate (500 mg, 13.76%) as an oil that later crystallized to a white solid upon standing. $^1$H NMR (500 MHz, $CDCl_3$) δ 8.43 (ddd, J=4.9, 2.0, 0.7 Hz, 1H), 7.95-7.75 (m, 1H), 7.31-7.24 (m, 1H), 7.15 (dt, J=8.2, 0.8 Hz, 1H), 1.72 (s, 6H), 1.77-1.66 (m, 3H).

Scheme: Preparation of tert-butyl ((2R, 6S, 7R, 13aS, 14aR, 16aS, Z)-14a-((cyclopropylsulfonyl)carbamoyl)-7-ethyl-2-hyroxy-9-methyl-5,16-dioxo-1,2,3,5,6,7,8,9,10,11,13a,14,14a,15,16,16a-hexadecahydrocyclopropa[e]pyrrolo[1,2-a] [1,4] diazacyclopentadecin-6-yl)carbamate

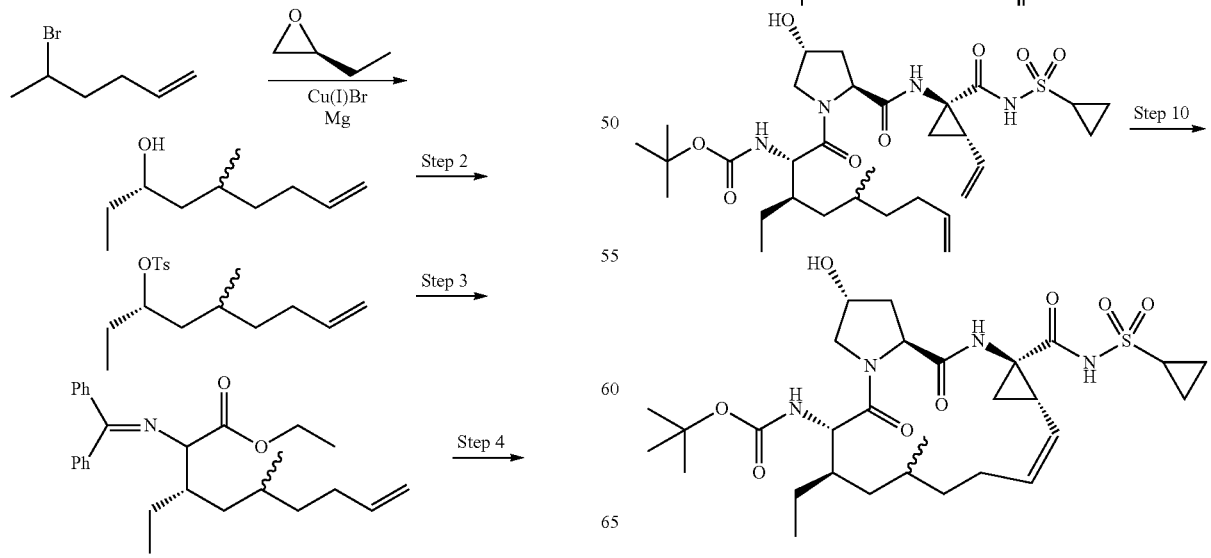

Step 1: Preparation of (S)-5-methylnon-8-en-3-ol

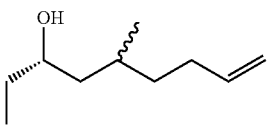

Magnesium turnings (3.03 g, 125 mmole) were suspended in dry THF (100 mL) and to the mixture was added iodine (100 mg) at room temperature. To this reaction mass was added a solution of 5-bromohex-1-ene (20.37 g, 125 mmole) in THF (200 mL). The reaction mass was heated with hot air gun to initiate the reaction. Upon full conversion of the bromide, the solution was transferred via cannula to a solution of (S)-2-ethyloxirane (6.05 g, 83 mmol) and copper bromide (1.19 g, 8.32 mmol) in THF (100 mL) at −78° C. The reaction mass was allowed to come to room temperature and was stirred overnight. The reaction mass was quenched with saturated aqueous ammonium chloride solution and extracted with diethyl ether (200 mL×3). The combined organic layers were dried over anhydrous $Na_2SO_4$; filtered; then concentrated at room temperature to get crude compound. The crude compound was purified by column chromatography (Silica gel, 10% TBME in pet ether) to get (S)-5-methylnon-8-en-3-ol (9.5 g, 73.1%) as an oily liquid. $^1$H NMR (400 MHz, $CDCl_3$): δ ppm 0.87-0.97 (m, 6H), 1.22-1.32 (m, 4H), 1.52-1.72 (m, 2H), 1.90-2.29 (m, 2H), 3.38-3.45 (m, 2H), 4.16-4.19 (m, 1H), 4.91-5.02 (m, 2H), 5.75-5.82 (m, 1H).

Step 2: Preparation of (S)-5-methylnon-8-en-3-yl 4-methylbenzenesulfonate

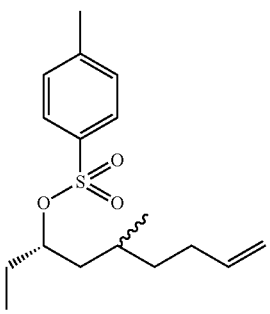 [SMILES: C=CCCC(C)C[C@H](CC)OS(=O)(=O)c1ccc(C)cc1]

To a solution of (S)-5-methylnon-8-en-3-ol (9.5 g, 61 mmol) in DCM (100 mL) was added pyridine (20 mL) followed by DMAP (0.74 g, 6.08 mmole) and the solution was stirred for 10 min. p-toluenesulfonyl chloride (17.39 g, 91 mmole) was added to the reaction mass at 0° C. The reaction mass was allowed to come to room temperature and stirred overnight. Solvent was removed under reduced pressure and the residue was diluted with ethyl acetate (100 mL). The organic solution was washed with aqueous 1.5 N HCl solution; saturated bicarbonate solution; brine solution; dried over anhydrous $Na_2SO_4$; filtered; and evaporated under reduced pressure to get crude compound (15 g, 79%). The crude compound was taken to the next step without further purification. MS: MS m/z 328.4 ($M^+$+18).

Step 3: Preparation of (3R)-ethyl 2-(diphenylmethyleneamino)-3-ethyl-5-methylnon-8-enoate

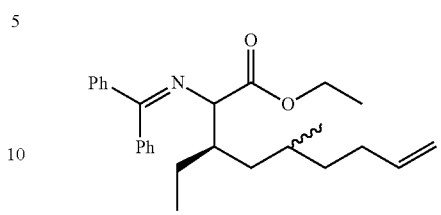

To a solution of (S)-5-methylnon-8-en-3-yl 4-methylbenzenesulfonate (15 g, 48 mmol) and N-(diphenylmethylene) glycinate ethyl ester (15.5 g, 58.0 mmol) in toluene (150 mL) at 0° C. was added lithium bis(trimethylsilyl)amide ("LiHMDS", 72.5 mL, 72.5 mmole, 1 M solution in THF). The reaction mass was allowed to come to room temperature, and then was heated at 110° C. for 2 h. The reaction mass was cooled to room temperature, quenched with water and extracted with ethyl acetate (100 mL×3). The combined organic layers were dried over anhydrous $Na_2SO_4$; filtered; then concentrated under reduced pressure to get crude compound (7.0 g, 35.7%). The crude compound was taken to the next step without further purification. MS: MS m/z 406.4 ($M^+$+1).

Step 4: Preparation of (3R)-ethyl 2-amino-3-ethyl-5-methylnon-8-enoate hydrochloride

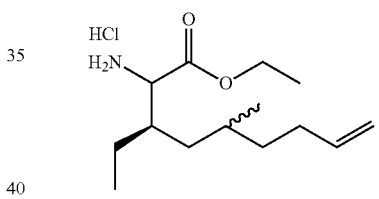

A solution of (3R)-ethyl 2-(diphenylmethyleneamino)-3-ethyl-5-methylnon-8-enoate (7.00 g, 17.3 mmole) in diethyl ether (20 mL) was added aqueous 1.5 N HCl solutions (100 mL) and the reaction mass was stirred at room temperature overnight. The reaction mass was washed with diethyl ether (100 mL). The aqueous solution was basified using saturated sodium bicarbonate solution and extracted with ethyl acetate (100 mL×3). The combined organic layers were dried over anhydrous $Na_2SO_4$; filtered; then concentrated under reduced pressure to get crude compound (2.6 g, 62.4%). The crude compound was taken to the next step without further purification. MS: MS m/z 242.4 ($M^+$+1).

Step 5: Preparation of (3R)-ethyl 2-(tert-butoxycarbonylamino)-3-ethyl-5-methylnon-8-enoate

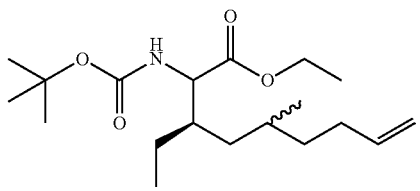 [SMILES: C=CCCC(C)C[C@@H](CC)C(NC(=O)OC(C)(C)C)C(=O)OCC]

A solution of (3R)-ethyl 2-amino-3-ethyl-5-methylnon-8-enoate hydrochloride (2.99 g, 10.8 mmole) in DCM (20 mL) was added N,N-diisopropylethylamine ("DIPEA", 1.08 mL, 10.8 mmole) followed by (Boc)₂O (2.39 mL, 10.8 mmole) at room temperature. The reaction mass was stirred at room temperature overnight. The reaction mass was diluted with DCM and washed with water. The organic layer was dried over anhydrous Na₂SO₄; filtered; then concentrated under reduced pressure to get crude compound. The crude compound was purified by column chromatography (Silica gel, 20% ethyl acetate in pet-ether) to get 2.3 g, (62.5%) of (3R)-ethyl 2-(tert-butoxycarbonylamino)-3,5-dimethylnon-8-enoate as an oily liquid. MS: MS m/z 342.4 (M⁺+1).

Step 6: Preparation of (3R)-2-(tert-butoxycarbonylamino)-3-ethyl-5-methylnon-8-enoic acid

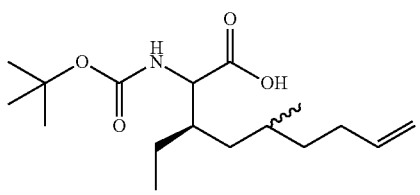 [SMILES: C=CCCC(C)C[C@@H](CC)C(NC(=O)OC(C)(C)C)C(=O)O]

To a solution of (3R)-ethyl 2-(tert-butoxycarbonylamino)-3-ethyl-5-methylnon-8-enoate (2.30 g, 6.74 mmole) in THF/water (50 mL, 1:1) was added methanol (10 mL) followed by LiOH (0.84 g, 20 mmol) at room temperature. The reaction mass was stirred at room temperature overnight. Solvent was evaporated under reduced pressure and the residue was diluted with water (10 mL). The aqueous solution was acidified with aqueous 1.5 N HCl solutions to pH ~3 and extracted with ethyl acetate (100 mL×3). The combined organic layer was dried over anhydrous Na₂SO₄; filtered; then concentrated under reduce pressure to get crude compound. The crude compound was purified by column chromatography (Silica gel, 2% methanol in DCM) to get 1.5 g (71%) of Intermediate 9 as an off-white solid. ¹H NMR (400 MHz, DMSO-d₆): δ ppm 1.27-1.09 (m, 8H), 1.02-1.35 (m, 3H), 1.39 (s, 11H), 1.91-1.97 (m, 1H), 1.99-2.02 (m, 2H), 4.03-4.12 (m, 1H), 4.90-5.03 (m, 2H), 5.74-5.84 (m, 1H), 6.80-6.83 (m, 1H), 12.47 (sb, 1H).

Step 7: Preparation of (2S,4R)-methyl 1-((2S,3R)-2-(tert-butoxycarbonylamino)-3-ethyl-5-methylnon-8-enoyl)-4-hydroxypyrrolidine-2-carboxylate

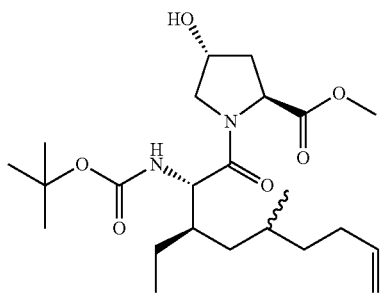 [SMILES: C=CCCC(C)C[C@@H](CC)[C@H](NC(=O)OC(C)(C)C)C(=O)N1C[C@H](O)C[C@H]1C(=O)OC]

To a solution of (3R)-2-(tert-butoxycarbonylamino)-3-ethyl-5-methylnon-8-enoic acid (2.0 g, 6.4 mmole) in dichloromethane (20 mL) was added DIPEA (1.93 mL, 19.2 mmole) and HATU (2.42 g, 6.38 mmole) followed by (2S,4R)-methyl 4-hydroxypyrrolidine-2-carboxylate (1.15 g, 6.38 mmole) at room temperature. The reaction mixture was stirred at room temperature for 2 h. The reaction mass was diluted with DCM and washed with water. The organic layer was dried over anhydrous Na₂SO₄; filtered; then concentrated under reduced pressure to get crude compound as mixture of diastereomers. The material was subjected to SFC purification to afford (2S,4R)-methyl 1-((2S,3R)-2-(tert-butoxycarbonylamino)-3-ethyl-5-methylnon-8-enoyl)-4-hydroxypyrrolidine-2-carboxylate (1.5 g, 53%). MS: MS m/z 441.6 (M⁺+1).

Step 8: Preparation of (2S,4R)-1-((2S,3R)-2-(tert-butoxycarbonylamino)-3-ethyl-5-methylnon-8-enoyl)-4-hydroxypyrrolidine-2-carboxylic acid

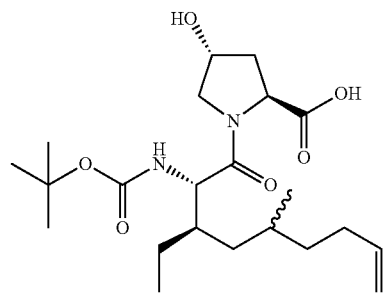 [SMILES: C=CCCC(C)C[C@@H](CC)[C@H](NC(=O)OC(C)(C)C)C(=O)N1C[C@H](O)C[C@H]1C(=O)O]

To a solution of (2S,4R)-methyl 1-((2S,3R)-2-(tert-butoxycarbonylamino)-3-ethyl-5-methylnon-8-enoyl)-4-hydroxypyrrolidine-2-carboxylate (1.5 g, 3.40 mmole) in THF:water (16 mL, 1:1) was added LiOH (286 mg, 6.80 mmole) followed by 3 mL of methanol at room temperature. The reaction mass was stirred at room temperature overnight. The solvent was evaporated under reduced pressure and the residue was diluted with water and acidified with aqueous 1.5 N HCl solutions. The aqueous solution was extracted with ethyl acetate (20 mL×3). The combined organic layers were dried over anhydrous Na₂SO₄; filtered; then concentrated under reduced pressure to afford (2S,4R)-1-((2S,3R)-2-(tert-butoxycarbonylamino)-3-ethyl-5-methylnon-8-enoyl)-4-hydroxypyrrolidine-2-carboxylic acid (1.3 g, 90%) as a white solid. ¹H NMR (400 MHz, DMSO-d₆): δ ppm 0.81-0.93 (m, 6H), 1.12-1.29 (m, 5H), 1.30-1.50 (m, 11H), 1.71-1.80 (m, 2H), 1.91-2.51 (m, 4H), 3.57-3.59 (m, 1H), 4.27-4.35 (m, 3H), 4.92-4.97 (m, 2H), 5.01-5.15 (m, 1H), 5.74-5.79 (m, 1H), 6.30-6.80 (m, 1H), 12.50 (sb, 1H). MS: MS m/z 427.6 (M⁺+1).

Step 9: Preparation of tert-butyl (2S,3R)-1-((2S,4R)-2-((1R,2S)-1-(cyclopropylsulfonylcarbamoyl)-2-vinylcyclopropylcarbamoyl)-4-hydroxypyrrolidin-1-yl)-3-ethyl-5-methyl-1-oxonon-8-en-2-ylcarbamate

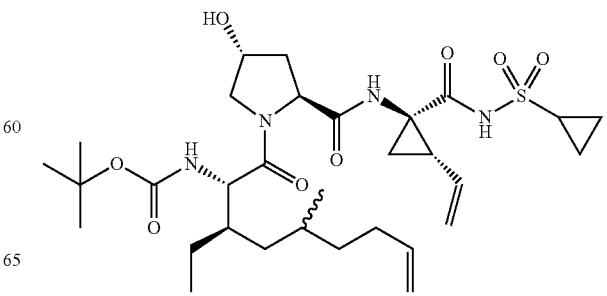

To a solution of (2S,4R)-1-((2S,3R)-2-(tert-butoxycarbonylamino)-3-ethyl-5-methylnon-8-enoyl)-4-hydroxypyrrolidine-2-carboxylic acid (1.3 g, 3.05 mmole) in dichloromethane (50 mL) was added HATU (1.15 g, 3.05 mmole) followed by DIPEA (1.6 mL, 9.13 mmole) at room temperature. The reaction mass was stirred at the same temperature for 10 min. (1R,2S)-1-amino-N-(cyclopropylsulfonyl)-2-vinylcyclopropanecarboxamide (1.22 g, 3.05 mmole) was added to the reaction mass and the mixture was stirred at room temperature for 1 h. The reaction mass was diluted with dichloromethane and washed with water. The organic layer was dried over anhydrous $Na_2SO_4$; filtered; then concentrated under reduced pressure to get the crude compound. The crude compound was purified by silica gel chromatography (6% methanol in chloroform) to get 1.7 g (87%) of tert-butyl (2S,3R)-1-((2S,4R)-2-((1R,2S)-1-(cyclopropylsulfonylcarbamoyl)-2-vinylcyclopropylcarbamoyl)-4-hydroxypyrrolidin-1-yl)-3-ethyl-5-methyl-1-oxonon-8-en-2-ylcarbamate as a white solid. MS: MS m/z 639.55 ($M^+$+1).

Step 10: Preparation of tert-butyl (2R,6S,7R,13aS,14aR,16aS,Z)-14a-(cyclopropylsulfonylcarbamoyl)-7-ethyl-2-hydroxy-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

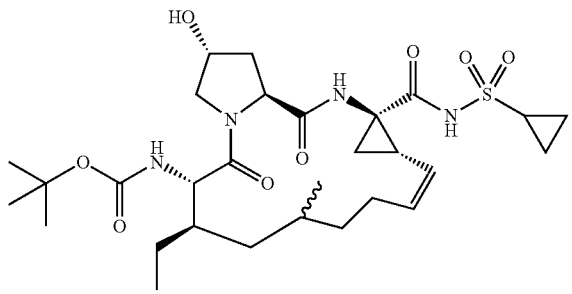 [SMILES: CC[C@@H]1CC(C)CC/C=C\[C@@H]2C[C@@]2(C(=O)NS(=O)(=O)C2CC2)NC(=O)[C@@H]2C[C@@H](O)CN2C(=O)[C@H]1NC(=O)OC(C)(C)C]

To a degassed solution of tert-butyl (2S,3R)-1-42S,4R)-2-41R,2S)-1-(cyclopropylsulfonylcarbamoyl)-2-vinylcyclopropylcarbamoyl)-4-hydroxypyrrolidin-1-yl)-3-ethyl-5-methyl-1-oxonon-8-en-2-ylcarbamate (1.7 g, 2.66 mmole) in dichloroethane (100 mL) was added (1,3-Bis-(2,4,6-trimethylphenyl)-2-imidazolidinylidene)dichloro(o-isopropoxyphenylmethylene)ruthenium ("Hoveyda-Grubbs II generation catalyst", 266 mg) at room temperature under nitrogen atmosphere. The reaction mass was heated at 95° C. overnight. The solvent was evaporated under reduced pressure and the residue was purified by silica gel chromatography (5% methanol in chloroform) to afford tert-butyl (2R,6S,7R,13aS,14aR,16aS,Z)-14a-(cyclopropylsulfonylcarbamoyl)-7-ethyl-2-hydroxy-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (770 mg, 47%) as a pale yellow crystalline solid. MS: MS m/z 609.20 ($M^+$−1).

Preparation of tert-butyl((2S,3R)-3-ethyl-14(2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-5-methyl-1-oxonon-8-en-2-yl)carbamate

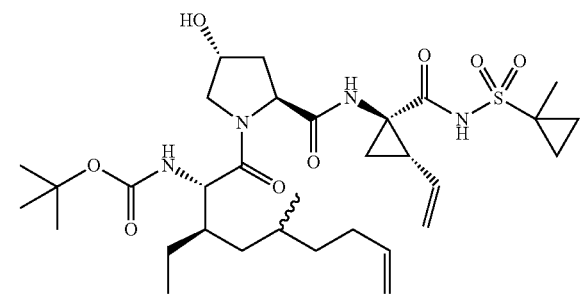 [SMILES: C=CCCC(C)C[C@@H](CC)[C@H](NC(=O)OC(C)(C)C)C(=O)N1C[C@H](O)C[C@H]1C(=O)N[C@]1(C(=O)NS(=O)(=O)C2(C)CC2)C[C@H]1C=C]

The same procedure was used as described for the preparation of tert-butyl((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate but(2S,4R)-1-((2S,3R)-2-(tert-butoxycarbonylamino)-3-ethyl-5-methylnon-8-enoyl)-4-hydroxypyrrolidine-2-carboxylic acid was used as starting material instead of (2S,4R)-1-((3R)-2-((tert-butoxycarbonyl)amino)-3,5-dimethylnon-8-enoyl)-4-hydroxypyrrolidine-2-carboxylic acid. $^1$H NMR (400 MHz, DMSO-$d_6$): δ ppm 10.42 (d, J=4.02 Hz, 1H) 8.83 (d, J=8.53 Hz, 1H) 6.24 (m, 1H) 5.81 (m, 1H) 5.57 (m, 1H) 5.05 (m, 5H) 4.32 (m, 3H) 3.59 (m, 2H) 1.92 (m, 8H) 1.25 (m, 21H) 0.84 (m, 8H) MS: MS m/z 653.4 ($M^+$+1)

Preparation of tert-butyl((2R,6S,7R,9R,13aS,14aR,16aS,Z)-7-ethyl-2-hydroxy-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

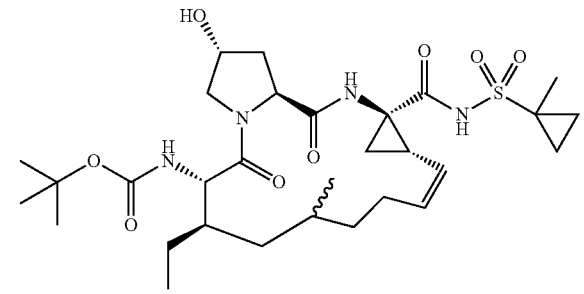 [SMILES: CC[C@@H]1CC(C)CC/C=C\[C@@H]2C[C@@]2(C(=O)NS(=O)(=O)C2(C)CC2)NC(=O)[C@@H]2C[C@@H](O)CN2C(=O)[C@H]1NC(=O)OC(C)(C)C]

The same procedure was used as described for of tert-butyl((2R,6S,7R,9R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate but tert-butyl((2S,3R)-3-ethyl-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-5-methyl-1-oxonon-8-en-2-yl)carbamate was used as a starting material instead of tert-butyl((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate. $^1$H NMR (400 MHz, DMSO-d$_6$): δ ppm 8.32 (s, 1H) 7.01 (d, J=9.54 Hz, 1H) 5.38 (m, 2H) 5.08 (m, 1H) 4.40 (br. s., 1H) 4.20 (t, J=7.78 Hz, 1H) 4.00 (m, 1H) 3.67 (m, 2H) 2.85 (q, J=7.53 Hz, 3H) 2.22 (d, J=8.03 Hz, 1H) 1.84 (m, 4H) 1.29 (m, 22H) 0.84 (m, 6H) 0.48 (m, 2H). MS: MS m/z 625.4 (M$^+$+1).

Scheme: Preparation of (3R)-2-((tert-butoxycarbonyl)amino)-3,5-dimethylnon-8-enoic acid

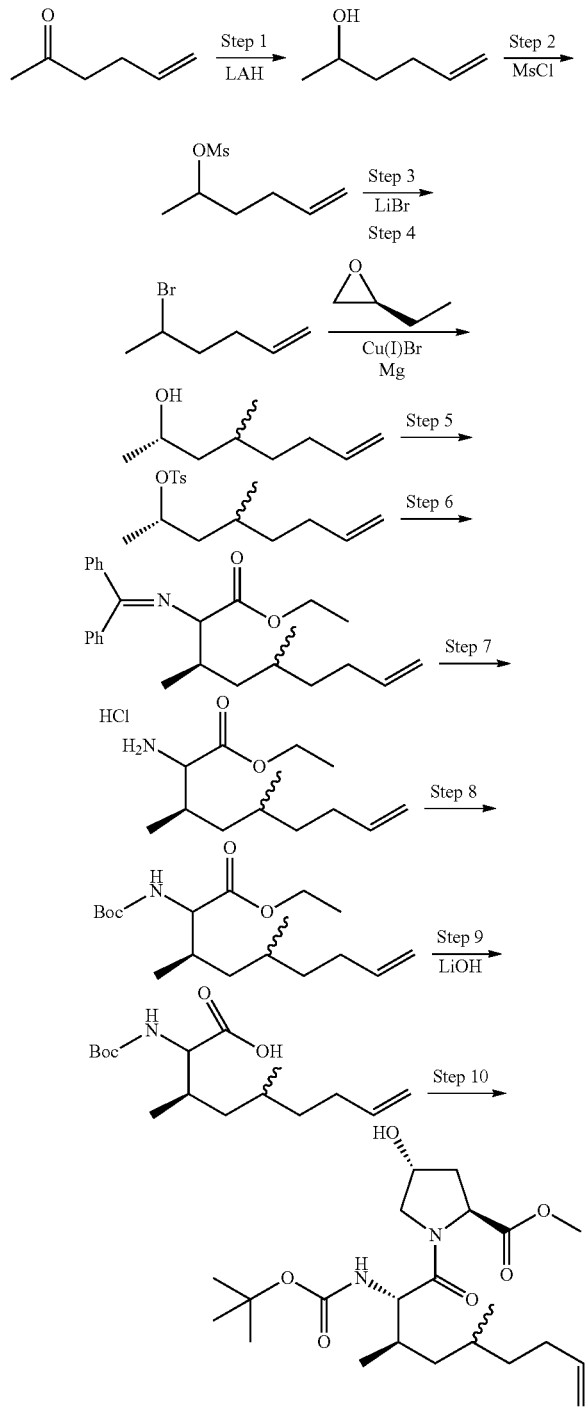

Step 1: Preparation of Hex-5-en-2-ol

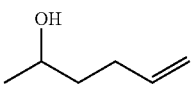

To a solution of lithium aluminum hydride in THF ("LAH", 20.1 g, 106 mmol, 509 mL, 1M solution) was added a solution of hex-5-en-2-one (50 g, 102 mmol) over a period of 30 min. at −20° C. under nitrogen. The reaction mass was allowed to warm to room temperature and stirred for 1 h. The solution was cooled to −20° C. and to it was added aqueous 10% NaOH solution (~100 mL). The organic layer was separated and the aqueous layer was extracted with ether. The combined organics were dried over anhydrous sodium sulfate and concentrated to get crude compound hex-5-en-2-ol as colorless liquid (50 g, 98%). $^1$H NMR (400 MHz, CDCl$_3$): δ ppm 5.87-5.02 (m, 1H), 4.99-4.95 (m, 2H), 3.81-3.83 (m, 1H), 2.17-2.13 (m, 2H), 1.58-1.53 (m, 2H), 1.20-1.19 (d, J=8 Hz, 3H).

Step 2: Preparation of Hex-5-en-2-yl methanesulfonate

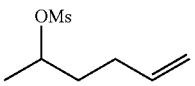

To a solution of hex-5-en-2-ol (50 g crude, 500 mmole) in dichloromethane was added triethylamine (103 m 5 L, 750 mmol) at room temperature. The reaction mass was cooled to 0° C. and to it was added a solution of methane sulfonyl chloride (50.4 mL, 650 mmol) in DCM over a period of 30 min. The reaction mass was allowed to come to room temperature and stirred for 2 h. The solution was washed with water, dried over anhydrous sodium sulfate, filtered and concentrated under reduced pressure to get crude hex-5-en-2-yl methanesulfonate as light brown oil (73 g, 82%). $^1$H NMR (400 MHz, CDCl$_3$): δ ppm 5.84-5.80 (m, 1H), 5.10-5.0 (m, 2H), 4.99-4.98 (m, 1H), 3.15 (s, 3H), 2.52-2.09 (m, 2H), 1.75-1.66 (m, 2H), 1.36-1.34 (d, J=6.4 Hz, 3H).

Step 3: Preparation of 5-bromohex-1-ene

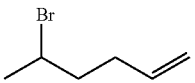

To a solution of hex-5-en-2-yl methanesulfonate (20 g, 0.112 moles) in dry THF (200 mL) was added LiBr (14.6 g, 0.168 moles) portion wise at room temperature over a period of 15 min. The reaction mass was heated at 70° C. for 3 h. The reaction mass was cooled to room temperature and was diluted with water (200 mL). The aqueous solution was extracted with ether (100 mL×3). The combined organics were dried over anhydrous Na$_2$SO$_4$ and concentrated at room temperature. The crude compound was distilled under reduced pressure at 115° C. to afford 5-bromohex-1-ene as colorless liquid (14.5 g, 80%). $^1$H NMR (400 MHz, CDCl$_3$): δ ppm 5.80-5.74 (m, 1H), 5.08-4.98 (m, 2H), 4.14-4.09 (m, 1H), 2.28-2.17 (m, 2H), 1.94-1.81 (m, 2H), 1.71-1.70 (d, J=6.8 Hz, 3H); MS: GC-MS m/z 162.

Step 4: Preparation of (2S)-4-methyloct-7-en-2-ol

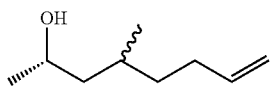

To magnesium turnings (7.44 g, 0.020 moles) in dry THF (100 mL) and was added iodine (100 mg) at room temperature. To this reaction mass was added a solution of 5-bromohex-1-ene (50.0 g, 362 mmoles) in THF (200 mL). The reaction mass was heated with hot air gun to initiate the reaction. Upon completion of the reaction the solution was transferred by cannula to a solution of (S)-propylene oxide (14 g, 241 mmol) and copper bromide (3.45 g, 24 mmol) in THF (100 mL) at −78° C. The reaction mass was allowed to come to room temperature and was stirred overnight. The reaction mass was quenched with saturated aq. ammonium chloride solution and extracted with diethyl ether (200 mL×3). The combined organic layers were dried over anhydrous Na$_2$SO$_4$; filtered; then concentrated in vacuo at room temperature to get crude compound. The crude compound was purified by column chromatography (Silica gel, 10% TBME in pet ether) to get (2S)-4-methyloct-7-en-2-ol (12.4 g, 30%) as an oil. $^1$H NMR (400 MHz, CDCl$_3$): δ ppm 5.84-5.77 (m, 1H), 5.02-4.92 (m, 2H), 4.05-3.85 (sb, 1H), 2.08-2.06 (m, 2H), 1.29-1.20 (m, 2H), 1.19-1.16 (m, 4H), 0.97-0.87 (m, 6H).

Step 5: Preparation of (2S)-4-methyloct-7-en-2-yl 4-methylbenzenesulfonate

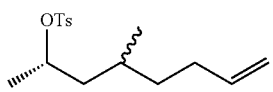 [SMILES: C=CCCC(C)C[C@H](C)OS(=O)(=O)c1ccc(C)cc1]

To a solution of (2S)-4-methyloct-7-en-2-ol (39.0 g, 0.274 moles) in pyridine (400 mL) was added 4-(dimethylamino)pyridine ("DMAP", 1.67 g, 0.013 moles) and the solution was stirred for 10 min. p-toluenesulfonyl chloride (60 g, 0.315 moles) was added to the reaction mass at 0° C. The reaction mass was allowed to come to room temperature and stirred overnight. Pyridine was removed under reduced pressure and the residue was diluted with ethyl acetate (200 mL). The organic solution was washed with aqueous 1.5 N HCl solution, saturated aq. Bicarbonate solution, brine solution, dried over anhydrous Na$_2$SO$_4$, filter, and concentrated under reduced pressure to get crude compound (2S)-4-methyloct-7-en-2-yl 4-methylbenzenesulfonate (54 g, 61%). The crude compound was taken to the next step without further purification.

Step 6: Preparation of (3R)-ethyl 2-((diphenylmethylene)amino)-3,5-dimethylnon-8-enoate

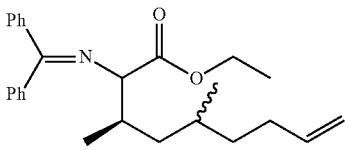 [SMILES: C=CCCC(C)C[C@@H](C)C(N=C(c1ccccc1)c1ccccc1)C(=O)OCC]

To a solution of (2S)-4-methyloct-7-en-2-yl 4-methylbenzenesulfonate (54 g, 0.182 moles) and N-(diphenylmethylene)glycinate ethyl ester (48.7 g, 0.182 moles) in toluene (500 mL) was added LiHMDS (36.5 g, 0.218 moles, 1 M solution in THF) at 0° C. The reaction mass was allowed to come to room temperature and was then heated at 110° C. for 2 h. The reaction mass was cooled to room temperature, quenched with water and extracted with ethyl acetate (200 mL×3). The combined organic layers were dried over anhydrous Na$_2$SO$_4$, filtered and concentrated under reduced pressure to get crude compound (3R)-ethyl 2-((diphenylmethylene)amino)-3,5-dimethylnon-8-enoate (75 g). The crude compound was taken to the next step without further purification.

Step 7: Preparation of (3R)-ethyl 2-amino-3,5-dimethylnon-8-enoate hydrochloride

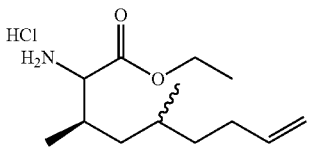 [SMILES: Cl ; C=CCCC(C)C[C@@H](C)C(N)C(=O)OCC]

To a solution of (3R)-ethyl 2-((diphenylmethylene)amino)-3,5-dimethylnon-8-enoate (20 g) in diethyl ether (20 mL) was added aqueous 1.5 N HCl solution (200 mL) and the reaction mass was stirred at room temperature overnight. The reaction mass was washed with diethyl ether (100 mL). The aqueous solution was basified using saturated sodium bicarbonate solution and was extracted with ethyl acetate (100 mL×3). The combined organic layers were dried over anhydrous Na$_2$SO$_4$, filtered, and concentrated under reduced pressure to get crude compound (3R)-ethyl 2-amino-3,5-dimethylnon-8-enoate hydrochloride (4 g, 30%). The crude compound was taken to the next step without further purification.

Step 8: Preparation of (3R)-ethyl 2-(tert-butoxycarbonylamino)-3,5-dimethylnon-8-enoate

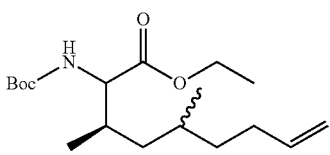 [SMILES: C=CCCC(C)C[C@@H](C)C(NC(=O)OC(C)(C)C)C(=O)OCC]

A solution of (3R)-ethyl 2-amino-3,5-dimethylnon-8-enoate hydrochloride (4 g, 0.017 moles) in DCM (40 mL) was added N,N-diisopropylethylamine ("DIPEA", 3.4 g, 0.026 moles) followed by di-tert-butyl dicarbonate (4.6 g, 0.021 moles) at room temperature. The reaction mass was stirred at room temperature overnight.

The reaction mass was diluted with DCM and washed with water. The organic layer was dried over anhydrous Na₂SO₄, filtered, and concentrated under reduced pressure to afford the crude compound. The crude compound was purified by column chromatography (Silica gel, 20% ethyl acetate in pet-ether) to get 4.7 g, (94%) of (3R)-ethyl 2-(tert-butoxycarbonylamino)-3,5-dimethylnon-8-enoate as an oil.

Step 9: Preparation of (3R)-2-(tert-butoxycarbonylamino)-3,5-dimethylnon-8-enoic acid

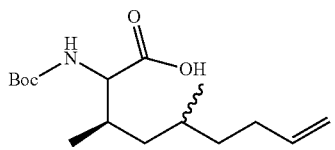 [SMILES: C=CCCC(C)C[C@@H](C)C(NC(=O)OC(C)(C)C)C(=O)O]

To a solution of (3R)-ethyl 2-(tert-butoxycarbonylamino)-3,5-dimethylnon-8-enoate (20 g, 0.061 moles) in THF/water (200 mL, 1:1) was added methanol (60 25 mL) followed by LiOH (7.7 g, 0.183 moles) at room temperature. The reaction mass was stirred at room temperature overnight. The solution was concentrated under reduced pressure and the residue was diluted with water (200 mL). The aqueous solution was acidified with aqueous 1.5 N HCl solution to pH ~3 and extracted with ethyl acetate (100 mLx3). The combined organic layers were dried over anhydrous Na₂SO₄ and concentrated under reduce pressure to get crude compound. The crude compound was purified by column chromatography (Silica gel, 3% methanol in DCM) to get 12.4 g (68%) of (3R)-2-(tert-butoxycarbonylamino)-3,5-dimethylnon-8-enoic acid as a gummy liquid. ¹H NMR (400 MHz, DMSO-d6): δ ppm 12.4 (sb, 1H), 6.92-6.85 (m, 1H), 5.81-5.75 (m, 1H), 5.04-4.93 (m, 2H), 4.12-3.91 (m, 1H), 2.18-1.98 (m, 4H), 1.5 (s, 9H), 1.35-1.02 (m, 3H), 0.98-0.85 (m, 6H).

Step 10: Preparation of (2S,4R)-methyl 1-((3R)-2-((tert-butoxycarbonyl)amino)-3,5-5 dimethylnon-8-enoyl)-4-hydroxypyrrolidine-2-carboxylate

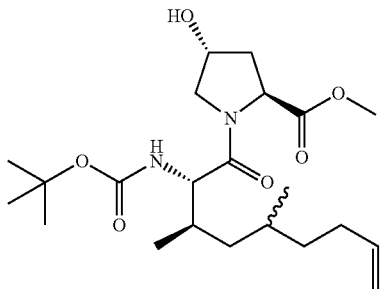 [SMILES: C=CCCC(C)C[C@@H](C)[C@H](NC(=O)OC(C)(C)C)C(=O)N1C[C@H](O)C[C@H]1C(=O)OC]

O-(7-Azabenzotriazol-1-yl)-N,N,N',N'-tetramethyluronium hexafluorophosphate (HATU, 31.7 g, 83 mmol) was added to a solution of (2S,4R)-methyl 4-hydroxypyrrolidine-2-carboxylate HCl (16.68 g, 92 mmol), (3R)-2-((tert-butoxycarbonyl)amino)-3,5-dimethylnon-8-enoic acid (25 g, 83 mmol) and NEt₃ (34.9 mL, 250 mmol) in DCM (250 mL) and stirred at RT for 16 h. The reaction was washed with 1N HCl (3x) and then brine. The organics were dried with magnesium sulfate, filtered and concentrated under vacuum. The crude material was purified via silica gel chromatography using 20-60% Acetone in hexanes to give the desired product (2S,4R)-methyl 1-((2S,3R)-2-((tert-butoxycarbonyl)amino)-3,5-dimethylnon-8-enoyl)-4-hydroxypyrrolidine-2-carboxylate (10.8 g, 30% yield), MS: MS m/z 427.2 (M⁺+1) and the undesired product (2S,4R)-methyl 142R,3R)-2-((tert-butoxycarbonyl)amino)-3,5-dimethylnon-8-enoyl)-4-hydroxypyrrolidine-2-carboxylate (12 g, 34% yield). MS: MS m/z 427.2 (M⁺+1).

Scheme: Preparation of tert-butyl ((2R, 6S, 7R, 9R, 13aS, 14aR, 16aS, Z)-2-hydroxy-7,9-dimethyl-14a-(((1-methylcyclopropyl)sulfonyl)carbamoyl)-5,16-dioxo-1, 2, 3, 5, 6, 7, 8, 9, 10, 11, 13a, 14, 14a, 15, 16, 16a-hexadecahydrocyclopropa[e]pyrrolo[1, 2-a] [1, 4] diazacyclopentadecin-6-yl)carbamate

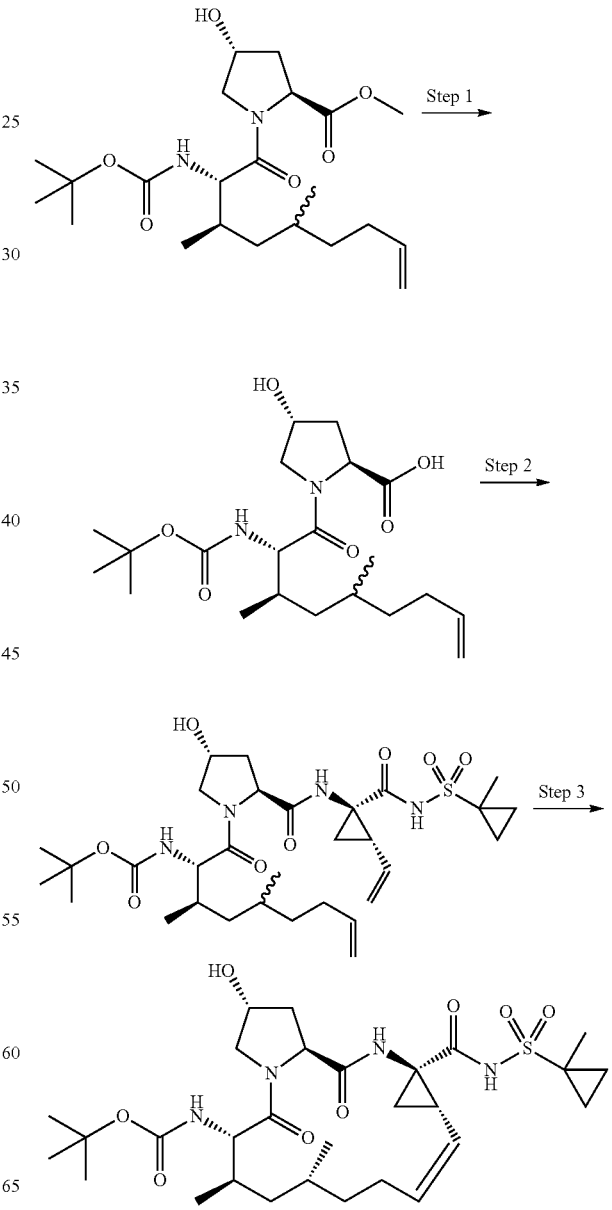

Step 1: Preparation of (2S,4R)-1-((3R)-2-((tert-butoxycarbonyl)amino)-3,5-dimethylnon-8-enoyl)-4-hydroxypyrrolidine-2-carboxylic acid

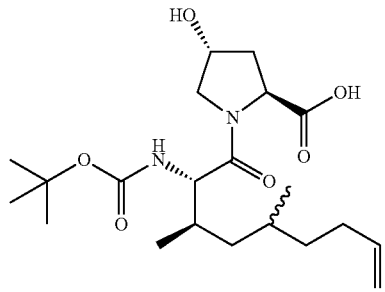 [SMILES: C=CCCC(C)C[C@@H](C)[C@H](NC(=O)OC(C)(C)C)C(=O)N1C[C@H](O)C[C@H]1C(=O)O]

(2S,4R)-methyl 1-((2S,3R)-2-((tert-butoxycarbonyl)amino)-3,5-dimethylnon-8-enoyl)-4-hydroxypyrrolidine-2-carboxylate (10.8 g, 25.3 mmol) was dissolved in THF (50 mL) and MeOH (50 mL) and to this solution was added LiOH (2.425 g, 101 mmol) in Water (50.0 mL). The reaction mixture was stirred at rt for 16 h. The solvent was removed under vacuum and the resulting aqueous residue was diluted with water, and EtOAc. The mixture was neutralized with 1 N HCl and adjusted the pH ~2.5 and the mixture was extracted with EtOAc. The organic layer was collected, washed with brine, dried over $Na_2SO_4$, and concentrated to give crude (2S,4R)-1-((2S,3R)-2-((tert-butoxycarbonyl)amino)-3,5-dimethylnon-8-enoyl)-4-hydroxypyrrolidine-2-carboxylic acid (12 g) as yellow viscous oil. MS: MS m/z 413.2 ($M^++1$).

Step 2: Preparation of tert-butyl((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate

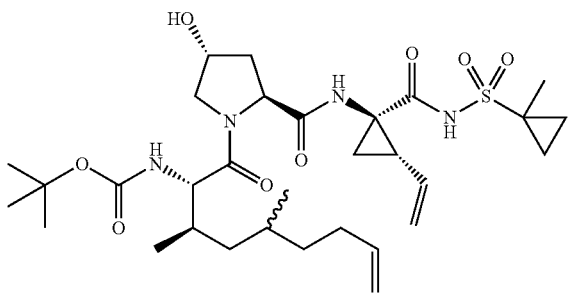 [SMILES: C=CCCC(C)C[C@@H](C)[C@H](NC(=O)OC(C)(C)C)C(=O)N1C[C@H](O)C[C@H]1C(=O)N[C@]1(C(=O)NS(=O)(=O)C2(C)CC2)C[C@H]1C=C]

HATU (7.60 g, 20.00 mmol) was added to a solution of (2S,4R)-1-((2S,3R)-2-((tert-butoxycarbonyl)amino)-3,5-dimethylnon-8-enoyl)-4-hydroxypyrrolidine-2-carboxylic acid (7.86 g, 19.05 mmol), (1R,2S)-1-amino-N-((1-methylcyclopropyl)5 sulfonyl)-2-vinylcyclopropanecarboxamide HCl (5.62 g, 20 mmol), and DIPEA (13.31 mL, 76 mmol) in DCM (110 mL). The reaction mixture was stirred at rt for 16 h. The mixture was washed with 1N HCl (3×), and then brine. The organic layer was collected, dried over sodium sulfate, and concentrated under vacuum. The crude material was purified by silica gel chromatography using a gradient of 20-60% Acetone in hexanes. The product fractions were collected and the solvent removed under vacuum to give tert-butyl((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate (9 g, 74% yield) as a light orange foam. MS: MS m/z 639.3 ($M^++1$).

Step 3: Preparation of tert-butyl((2R,6S,7R,9R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

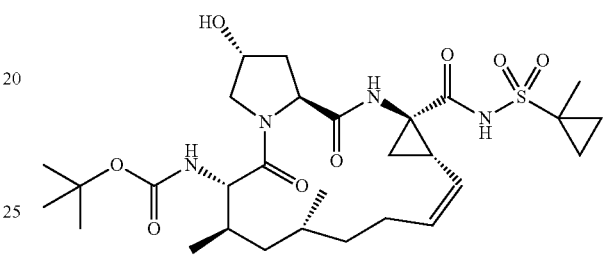

A solution of tert-butyl((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate (8.4 g, 13.15 mmol) in DCE (1500 ml) was degassed with nitrogen for 30 min. and then (1,3-Bis-(2,4,6-trimethylphenyl)-2-imidazolidinylidene)dichloro(o-isopropoxyphenylmethylene)ruthenium) ("Hoveyda-Grubbs Catalyst 2nd Generation", 0.413 g, 0.657 mmol) was added. The reaction solution was heated to 80° C. for 2 h. The reaction solution was concentrated in vacuo the and resulting residue was purified by silica gel chromatography using a gradient of 20-60% Acetone in hexanes to give the mixture of diastereomers as a brown solid (5.6 g, 70% yield). The material was further purified by SFC to afford the single diastereomer tert-butyl((2R,6S,7R,13aS,14aR,16aS,Z)-2-hydroxy-7,9-dimethyl-14a-4(1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 611.3 ($M^++1$).

Scheme: Preparation of 1-methylcyclopropane-1-sulfonamide
Synthesis of 1-Methylcyclopropane-1-sulfonamide:

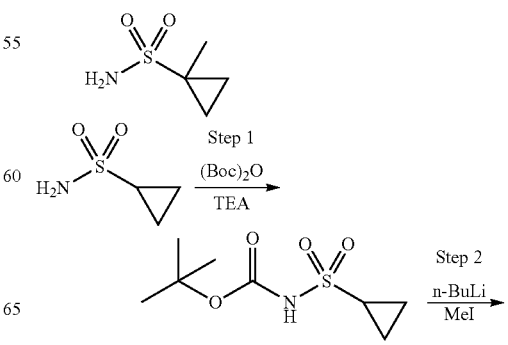

-continued

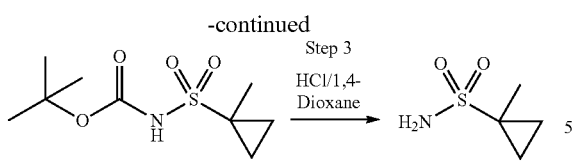

Step 1: Preparation of tert-butyl cyclopropylsulfonylcarbamate

To a solution of cyclopropanesulfonamide (100 g, 82.6 mmol) in DCM (800 ml) was added triethylamine (234 ml, 165 mmol) followed by DMAP (10.28 g, 82.6 mmol) at 0° C. under nitrogen. To this reaction mixture Boc anhydride (247 ml, 107 mmol) in DCM (400 ml) was added slowly. The resulting mixture was stirred for 4 h at room temperature. The reaction mixture was diluted with water and extracted with ethyl acetate. The combine organic layer was washed with 1.5 N HCl solution and 10% NaHCO$_3$ and dried over anhydrous sodium sulfate, filtered and evaporated under reduced pressure to get crude compound (143 g, 65%) as a solid. The crude compound was directly taken for the next step. $^1$H NMR (400 MHz, DMSO-d6): δ ppm 11.08 (s, 1H), 2.90 (m, 1H), 1.48 (s, 9H), 1.06 (m, 4H).

Step 2: Preparation of tert-butyl (1-methylcyclopropyl) sulfonylcarbamate

A solution of tert-butyl cyclopropylsulfonylcarbamate (4.3 g, 20 mmol) was dissolved in dry THF (100 ml) and cooled to −78° C. To this solution was added n-BuLi (17.6 ml, 44 mmol, 2.5 M in hexane) slowly. The reaction mixture was allowed to warm to room temperature over a period of 1.5 h. This mixture was then cooled to −78° C., and a solution of n-BuLi (20 mmol, 8 ml, 2.5M in hexane) was added, stirred for 1 h and a neat solution of methyl iodide (5.68 g, 40 mmol) was added. The reaction mixture was allowed to warm to room temperature with stirring overnight; then was quenched with aqueous saturated NH$_4$Cl (100 ml) at room temperature. The mixture was extracted with EtOAc (100 ml). The organic layer was washed with brine; dried over Na$_2$SO$_4$, filtered and concentrated under reduced pressure to give a yellow oil which was crystallized from hexane to afford the product as a slightly yellow solid (3.1 g, 81%). $^1$H NMR (400 MHz, DMSO-d6): δ ppm 10.97 (s, 1H), 1.44 (s, 12H), 1.35-1.33 (m, 2H), 0.93-0.91 (m, 2H).

Step 3: Preparation of 1-methylcyclopropane-1-sulfonamide

A solution of N-tert-butyl-(1-methyl)-cyclopropyl-sulfonamide (1.91 g, 10 mmol) was dissolved in 4M HCl in dioxane (30 ml) and the reaction mixture stirred at rt for 16 h. The solvent was removed in vacuo to give a yellow oil which was crystallized from EtOAc/hexane (1:4, 40 ml) to yield 1-methyl-cyclopropylsulfonamide, as a white solid (1.25 g, 96%). $^1$H NMR (400 MHz, CDCl$_3$): δ ppm 6.73 (s, 2H), 1.43 (s, 3H), 1.14-1.12 (m, 2H), 0.75-0.73 (m, 2H).

Preparation of tert-butyl((1R,2S)-1-(((1-methylcyclopropyl)sulfonyl)carbamoyl)-2-vinylcyclopropyl) carbamate

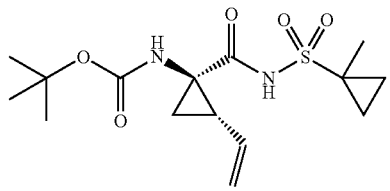 [SMILES: C=C[C@@H]1C[C@]1(NC(=O)OC(C)(C)C)C(=O)NS(=O)(=O)C1(C)CC1]

To a solution of (1R,2S)-1-(tert-butoxycarbonylamino)-2-vinylcyclopropanecarboxylic acid (25 g, 110 mmol) in THF (300 mL) was added CDI (205 g, 127 mmol) and the reaction mass was heated at 85° C. for 1 h. The reaction mass was cooled to rt and to this reaction mass was added 1-methylcyclopropane-1-sulfonamide (17.7 g, 131 mmol) followed by DBU (33.2 mL, 33.5 mmol). The reaction mixture was stirred at rt for 18 h. The solvent was evaporated under reduced pressure and the residue was diluted with water and acidified to pH ~2 by using aq. 1.5 N HCl solution. The precipitated solid was isolated via filtration and washed with water to get desired compound (22 g, 58%) as off-white solid. $^1$H NMR (400 MHz, DMSO-d$_6$) δ ppm 11.01-11.17 (m, 1H), 7.17-7.33 (m, 1H), 5.35-5.51 (m, 1H), 5.18-5.29 (m, 1H), 4.99-5.09 (m, 1H), 2.21 (s, 1H), 1.69 (dd, J=7.78, 5.27 Hz, 1H), 1.40 (d, J=3.01 Hz, 14H), 1.20 (dd, J=9.29, 5.27 Hz, 1H), 0.82-0.96 (m, 2H). MS: MS m/z 343 (M$^+$+1).

Preparation of (1R,2S)-1-amino-N-((1-methylcyclopropyl)sulfonyl)-2-vinylcyclopropanecarboxamide hydrochloride

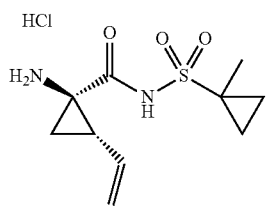 [SMILES: Cl ; C=C[C@@H]1C[C@]1(N)C(=O)NS(=O)(=O)C1(C)CC1]

A solution of tert-butyl((1R,2S)-1-(((1-methylcyclopropyl)sulfonyl)carbamoyl)-2-vinylcyclopropyl)carbamate (40 g, 116 mmol) in 4 N HCl in dioxane (400 mL) was stirred at room temperature for 1 h. The solvent was evaporated under reduced pressure and the residue was washed with diethyl ether to get crude compound (31 g, 95%). The crude compound was used without further purification. $^1$H NMR (400 MHz, DMSO-d$_6$) δ ppm 8.97-9.29 (m, 2H), 5.47-5.66 (m, 1H), 5.32-5.44 (m, 1H), 5.22 (dd, J=10.04, 1.51 Hz, 1H), 2.38 (s, 1H), 2.03 (s, 1H), 1.71 (d, J=3.51 Hz, 1H), 1.46-1.52 (m, 4H), 1.25-1.35 (m, 1H), 0.88-1.01 (m, 2H). MS: MS m/z 245.14 (M$^+$+1).

Preparation of tert-butyl((2R,6S,7R,13aS,14aR,
16aS,Z)-14a-(((1-(fluoromethyl)cyclopropyl)sulfo-
nyl)carbamoyl)-2-hydroxy-7,9-dimethyl-5,16-dioxo-
1,2,3,5,6,7,8,9,10,11,13a,14,14a,15,16,16a-
hexadecahydrocyclopropa[e]pyrrolo[1,2-a][1,4]
diazacyclopentadecin-6-yl)carbamate

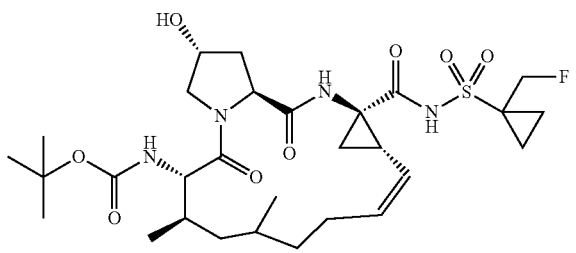 [SMILES: CC1CC/C=C\[C@@H]2C[C@@]2(C(=O)NS(=O)(=O)C2(CF)CC2)NC(=O)[C@@H]2C[C@@H](O)CN2C(=O)[C@@H](NC(=O)OC(C)(C)C)[C@H](C)C1]

Scheme

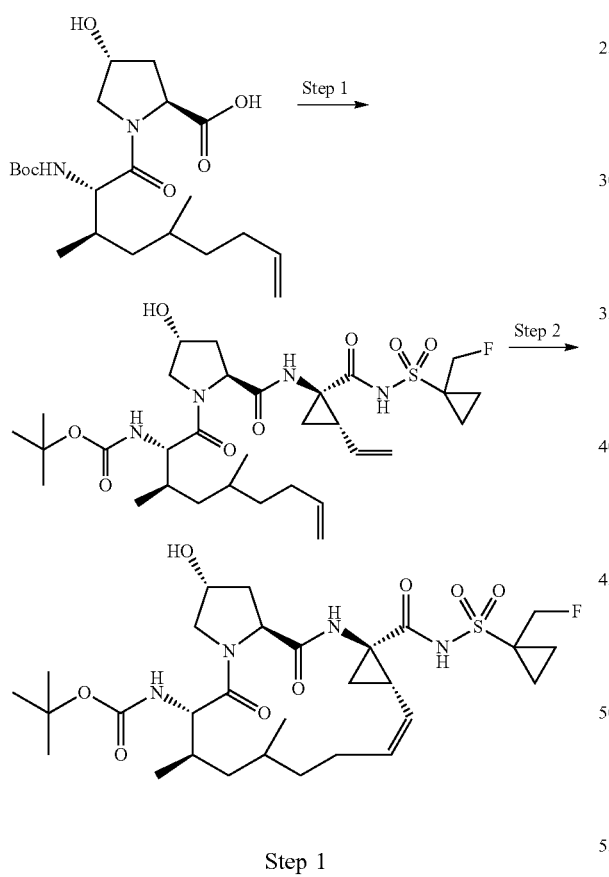

Step 1

To a solution of (2S,4R)-1-((2S,3R)-2-((tert-butoxycarbonyl)amino)-3,5-dimethylnon-8-enoyl)-4-hydroxypyrrolidine-2-carboxylic acid (10.5 g, 25.5 mmol), (1R,2S)-1-amino-N-((1-(fluoromethyl)cyclopropyl)sulfonyl)-2-vinylcyclopropanecarboxamide HCl (8.37 g, 28 mmol), and triethylamine (14.2 mL, 102 mmol) in DCM (220 mL) was added 1-[bis(dimethylamino)methylene]-1H-1,2,3-triazolo[4,5-b]pyridinium 3-oxid hexafluorophosphate ("HATU", 11.61 g, 30.5 mmol). The mixture was stirred at room temperature overnight. The mixture was washed with aq. 1N HCl (3×) and then with brine; dried over MgSO$_4$; filtered; then concentrated in vacuo. The crude material was purified by silica gel chromatography using 20-40% acetone in hexanes. The product fractions were collected and the solvent removed under vacuum to afford tert-butyl((2S,3R)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3,5-dimethyl-1-oxonon-8-en-2-yl)carbamate (15 g, 90% yield). MS: MS m/z 657.3 (M$^+$+1).

Step 2

A solution of tert-butyl((2S,3R)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3,5-dimethyl-1-oxonon-8-en-2-yl)carbamate (7.5 g, 22.84 mmol) in DCE (2855 ml) was sparged with nitrogen for 30 min. and then Hoveyda-Grubbs Catalyst 2nd Generation (0.718 g, 1.142 mmol) was added and the reaction was heated to 80° C. for 2 hrs. The solution was concentrated in vacuo and the resulting residue was purified by flash chromatography on silica gel (20-60% Acetone in hexanes) to afford tert-butyl((2R,6S,7R,13aS,14aR,16aS,Z)-14a-(((1-(fluoromethyl)cyclopropyl)sulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (4 g, 28% yield). MS: MS m/z 629.3 (M$^+$+1).

Scheme: Preparation of 4-(tert-butyl)-2-(1-chloro-6-methoxyisoquinolin-4-yl)thiazole

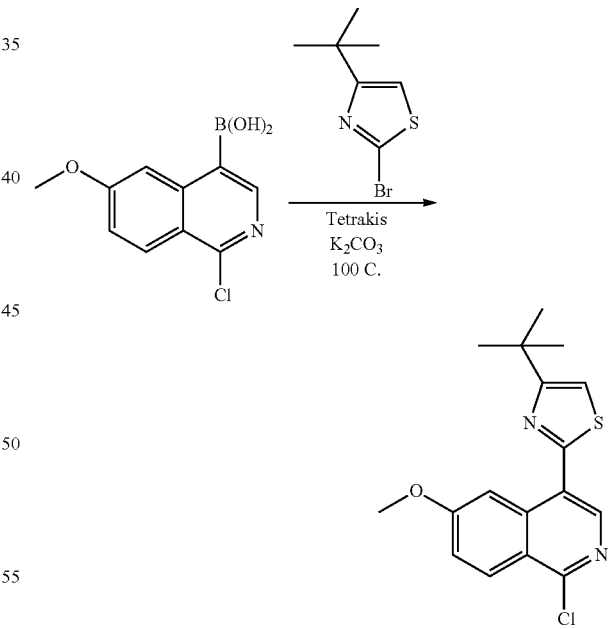

(1-chloro-6-methoxyisoquinolin-4-yl)boronic acid (0.1 g, 0.421 mmol) and 2-bromo-4-(tert-butyl)thiazole (0.111 g, 0.505 mmol) were dissolved in DME (1 mL):water (0.5 mL):ethanol (0.25 mL). The solution was sparged with nitrogen gas for 5 min. Potassium carbonate (0.175 g, 1.263 mmol) was added to the solution, then to the solution was added Pd(PPh$_3$)$_4$ (0.024 g, 0.021 mmol). The solution was heated at 100° C. for 1 h. The reaction mixture was poured into water, extracted with ethyl acetate. The combined organic layers were dried over anhydrous sodium sulfate and concentrated under reduced pressure. The crude sample was purified by silica gel chromatography using 15% ethyl acetate in Pet-ether to afford 4-(tert-butyl)-2-(1-chloro-6-methoxyisoquinolin-4-yl)thiazole (0.06 g, 41% yield) as white solid. $^1$H NMR (400 MHz, CDCl$_3$): δ ppm 7.34 (dd, J=9.26, 2.50 Hz, 1H) 7.26 (s, 3H) 7.05 (s, 1H) 3.97 (s, 3H) 1.47 (s, 9H). MS: MS m/z 333.5 (M$^+$+1).

combined organic layers were dried over anhydrous sodium sulfate and concentrated under reduced pressure to get crude compound. The crude compound was purified by silica gel chromatography to get a mixture of 4-chloro-2-(1H-imidazol-1-yl)-7-methoxyquinoline and 2-chloro-4-(1H-imidazol-1-yl)-7-methoxyquinoline. MS: MS m/z 260.1 (M$^+$+2).

Scheme: Preparation of 4-chloro-2-(1H-imidazol-1-yl)-7-methoxyquinoline and 2-chloro-4-(1H-imidazol-1-yl)-7-methoxyquinoline

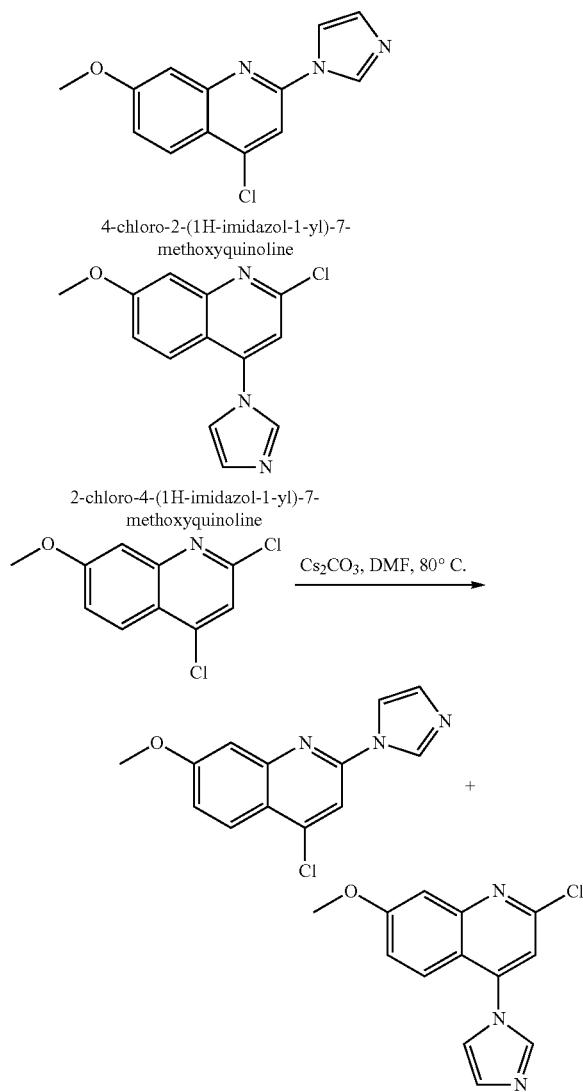

Scheme: Preparation of N-(1-chloro-6-methoxyisoquinolin-4-yl)-N-methylbenzamide

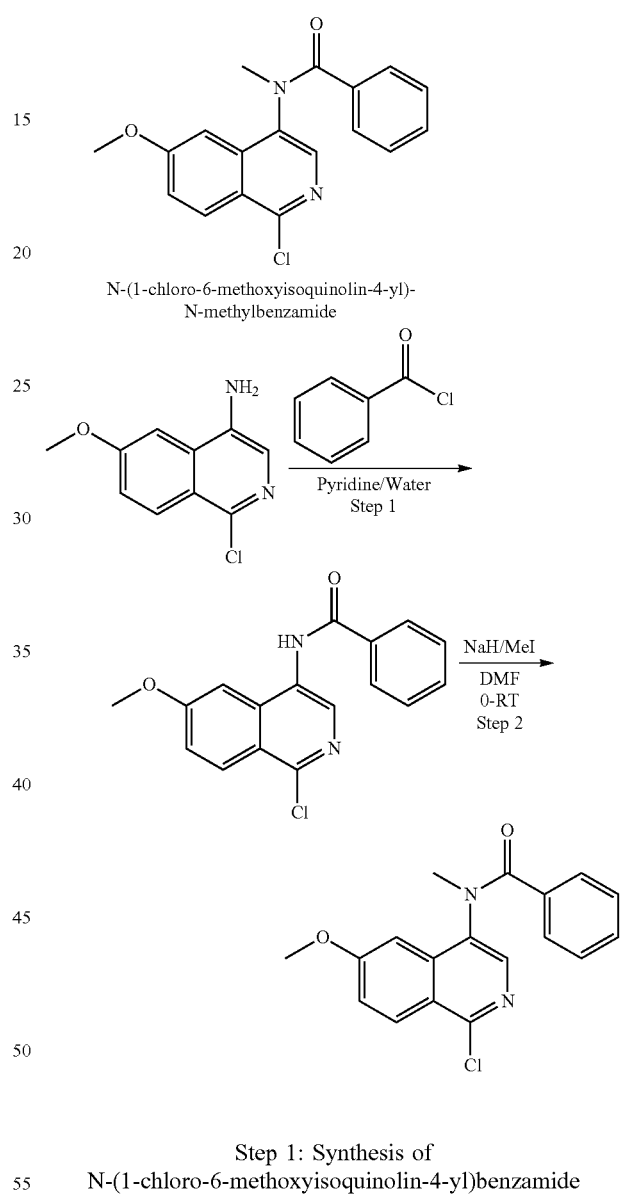

Step 1: 4-chloro-2-(1H-imidazol-1-yl)-7-methoxyquinoline and 2-chloro-4-(1H-imidazol-1-yl)-7-methoxyquinoline To a solution of 2,4-dichloro-7-methoxyisoquinolin (0.5 g, 2.19 mmol) in DMF (5 ml) was added Cs$_2$CO$_3$ (1.54 g, 4.74 mmol) followed by imidazole (0.16 g, 2.41 mmol). The reaction mixture was heated to 80° C. for 18 h. The reaction mass was concentrated under reduced pressure. The residue was diluted with water and extracted with ethyl acetate. The Step 1: Synthesis of N-(1-chloro-6-methoxyisoquinolin-4-yl)benzamide To a suspension of 1-chloro-6-methoxyisoquinolin-4-amine (0.2 g, 0.959 mmol) in pyridine (2 mL) was added benzoyl chloride (0.135 g, 0.959 mmol). The mixture was stirred at room temperature until completion of the reaction. To the solution was added water (4 mL). The mixture was stirred for 10 min, upon which a white solid precipitated. The solid was isolated via filtration, washed with water and dried to afford N-(1-chloro-6-methoxyisoquinolin-4-yl)benzamide (0.26 g, 0.815 mmol, 85% yield) as off-white solid. $^1$H NMR (400 MHz, DMSO-d6): δ ppm 10.48 (s, 1H) 8.40 (s, 1H) 8.25 (d, J=9.03 Hz, 1H) 8.06-8.12 (m, 2H) 7.56-7.68

(m, 3H) 7.50 (dd, J=9.29, 2.51 Hz, 1H) 7.37 (d, J=2.51 Hz, 1H) 3.94 (s, 3H). MS: MS m/z 313.5 (M⁺+1).

Step 2: Synthesis of N-(1-chloro-6-methoxyisoquinolin-4-yl)-N-methylbenzamide

To a 2-neck round-bottom flask under nitrogen, charged with DMF (5 mL) and cooled to 0° C. was added NaH (0.017 g, 0.703 mmol, 60% weight in oil). To the mixture was added N-(1-chloro-6-methoxyisoquinolin-4-yl)benzamide (0.2 g, 0.639 mmol), and the mixture was stirred for 30 min. To the mixture was added methyl iodide (0.040 mL, 0.639 mmol), and the mixture was stirred at room temperature for 18 h. The reaction mixture was poured into ice and extracted with ethyl acetate. The combined organic layers were dried over anhydrous sodium sulfate and concentrated under reduced pressure. The resulting residue was purified by silica gel chromatography using 20% ethyl acetate in pet-ether to afford N-(1-chloro-6-methoxyisoquinolin-4-yl)-N-methyl benzamide (0.21 g, 0.611 mmol, 95% yield) as white solid. $^1$H NMR (400 MHz, DMSO-d6): δ ppm 8.18 (d, J=9.29 Hz, 1H) 8.06 (s, 1H) 7.48 (dd, J=9.29, 2.26 Hz, 1H) 7.35 (s, 1H) 7.08-7.25 (m, 4H) 4.05 (s, 3H) 3.42 (s, 3H). MS: MS m/z 327.2 (M⁺+1).

Scheme: Preparation of 2-(1-chloro-6-methoxyisoquinolin-4-yl)thiazole

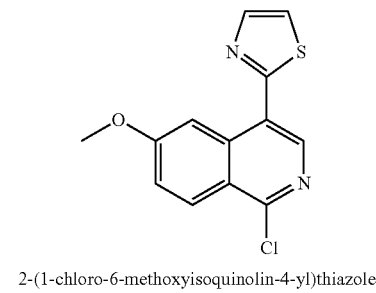

2-(1-chloro-6-methoxyisoquinolin-4-yl)thiazole

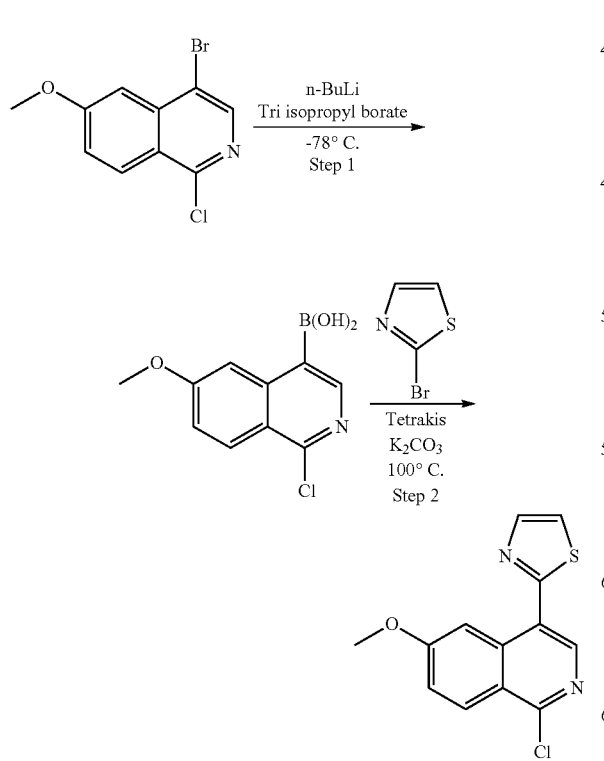

Step 1: Synthesis of (1-chloro-6-methoxyisoquinolin-4-yl)boronic acid

To a stirred solution of 4-bromo-1-chloro-6-methoxyisoquinoline (0.75 g, 2.75 mmol) in THF (50 mL) at −78° C. was added n-BuLi (2.27 mL, 3.58 mmol, 1.6 M in hexanes). The reaction solution was stirred for 1 h. To the solution was added triisopropylborate (1.278 mL, 5.50 mmol), and the solution was stirred at the same temperature for 2 h. The solution was allowed to warm to room temperature and then was quenched with water. The volatiles were removed under reduced pressure. The residue was diluted with water; adjusted the pH ~1 using 1.5 N HCl solution; and the precipitated solid was isolated via filtration, then was washed with water and dried to afford (1-chloro-6-methoxyisoquinolin-4-yl)boronic acid (0.34 g, 1.289 mmol, 47% yield) as white solid. MS: MS m/z 239.1 (M⁺+2).

Step 2: Synthesis of 2-(1-chloro-6-methoxyisoquinolin-4-yl)thiazole (1-chloro-6-methoxyisoquinolin-4-yl)boronic acid (0.1 g, 0.421 mmol) and 2-bromothiazole (0.083 g, 0.505 mmol) were dissolved in DME (1 mL):Water (0.5 mL):Ethanol (0.25 mL). The solution was sparged with nitrogen gas for 5 min. Potassium carbonate (0.175 g, 1.263 mmol) was added to the solution, then to the solution was added Pd(PPh₃)₄ (0.024 g, 0.021 mmol). The solution was heated to 100° C. for 1 h. The reaction mixture was poured into water, extracted with ethyl acetate. The combined organic layers were dried over anhydrous sodium sulfate; then concentrated under reduced pressure. The crude sample was purified by silica gel chromatography using 15% ethyl acetate in Pet-ether to afford 2-(1-chloro-6-methoxyisoquinolin-4-yl)thiazole (0.048 g, 0.139 mmol, 32.9% yield) as white solid.

$^1$H NMR (400 MHz, DMSO-d6): δ ppm 8.66 (s, 1H) 8.46 (s, 1H) 8.34 (s, 1H) 8.19 (s, 1H) 8.03 (s, 1H) 7.57 (dd, J=9.29, 2.51 Hz, 1H) 3.97 (s, 3H) MS: MS m/z 278.5 (M⁺+1).

Preparation of N-(1-chloro-6-methoxyisoquinolin-4-yl)-N-ethylbenzamide

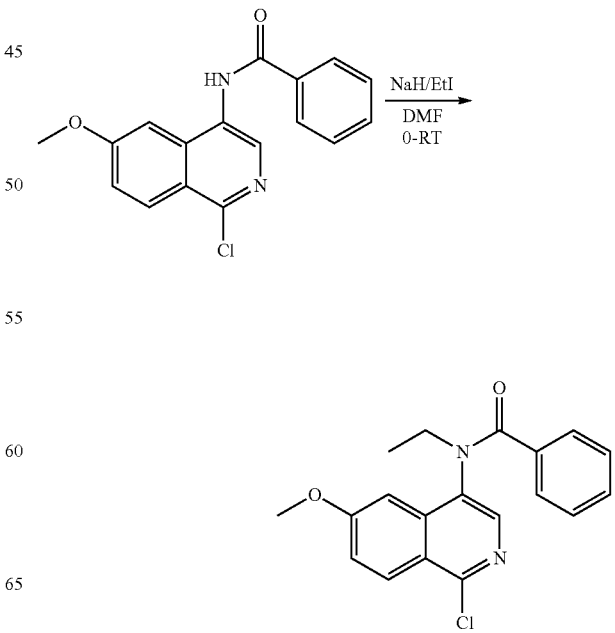

To a two-neck round-bottom flask charged under nitrogen and charged with DMF (3 mL) at 0° C. was added NaH (0.019 g, 0.799 mmol). To the mixture was added N-(1-chloro-6-methoxyisoquinolin-4-yl)benzamide (0.1 g, 0.320 mmol). The mixture was stirred for 30 min. Iodoethane (0.031 mL, 0.384 mmol) was added; the mixture was stirred at room temperature for 18 h. The reaction mixture was poured into ice and extracted with ethyl acetate. The combined organic layers were dried over anhydrous sodium sulfate and concentrated under reduced pressure. The crude sample was purified by silica gel chromatography using 30% ethyl acetate in Pet-ether as eluent to afford N-(1-chloro-6-methoxyisoquinolin-4-yl)-N-ethylbenzamide (0.04 g, 0.094 mmol, 29.4% yield) as solid. $^1$H NMR (400 MHz, DMSO-d6): δ ppm 8.18 (d, J=9.03 Hz, 1H) 8.06 (br. s., 1H) 7.47 (d, J=9.54 Hz, 1H) 7.33 (br. s., 1H) 7.07-7.26 (m, 5H) 4.04 (s, 3H) 3.51-3.60 (m, 2H) 1.16 (t, J=6.90 Hz, 3H). MS: MS m/z 341.2 ($M^+$+1).

Scheme: Preparation of 4-chloro-2-(3-isopropyl-1H-pyrazol-1-yl)-7-methoxyquinoline

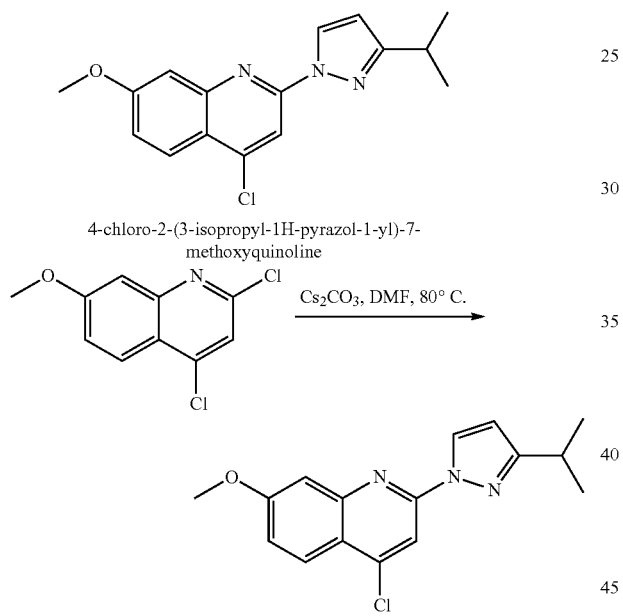

4-chloro-2-(3-isopropyl-1H-pyrazol-1-yl)-7-methoxyquinoline

Step 1: Preparation of 4-chloro-2-(3-isopropyl-1H-pyrazol-1-yl)-7-methoxyquinoline To a solution of 2,4-dichloro-7-methoxyisoquinolin (0.54 g, 2.36 mmol) in DMF (5 ml) was added Cs$_2$CO$_3$ (1.54 g, 4.74 mmol) followed by 3-isopropyl-1H-pyrazole (0.78 g, 7.10 mmol). The reaction mixture was heated to 80° C. for 18 h. The reaction mass was concentrated under reduced pressure. The residue was diluted with water and extracted with ethyl acetate. The combined organic layers were dried over anhydrous Na$_2$SO$_4$ and then concentrated under reduced pressure to get crude compound. The crude compound was silica gel chromatography to get desired compound (0.1 g, 14%) as white solid. $^1$H NMR (400 MHz, CDCl$_3$): δ ppm 8.60 (d, J=2.51 Hz, 1H) 8.07 (d, J=9.04 Hz, 1H) 8.15 (s, 1H) 8.07 (d, J=9.04 Hz, 1H) 8.15 (s, 1H) 7.26 (s, 2H) 7.16-7.22 (m, 1H) 6.35 (d, J=2.51 Hz, 1H) 3.97-3.99 (m, 4H) 3.10 (quin, J=7.03 Hz, 1H) 1.36 (s, 4H) 1.34 (s, 3H). MS: MS m/z 302.1 ($M^+$+1).

Scheme: Preparation of 5-(1-chloro-6-methoxyisoquinolin-4-yl)oxazole

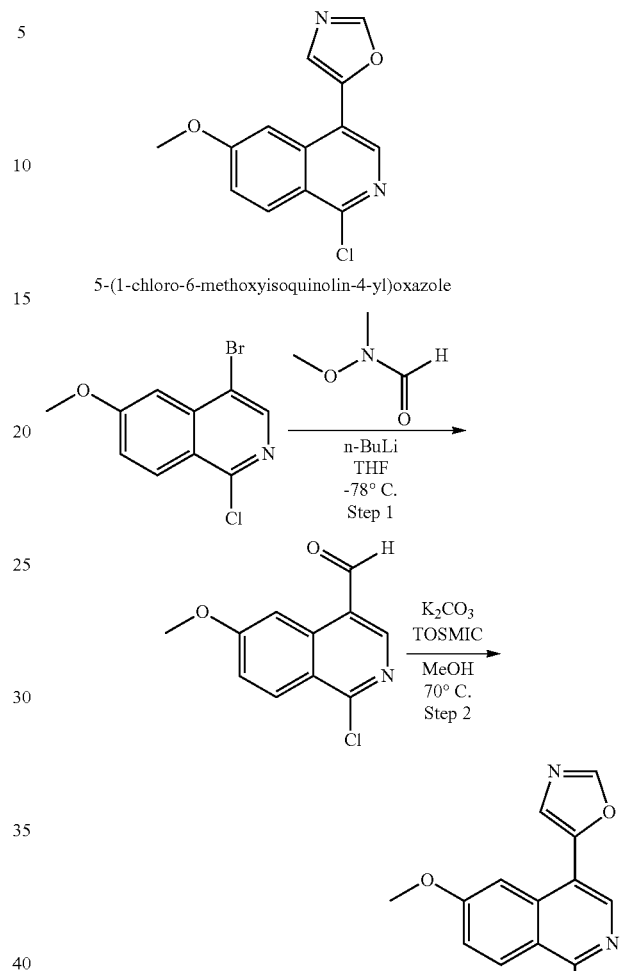

5-(1-chloro-6-methoxyisoquinolin-4-yl)oxazole

Step 1: Synthesis of 1-chloro-6-methoxyisoquinoline-4-carbaldehyde

To a stirred solution of 4-bromo-1-chloro-6-methoxyisoquinoline (0.25 g, 0.917 mmol) in THF (10 mL) at −78° C. was added n-BuLi (0.860 mL, 1.376 mmol, 1.6 M in hexanes). Stirred the reaction mixture for 1 h. N-methoxy-N-methylformamide (0.123 g, 1.376 mmol) was added to the solution; stirred at the same temperature for 1 h. The mixture was allowed to warm to room temperature and then was quenched with aq. 1.5N HCl solution; extracted with ethyl acetate. The combined organic layers were washed with brine solution; dried over sodium sulfate and concentrated under reduced pressure. The crude sample was purified by silica gel chromatography using 25% ethyl acetate in Pet-ether to afford 1-chloro-6-methoxyisoquinoline-4-carbaldehyde (0.15 g, 0.474 mmol, 51.6% yield) as white solid. $^1$H NMR (400 MHz, DMSO-d6): δ ppm 8.86 (s, 1H) 8.58 (s, 1H) 8.37 (d, J=9.29 Hz, 1H) 8.15-8.23 (m, 1H) 7.56 (dd, J=9.29, 2.51 Hz, 1H) 4.01 (s, 3H). MS: MS m/z 221.8 ($M^+$+1).

Step 2: Synthesis of 5-(1-chloro-6-methoxyisoquinolin-4-yl)oxazole

To a stirred solution of 1-chloro-6-methoxyisoquinoline-4-carbaldehyde (0.15 g, 0.677 mmol) in methanol (10 mL) was added toluenesulphonylmethyl isocyanide ("TOSMIC", 0.145 g, 0.744 mmol). The solution was heated at reflux for 1 h. Removed the volatiles under reduced pressure. To the resulting residue was added water. The mixture was extracted with ethyl acetate. The combined organic layers were dried over anhydrous sodium sulfate and then concentrated under reduced pressure. The crude sample was purified by silica gel chromatography using 35% ethyl acetate in Pet-ether to afford 5-(1-chloro-6-methoxyisoquinolin-4-yl)oxazole (0.08 g, 0.307 mmol, 45.3% yield) as a white solid. $^1$H NMR (400 MHz, DMSO-d6): δ ppm 8.68 (s, 1H) 8.52 (s, 1H) 8.32 (d, J=9.29 Hz, 1H) 7.92 (s, 1H) 7.52-7.60 (m, 2H) 4.00 (s, 3H). MS: MS m/z 261.1 ($M^+$+1).

Scheme: Preparation of 2-chloro-3-(trifluoromethyl)pyrido[2,3-b]pyrazine and 3-chloro-2-(trifluoromethyl)pyrido[2,3-b]pyrazine

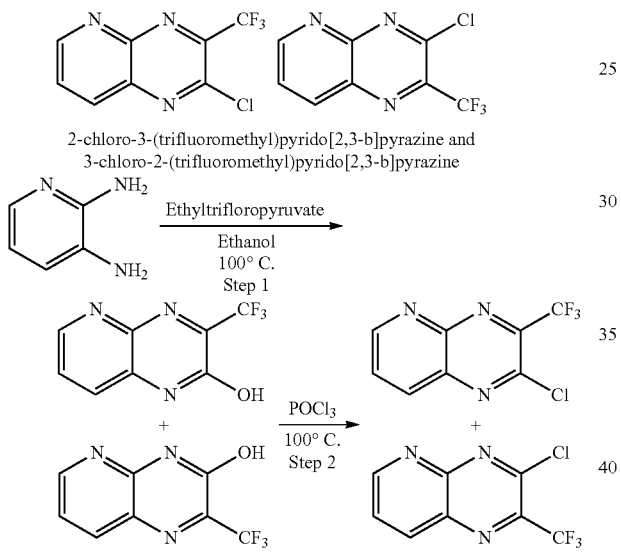

Step 1: Synthesis of 3-(trifluoromethyl)pyrido[2,3-b]pyrazin-2-ol and 2-(trifluoromethyl)pyrido[2,3-b]pyrazin-3-ol To a suspension of pyridine-2,3-diamine (1 g, 9.16 mmol) in ethanol (10 mL) was added ethyl trifluoropyruvate (1.11 mL, 9.16 mmol). The reaction mixture was refluxed at 90° C. for 16 h. The solvent was removed under reduced pressure and the residue was diluted with pet-ether. The precipitated solid was isolated via filtration to get a mixture of 3-(trifluoromethyl)pyrido[2,3-b]pyrazin-2-ol and 2-(trifluoromethyl)pyrido[2,3-b]pyrazin-3-ol (0.70 g, 3.25 mmol). MS: MS m/z 216.0 ($M^+$+1).

Step 2: Synthesis of 2-chloro-3-(trifluoromethyl)pyrido[2,3-b]pyrazine and 3-chloro-2-(trifluoromethyl)pyrido[2,3-b]pyrazine The suspension of 3-(trifluoromethyl)pyrido[2,3-b]pyrazin-2-ol and 2-(trifluoromethyl)pyrido[2,3-b]pyrazin-3-ol (0.70 g, 3.25 mmol) in POCl$_3$ (10 mL) was refluxed at 100° C. for 2 h. The solvent was removed under reduced pressure and the residue was diluted with ice cold water. The aqueous solution was basified to pH ~9.0 by using sodium bicarbonate, then was extracted with ethyl acetate. The combined organic layers were dried over anhydrous sodium sulfate and concentrated under reduced pressure to get crude compound. The crude compound was purified by silica gel chromatography using 10% ethyl acetate in Pet-ether to get a mixture of 2-chloro-3-(trifluoromethyl)pyrido[2,3-b]pyrazine and 3-chloro-2-(trifluoromethyl)pyrido[2,3-b]pyrazine (0.32 g, 1.233 mmol, 37.9% yield). MS: MS m/z 234.0 ($M^+$+1). The mixture was used without further purification.

Scheme: Preparation of 2-chloro-7-methoxy-3-(trifluoromethyl)pyrido[3,4-b]pyrazine and 3-chloro-7-methoxy-2-(trifluoromethyl)pyrido[3,4-b]pyrazine

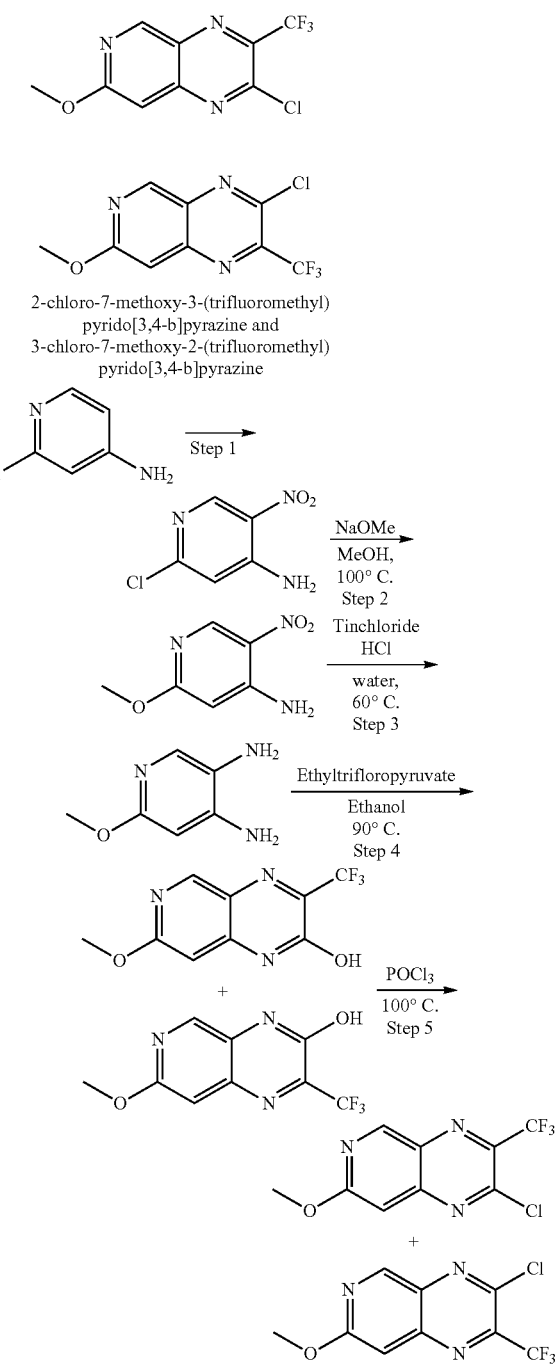

Step 1: Synthesis of 2-chloro-5-nitropyridin-4-amine

To a solution of 2-chloropyridin-4-amine (10 g, 78 mmol) in conc. sulfuric acid (60 mL) at 0° C. was slowly added fuming nitric acid (30 mL). Then reaction mixture was stirred for 30 min. The reaction mixture was slowly poured into ice; the pH was adjusted to ~3 with using ammonia solution. The resultant white solid was isolated via filtration. The solid was dissolved in conc. sulfuric acid, then heated to 100° C. for 2 h. The reaction mixture was cooled to room temperature and poured into ice. The aqueous solution was adjusted to pH ~3 using ammonia solution; then was extracted with ethyl acetate. The organic layer was dried over anhydrous sodium sulfate and concentrated under reduced pressure. The resultant residue was purified by silica gel chromatography using 30% ethyl acetate in Pet-ether to afford 2-chloro-5-nitropyridin-4-amine (1.2 g, 6.91 mmol, 8.89% yield) and 2-chloro-3-nitropyridin-4-amine (6 g, 34.6 mmol, 44.4% yield) as yellow solids. $^1$H NMR (400 MHz, DMSO-d6): δ ppm 7.90 (d, J=5.77 Hz, 1H) 7.34 (br. s., 2H) 6.83 (s, 1H). MS: MS m/z 172.2 (M$^+$−1).

Step 2: Synthesis of 2-methoxy-5-nitropyridin-4-amine

To a solution of 2-chloro-5-nitropyridin-4-amine (0.5 g, 2.88 mmol) in Methanol was added and sodium methoxide (0.233 g, 4.32 mmol) under nitrogen atmosphere and heated to reflux at t 70° C. for 3 h. Removed the volatiles under reduced pressure, quenched by pouring into ice water, filtered the resulting precipitate, washed with cold water and dried to afford 2-methoxy-5-nitropyridin-4-amine (0.4 g, 2.247 mmol, 78% yield) as pale yellow solid. MS: MS m/z 170.2 (M$^+$+1).

Step 3: Synthesis of 6-methoxypyridine-3,4-diamine

Aq. conc. HCl (1 ml, 32.9 mmol) was diluted with water. To the solution was added tin (II) chloride (0.448 g, 2.365 mmol), followed by 2-methoxy-5-nitropyridin-4-amine (0.1 g, 0.591 mmol). The mixture was heated to 60° C. for 18 h. The reaction mixture was cooled to room temperature, then basified using 10% NaOH solution. The mixture was extracted with ethyl acetate. The combined organic layers were dried over anhydrous sodium sulfate and concentrated under reduced pressure. The resultant crude compound was triturated with 10% ethyl acetate in Pet-ether to afford 6-methoxypyridine-3,4-diamine (0.06 g, 0.366 mmol, 62.0% yield) as a solid. $^1$H NMR (400 MHz, DMSO-d6): δ ppm 7.21 (s, 1H), 5.83 (s, 1H), 5.39 (b s, 2H), 4.04 (b s, 2H), 3.62 (s, 3H).

Step 4: Synthesis of 7-methoxy-3-(trifluoromethyl)pyrido[3,4-b]pyrazin-2-ol and 7-methoxy-2-(trifluoromethyl)pyrido[3,4-b]pyrazin-3-ol To a solution of 6-methoxypyridine-3,4-diamine (0.45 g, 3.23 mmol) in ethanol was added ethyl trifluoropyruvate (0.393 mL, 3.23 mmol). The reaction mixture was heated to reflux at 90° C. for 16 h. The volatiles were removed under reduced pressure. To the residue was added Pet-ether. The resultant solid was isolated via filtration and dried to afford 7-methoxy-3-(trifluoromethyl)pyrido[3,4-b]pyrazin-2-ol and 7-methoxy-2-(trifluoromethyl)pyrido[3,4-b]pyrazin-3-ol as mixture of regioisomer (0.37 g 46% yield). MS: MS m/z 246.2 (M$^+$+1).

Step 5: Synthesis of 2-chloro-7-methoxy-3-(trifluoromethyl)pyrido[3,4-b]pyrazine and 3-chloro-7-methoxy-2-(trifluoromethyl)pyrido[3,4-b]pyrazine A solution of 7-methoxy-3-(trifluoromethyl)pyrido[3,4-b]pyrazin-2-ol and 7-methoxy-2-(trifluoromethyl)pyrido[3,4-b]pyrazin-3-ol (0.37 g, 1.509 mmol) in POCl$_3$ (5 mL) was heated to 100° C. for 2 h. The solvent was removed under reduced pressure and the residue was diluted with ice cold water. The aqueous solution was basified to pH ~9.0 by using sodium bicarbonate, then was extracted with ethyl acetate. The combined organic layers were dried over anhydrous sodium sulfate and concentrated under reduced pressure to get crude compound. The crude compound was purified by silica gel chromatography using 10% ethyl acetate in Pet-ether to get 2-chloro-7-methoxy-3-(trifluoromethyl)pyrido[3,4-b]pyrazine (0.135 g, 0.435 mmol, 28.8% yield) and 3-chloro-7-methoxy-2-(trifluoromethyl)pyrido[3,4-b]pyrazine (0.035 g, 0.435 mmol, 4.8% yield) as yellow solids.

2-chloro-7-methoxy-3-(trifluoromethyl)pyrido[3,4-b]pyrazine: $^1$H NMR (400 MHz, DMSO-d6): δ ppm 9.40 (d, J=0.75 Hz, 1H) 7.60 (s, 1H) 4.08 (s, 3H). MS: MS m/z 264.2 (M'+1).

3-chloro-7-methoxy-2-(trifluoromethyl)pyrido[3,4-b]pyrazine: MS: MS m/z 264.2 (M$^+$+1).

Preparation of 2-chloro-3-cyclopropyl-6-methoxyquinoxaline

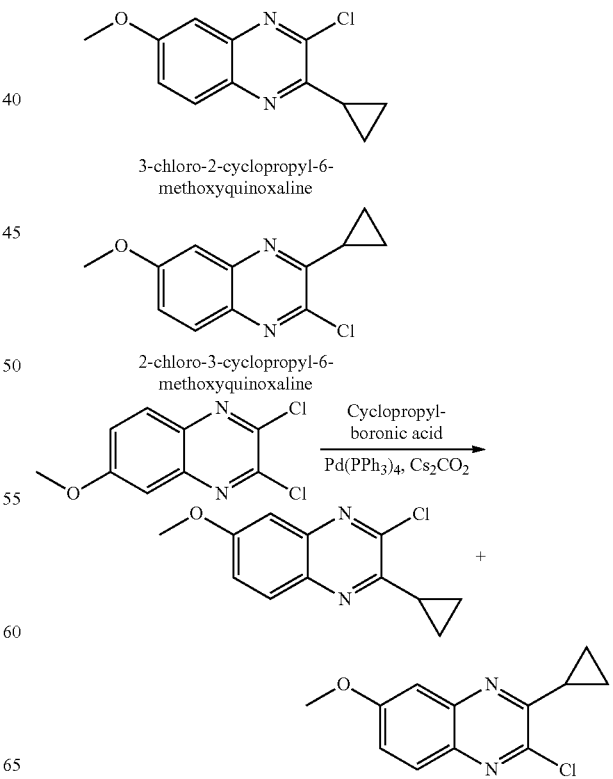

Preparation of 2-chloro-3-cyclopropyl-6-methoxyquinoxaline

A solution of 2,3-dichloro-6-methoxyquinoxaline (100 mg, 0.437 mmol), cyclopropyl boronic acid (82 mg. 0.96 mmol) and cesium carbonate (284 mg, 0.873 mmol) in dioxane (5 mL) was sparged with nitrogen for 30 min. To this reaction mass was added Pd(PPh$_3$)$_4$ (15 mg, 0.013 mmol) and resultant mixture was heated in a pressure tube at 100° C. for 16 h. The reaction mixture was diluted with EtOAc and washed with water followed by brine solution. The organic layer was dried over anhydrous sodium sulphate and evaporated under reduced pressure to get crude compound. The crude compound was purified by silica gel chromatography (4% EtOAc in pet ether) to afford a mixture of regioisomer. The material was further purified by SFC to separate the regioisomers and afford 2-chloro-3-cyclopropyl-6-methoxyquinoxaline (30 mg, 0.128 mmol, 29.3% yield) as a white solid and 2-chloro-3-cyclopropyl-6-methoxyquinoxaline (5 mg) as a white solid. 2-Chloro-3-cyclopropyl-6-methoxyquinoxaline: $^1$H NMR (400 MHz, CDCl$_3$) 7.88 (d, J=8 Hz, 1H) 7.43-7.40 (m, 1H) 7.32 (d, J=2.8, 1H) 3.93 (s, 3H) 2.69 (m, 1H) 1.23 (m, 4H). MS: MS m/z 234.94 (M$^+$+1).

Preparation of pyridin-2-yl (1,1,1-trifluoro-2-methylpropan-2-yl) carbonate

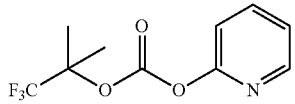 [SMILES: CC(C)(OC(=O)Oc1ccccn1)C(F)(F)F]

To a solution of 1,1,1-trifluoro-2-methylpropan-2-ol (10 g, 78 mmol) in DIPEA (40.9 ml, 234 mmol) was added DMAP (9.54 g, 78 mmol) and the solution was stirred 10 min at room temperature. To the solution was added dipyridin-2-yl carbonate (16.8 g, 78 mmol). The solution was stirred overnight. The reaction mass was filtered, washing with DIPEA (2*10 mL); the filtrate was concentrated under vacuum and then diluted with DCM (300 mL). The solution was washed with aq. 1.5N HCl solution (2×150 mL), followed by brine solution (100 mL). The organic phase was dried over Na$_2$SO$_4$, filtered and concentrated under reduced pressure to afford crude product as red color liquid. The crude compound was purified by silica gel chromatography eluting with EtOAc in pet-ether [0-5% over 25 min] as gradient, using 40 g silica column, collected the product fractions and concentrated to afford pyridin-2-yl (1,1,1-trifluoro-2-methylpropan-2-yl) carbonate (9.0 g, 36 mmol, 46% yield) as colorless liquid. $^1$H NMR (400 MHz, CDCL3) δ ppm 8.41-8.40 (d, J=4.8 Hz, 1H), 7.84-7.79 (m, 1H), 7.28-7.24 (m, 1H), 7.13-7.10 (d, J=10 Hz, 1H), 1.78 (s, 6H). MS: MS m/z 250.54 (M$^+$+1).

Preparation of Compound 4303

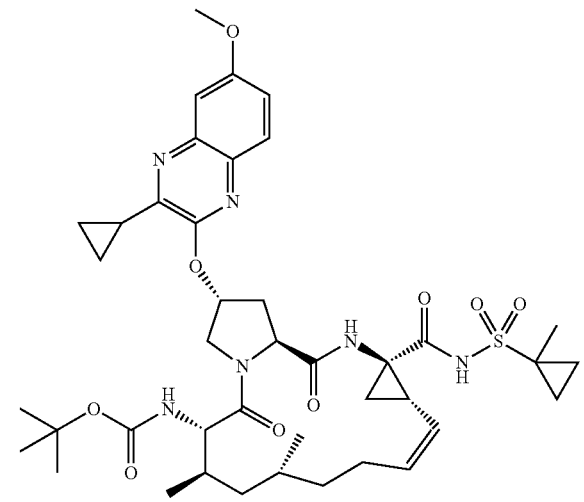

Compound 4303

To a solution of tert-butyl((2R,6S,7R,9R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (50 mg, 0.082 mmole) and 2-chloro-3-cyclopropyl-6-methoxyquinoxaline 19.21 mg, 0.082 mmole) in DMSO (5 mL) was added t-BuOK (0.164 mL, 0.164 mmol, 1M solution in THF) at room temperature under nitrogen atmosphere. The reaction mixture was stirred at room temperature for 2 h. The reaction mass was quenched with aqueous citric acid solution and extracted with ethyl acetate (50 mL×3). The combined organic layer was washed with water, brine solution, dried over anhydrous Na$_2$SO$_4$ and evaporated under reduced pressure to get crude compound. The crude compound was purified by prep-HPLC to get 15 mg (21%) of desired compound as a white solid.

Compound 4303: tert-butyl((2R,6S,7R,9R,13aS,14aR,16aS,Z)-2-(((3-cyclopropyl-6-methoxyquinoxalin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.65-7.78 (m, 1H) 7.26 (dq, J=4.83, 2.57 Hz, 2H) 5.83-6.00 (m, 1H) 5.63 (td, J=10.04, 5.52 Hz, 1H) 4.93-5.09 (m, 1H) 4.74 (d, J=11.04 Hz, 1H) 4.54-4.68 (m, 1H) 4.02-4.18 (m, 1H) 3.82-3.98 (m, 4H) 2.67-2.86 (m, 2H) 2.36-2.63 (m, 3H) 1.73-2.09 (m, 4H) 1.60-1.72 (m, 1H) 1.38-1.61 (m, 7H) 1.11-1.34 (m, 11H) 0.79-1.10 (m, 11H). MS: MS m/z 809.4 (M$^+$+1).

Preparation of Compound 4306 and Compound 4307

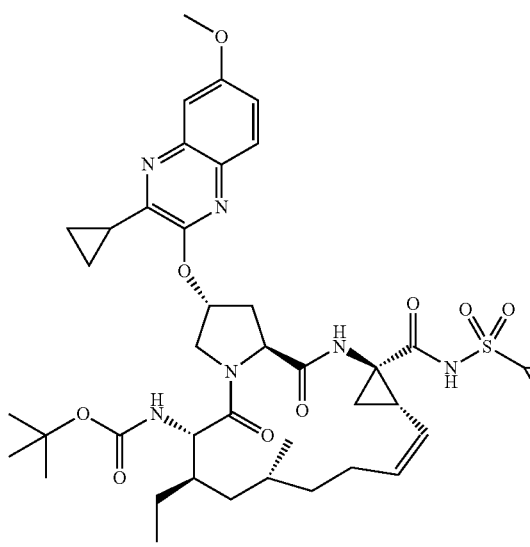

Compound 4306

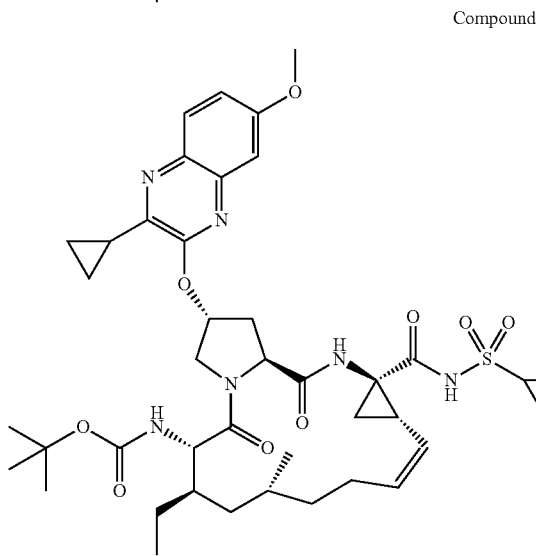

Compound 4307

Compound 4306 and 4307 were prepared using the intermediates described herein and by following the general procedure described for the synthesis of Compound 4303 but 3-chloro-2-cyclopropyl-6-methoxyquinoxaline and 2-chloro-3-cyclopropyl-6-methoxyquinoxaline (as a mixture) was used instead of 2-chloro-3-cyclopropyl-6-methoxyquinoxaline.

Compound 4306: tert-butyl((2R,6S,7R,9R,13aS,14aR, 16aS,Z)-2-(((3-cyclopropyl-6-methoxyquinoxalin-2-yl) oxy)-14a-((cyclopropylsulfonyl)carbamoyl)-7-ethyl-9-methyl-5,16-dioxo-1,2,3,5,6,7,8,9,10,11,13a,14,14a,15,16, 16a-hexadecahydrocyclopropa[e]pyrrolo[1,2-a][1,4] diazacyclopentadecin-6-yl)carbamate. $^1$H NMR (400 MHz, CD$_3$OD): δ 7.60-7.81 (m, 1H) 7.16-7.32 (m, 2H) 5.90 (br. s., 1H) 5.60 (br. s., 1H) 4.73 (d, J=11.55 Hz, 1H) 4.50-4.67 (m, 1H) 4.01-4.18 (m, 2H) 3.91 (s, 3H) 2.91 (br. s., 1H) 2.63-2.82 (m, 1H) 2.41-2.64 (m, 1H) 1.96 (d, J=11.55 Hz, 2H) 1.76 (br. s., 1H) 1.41-1.67 (m, 6H) 0.73-1.39 (m, 3H). MS: MS m/z 807.0 (M$^+$−1).

Compound 4307: tert-butyl((2R,6S,7R,9R,13aS,14aR, 16aS,Z)-2-(((3-cyclopropyl-7-methoxyquinoxalin-2-yl) oxy)-14a-((cyclopropylsulfonyl)carbamoyl)-7-ethyl-9-methyl-5,16-dioxo-1,2,3,5,6,7,8,9,10,11,13a,14,14a,15,16, 16a-hexadecahydrocyclopropa[e]pyrrolo[1,2-a][1,4] diazacyclopentadecin-6-yl)carbamate. $^1$H NMR (400 MHz, CD$_3$OD): δ ppm 7.70 (m, 1H) 7.19 (m, 2H) 5.92 (br. s., 1H) 4.73 (d, J=18.07 Hz, 1H) 4.57 (br. s., 1H) 4.19 (m, 2H) 3.91 (m, 3H) 2.72 (s, 1H) 2.50 (m, 1H) 2.02 (m, 1H) 1.67 (m, 2H) 1.37 (m, 4H) 1.09 (br. s., 11H) 0.94 (m, 11H). MS: MS m/z 806.9 (M$^+$−1).

Preparation of (2R,6S,7R,9R,13aS,14aR,16aS,Z)-6-amino-2-((3-cyclopropyl-6-methoxyquinoxalin-2-yl) oxy)-N-(cyclopropylsulfonyl)-7-ethyl-9-methyl-5, 16-dioxo-1,2,3,5,6,7,8,9,10,11,13a,14,14a,15,16,16a-hexadecahydrocyclopropa[e]pyrrolo[1,2]-[1,4] diazacyclopentadecine-14a-carboxamide compound with (2R,6S,7R,9R,13aS,14aR,16aS,Z)-6-amino-2-((3-cyclopropyl-7-methoxyquinoxalin-2-yl)oxy)-N-(cyclopropylsulfonyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4] diazacyclopentadecine-14a-carboxamide (1:1) dihydrochloride

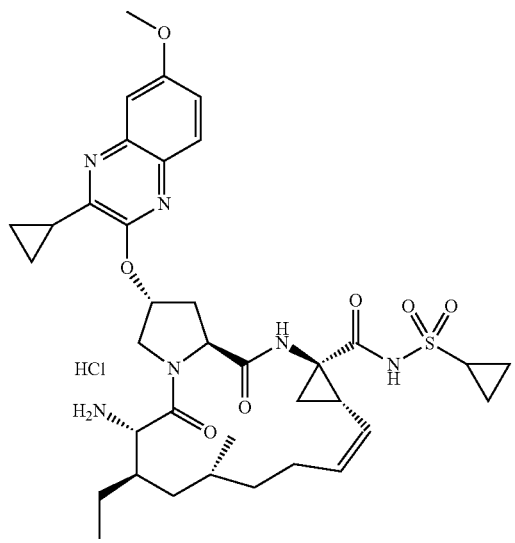

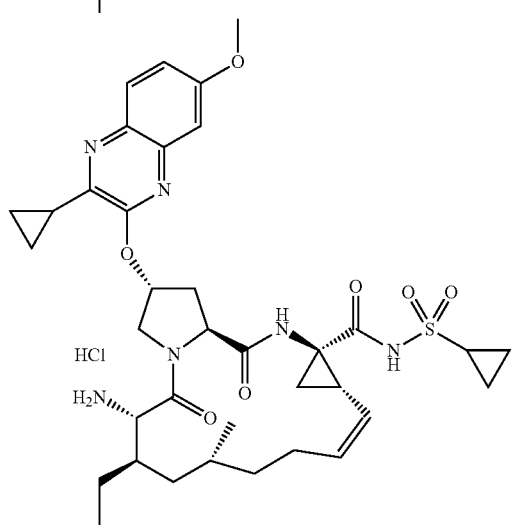

A mixture of compounds 4306 and 4307 (110 mg, 0.136 mmole) was treated with HCl in dioxane (4M). The solution was stirred at room temperature for 30 min. The volatiles were removed under reduced pressure to afford a 1:1 mixture of (2R,6S,7R,9R,13aS,14aR,16aS,Z)-6-amino-2-(((3-cyclopropyl-6-methoxyquinoxalin-2-yl)oxy)-N-(cyclopropylsulfonyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide and (2R,6S,7R,9R,13aS,14aR,16aS,Z)-6-amino-2-(((3-cyclopropyl-7-methoxyquinoxalin-2-yl)oxy)-N-(cyclopropylsulfonyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide as the HCl salts (90 mg, 84%). The crude material was used without further purification. MS: MS m/z 709.4 (M$^+$+1).

Preparation of Compound 4308 and Compound 4309

Compound 4308

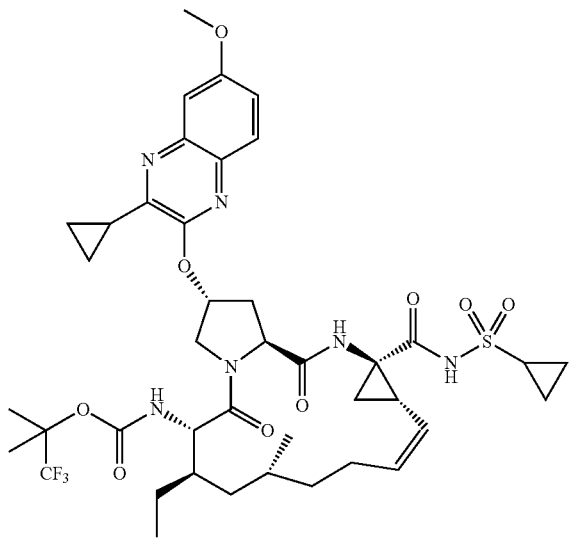

Compound 4309

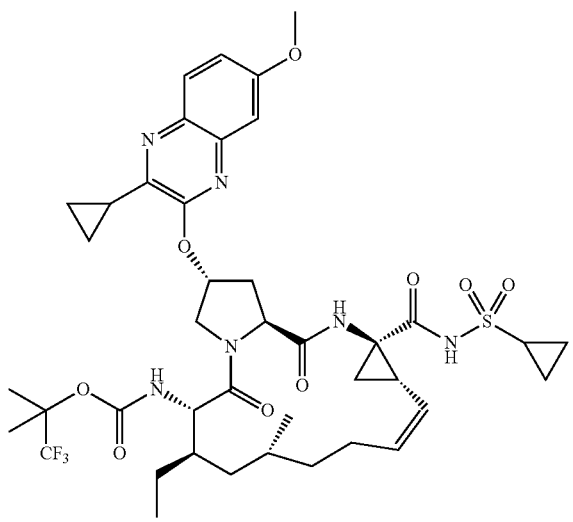

A 1:1 mixture of (2R,6S,7R,9R,13aS,14aR,16aS,Z)-6-amino-2-((3-cyclopropyl-6-methoxyquinoxalin-2-yl)oxy)-N-(cyclopropylsulfonyl)-7-ethyl-9-methyl-5,16-dioxo-1,2, 3,5,6,7,8,9,10,11,13a,14,14a,15,16,16a-hexadecahydrocyclopropa[e]pyrrolo[1,2-a][1,4]diazacyclopentadecine-14a-carboxamide and (2R,6S,7R,9R,13aS,14aR,16aS,Z)-6-amino-2-((3-cyclopropyl-7-methoxyquinoxalin-2-yl)oxy)-N-(cyclopropylsulfonyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide as the HCl salts (90 mg, 0.127 mmol) was dissolved in DCM (4 mL). To the solution at room temperature was added DIPEA (0.067 mL, 0.381 mmole) followed by pyridin-2-yl (1,1,1-trifluoro-2-methylpropan-2-yl) carbonate (38 mg, 0.152 mmole). The reaction mixture was stirred at room temperature for 30 min. The reaction mass was diluted with DCM and washed with water. The organic layer was dried over anhydrous Na$_2$SO$_4$ and evaporated under reduced pressure to get crude compound. The crude compound was purified by prep-HPLC to get compound 4308 (22 mg, 20%) and Compound 4309 (9 mg, 8%) as white solids.

Compound 4308: 1,1,1-trifluoro-2-methylpropan-2-yl ((2R,6S,7R,9R,13aS,14aR,16aS,Z)-2-(((3-cyclopropyl-6-methoxyquinoxalin-2-yl)oxy)-14a-((cyclopropylsulfonyl)carbamoyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (400 MHz, CD$_3$OD): δ ppm 7.72 (m, 1H) 7.27 (m, 2H) 5.89 (br. s., 1H) 5.65 (m, 1H) 5.01 (m, 1H) 4.77 (d, J=11.55 Hz, 1H) 4.62 (m, 1H) 4.07 (d, J=11.55 Hz, 2H) 3.92 (s, 3H) 3.07 (q, J=7.53 Hz, 1H) 2.93 (br. s., 1H) 2.75 (m, 2H) 2.50 (m, 2H) 2.00 (br. s., 2H) 1.79 (m, 1H) 1.54 (m, 5H) 1.30 (m, 12H) 1.02 (m, 11H). $^{19}$F NMR: δ ppm −85.01 (1 F). MS: MS m/z 860.9 (M$^+$−1).

Compound 4309: 1,1,1-trifluoro-2-methylpropan-2-yl ((2R,6S,7R,9R,13aS,14aR,16aS,Z)-2-(((3-cyclopropyl-7-methoxyquinoxalin-2-yl)oxy)-14a-((cyclopropylsulfonyl)carbamoyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (400 MHz, CD$_3$OD): δ ppm 7.73 (m, 1H) 7.27 (d, J=3.01 Hz, 1H) 7.19 (m, 1H) 5.92 (br. s., 1H) 5.62 (br. s., 1H) 4.76 (d, J=11.55 Hz, 1H) 4.62 (m, 1H) 4.08 (m, 2H) 3.94 (m, 3H) 3.05 (m, 1H) 2.93 (br. s., 1H) 2.75 (dd, J=14.05, 7.03 Hz, 1H) 2.49 (m, 2H) 1.98 (m, 2H) 1.78 (br. s., 1H) 1.54 (m, 6H) 1.29 (m, 11H) 1.04 (m, 10H) 0.87 (m, 4H). $^{19}$F NMR: δ ppm −85.01 (1 F). MS: MS m/z 860.9 (M$^+$−1).

Preparation of Compound 4280

Compound 4280

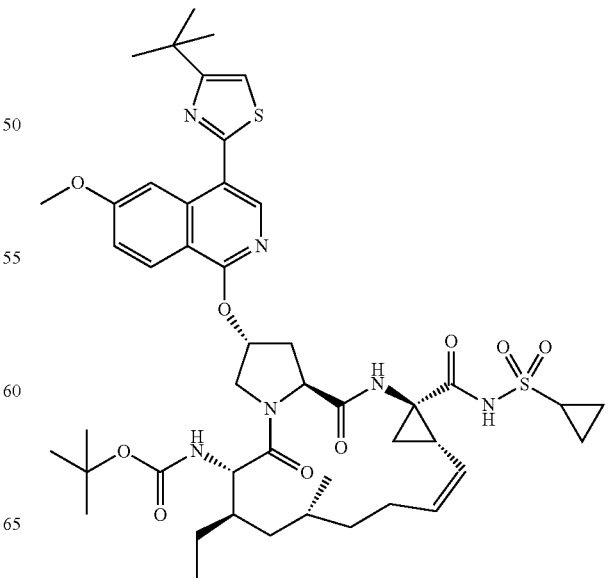

Compound 4280 was prepared using the intermediates described herein and by following the general procedure described for the synthesis of Compound 4303.

Compound 4280: tert-butyl((2R,6S,7R,9R,13aS,14aR,16aS,Z)-2-((4-(4-(tert-butyl)thiazol-2-yl)-6-methoxyisoquinolin-1-yl)oxy)-14a-((cyclopropylsulfonyl)carbamoyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.

$^1$H NMR (400 MHz, CD$_3$OD): δ ppm 8.33-8.53 (m, 1H) 8.21 (d, J=9.29 Hz, 1H) 6.90-7.35 (m, 1H) 5.96 (br. s., 1H) 5.51-5.73 (m, 1H) 5.05 (t, J=9.91 Hz, 1H) 4.65 (dd, J=10.42, 7.15 Hz, 1H) 4.01-4.19 (m, 1H) 3.94 (s, 2H) 3.50 (dt, J=3.26, 1.63 Hz, 1H) 3.15 (dt, J=3.14, 1.69 Hz, 1H) 2.87-3.02 (m, 1H) 2.68-2.86 (m, 1H) 2.30-2.59 (m, 1H) 1.97 (d, J=9.54 Hz, 1H) 1.75-1.87 (m, 1H) 1.52-1.68 (m, 3H) 1.48 (s, 7H) 1.23-1.46 (m, 4H) 0.97-1.21 (m, 11H) 0.73-0.94 (m, 3H). MS: MS m/z 907.76 (M$^+$+1).

Preparation of Compound 4281

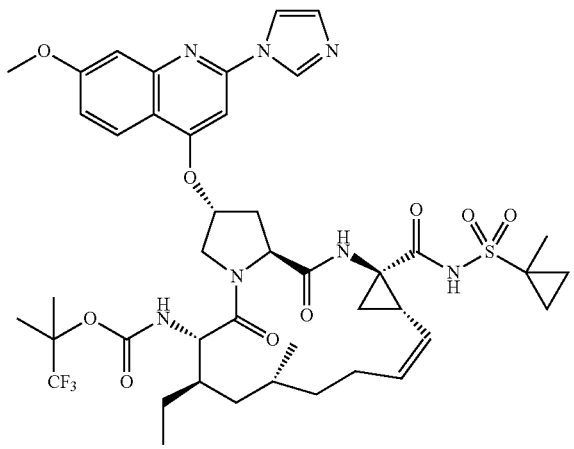

Compound 4281

Compound 4281 was prepared using the intermediates described herein and by following the general procedure described for the synthesis of Compound 4308.

Compound 4281: 1,1,1-trifluoro-2-methylpropan-2-yl ((2R,6S,7R,9R,13aS,14aR,16aS,Z)-2-((2-(1H-imidazol-1-yl)-7-methoxyquinolin-4-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 9.82 (br. s., 1H) 8.58 (br. s., 1H) 8.12 (d, J=9.29 Hz, 1H) 7.78 (br. s., 1H) 7.37-7.59 (m, 2H) 7.21 (dd, J=9.29, 2.51 Hz, 1H) 5.47-5.77 (m, 2H) 4.94-5.14 (m, 2H) 3.85-4.26 (m, 3H) 2.86 (dd, J=13.93, 7.15 Hz, 1H) 2.73 (d, J=9.03 Hz, 1H) 2.54 (ddd, J=14.05, 10.16, 3.89 Hz, 1H) 2.42 (d, J=13.55 Hz, 1H) 1.89-2.10 (m, 1H) 1.79 (dd, J=8.41, 5.65 Hz, 1H) 1.67-1.76 (m, 1H) 1.48-1.67 (m, 7H) 1.43 (dd, J=9.41, 4.89 Hz, 1H) 1.30-1.39 (m, 3H) 1.10-1.29 (m, 2H) 0.99-1.07 (m, 4H) 0.65-0.96 (m, 4H). MS: MS m/z 902.8 (M$^+$+1).

Preparation of Compound 4282

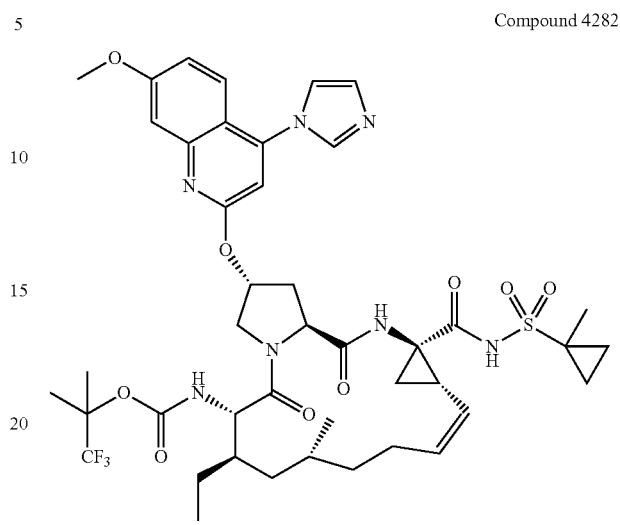

Compound 4282

Compound 4282 was prepared using the intermediates described herein and by following the general procedure described for the synthesis of Compound 4308.

Compound 4282: 1,1,1-trifluoro-2-methylpropan-2-yl ((2R,6S,7R,9R,13aS,14aR,16aS,Z)-2-((4-(1H-imidazol-1-yl)-7-methoxyquinolin-2-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.07 (s, 1H) 7.92 (s, 1H) 7.62 (d, J=9.29 Hz, 1H) 7.55 (s, 1H) 7.42-7.45 (m, 1H) 7.30 (s, 1H) 7.18 (s, 1H) 6.90 (s, 1H) 6.01 (br. s., 1H) 4.81 (s, 1H) 4.66-4.68 (m, 1H) 4.64-4.66 (m, 1H) 4.58 (s, 1H) 4.14 (s, 1H) 4.00 (s, 3H) 3.51 (s, 1H) 3.27-3.30 (m, 1H) 3.16 (s, 1H) 2.63-2.71 (m, 1H) 1.98-2.04 (m, 1H) 1.75-1.81 (m, 1H) 1.52-1.63 (m, 7H) 1.41 (s, 3H) 1.31 (s, 3H) 1.22 (s, 3H) 1.02 (d, J=6.53 Hz, 3H) 0.88-0.93 (m, 1H) 0.86 (s, 1H) 0.84 (s, 1H) 0.83 (s, 1H). MS: MS m/z 902.8 (M$^+$+1).

Preparation of Compound 4248

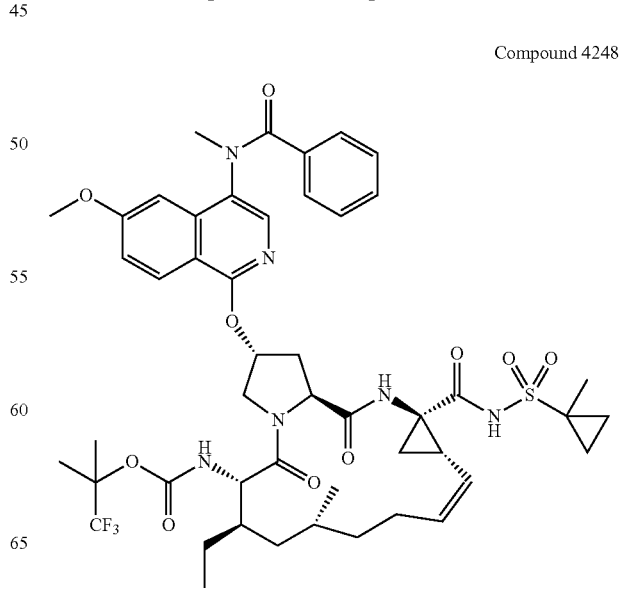

Compound 4248

Compound 4248 was prepared using the intermediates described herein and by following the general procedure described for the synthesis of Compound 4308.

Compound 4248: 1,1,1-trifluoro-2-methylpropan-2-yl ((2R,6S,7R,9R,13aS,14aR,16aS,Z)-7-ethyl-2-((6-methoxy-4-(N-methylbenzamido)isoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.06-8.16 (m, 1H) 7.30 (d, J=7.03 Hz, 2H) 7.07-7.24 (m, 6H) 3.99-4.05 (m, 4H) 2.62-2.78 (m, 3H) 2.41 (d, J=14.31 Hz, 3H) 1.97 (br. s., 2H) 1.72-1.82 (m, 1H) 1.39-1.61 (m, 14H) 1.25-1.37 (m, 5H) 0.96-1.05 (m, 4H) 0.80-0.94 (m, 8H). MS: MS m/z 969.8 (M$^+$+1).

Preparation of Compound 4255

Compound 4255

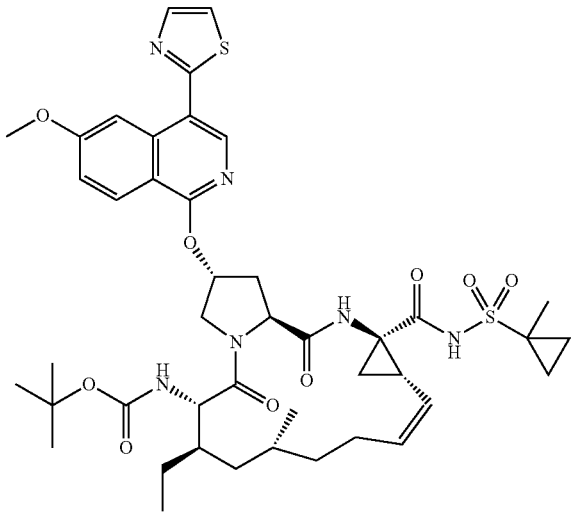

Compound 4255 was prepared using the intermediates described herein and by following the general procedure described for the synthesis of Compound 4303.

Compound 4255: tert-butyl((2R,6S,7R,9R,13aS,14aR,16aS,Z)-7-ethyl-2-((6-methoxy-4-(thiazol-2-yl)isoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.37 (s, 1H) 8.24 (s, 1H) 8.13 (s, 1H) 8.05 (s, 1H) 7.72 (s, 1H) 7.21 (dd, J=9.16, 2.38 Hz, 1H) 5.98 (br. s., 1H) 5.63 (td, J=10.16, 5.77 Hz, 1H) 5.01 (t, J=9.91 Hz, 1H) 4.63-4.69 (m, 1H) 4.05-4.13 (m, 1H) 3.93 (s, 2H) 2.70-2.83 (m, 2H) 2.40-2.51 (m, 1H) 1.96 (br. s., 2H) 1.77 (dd, J=8.28, 5.77 Hz, 1H) 1.50-1.68 (m, 8H) 1.38-1.47 (m, 2H) 1.06-1.19 (m, 8H) 1.02 (d, J=6.53 Hz, 3H) 0.81-0.93 (m, 5H). MS: MS m/z 865.7 (M$^+$+1).

Preparation of Compound 4258

Compound 4258

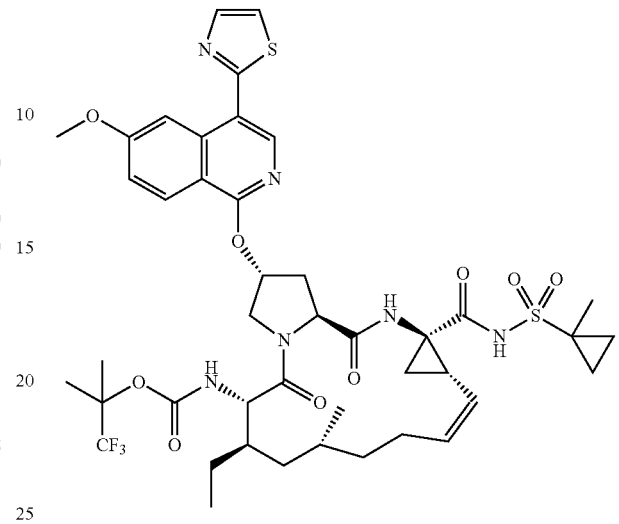

Compound 4258 was prepared using the intermediates described herein and by following the general procedure described for the synthesis of Compound 4308.

Compound 4258: 1,1,1-trifluoro-2-methylpropan-2-yl ((2R,6S,7R,9R,13aS,14aR,16aS,Z)-7-ethyl-2-((6-methoxy-4-(thiazol-2-yl)isoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 9.08 (s, 1H) 8.39 (s, 1H) 8.24 (s, 1H) 8.15 (s, 1H) 8.07 (s, 1H) 7.73 (s, 1H) 7.21-7.26 (m, 1H) 5.99 (br. s., 1H) 5.60-5.69 (m, 1H) 5.02 (s, 2H) 4.67-4.74 (m, 2H) 4.03-4.10 (m, 3H) 3.94 (s, 4H) 2.69-2.84 (m, 4H) 2.49 (ddd, J=13.87, 10.10, 3.89 Hz, 3H) 1.94-2.05 (m, 3H) 1.76-1.82 (m, 1H) 1.41-1.70 (m, 18H) 1.27-1.37 (m, 6H) 0.80-1.05 (m, 17H). MS: MS m/z 919.8 (M$^+$+1).

Preparation of Compound 4264

Compound 4264

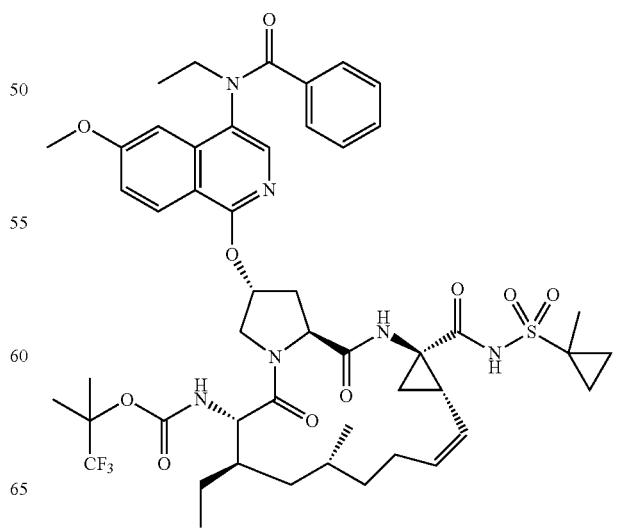

Compound 4264 was prepared using the intermediates described herein and by following the general procedure described for the synthesis of Compound 4308.

Compound 4264: 1,1,1-trifluoro-2-methylpropan-2-yl ((2R,6S,7R,9R,13aS,14aR,16aS,Z)-7-ethyl-2-(4-(N-ethyl-benzamido)-6-methoxyisoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.07-8.15 (m, 1H) 7.68-7.74 (m, 1H) 7.26-7.33 (m, 2H) 7.18-7.24 (m, 3H) 7.08-7.15 (m, 2H) 5.01 (t, J=10.42 Hz, 1H) 4.65 (dd, J=9.91, 6.90 Hz, 1H) 4.46 (dd, J=13.43, 7.15 Hz, 2H) 3.96-4.06 (m, 5H) 2.61-2.78 (m, 3H) 2.35-2.50 (m, 3H) 1.97 (br. s., 2H) 1.78 (dd, J=8.41, 5.65 Hz, 1H) 1.46-1.68 (m, 13H) 1.25-1.38 (m, 13H) 0.78-1.05 (m, 13H). MS: MS m/z 983.18 (M$^+$+1).

Preparation of Compound 4274

Compound 4274

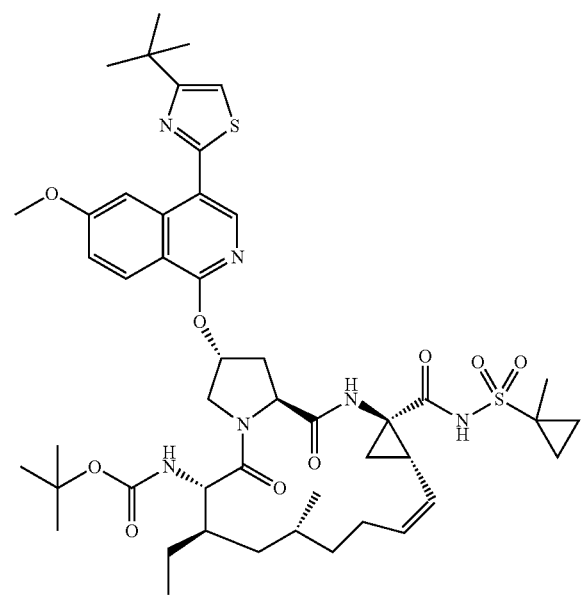

Compound 4274 was prepared using the intermediates described herein and by following the general procedure described for the synthesis of Compound 4303.

Compound 4274: tert-butyl((2R,6S,7R,9R,13aS,14aR,16aS,Z)-2-((4-(4-(tert-butyl)thiazol-2-yl)-6-methoxyisoquinolin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.45 (d, J=2.26 Hz, 1H) 8.39 (s, 1H) 8.21 (d, J=9.29 Hz, 1H) 7.17-7.24 (m, 2H) 6.64 (d, J=9.03 Hz, 1H) 5.97 (br. s., 1H) 5.63 (td, J=10.04, 5.77 Hz, 1H) 5.01 (t, J=10.04 Hz, 1H) 4.66 (dd, J=10.04, 7.03 Hz, 1H) 4.03-4.15 (m, 3H) 3.94 (s, 4H) 2.70-2.84 (m, 3H) 2.39-2.51 (m, 3H) 1.97 (d, J=13.55 Hz, 3H) 1.77 (dd, J=8.28, 5.77 Hz, 1H) 1.39-1.69 (m, 29H) 1.26-1.36 (m, 4H) 0.97-1.20 (m, 19H) 0.80-0.94 (m, 8H). MS: MS m/z 921.6 (M$^+$+1).

Preparation of Compound 4275

Compound 4275

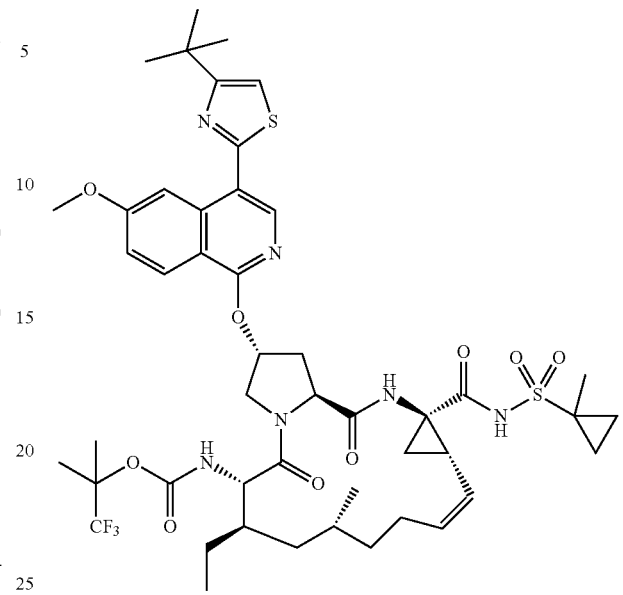

Compound 4275 was prepared using the intermediates described herein and by following the general procedure described for the synthesis of Compound 4308.

Compound 4275: 1,1,1-trifluoro-2-methylpropan-2-yl ((2R,6S,7R,9R,13aS,14aR,16aS,Z)-2-(4-(4-(tert-butyl)thiazol-2-yl)-6-methoxyisoquinolin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.47 (d, J=2.51 Hz, 1H) 8.41 (s, 1H) 8.21 (d, J=9.04 Hz, 1H) 7.19-7.25 (m, 2H) 5.96 (br. s., 1H) 5.59-5.68 (m, 1H) 5.02 (t, J=10.04 Hz, 2H) 4.70 (dd, J=10.04, 7.03 Hz, 1H) 4.05 (d, J=11.04 Hz, 2H) 3.95 (s, 3H) 2.70-2.83 (m, 3H) 2.41-2.53 (m, 2H) 1.95-2.04 (m, 2H) 1.78 (dd, J=8.41, 5.65 Hz, 1H) 1.39-1.70 (m, 25H) 1.29-1.35 (m, 6H) 1.02 (d, J=6.78 Hz, 3H) 0.89-0.95 (m, 6H) 0.83 (t, J=7.40 Hz, 3H). MS: MS m/z 975.8 (M$^+$+1).

Preparation of Compound 4285

Compound 4285

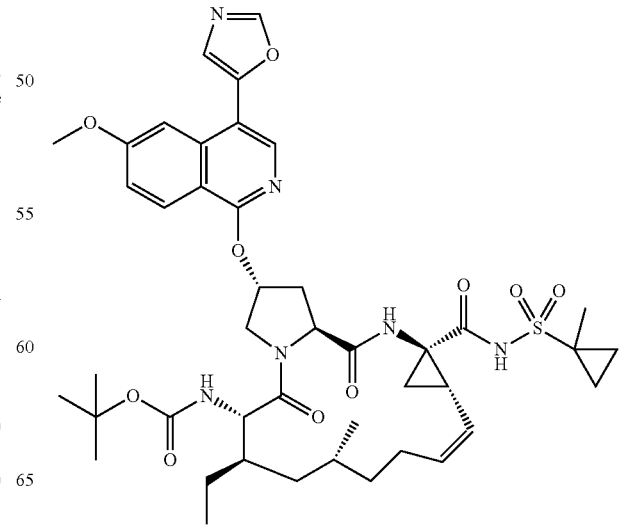

Compound 4285 was prepared using the intermediates described herein and by following the general procedure described for the synthesis of Compound 4303.

Compound 4285: tert-butyl((2R,6S,7R,9R,13aS,14aR,16aS,Z)-7-ethyl-2-((6-methoxy-4-(oxazol-5-yl)isoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.42 (s, 1H) 8.20-8.26 (m, 3H) 7.52 (s, 1H) 7.42 (d, J=2.01 Hz, 1H) 7.21 (dd, J=9.03, 2.26 Hz, 1H) 5.96 (br. s., 1H) 5.58-5.66 (m, 1H) 4.97-5.07 (m, 1H) 4.66 (dd, J=10.04, 7.03 Hz, 2H) 4.04-4.11 (m, 3H) 3.95 (s, 5H) 2.69-2.82 (m, 3H) 2.46 (dd, J=13.55, 4.02 Hz, 3H) 1.97 (d, J=14.05 Hz, 3H) 1.77 (dd, J=8.16, 5.65 Hz, 2H) 1.40-1.66 (m, 18H) 0.99-1.16 (m, 21H) 0.79-0.92 (m, 9H). MS: MS m/z 849.7 (M$^+$+1).

Preparation of Compound 4291

Compound 4291

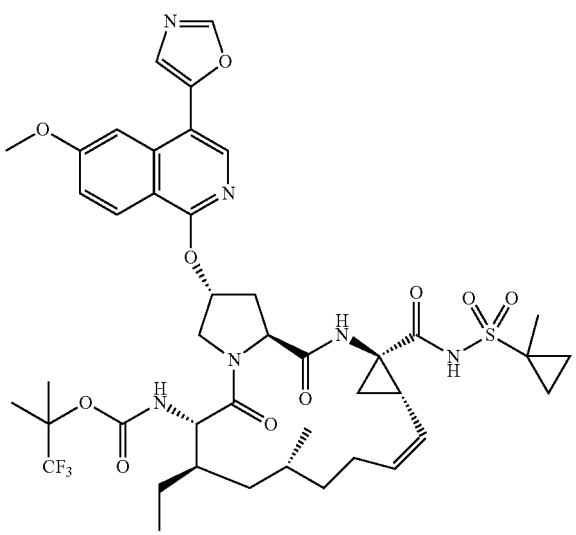

Compound 4291 was prepared using the intermediates described herein and by following the general procedure described for the synthesis of Compound 4308.

Compound 4291: 1,1,1-trifluoro-2-methylpropan-2-yl ((2R,6S,7R,9R,13aS,14aR,16aS,Z)-7-ethyl-2-((6-methoxy-4-(oxazol-5-yl)isoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.44 (s, 1H) 8.21-8.28 (m, 3H) 7.54 (s, 1H) 7.43 (d, J=2.26 Hz, 1H) 7.24 (dd, J=9.16, 2.38 Hz, 1H) 5.96 (br. s., 1H) 5.64 (td, J=9.98, 6.40 Hz, 1H) 5.02 (t, J=10.04 Hz, 2H) 4.68-4.73 (m, 1H) 4.02-4.08 (m, 3H) 3.96 (s, 4H) 2.71-2.83 (m, 3H) 2.37-2.52 (m, 3H) 1.93-2.05 (m, 3H) 1.78 (dd, J=8.41, 5.65 Hz, 1H) 1.50-1.70 (m, 14H) 1.40-1.46 (m, 2H) 1.30-1.36 (m, 6H) 1.13 (t, J=12.55 Hz, 2H) 1.02 (d, J=6.78 Hz, 4H) 0.90-0.95 (m, 7H) 0.83 (t, J=7.40 Hz, 4H). MS: MS m/z 903.8 (M$^+$+1).

Preparation of Compound 4293

Compound 4293

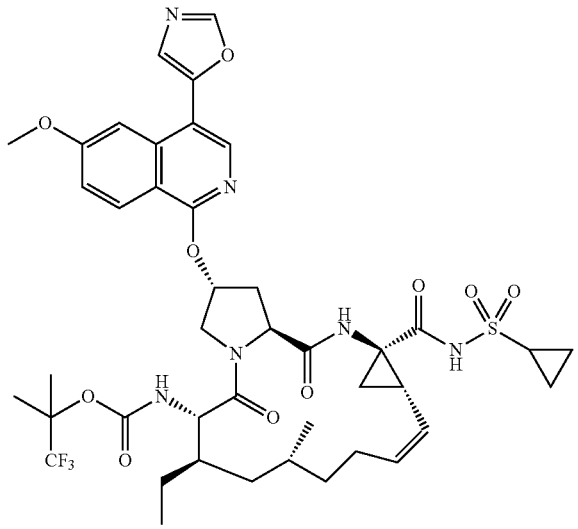

Compound 4291 was prepared using the intermediates described herein and by following the general procedure described for the synthesis of Compound 4308.

Compound 4293: 1,1,1-trifluoro-2-methylpropan-2-yl ((2R,6S,7R,9R,13aS,14aR,16aS,Z)-14a-((cyclopropylsulfonyl)carbamoyl)-7-ethyl-2-((6-methoxy-4-(oxazol-5-yl)isoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.44 (s, 1H) 8.21-8.28 (m, 3H) 7.54 (s, 1H) 7.43 (d, J=2.26 Hz, 1H) 7.24 (dd, J=9.16, 2.38 Hz, 1H) 5.96 (br. s., 1H) 5.64 (td, J=9.98, 6.40 Hz, 1H) 5.02 (t, J=10.04 Hz, 2H) 4.68-4.73 (m, 1H) 4.02-4.08 (m, 3H) 3.96 (s, 4H) 2.90-2.99 (m, 1H) 2.71-2.83 (m, 3H) 2.37-2.52 (m, 3H) 1.93-2.05 (m, 3H) 1.78 (dd, J=8.41, 5.65 Hz, 1H) 1.50-1.70 (m, 14H) 1.40-1.46 (m, 2H) 1.30-1.36 (m, 3H) 1.13 (t, J=12.55 Hz, 2H) 1.02 (d, J=6.78 Hz, 4H) 0.90-0.95 (m, 7H) 0.83 (t, J=7.40 Hz, 4H). MS: MS m/z 889.7 (M$^+$+1).

Preparation of Compound 4329

Compound 4329

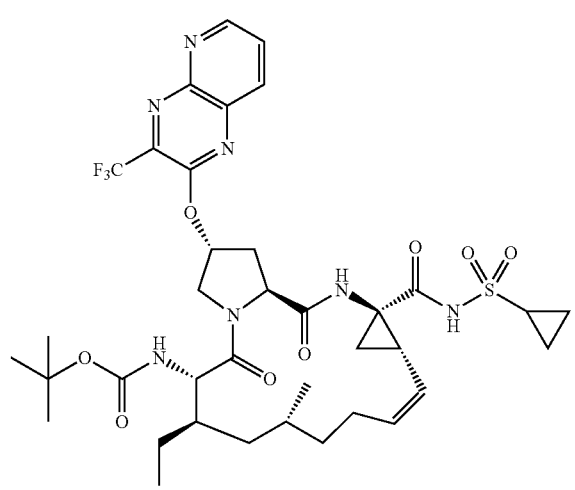

Compound 4329 was prepared using the intermediates described herein and by following the general procedure described for the synthesis of Compound 4303.

Compound 4329: tert-butyl((2R,6S,7R,9R,13aS,14aR,16aS,Z)-14a-((cyclopropylsulfonyl)carbamoyl)-7-ethyl-9-methyl-5,16-dioxo-2-((3-(trifluoromethyl)pyrido[2,3-b]pyrazin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 9.15 (dd, J=4.52, 1.76 Hz, 1H) 8.63 (dd, J=8.28, 1.76 Hz, 1H) 7.85 (dd, J=8.41, 4.39 Hz, 1H) 6.04 (br. s., 1H) 5.57 (br. s., 1H) 4.93-5.00 (m, 2H) 4.61 (d, J=7.78 Hz, 1H) 4.08 (dd, J=11.92, 3.14 Hz, 1H) 3.96 (d, J=11.04 Hz, 1H) 3.05 (q, J=7.36 Hz, 6H) 2.90 (br. s., 2H) 2.78 (dd, J=13.43, 6.90 Hz, 2H) 2.49-2.61 (m, 2H) 2.37 (br. s., 1H) 1.85-2.05 (m, 3H) 1.74 (br. s., 1H) 1.40-1.64 (m, 10H) 1.32 (t, J=7.28 Hz, 15H) 0.97-1.12 (m, 22H) 0.77 (t, J=7.53 Hz, 4H). MS: MS m/z 808.7 (M$^+$+1).

Preparation of Compound 4330

Compound 4330

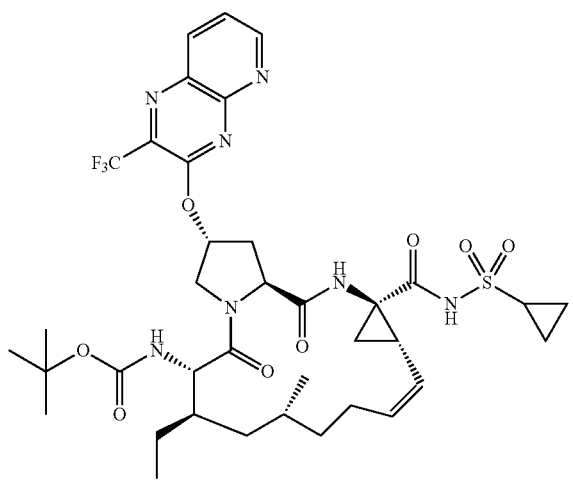

Compound 4280 was prepared using the intermediates described herein and by following the general procedure described for the synthesis of Compound 4303.

Compound 4330: tert-butyl((2R,6S,7R,9R,13aS,14aR,16aS,Z)-14a-((cyclopropylsulfonyl)carbamoyl)-7-ethyl-9-methyl-5,16-dioxo-2-((2-(trifluoromethyl)pyrido[2,3-b]pyrazin-3-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 9.06 (dd, J=4.27, 1.76 Hz, 1H) 8.49-8.56 (m, 1H) 7.93-8.00 (m, 1H) 6.01 (br. s., 1H) 5.56 (br. s., 1H) 4.59 (d, J=7.78 Hz, 2H) 4.05-4.12 (m, 2H) 3.97 (d, J=11.04 Hz, 1H) 3.04 (q, J=7.28 Hz, 4H) 2.90 (br. s., 1H) 2.76 (dd, J=14.18, 6.65 Hz, 2H) 2.55 (br. s., 2H) 2.35 (br. s., 2H) 1.87-2.04 (m, 3H) 1.72 (br. s., 2H) 1.46-1.63 (m, 8H) 1.25-1.37 (m, 12H) 0.99-1.10 (m, 21H) 0.91 (d, J=12.05 Hz, 3H) 0.78 (t, J=7.40 Hz, 4H). MS: MS m/z 808.7 (M$^+$+1).

Preparation of Compound 4368

Compound 4368

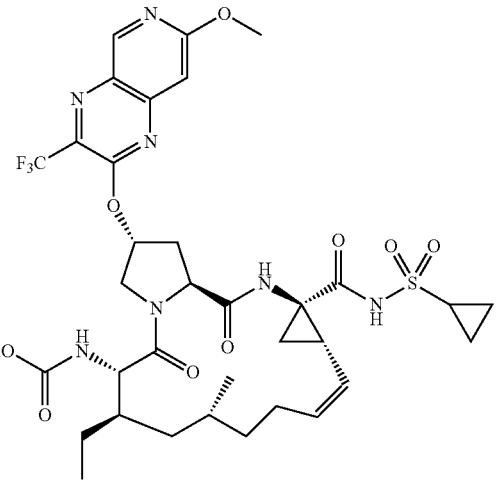

Compound 4368 was prepared using the intermediates described herein and by following the general procedure described for the synthesis of Compound 4303.

Compound 4368: tert-butyl((2R,6S,7R,9R,13aS,14aR,16aS,Z)-14a-((cyclopropylsulfonyl)carbamoyl)-7-ethyl-2-((7-methoxy-3-(trifluoromethyl)pyrido[3,4-b]pyrazin-2-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.

$^1$H NMR (400 MHz, CD$_3$OD): δ ppm 9.15 (s, 1H) 9.07-9.12 (m, 1H) 7.20 (s, 1H) 6.02 (br. s., 1H) 5.63 (td, J=9.98, 5.90 Hz, 2H) 5.05 (t, J=9.91 Hz, 2H) 4.62 (dd, J=10.16, 7.15 Hz, 1H) 4.03-4.13 (m, 6H) 3.96 (d, J=11.29 Hz, 1H) 2.90-2.98 (m, 2H) 2.66-2.78 (m, 3H) 2.35-2.54 (m, 3H) 1.88-2.04 (m, 3H) 1.78 (dd, J=8.41, 5.65 Hz, 2H) 1.44-1.67 (m, 10H) 1.25-1.37 (m, 7H) 0.97-1.18 (m, 25H) 0.86-0.95 (m, 2H) 0.80 (t, J=7.40 Hz, 4H). MS: MS m/z 892.7 (M$^+$+1).

Preparation of Compound 4288

Compound 4288

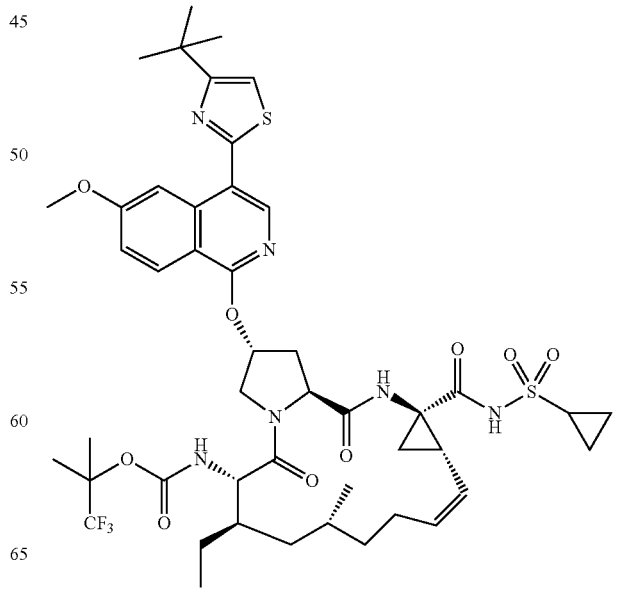

Compound 4288 was prepared using the intermediates described herein and by following the general procedure described for the synthesis of Compound 4308.

Compound 4288: 1,1,1-trifluoro-2-methylpropan-2-yl ((2R,6S,7R,9R,13aS,14aR,16aS,Z)-2-(4-(4-(tert-butyl)thiazol-2-yl)-6-methoxyisoquinolin-1-yl)oxy)-14a-((cyclopropylsulfonyl)carbamoyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.46 (d, J=2.51 Hz, 1H) 8.40 (s, 1H) 8.21 (s, 1H) 7.19-7.23 (m, 3H) 5.95 (br. s., 1H) 5.60-5.68 (m, 1H) 5.04 (t, J=9.91 Hz, 1H) 4.69 (dd, J=10.29, 7.03 Hz, 1H) 4.00-4.08 (m, 3H) 3.94 (s, 4H) 2.91-2.97 (m, 1H) 2.70-2.82 (m, 3H) 2.38-2.50 (m, 3H) 1.97 (d, J=11.80 Hz, 3H) 1.79 (dd, J=8.28, 5.52 Hz, 1H) 1.44-1.63 (m, 21H) 1.27-1.38 (m, 8H) 1.00-1.18 (m, 10H) 0.93 (s, 4H) 0.83 (t, J=7.40 Hz, 4H). MS: MS m/z 961.6 (M$^+$+1).

Scheme: Preparation of tert-butyl ((2R,6S,7R,9R,13aS,14aR,16aS,Z)-2-((2-ethoxy-7-methoxypyrido[3,4-b]pyrazin-3-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

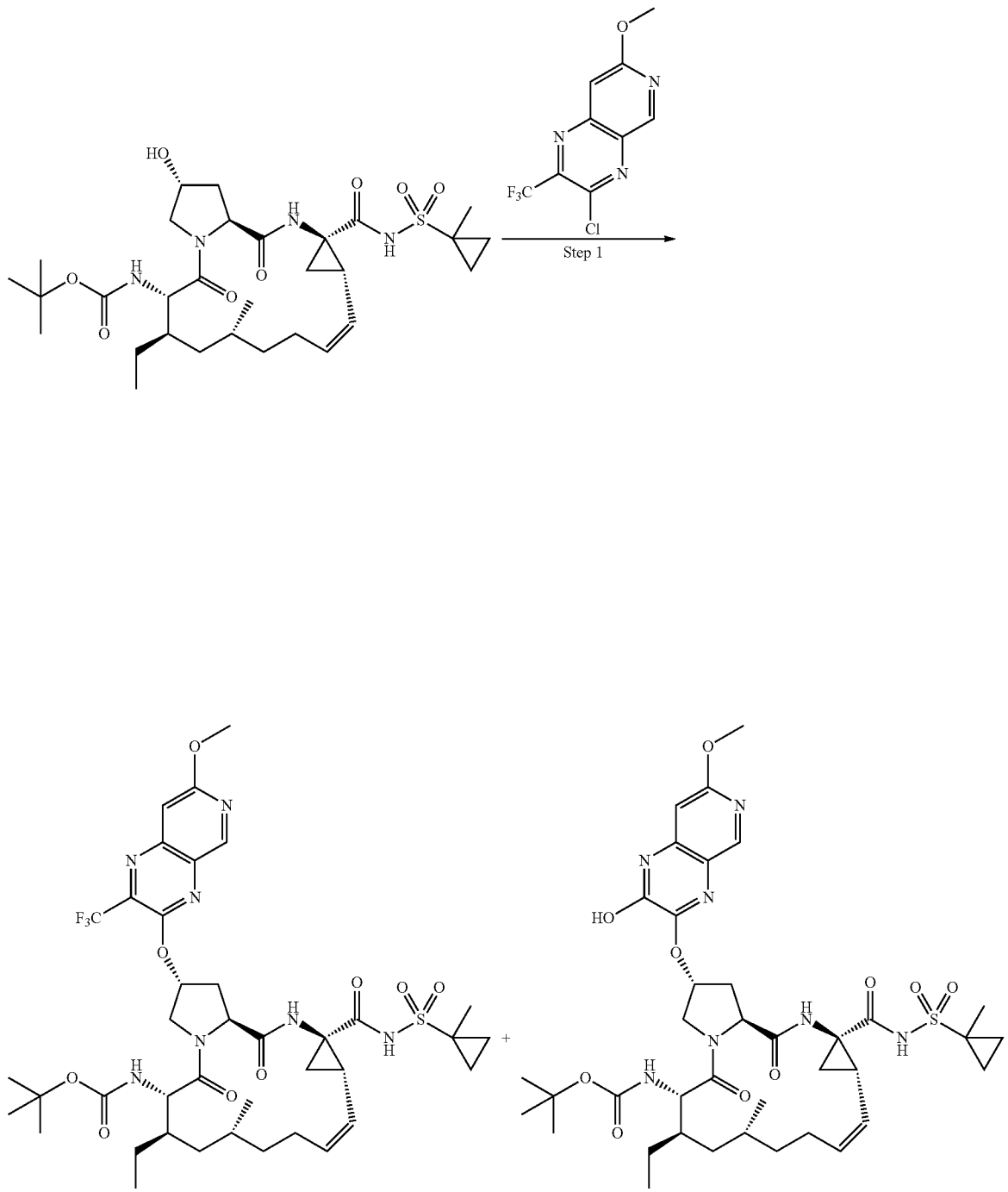

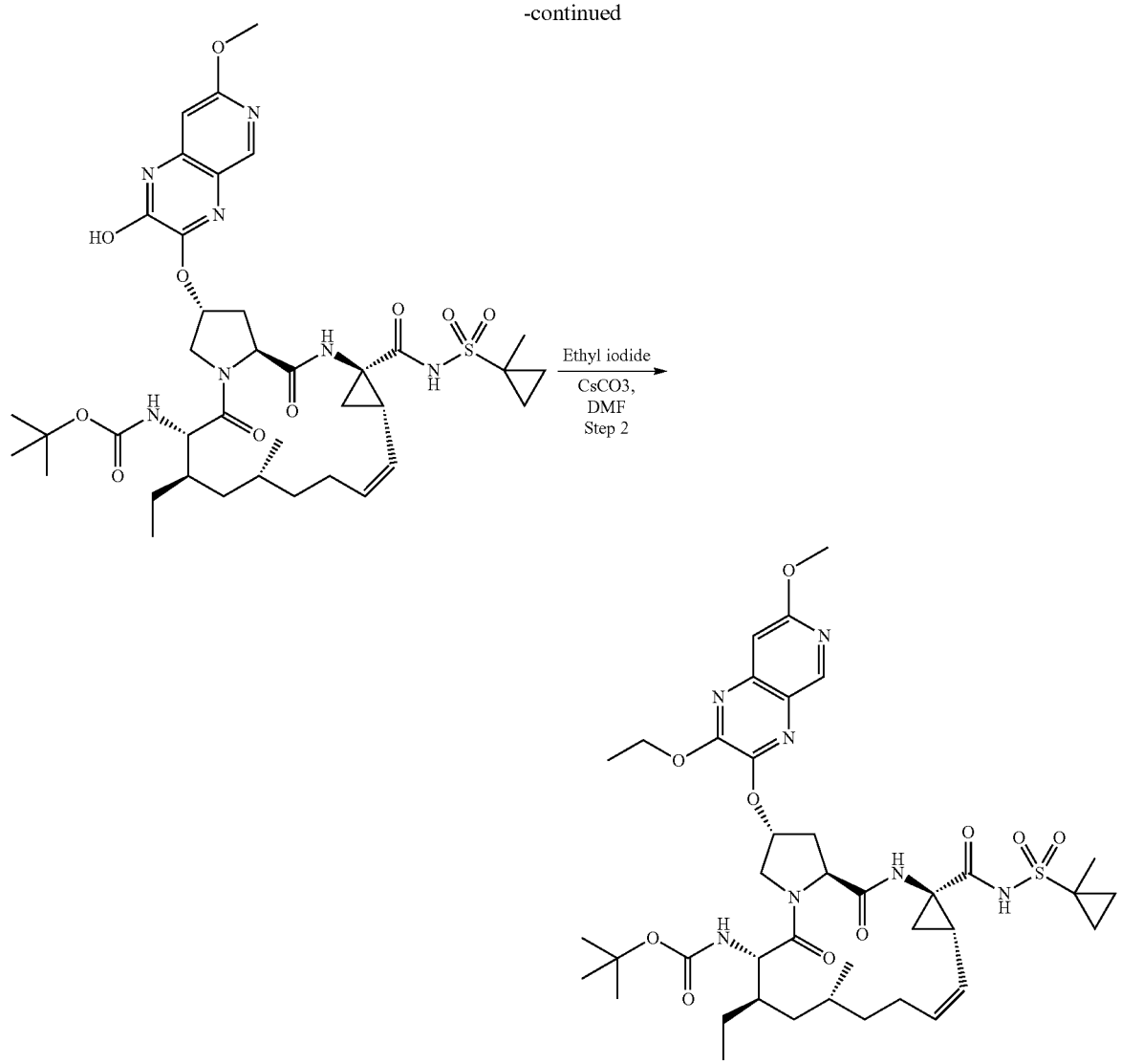

Step 1: Preparation of tert-butyl((2R,6S,7R,9R,13aS,14aR,16aS,Z)-7-ethyl-2-((7-methoxy-2-(trifluoromethyl)pyrido[3,4-b]pyrazin-3-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate The same procedure was followed as described for the preparation of Compound 4303 but tert-butyl((2R,6S,7R,9R,13aS,14aR,16aS,Z)-7-ethyl-2-hydroxy-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate and 3-chloro-7-methoxy-2-(trifluoromethyl)pyrido[3,4-b]pyrazine were used as starting materials. MS: MS m/z 852.83 (M$^+$+1). During this conversion tert-butyl((2R,6S,7R,9R,13aS,14aR,16aS,Z)-7-ethyl-2-((2-hydroxy-7-methoxypyrido[3,4-b]pyrazin-3-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate was isolated as by product. MS: MS m/z 800.3 (M$^+$+1).

Step 2: Preparation of tert-butyl((2R,6S,7R,9R,13aS,14aR,16aS,Z)-2-((2-ethoxy-7-methoxypyrido[3,4-b]pyrazin-3-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate To a solution of tert-butyl((2R,6S,7R,9R,13aS,14aR,16aS,Z)-7-ethyl-2-((2-hydroxy-7-methoxypyrido[3,4-b]pyrazin-3-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (60 mg, 0.075 mmol) in DMF (2 mL) was added Iodoethane (6.06 μl, 0.075 mmol) followed by cesium carbonate (24.44 mg, 0.075 mmol) at room temperature. The reaction mass was stirred at room temperature for 18 h. The solvent was removed under reduced pressure and the residue was diluted with water and extracted with ethyl acetate. The combined organic volume was dried over sodium sulfate and evaporated under reduced pressure to get crude compound. The crude compound was purified by prep HPLC to get tert-butyl((2R,6S,7R,9R,13aS,14aR,16aS,Z)-2-((2-ethoxy-6-methoxypyrido[2,3-b]pyrazin-3-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (40 mg, 0.048 mmol, 64.4% yield) as white solid. MS: MS m/z 828.4 (M$^+$+1).

Preparation of Compound 4359

Compound 4359

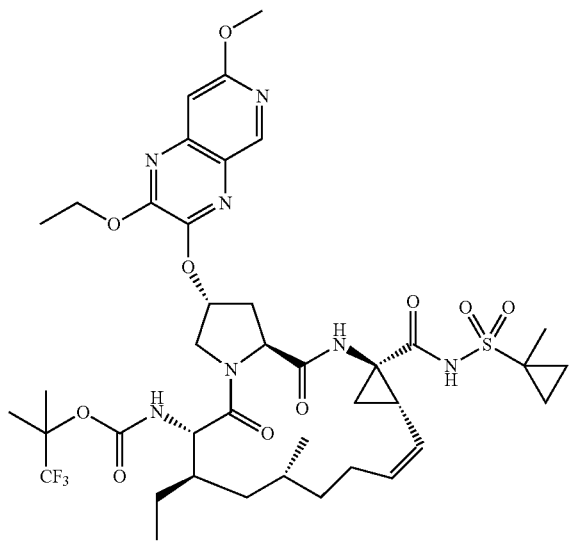

Compound 4359 was prepared using the intermediates described herein and by following the general procedure described for the synthesis of Compound 4308. tert-butyl ((2R,6S,7R,9R,13aS,14aR,16aS,Z)-2-((2-ethoxy-7-methoxypyrido[3,4-b]pyrazin-3-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate was used as a starting material.

Compound 4359: 1,1,1-trifluoro-2-methylpropan-2-yl ((2R,6S,7R,9R,13aS,14aR,16aS,Z)-2-((2-ethoxy-7-methoxypyrido[3,4-b]pyrazin-3-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.81 (br. s., 1H) 8.49 (s, 1H) 7.96 (br. s., 1H) 6.81 (s, 1H) 5.79 (br. s., 1H) 5.62 (td, J=9.91, 6.02 Hz, 1H) 4.65 (dd, J=9.66, 7.15 Hz, 1H) 4.29-4.37 (m, 1H) 4.13-4.25 (m, 2H) 3.99-4.07 (m, 5H) 2.65-2.74 (m, 2H) 2.44 (ddd, J=13.99, 9.72, 4.64 Hz, 2H) 1.95-2.02 (m, 2H) 1.77 (dd, J=8.28, 5.77 Hz, 1H) 1.49-1.69 (m, 11H) 1.24-1.43 (m, 20H) 0.79-1.04 (m, 14H). MS: MS m/z 882.8 (M$^+$+1).

Preparation of Compound 4364

Compound 4364

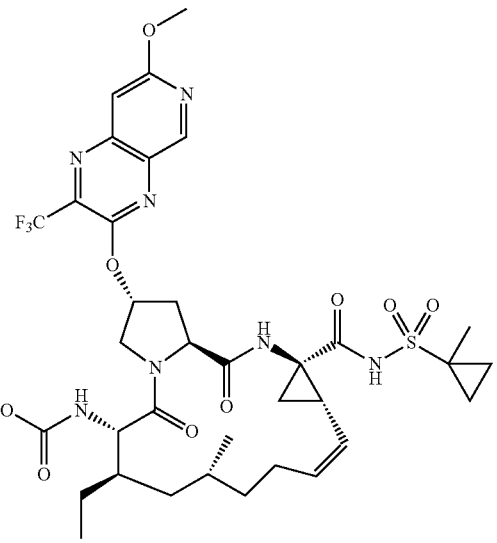

Compound 4364 was prepared using the intermediates described herein and by following the general procedure described for the synthesis of Compound 4303.

Compound 4364: tert-butyl((2R,6S,7R,9R,13aS,14aR,16aS,Z)-7-ethyl-2-((7-methoxy-2-(trifluoromethyl)pyrido[3,4-b]pyrazin-3-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 9.19 (s, 1H) 9.09-9.12 (m, 1H) 7.37 (s, 1H) 5.98-6.05 (m, 1H) 5.59-5.67 (m, 2H) 5.02 (t, J=10.04 Hz, 2H) 4.63 (dd, J=10.16, 7.15 Hz, 2H) 4.06-4.13 (m, 6H) 3.97 (d, J=11.04 Hz, 2H) 2.68-2.78 (m, 4H) 2.38-2.55 (m, 3H) 1.90-2.02 (m, 3H) 1.77 (dd, J=8.41, 5.65 Hz, 2H) 1.63-1.69 (m, 2H) 1.40-1.61 (m, 17H) 1.07-1.15 (m, 16H) 1.01 (d, J=6.78 Hz, 5H) 0.77-0.92 (m, 9H). MS: MS m/z 906.8 (M$^+$+1).

Preparation of Compound 5490 and Compound 5491

Compound 5490

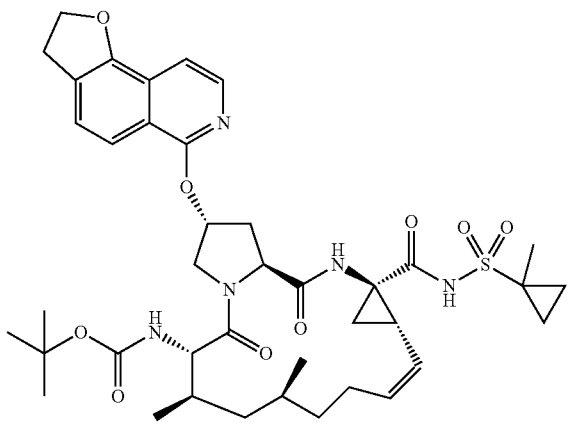

105

-continued

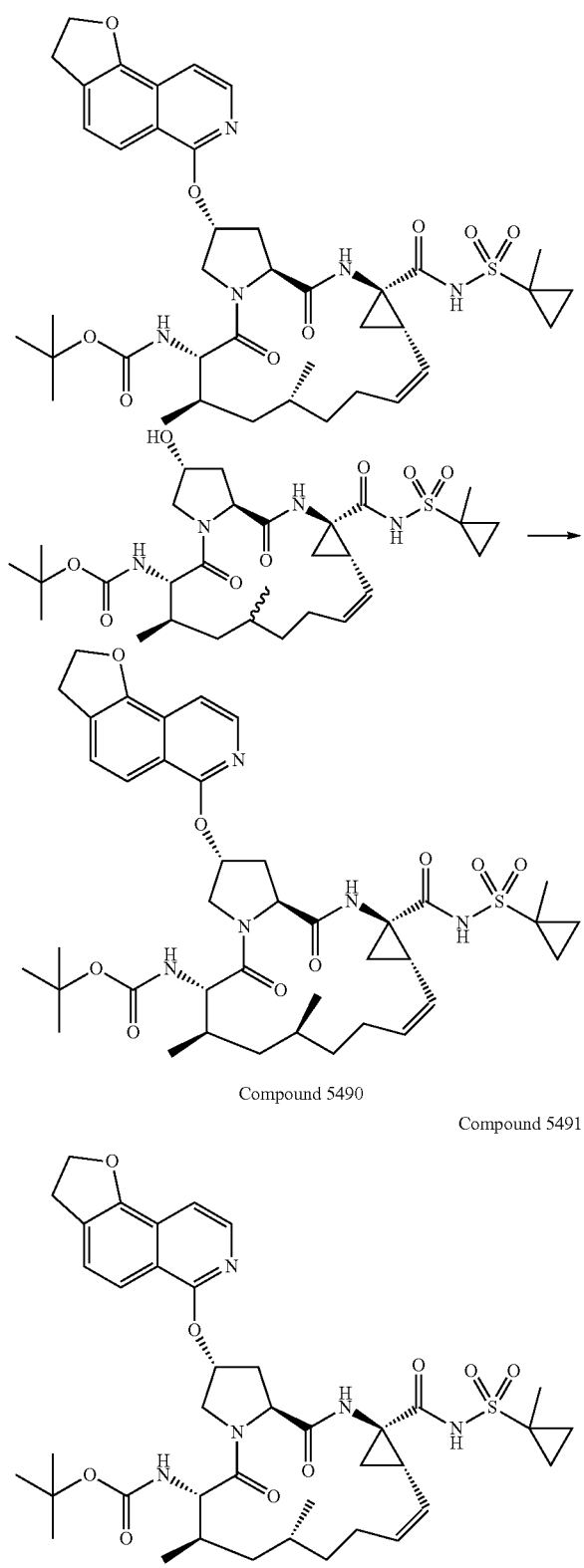

Compound 5491

Compound 5490

Compound 5491

To a mixture of tert-butyl((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a]

106

[1,4]diazacyclopentadecin-6-yl)carbamate (9.16 mg, 0.015 mmol), 6-chloro-2,3-dihydrofuro[2,3-f]isoquinoline (3.08 mg, 0.015 mmol), and tert-BuOK (1.683 mg, 0.015 mmol) was added DMSO (3 mL). The mixture was then sonicated for 15 min. The resulting solution was stirred for 4 h. The reaction was quenched with water, acidified with aq. 6 N HCl, extracted with EtOAc, washed with brine, dried over MgSO$_4$. After concentration, the residue was purified by prep HPLC to afford 1.7 mg of Compound 5490 as a solid and 1.1 mg of Compound 5491 as a solid.

Compound 5490: tert-butyl((2R,6S,7R,9S,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 780.7 (M$^+$+1).

Compound 5491: tert-butyl((2R,6S,7R,9R,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 780.7 (M$^+$+1).

Preparation of Compound 5492 and Compound 5493

Compound 5492

Compound 5493

Compounds 5492 and 5493 were prepared using the intermediates described herein and by following the general procedure described for the synthesis of Compounds 5490 and 5491:

Compound 5492: tert-butyl((2R,6S,7R,9S,13aS,14aR,16aS,Z)-2-((2,3-dihydrofuro[2,3-f]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 794.7 (M⁺+1).

Compound 5493: tert-butyl((2R,6S,7R,9R,13aS,14aR,16aS,Z)-2-((2,3-dihydrofuro[2,3-f]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 794.7 (M⁺+1).

Preparation of Compound 5494 and Compound 5495

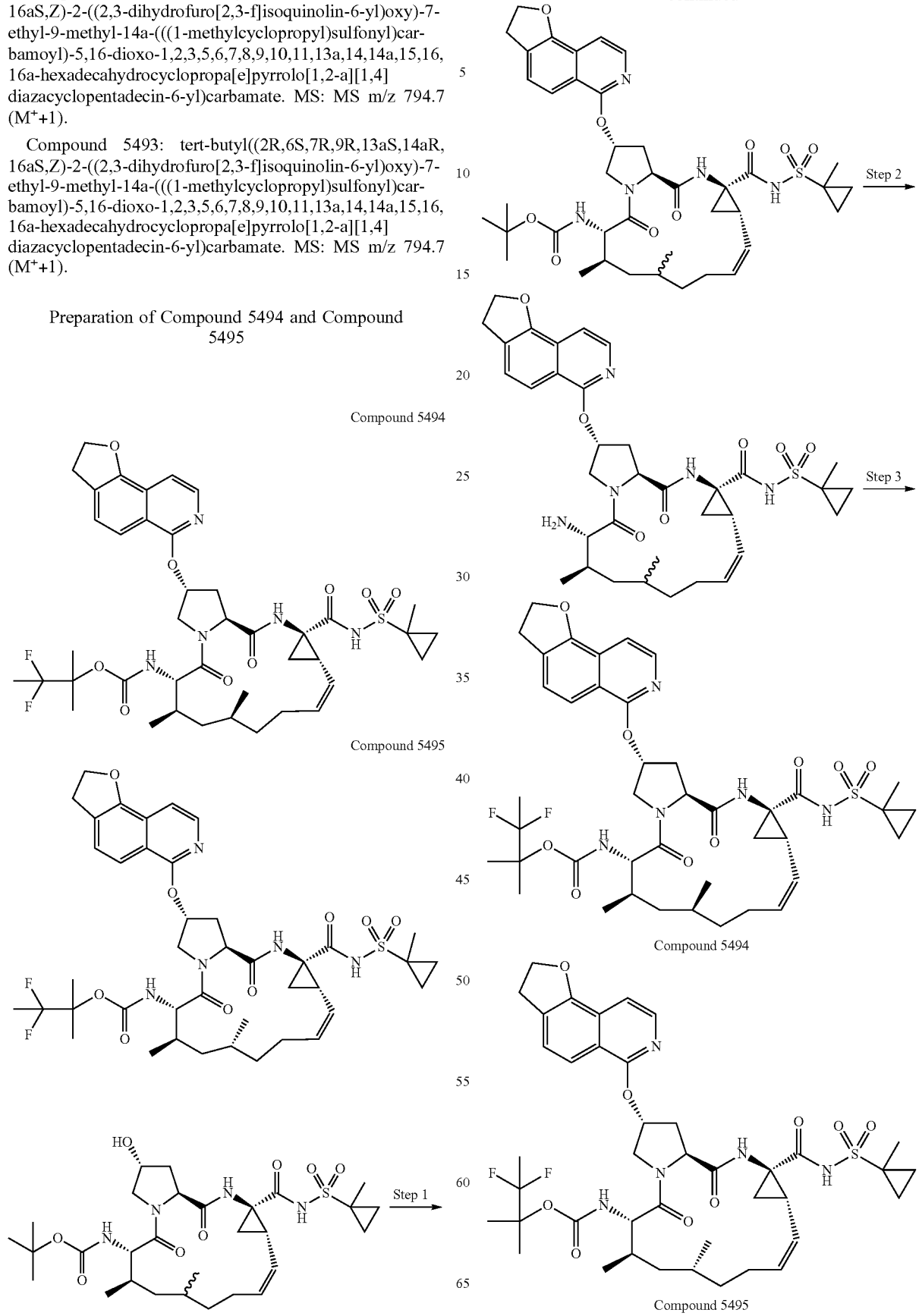

Step 1

To a mixture of tert-butyl((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (0.092 g, 0.15 mmol), 6-chloro-2,3-dihydrofuro[2,3-f]isoquinoline (0.037 g, 0.180 mmol), and tert-BuOK (0.084 g, 0.750 mmol) was added DMSO (5 mL) and the mixture was then sonicated for 15 min. The resulting solution was stirred for 4 h. The reaction was quenched with water, acidified with aq. 6 N HCl, extracted with EtOAc, washed with brine, dried over MgSO$_4$. Concentration gave 150 mg of tert-butyl((2R,6S,7R,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate that was used in the next step without further purification.

Step 2

To a solution of tert-butyl((2R,6S,7R,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (0.078 g, 0.10 mmol) in CH$_2$Cl$_2$ (1 mL) was added TFA (0.077 mL, 1.0 mmol). After stirring for 1 h, concentration gave 79 mg of (2R,6S,7R,13aS,14aR,16aS,Z)-6-amino-2-((2,3-dihydrofuro[2,3-f]isoquinolin-6-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide as the TFA salt.

Step 3

A solution of (2R,6S,7R,13aS,14aR,16aS,Z)-6-amino-2-((2,3-dihydrofuro[2,3-f]isoquinolin-6-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA salt (40 mg, 0.050 mmol), 3,3-difluoro-2-methylbutan-2-yl pyridin-2-yl carbonate (14 mg, 0.060 mmol), and N-ethyl-N-isopropylpropan-2-amine (0.044 mL, 0.250 mmol) in CH$_2$Cl$_2$ (1 mL) was stirred for 16 h. After concentration, the residue was purified by prep HPLC to afford 3.7 mg of Compounds 5494 as a solid and 5.8 mg of Compound 5995 as a solid.

Compound 5494: 3,3-difluoro-2-methylbutan-2-yl((2R,6S,7R,9S,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 830.7 (M$^+$+1).

Compound 5495: 3,3-difluoro-2-methylbutan-2-yl((2R,6S,7R,9R,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 830.7 (M$^+$+1).

Preparation of Compound 5496 and Compound 5497

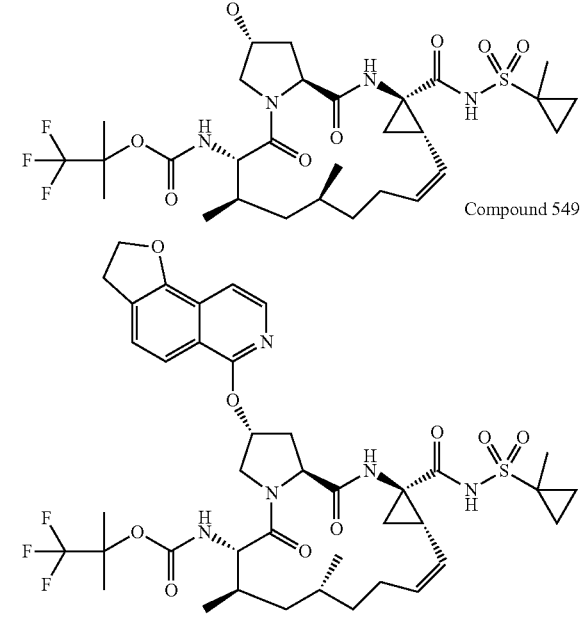

Compound 5496

Compound 5497

Compounds 5496 and 5497 were prepared using the intermediates described herein and by following the general procedure described for the synthesis of Compounds 5494 and 5495:

Compound 5496: 1,1,1-trifluoro-2-methylpropan-2-yl ((2R,6S,7R,9S,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 834.6 (M$^+$+1).

Compound 5497: 1,1,1-trifluoro-2-methylpropan-2-yl ((2R,6S,7R,9R,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 834.6 (M$^+$+1).

Preparation of Compound 5498

Compound 5498

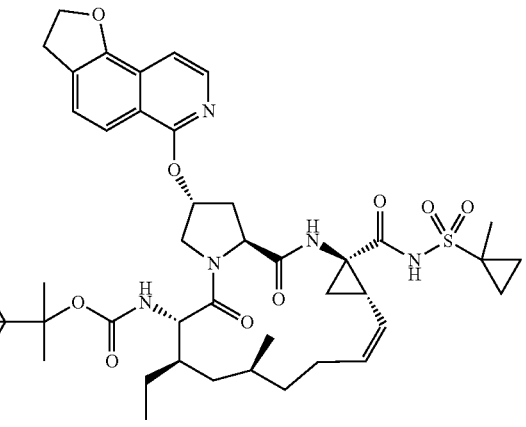

Compound 5498 was prepared using the intermediates described herein and by following the general procedure described for the synthesis of Compound 5494:

Compound 5498: 1,1,1-trifluoro-2-methylpropan-2-yl ((2R,6S,7R,9S,13aS,14aR,16aS,Z)-2-((2,3-dihydrofuro[2,3-f]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 848.7 (M$^+$+1).

Preparation of Compound 5499 and Compound 5500

Compound 5499

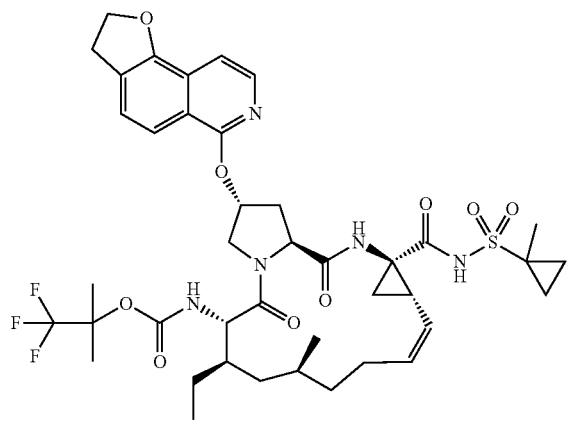

Compound 5500

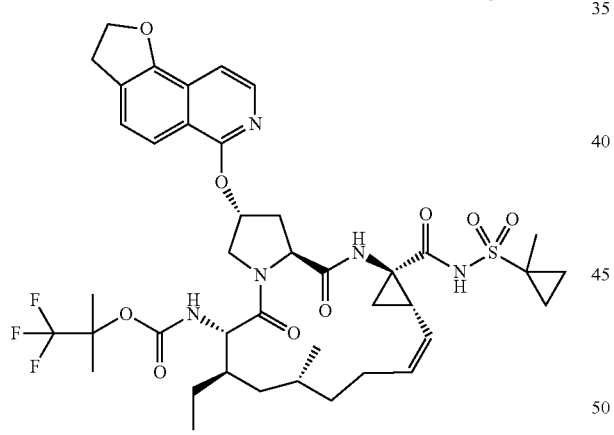

Compounds 5499 and 5500 were prepared using the intermediates described herein and by following the general procedure described for the synthesis of Compounds 5494 and 5495:

Compound 5499: 1,1,1-trifluoro-2-methylpropan-2-yl ((2R,6S,7R,9S,13aS,14aR,16aS,Z)-2-((2,3-dihydrofuro[2,3-f]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 848.7 (M$^+$+1).

Compound 5500: 1,1,1-trifluoro-2-methylpropan-2-yl ((2R,6S,7R,9R,13aS,14aR,16aS,Z)-2-((2,3-dihydrofuro[2,3-f]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 848.7 (M$^+$+1).

Preparation of Compound 6121 and Compound 6122

Compound 6121

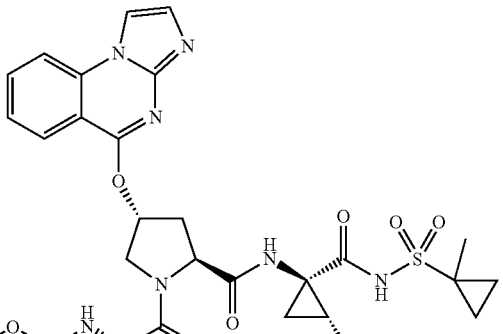

Compound 6122

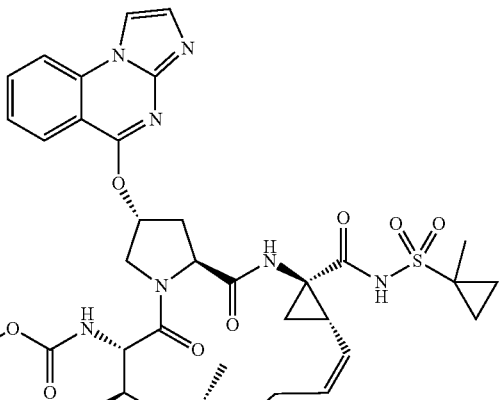

Scheme

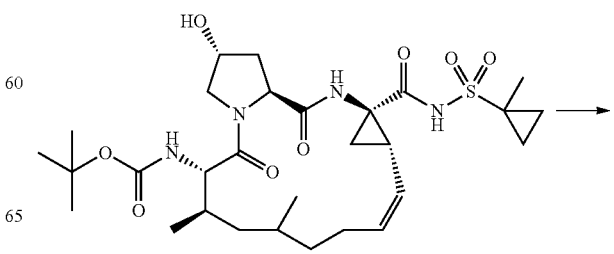

-continued

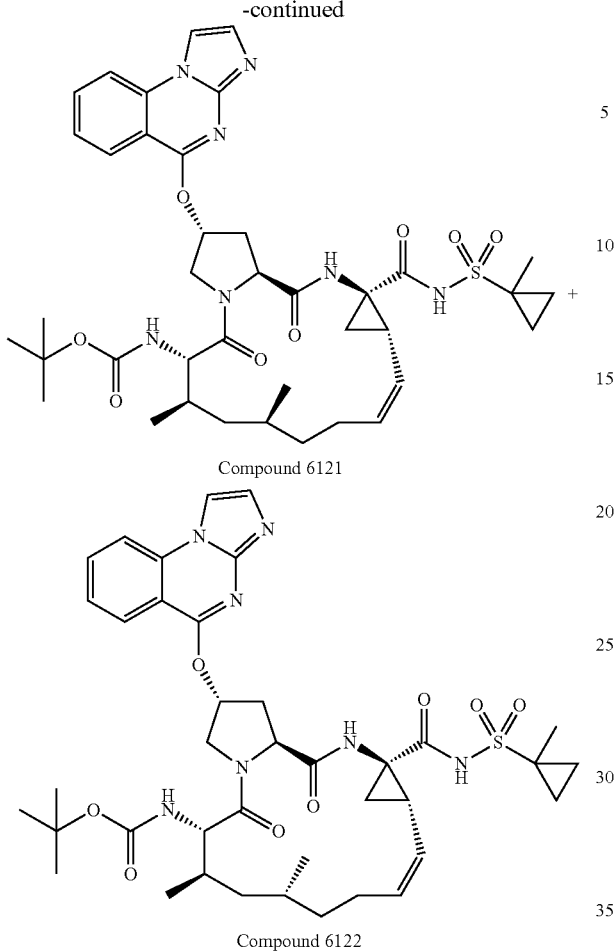

Compound 6121

Compound 6122

To a THF (4 mL) solution of tert-butyl((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (70 mg, 0.12 mmol) was added NaH (23 mg, 0.57 mmol) then DMSO (2 mL). The mixture was stirred for 20 min. The mixture was then cooled with an ice bath and 5-chloroimidazo[1,2-a]quinazoline (28.0 mg, 0.138 mmol) was added in one portion. The reaction was complete after 0.5 h. The reaction was quenched with water, acidified with aq. 6 N HCl to pH=4, and extracted with EtOAc. The organic layer was collected, washed with brine, dried over MgSO$_4$, filtered. After concentration, the residue was purified by prep HPLC to give 1.1 mg of Compound 6121 as a solid and 6.1 mg of Compound 6122 as a solid.

Compound 6121: tert-butyl((2R,6S,7R,9S,13aS,14aR,16aS,Z)-2-(imidazo[1,2-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 778.5 (M$^+$+1).

Compound 6122: tert-butyl((2R,6S,7R,9R,13aS,14aR,16aS,Z)-2-(imidazo[1,2-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 778.5 (M$^+$+1).

Preparation of Compound 6119 and Compound 6120

Compound 6119

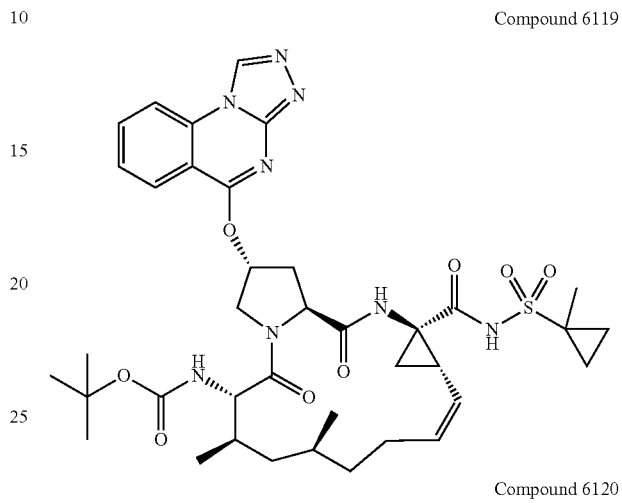

Compound 6120

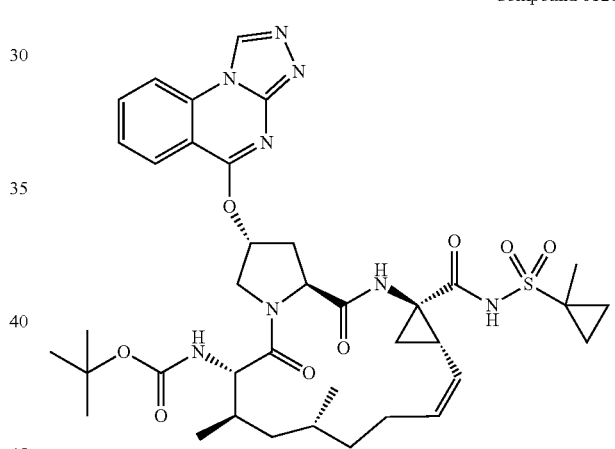

Compounds 6119 and 6120 were prepared using the intermediates described herein and by following the general procedure described for the synthesis of Compound 6121 and Compound 6122:

Compound 6119: tert-butyl((2R,6S,7R,9S,13aS,14aR,16aS,Z)-2-([1,2,4]triazolo[4,3-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 779.8 (M$^+$+1).

Compound 6120: tert-butyl((2R,6S,7R,9R,13aS,14aR,16aS,Z)-2-([1,2,4]triazolo[4,3-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.07 (br. s., 1H), 9.71 (s, 1H), 9.19 (br. s., 1H), 8.38 (d, J=8.2 Hz, 1H), 8.14 (d, J=7.6 Hz, 1H), 8.03 (t, J=7.9 Hz, 1H), 7.62 (t, J=7.8 Hz, 1H), 7.22 (d, J=7.0 Hz, 1H), 5.89 (br. s., 1H), 5.53 (m, 1H), 4.97 (m, 1H), 4.84 (d, J=11.9 Hz, 1H), 4.61-4.49 (m, 1H), 3.99-3.91 (m, 1H), 3.64 (dd, J=10.7, 7.6 Hz, 1H), 2.78-2.62 (m, 2H), 2.45-2.32 (m, 3H), 1.94-1.85 (m, 1H), 1.79 (d, J=6.1 Hz, 1H), 1.69 (m, 1H), 1.63 (m, 1H), 1.54 (m, 1H), 1.42 (s, 3H), 1.36-1.16 (m, 6H), 1.02-0.82 (m, 15H), 0.76 (t, J=11.6 Hz, 1H); MS: MS m/z 779.8 (M⁺+1).

Preparation of Compound 6123

Compound 6123

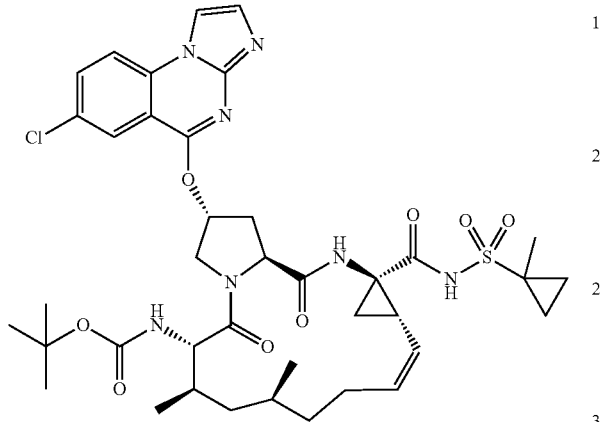

Compounds 6123 was prepared using the intermediates described herein and by following the general procedure described for the synthesis of Compound 6121:

Compound 6123: tert-butyl((2R,6S,7R,9S,13aS,14aR,16aS,Z)-2-((7-chloroimidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 812.8 (M⁺+1).

Preparation of Compound 6126 and Compound 6127

Compound 6126

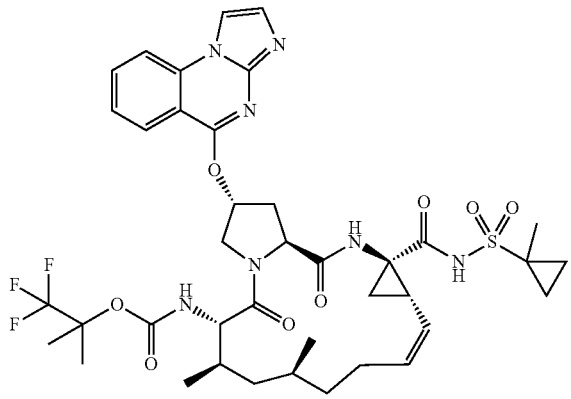

Compound 6127

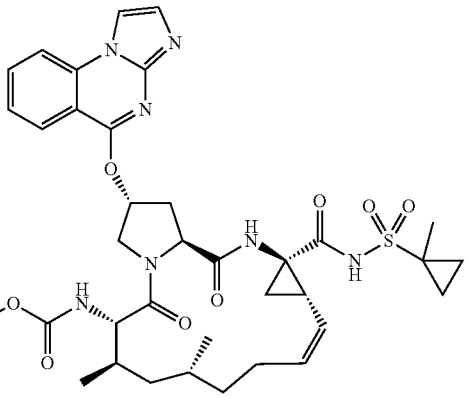

Scheme

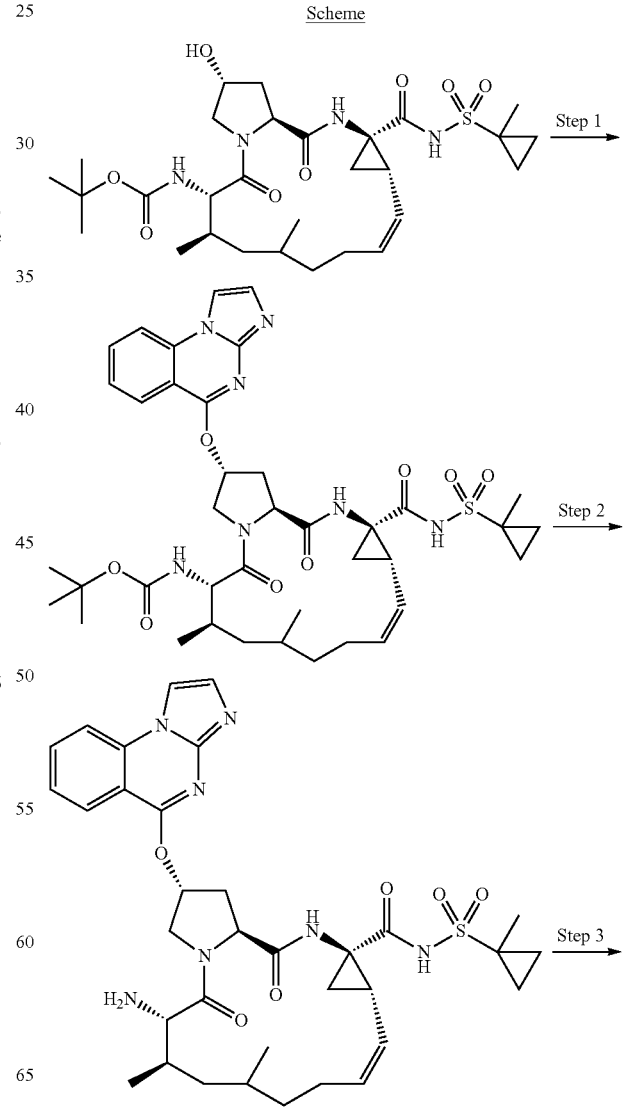

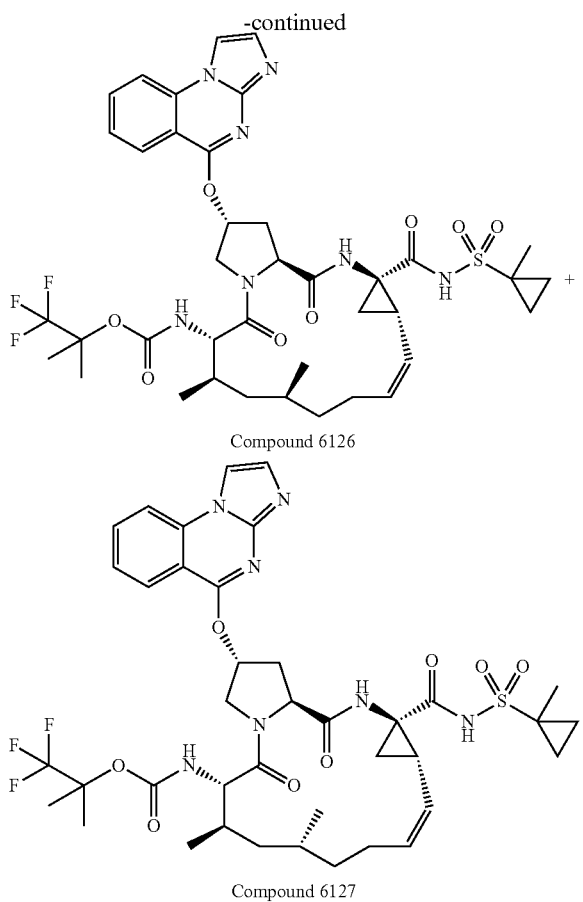

Compound 6126

Compound 6127

Step 1

To a THF (4 mL) solution of tert-butyl((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (70 mg, 0.12 mmol) was added NaH (23 mg, 0.57 mmol) then DMSO (2 mL). The mixture was stirred for 20 min. The mixture was then cooled with an ice bath and 5-chloroimidazo[1,2-a]quinazoline (28.0 mg, 0.138 mmol) was added in one portion. The reaction was complete after 0.5 h. The reaction was quenched with water, acidified with aq. 6 N HCl to pH=4, and extracted with EtOAc. The organic layer was collected, washed with brine, dried over MgSO$_4$, filtered, and concentrated to give the crude product tert-butyl ((2R,6S,7R,13aS,14aR,16aS,Z)-2-(imidazo[1,2-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate that was used in the next step as is. MS: MS m/z 778.5 (M$^+$+1).

Step 2

To a solution of tert-butyl((2R,6S,7R,13aS,14aR,16aS,Z)-2-(imidazo[1,2-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (60 mg, 0.077 mmol) in DCM (2 mL) was added trifluoroacetic acid ("TFA", 2 mL). The reaction was stirred for 1 h at room temperature. The volatiles were removed under vacuum to give (2R,6S,7R,13aS,14aR,16aS,Z)-6-amino-2-(imidazo[1,2-a]quinazolin-5-yloxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA salt (52 mg) which was used in the next step without further purification. MS: MS m/z 678.9 (M$^+$+1).

Step 3

To a solution of (2R,6S,7R,13aS,14aR,16aS,Z)-6-amino-2-(imidazo[1,2-a]quinazolin-5-yloxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA salt (30 mg, 0.044 mmol) and pyridin-2-yl (1,1,1-trifluoro-2-methylpropan-2-yl) carbonate (13.2 mg, 0.053 mmol) in CH$_2$Cl$_2$ (1 mL) was added N-ethyl-N-isopropylpropan-2-amine ("Hunig's Base", 0.039 mL, 0.22 mmol). The reaction was stirred for 16 h. After concentration, the residue was purified by prep HPLC to give 0.9 mg of Compound 6126 as a solid and 12.2 mg of Compound 6127 as a solid.

Compound 6126: 1,1,1-trifluoro-2-methylpropan-2-yl ((2R,6S,7R,9S,13aS,14aR,16aS,Z)-2-(imidazo[1,2-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 832.5 (M$^+$+1).

Compound 6127: 1,1,1-trifluoro-2-methylpropan-2-yl ((2R,6S,7R,9R,13aS,14aR,16aS,Z)-2-(imidazo[1,2-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.06 (br. s., 1H), 9.20 (br. s., 1H), 8.38-8.25 (m, 2H), 8.11 (d, J=7.9 Hz, 1H), 7.98 (t, J=7.5 Hz, 1H), 7.84 (d, J=7.3 Hz, 1H), 7.56 (t, J=7.6 Hz, 1H), 7.45 (d, J=1.5 Hz, 1H), 5.87 (br. s., 1H), 5.54 (m, 1H), 4.98 (m, 1H), 4.71 (d, J=11.0 Hz, 1H), 4.58 (m, 1H), 3.95 (d, J=9.2 Hz, 1H), 3.66 (dd, J=11.0, 7.6 Hz, 1H), 2.70 (m, 2H), 2.65 (m, 1H), 2.44-2.25 (m, 2H), 1.95-1.54 (m, 5H), 1.42 (m, 6H), 1.36 (m, 1H), 1.29 (m, 1H), 1.19 (s, 3H), 0.98-0.84 (m, 10H), 0.79 (m, 1H); MS: MS m/z 832.5 (M$^+$+1).

Preparation of Compound 6124 and Compound 6125

Compound 6124

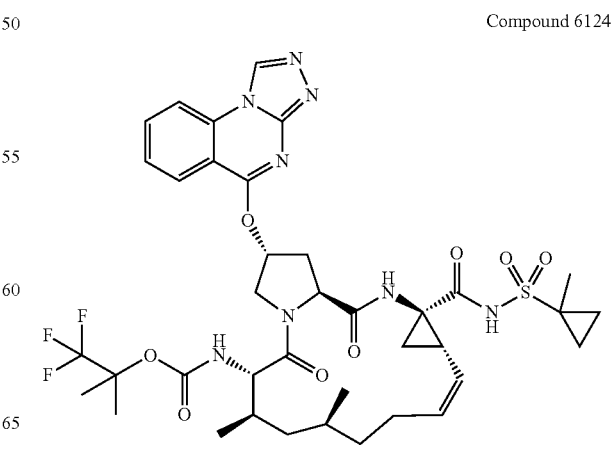

Compound 6125

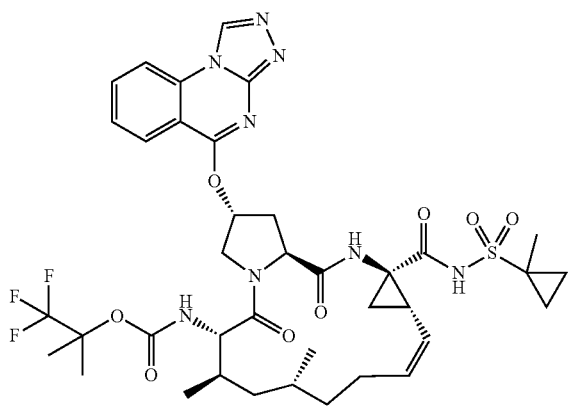

Compounds 6124 and 6125 were prepared using the intermediates described herein and by following the general procedure described for the synthesis of Compound 6126 and Compound 6127:

Compound 6124: 1,1,1-trifluoro-2-methylpropan-2-yl ((2R,6S,7R,9S,13aS,14aR,16aS,Z)-2-([1,2,4]triazolo[4,3-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 833.5 (M$^+$+1).

Compound 6125: 1,1,1-trifluoro-2-methylpropan-2-yl ((2R,6S,7R,9R,13aS,14aR,16aS,Z)-2-([1,2,4]triazolo[4,3-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (500 MHz, METHANOL-d$_4$) δ 9.58 (s, 1H), 8.36-8.25 (m, 2H), 8.10-7.98 (m, 1H), 7.69 (t, J=7.6 Hz, 1H), 6.06-5.94 (m, 1H), 5.58 (td, J=10.3, 5.6 Hz, 1H), 5.19 (t, J=10.1 Hz, 1H), 4.68 (dd, J=10.1, 7.0 Hz, 1H), 4.07 (dd, J=12.1, 3.2 Hz, 1H), 3.77 (d, J=10.7 Hz, 1H), 2.92-2.84 (m, 1H), 2.68-2.49 (m, 2H), 2.40 (d, J=13.7 Hz, 1H), 1.88-1.70 (m, 4H), 1.67 (d, J=9.5 Hz, 1H), 1.57 (dd, J=9.6, 5.3 Hz, 2H), 1.51 (s, 3H), 1.50-1.36 (m, 4H), 1.22 (s, 3H), 1.04-0.91 (m, 9H), 0.88-0.78 (m, 3H); MS: MS m/z 833.5 (M$^+$+1).

Preparation of Compound 6128 and Compound 6129

Compound 6129

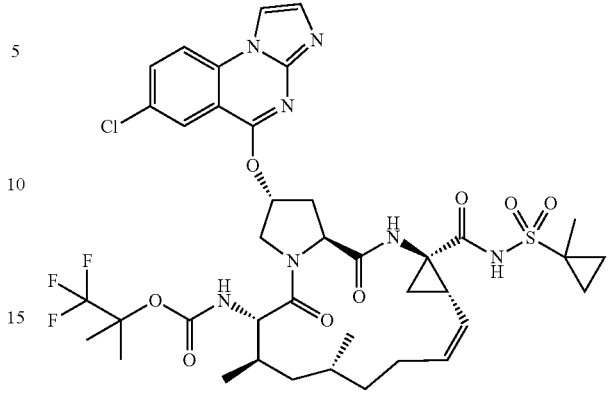

Compounds 6128 and 6129 were prepared using the intermediates described herein and by following the general procedure described for the synthesis of Compound 6126 and Compound 6127:

Compound 6128: 1,1,1-trifluoro-2-methylpropan-2-yl ((2R,6S,7R,9S,13aS,14aR,16aS,Z)-2-((7-chloroimidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 866.5 (M$^+$+1).

Compound 6129: 1,1,1-trifluoro-2-methylpropan-2-yl ((2R,6S,7R,9R,13aS,14aR,16aS,Z)-2-((7-chloroimidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (500 MHz, METHANOL-d$_4$) δ 8.22-8.07 (m, 3H), 7.93 (dd, J=8.9, 2.4 Hz, 1H), 7.46 (d, J=1.5 Hz, 1H), 5.95 (br. s., 1H), 5.59 (td, J=10.3, 5.6 Hz, 1H), 5.04 (t, J=9.9 Hz, 1H), 4.93 (d, J=11.9 Hz, 1H), 4.71 (dd, J=10.4, 7.0 Hz, 1H), 4.04 (dd, J=12.1, 3.2 Hz, 1H), 3.72 (d, J=11.0 Hz, 1H), 2.83 (dd, J=13.9, 6.9 Hz, 1H), 2.69 (q, J=9.2 Hz, 1H), 2.57-2.34 (m, 2H), 2.01-1.89 (m, 2H), 1.87-1.73 (m, 3H), 1.68-1.54 (m, 2H), 1.52 (s, 3H), 1.49-1.36 (m, 3H), 1.29-1.19 (m, 1H), 1.14 (s, 3H), 0.97 (d, J=6.4 Hz, 2H), 1.00 (d, J=6.7 Hz, 3H), 0.94-0.75 (m, 6H); MS: MS m/z 866.5 (M$^+$+1).

Preparation of Compound 6130 and Compound 6131

Compound 6128

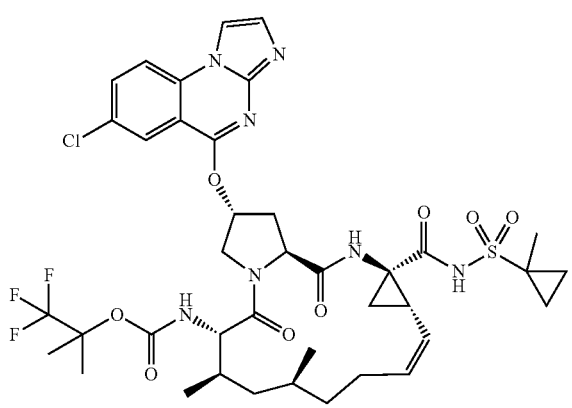

Compound 6130

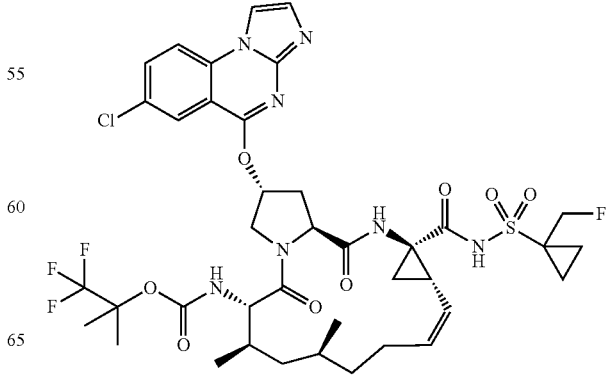

Compound 6131

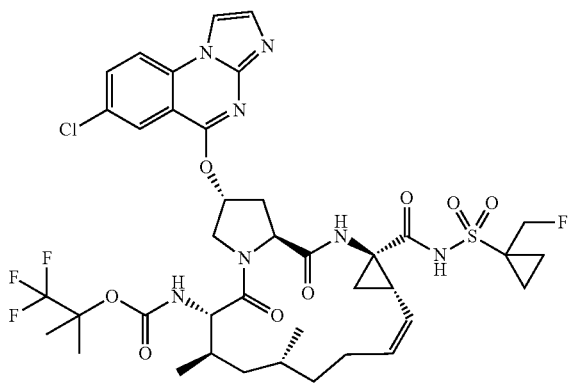

Compounds 6130 and 6131 were prepared using the intermediates described herein and by following the general procedure described for the synthesis of Compound 6126 and Compound 6127:

Compound 6130: 1,1,1-trifluoro-2-methylpropan-2-yl ((2R,6S,7R,9S,13aS,14aR,16aS,Z)-2-((7-chloroimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 884.6 (M$^+$+1).

Compound 6131: 1,1,1-trifluoro-2-methylpropan-2-yl ((2R,6S,7R,9R,13aS,14aR,16aS,Z)-2-((7-chloroimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.30 (br. s., 1H), 9.13 (br. s., 1H), 8.43-8.33 (m, 2H), 8.08 (dd, J=8.9, 2.4 Hz, 1H), 7.99 (d, J=2.4 Hz, 1H), 7.83 (d, J=6.7 Hz, 1H), 7.48 (d, J=1.5 Hz, 1H), 5.86 (br. s., 1H), 5.53 (br. s., 1H), 5.00 (m, 1H), 4.68 (d, J=11.3 Hz, 1H), 4.65-4.55 (m, 1H), 4.02-3.85 (m, 1H), 3.61 (dd, J=10.8, 7.5 Hz, 1H), 2.73 (d, J=17.4 Hz, 1H), 2.65 (m, 2H), 2.47-2.35 (m, 1H), 2.31 (d, J=11.9 Hz, 1H), 1.90-1.75 (m, 2H), 1.70 (m, 2H), 1.65-1.47 (m, 4H), 1.38 (d, J=15.3 Hz, 2H), 1.26 (d, J=12.8 Hz, 2H), 1.20-1.03 (m, 4H), 0.98-0.91 (m, 6H), 0.88 (d, J=6.1 Hz, 3H), 0.77 (t, J=12.1 Hz, 1H); MS: MS m/z 884.6 (M$^+$+1).

Preparation of Compound 6132 and Compound 6133

Compound 6132

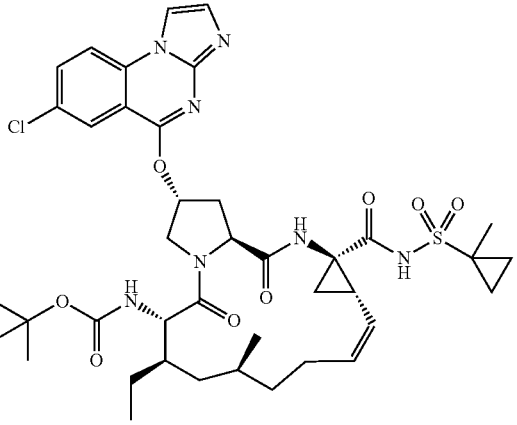

Compound 6133

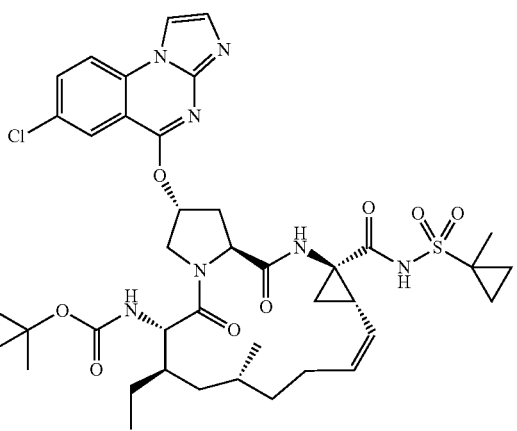

Compounds 6132 and 6133 were prepared using the intermediates described herein and by following the general procedure described for the synthesis of Compound 6126 and Compound 6127:

Compound 6132: 1,1,1-trifluoro-2-methylpropan-2-yl ((2R,6S,7R,9S,13aS,14aR,16aS,Z)-2-((7-chloroimidazo[1,2-a]quinazolin-5-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 880.7 (M$^+$+1).

Compound 6133: 1,1,1-trifluoro-2-methylpropan-2-yl ((2R,6S,7R,9R,13aS,14aR,16aS,Z)-2-((7-chloroimidazo[1,2-a]quinazolin-5-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.05 (br. s., 1H), 9.19 (br. s., 1H), 8.48-8.30 (m, 2H), 8.08 (dd, J=8.9, 2.4 Hz, 1H), 7.98 (d, J=2.1 Hz, 1H), 7.88 (d, J=7.9 Hz, 1H), 7.48 (d, J=1.5 Hz, 1H), 5.90 (br. s., 1H), 5.53 (br. s., 1H), 4.99 (br. s., 1H), 4.70-4.54 (m, 2H), 3.99 (d, J=8.9 Hz, 1H), 3.80 (dd, J=11.1, 8.1 Hz, 1H), 2.77-2.64 (m, 2H), 2.45-2.25 (m, 2H), 2.00-1.84 (m, 2H), 1.68-1.58 (m, 1H), 1.56 (br. s., 1H), 1.52-1.34

(m, 9H), 1.33-1.28 (m, 1H), 1.15 (s, 3H), 1.03 (t, J=12.2 Hz, 1H), 0.97-0.89 (m, 9H), 0.71 (t, J=7.5 Hz, 3H); MS: MS m/z 880.7 (M$^+$+1).

Preparation of Compound 6134 and Compound 6135

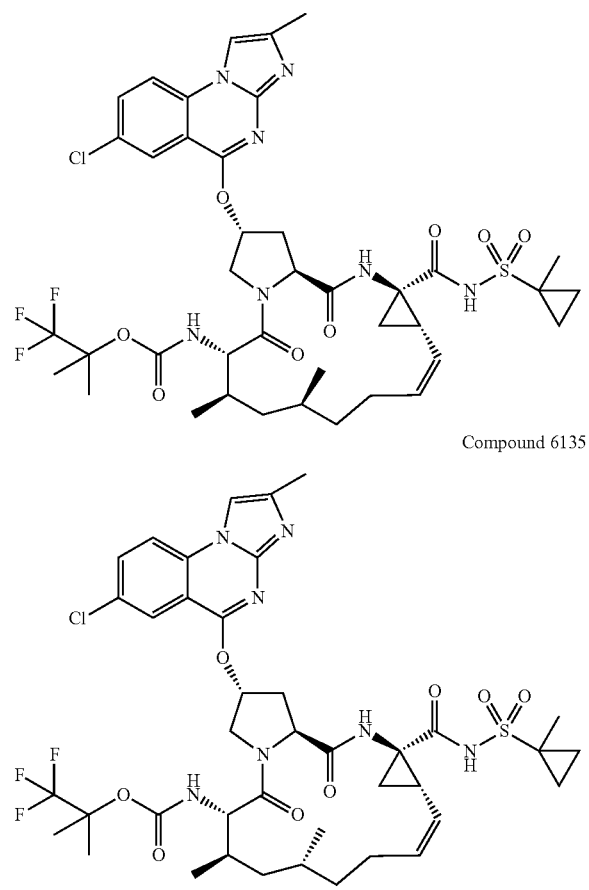

Compounds 6134 and 6135 were prepared using the intermediates described herein and by following the general procedure described for the synthesis of Compound 6126 and Compound 6127:

Compound 6134: 1,1,1-trifluoro-2-methylpropan-2-yl ((2R,6S,7R,9S,13aS,14aR,16aS,Z)-2-((7-chloro-2-methyl-imidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 880.6 (M$^+$+1).

Compound 6135: 1,1,1-trifluoro-2-methylpropan-2-yl ((2R,6S,7R,9R,13aS,14aR,16aS,Z)-2-((7-chloro-2-methyl-imidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 880.6 (M$^+$+1).

Preparation of Compound 6136 and Compound 6137

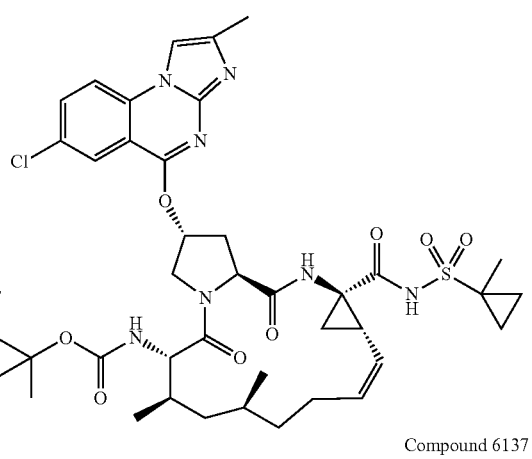

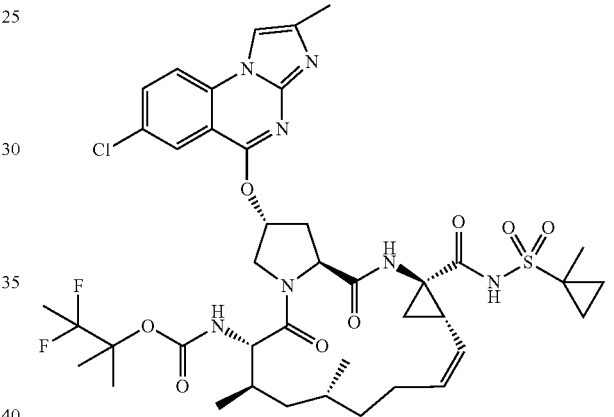

Compounds 6136 and 6137 were prepared using the intermediates described herein and by following the general procedure described for the synthesis of Compound 6126 and Compound 6127:

Compound 6136: 3,3-difluoro-2-methylbutan-2-yl((2R, 6S,7R,9S,13aS,14aR,16aS,Z)-2-((7-chloro-2-methylimi-dazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 876.6 (M$^+$+1).

Compound 6137: 3,3-difluoro-2-methylbutan-2-yl((2R, 6S,7R,9R,13aS,14aR,16aS,Z)-2-((7-chloro-2-methylimi-dazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.05 (br. s., 1H), 9.19 (br. s., 1H), 8.22 (d, J=8.9 Hz, 1H), 8.07-7.86 (m, 3H), 7.55 (d, J=7.6 Hz, 1H), 5.81 (br. s., 1H), 5.59-5.38 (m, 1H), 4.99 (br. s., 1H), 4.69 (d, J=12.2 Hz, 1H), 4.60 (dd, J=10.4, 6.7 Hz, 1H), 3.92 (m, 1H), 3.56 (dd, J=10.4, 7.9 Hz, 3H), 2.74-2.58 (m, 2H), 2.37 (t, J=10.1 Hz, 1H), 2.30 (s, 3H), 1.94-1.82 (m, 1H), 1.76 (m, 1H), 1.73-1.58 (m, 2H), 1.50 (t, J=19.5 Hz, 4H), 1.41 (m, 4H), 1.33-1.25 (m, 1H), 0.98-0.89 (m, 8H), 0.87 (m, 5H), 0.72 (m, 4H); MS: MS m/z 876.6 (M⁺+1).

Preparation of Compound 6138 and Compound 6139

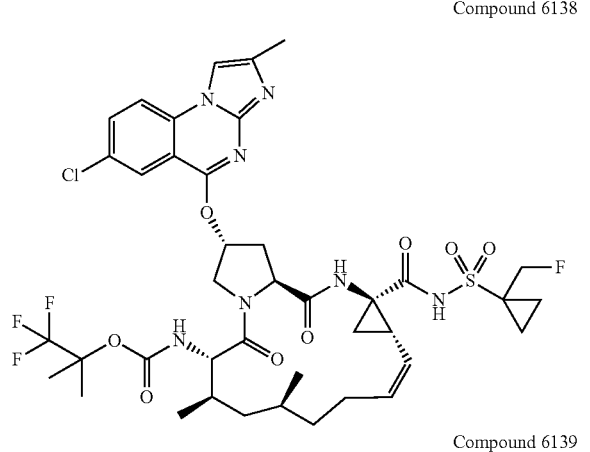

Compound 6138

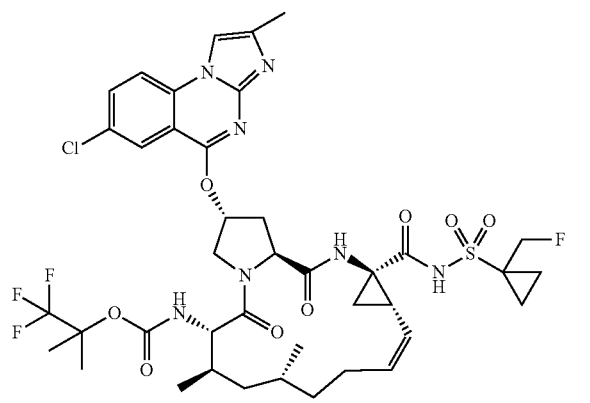

Compound 6139

Compounds 6138 and 6139 were prepared using the intermediates described herein and by following the general procedure described for the synthesis of Compound 6126 and Compound 6127:

Compound 6138: 1,1,1-trifluoro-2-methylpropan-2-yl ((2R,6S,7R,9S,13aS,14aR,16aS,Z)-2-((7-chloro-2-methylimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 898.6 (M⁺+1).

Compound 6139: 1,1,1-trifluoro-2-methylpropan-2-yl ((2R,6S,7R,9R,13aS,14aR,16aS,Z)-2-((7-chloro-2-methylimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ 11.05 (br. s., 1H), 9.19 (br. s., 1H), 8.23 (d, J=8.9 Hz, 1H), 8.10-7.97 (m, 2H), 7.95 (d, J=2.1 Hz, 1H), 7.78 (d, J=6.7 Hz, 1H), 5.81 (br. s., 1H), 5.48 (m, 1H), 5.03 (m, 1H), 4.68-4.46 (m, 3H), 3.95-3.86 (m, 1H), 3.64-3.54 (m, 1H), 2.65 (m, 1H), 2.39 (t, J=9.8 Hz, 1H), 2.31 (m, 4H), 1.86 (m, 1H), 1.82-1.73 (m, 1H), 1.70 (m, 1H), 1.54 (m, 2H), 1.48 (m, 2H), 1.35 (d, J=17.1 Hz, 3H), 1.23 (m, 1H), 1.17 (m, 2H), 1.09 (s, 3H), 0.96-0.81 (m, 10H), 0.77-0.68 (m, 1H); MS: MS m/z 898.6 (M⁺+1).

Preparation of Compound 6140 and Compound 6141

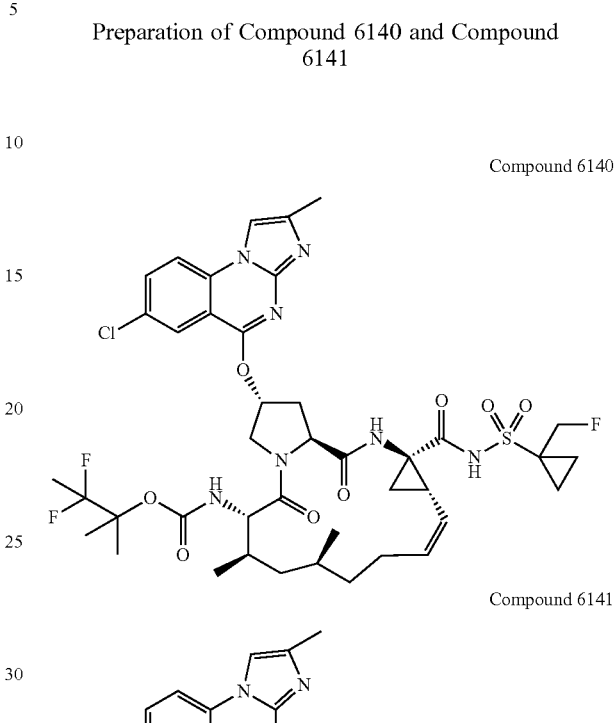

Compound 6140

Compound 6141

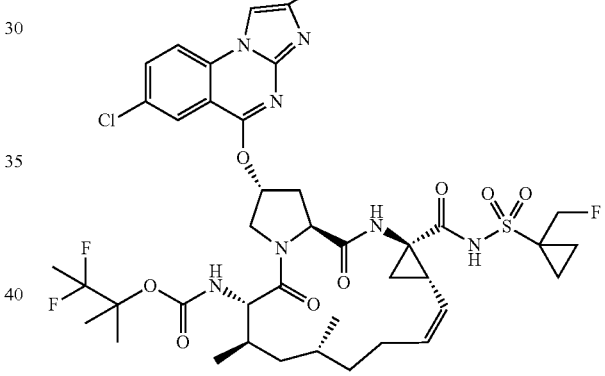

Compounds 6140 and 6141 were prepared using the intermediates described herein and by following the general procedure described for the synthesis of Compound 6126 and Compound 6127:

Compound 6140: 3,3-difluoro-2-methylbutan-2-yl((2R,6S,7R,9S,13aS,14aR,16aS,Z)-2-((7-chloro-2-methylimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 894.8 (M⁺+1).

Compound 6141: 3,3-difluoro-2-methylbutan-2-yl((2R,6S,7R,9R,13aS,14aR,16aS,Z)-2-((7-chloro-2-methylimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, METHANOL-d₄) δ 8.10-8.00 (m, 2H), 7.89 (dd, J=8.9, 2.4 Hz, 1H), 7.81 (s, 1H), 5.98-5.87 (m, 1H), 5.56 (td, J=10.2, 5.5 Hz, 1H), 5.09 (t, J=9.4 Hz, 1H), 4.77 (d, J=11.3 Hz, 1H), 4.72-4.60 (m, 2H), 4.53 (d, J=11.3 Hz, 1H), 4.02 (dd, J=11.9, 3.1 Hz, 1H), 3.71 (d, J=10.8 Hz, 1H), 2.81 (dd, J=14.1, 6.8 Hz, 1H), 2.64 (q, J=9.1 Hz, 1H), 2.51 (ddd, J=14.1, 10.3, 4.0 Hz, 1H), 2.42-2.33 (m, 4H), 1.98-1.85 (m, 1H), 1.85-1.75 (m, 2H), 1.73-1.52 (m, 5H), 1.51-1.39 (m, 4H), 1.31-1.10 (m, 4H), 1.07-0.94 (m, 9H), 0.81 (s, 3H); MS: MS m/z 894.8 (M$^+$+1).

Preparation of 3,3-difluoro-2-methylbutan-2-yl pyridin-2-yl carbonate

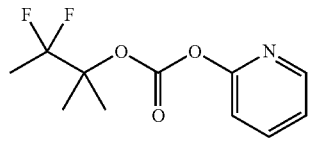 [SMILES: CC(F)(F)C(C)(C)OC(=O)Oc1ccccn1]

Scheme:

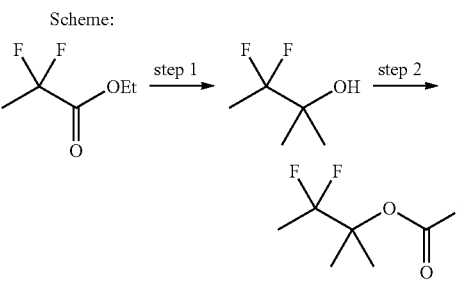

Step 1

Methylmagnesium bromide (24.9 mL, 74.7 mmol) was added dropwise via syringe to a solution of ethyl 2,2-difluoropropanoate (3.44 g, 24.91 mmol) in diethyl ether (50 mL) at −20° C. and stirred at this temp for 1 h before warming up to room temperature. The reaction was quenched with sat. ammonium chloride and extracted with ether. The organic layer was washed with brine; dried over MgSO$_4$; filtered and concentrated in vacuo to afford the crude 3,3-difluoro-2-methylbutan-2-ol (1.84 g, 59.5% yield) as an oil. $^1$H NMR (500 MHz, CDCl$_3$) δ 1.68-1.58 (m, 3H), 1.31 (t, J=1.2 Hz, 6H).

Preparation of tert-butyl 3-chloro-2-(trifluoromethyl)quinoxaline-6-carboxylate

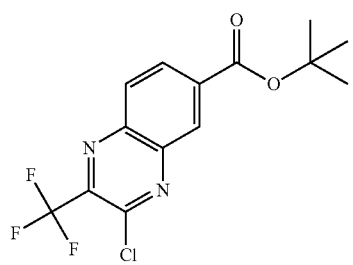 [SMILES: CC(C)(C)OC(=O)c1ccc2nc(C(F)(F)F)c(Cl)nc2c1]

Scheme:

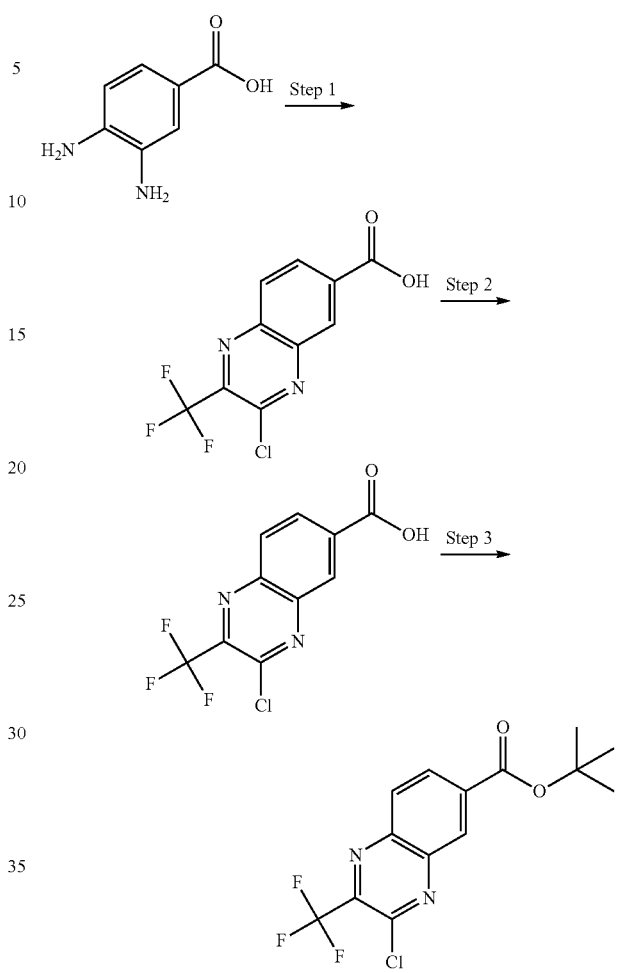

Step 1

To a 30 mL vial equipped with a stir bar was added 3,4-diaminobenzoic acid (3.00 g, 19.7 mmol) and ethanol (30 mL). To the homogenous, dark purple solution was added ethyl 3,3,3-trifluoro-2-oxopropanoate (4.02 g, 23.7 mmol). The vial was placed in a 75° C. heating block with stirring for 16 h. The mixture was cooled to room temperature and then filtered to isolate the solids. Residual solvent was removed in vacuo to afford a light-purple solid, 3-hydroxy-2-(trifluoromethyl)quinoxaline-6-carboxylic acid, 2.57 g (51%). This material was used directly in the next step.

Step 2

To a 15 mL vial equipped with a stir bar was added 3-hydroxy-2-(trifluoromethyl)quinoxaline-6-carboxylic acid (2.57 g, 9.97 mmol), then POCl$_3$ (6 ml, 64.4 mmol), then DMF (0.154 ml, 1.99 mmol). The vial was sealed and then placed in a 90° C. heating block with stirring for 5 h. The crude reaction solution was added to a 1 L separatory funnel charged with approximately 500 mL ice. The mixture was shaken and then allowed to stand until the mixture had warmed to room temperature. The mixture was extracted with EtOAc (2×150 mL). The combined organics were dried over MgSO$_4$; filtered; then concentrated in vacuo to afford 3-chloro-2-(trifluoromethyl)quinoxaline-6-carboxylic acid as a purple solid, 2.991 g. This material was used directly in the next step.

Step 3

A dry 100 mL r.b. flask equipped with a stir bar was fitted with a Schlenk gas adapter and the top of the Schlenk adapter was sealed with a rubber septum vented to an oil bubbler. The system was placed under a constant slow stream of N$_2$ gas. To the flask was added 3-chloro-2-(trifluoromethyl)quinoxaline-6-carboxylic acid (2.991 g, 10.81 mmol) in DMF (5 mL). To the flask was slowly added 1,1-di-tert-butoxy-N,N-dimethylmethanamine (20 mL, 83 mmol) upon which a white smoke was immediately evolved and an exotherm leading to mild reflux was noted. The addition rate was controlled to maintain a mild reflux. The flask was placed in a 100° C. oil bath with stirring for 30 minutes. The reaction solution was concentrated in vacuo onto Celite and the resulting powder was subjected to SiO$_2$ chromatography to afford tert-butyl 3-chloro-2-(trifluoromethyl)quinoxaline-6-carboxylate as a white solid, 1.2811 g (36% over three steps). $^1$H-NMR (500 MHz, CDCl$_3$) δ 8.74 (d, J=1.6 Hz, 1H), 8.45 (dd, J=8.7, 1.8 Hz, 1H), 8.27 (d, J=8.8 Hz, 1H), 1.67 (s, 9H).

Preparation of 3-chloro-N-(prop-2-yn-1-yl)-2-(trifluoromethyl)quinoxaline-6-carboxamide

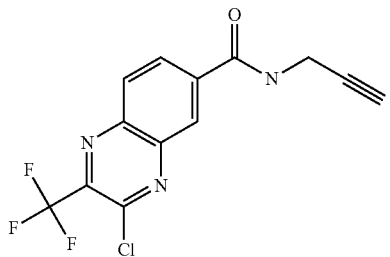 [SMILES: C#CCNC(=O)c1ccc2nc(C(F)(F)F)c(Cl)nc2c1]

To a 40 mL vial equipped with a stir bar was added 3-chloro-2-(trifluoromethyl)quinoxaline-6-carboxylic acid (0.500 g, 1.81 mmol) and prop-2-yn-1-amine (0.100 g, 1.81 mmol), then CH$_2$Cl$_2$ (10 mL), then diisopropylethylamine (0.95 mL, 5.4 mmol). To the stirred solution was added HATU (0.756 g, 1.99 mmol). The solution was stirred at room temperature for 30 minutes. The reaction mixture was transferred to a 500 mL separatory funnel and was diluted with EtOAc (200 mL). The solution was washed with aq. 2M HCl (2×50 mL); then brine. The organic phase was dried over MgSO$_4$; filtered; then concentrated in vacuo to afford a brown solid. This material was purified by silica gel chromatography to afford 3-chloro-N-(prop-2-yn-1-yl)-2-(trifluoromethyl)quinoxaline-6-carboxamide as a yellow solid, 0.35 g (62%). $^1$H-NMR (400 MHz, CD$_3$OD) δ 8.55 (d, J=1.5 Hz, 1H), 8.40-8.32 (m, 2H), 4.24 (d, J=2.5 Hz, 2H), 2.67 (t, J=2.5 Hz, 1H).

Preparation of (2R,6S,7R,9R,13aS,14aR,16aS,Z)-6-amino-2-hydroxy-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA salt and (2R,6S,7R,9R,13aS,14aR,16aS,Z)-6-amino-7-ethyl-2-hydroxy-9-methyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA salt (2R,6S,7R,9R,13aS,14aR,16aS,Z)-6-amino-2-hydroxy-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA salt was prepared by treating tert-butyl ((2R,6S,7R,9R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate with a 1:1 solution of CH$_2$Cl$_2$:trifluoroacetic acid for 1 h. The volatiles were then removed in vacuo to afford the product in quantitative yield.

Likewise, (2R,6S,7R,9R,13aS,14aR,16aS,Z)-6-amino-7-ethyl-2-hydroxy-9-methyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA salt was prepared from tert-butyl((2R,6S,7R,9R,13aS,14aR,16aS,Z)-7-ethyl-2-hydroxy-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate following the same procedure.

Preparation of 2-(3-chloro-2-(trifluoromethyl)quinoxalin-6-yl)-5-methyloxazole

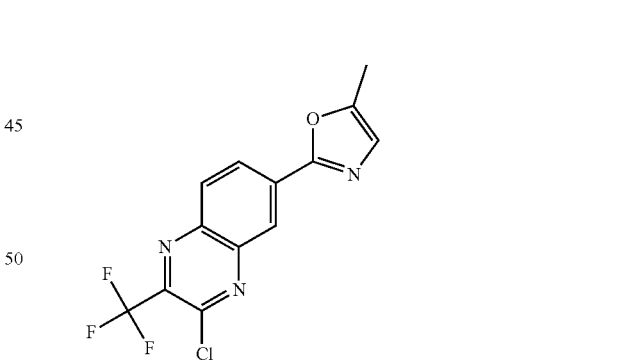

To a 7 mL vial equipped with a stir bar was added 3-chloro-N-(prop-2-yn-1-yl)-2-(trifluoromethyl)quinoxaline-6-carboxamide (100 mg, 0.319 mmol) and dioxane (1 mL). To the solution was added triflic acid (0.028 mL, 0.319 mmol). The vial was capped and placed in a 90° C. heat block with stirring for 16 h. The solution was concentrated onto diatomaceous earth (Celite®) in vacuo and the resulting powder was subjected to SiO$_2$ chromatography (30 g SiO$_2$, hexanes:EtOAc 100:0→70:30 over 12 CV, only one peak elutes, detected at 245 nm) to afford 2-(3-chloro-2-(trifluoromethyl)quinoxalin-6-yl)-5-methyloxazole as a pale yellow solid, 53 mg (53%). $^1$H NMR (500 MHz, CDCl$_3$) δ

8.66 (d, J=1.7 Hz, 1H), 8.55 (dd, J=8.8, 1.9 Hz, 1H), 8.27 (d, J=8.8 Hz, 1H), 7.01 (q, J=1.1 Hz, 1H), 2.49 (d, J=1.3 Hz, 3H).

Preparation of Compound 7001

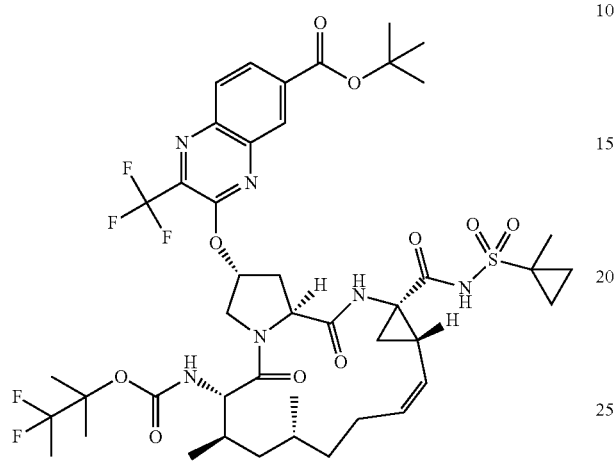

Compound 7001

To a 2 mL vial equipped with a stir bar was added tert-butyl 3-chloro-2-(trifluoromethyl)quinoxaline-6-carboxylate (7.2 mg, 0.022 mmol) and (2R,6S,7R,9R,13aS,14aR,16aS,Z)-6-amino-2-hydroxy-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA salt (18 mg, 0.022 mmol), then THF (0.2 mL). To the solution was added potassium tert-butoxide in THF (0.11 mL, 0.11 mmol). The solution was stirred at 23° C. for 15 minutes. To the vial was added acetic acid (6.2 µl, 0.11 mmol) and diisopropylethylamine (0.057 mL, 0.32 mmol) as a solution in THF (0.100 mL). To the vial was then added 3,3-difluoro-2-methylbutan-2-yl pyridin-2-yl carbonate (16 mg, 0.065 mmol) as a solution in THF (0.100 mL). The reaction solution was stirred at room temperature for 10 min. The volatiles were evaporated under a stream of nitrogen and the resulting residue was then dissolved in MeOH. The resulting solution was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 70-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-85% B over 40 minutes, then a 5-minute hold at 100% B; Flow: 20 mL/min. Fractions containing the desired product were combined and dried via centrifugal evaporation to afford the title compound, 6.6 mg (32%).

Compound 7001: tert-butyl 3-(((2R,6S,7R,9R,13aS,14aR,16aS,Z)-6-((((3,3-difluoro-2-methylbutan-2-yl)oxy)carbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl)oxy)-2-(trifluoromethyl)quinoxaline-6-carboxylate.

$^1$H NMR (400 MHz, CD$_3$OD) δ 8.55 (d, J=1.7 Hz, 1H), 8.28-8.22 (m, 1H), 8.21-8.15 (m, 1H), 7.09 (d, J=8.1 Hz, 1H), 6.00 (br. s., 1H), 5.61 (td, J=10.3, 5.6 Hz, 1H), 5.03 (t, J=10.0 Hz, 1H), 4.93-4.90 (m, 1H), 4.66 (dd, J=10.3, 6.8 Hz, 1H), 4.08 (dd, J=12.1, 3.1 Hz, 1H), 3.76-3.68 (m, 1H), 2.77 (dd, J=14.1, 7.0 Hz, 1H), 2.72-2.65 (m, 1H), 2.52 (ddd, J=13.9, 10.3, 3.9 Hz, 1H), 2.48-2.36 (m, 1H), 2.01-1.89 (m, 1H), 1.89-1.73 (m, 3H), 1.69 (s, 9H), 1.68-1.55 (m, 3H), 1.52 (s, 6H), 1.50-1.35 (m, 4H), 1.31-1.17 (m, 1H), 1.07 (s, 3H), 1.03 (s, 3H), 1.01 (d, J=6.8 Hz, 3H), 0.95 (d, J=6.6 Hz, 3H), 0.91-0.87 (m, 2H), 0.87-0.78 (m, 1H). MS: MS m/z 955.7 (M$^-$−1).

Preparation of Compound 7002

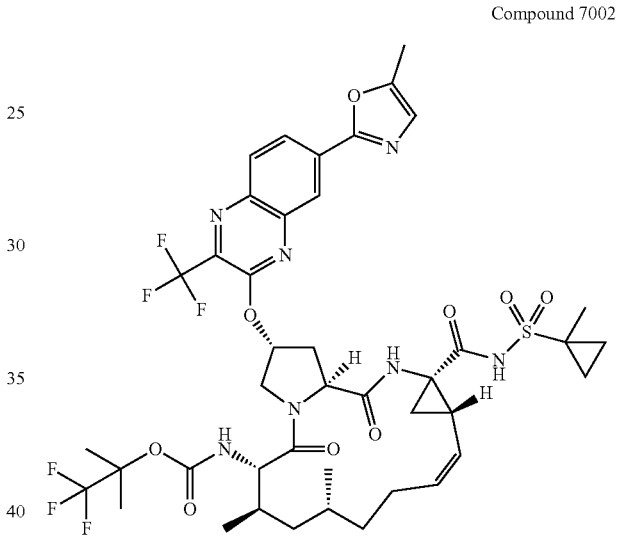

Compound 7002

To a 2 mL vial equipped with a stir bar was added 2-(3-chloro-2-(trifluoromethyl)quinoxalin-6-yl)-5-methyloxazole (8.32 mg, 0.027 mmol) and (2R,6S,7R,9R,13aS,14aR,16aS,Z)-6-amino-2-hydroxy-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA salt (15 mg, 0.022 mmol), then THF (0.2 mL). To the solution was added potassium tert-butoxide in THF (0.11 mL, 0.11 mmol). The solution was stirred at 23° C. for 10 minutes. To the vial was added acetic acid (6.32 µl, 0.110 mmol) and diisopropylethylamine (0.058 mL, 0.33 mmol) as a solution in THF (0.10 mL). To the vial was then added pyridin-2-yl (1,1,1-trifluoro-2-methylpropan-2-yl) carbonate (16.5 mg, 0.066 mmol) as a solution in THF (0.100 mL). The reaction solution was stirred at room for 10 minutes. The reaction mixture was concentrated under a stream of N$_2$ and the resulting residue was dissolved in MeOH, and then was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 50-100% B over 25 minutes, then a 5-minute hold at 100% B; Flow: 20 mL/min. Fractions containing the desired product were combined and dried via centrifugal evaporation to afford the title compound, 8.2 mg (38%).

Compound 7002: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-2-((7-(5-methyloxazol-2-yl)-3-(trifluoromethyl)quinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD) δ 8.45 (d, J=1.8 Hz, 1H), 8.27 (dd, J=8.7, 1.9 Hz, 1H), 8.15 (d, J=8.8 Hz, 1H), 7.03 (d, J=1.0 Hz, 1H), 5.95 (br. s., 1H), 5.57 (td, J=10.2, 5.6 Hz, 1H), 5.00 (t, J=9.8 Hz, 1H), 4.83 (s, 1H), 4.61 (dd, J=10.4, 6.9 Hz, 1H), 4.04 (dd, J=12.2, 3.1 Hz, 1H), 3.68 (d, J=10.8 Hz, 1H), 2.73 (dd, J=13.9, 6.7 Hz, 1H), 2.68-2.60 (m, 1H), 2.54-2.30 (m, 5H), 1.97-1.69 (m, 5H), 1.67-1.50 (m, 3H), 1.48 (s, 3H), 1.47-1.30 (m, 4H), 1.25-1.19 (m, 1H), 1.18 (s, 3H), 1.11 (s, 3H), 0.96 (d, J=6.8 Hz, 3H), 0.90 (d, J=6.5 Hz, 3H), 0.87-0.83 (m, 2H), 0.83-0.73 (m, 1H). MS: MS m/z 942.8 (M$^+$+1).

Preparation of Compound 7003

Compound 7003

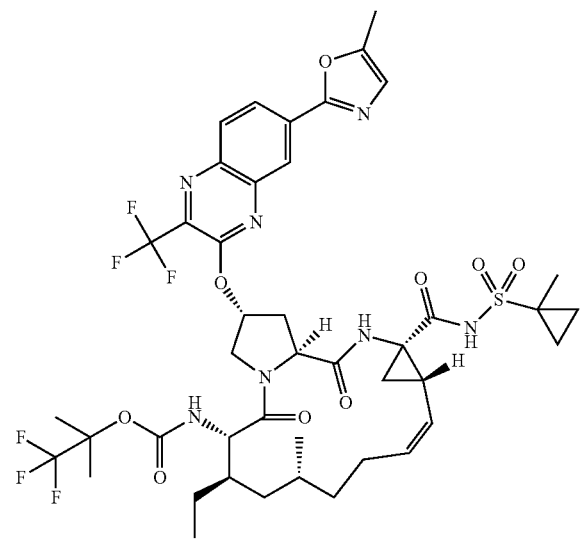

To a 2 mL vial equipped with a stir bar was added 2-(3-chloro-2-(trifluoromethyl)quinoxalin-6-yl)-5-methyloxazole (7.5 mg, 0.024 mmol) and (2R,6S,7R,9R,13aS,14aR,16aS,Z)-6-amino-7-ethyl-2-hydroxy-9-methyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA salt (15 mg, 0.022 mmol), then THF (0.2 mL). To the solution was added potassium tert-butoxide in THF (0.11 mL, 0.11 mmol). The solution was stirred at 23° C. for 10 minutes. To the vial was added acetic acid (6.22 μl, 0.109 mmol) and diisopropylethylamine (0.057 mL, 0.33 mmol) as a solution in THF (0.100 mL). To the vial was then added pyridin-2-yl (1,1,1-trifluoro-2-methylpropan-2-yl) carbonate (16.25 mg, 0.065 mmol) as a solution in THF (0.100 mL). The reaction solution was stirred at room for 10 minutes, then was concentrated under a N$_2$ stream and the resulting residue was dissolved in MeOH and was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 60-100% B over 20 minutes, then a 5-minute hold at 100% B; Flow: 20 mL/min. Fractions containing the desired product were combined and dried via centrifugal evaporation to afford the title compound, 1.3 mg (6%).

Compound 7003: 1,1,1-trifluoro-2-methylpropan-2-yl ((2R,6S,7R,9R,13aS,14aR,16aS,Z)-7-ethyl-9-methyl-14a-(((1-methylcyclopropyl)sulfonyl)carbamoyl)-2-(7-(5-methyloxazol-2-yl)-3-(trifluoromethyl)quinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD) δ 8.52 (d, J=1.8 Hz, 1H), 8.31 (dd, J=8.8, 1.8 Hz, 1H), 8.18 (d, J=8.8 Hz, 1H), 7.04 (d, J=1.0 Hz, 1H), 6.01 (br. s., 1H), 5.62-5.51 (m, 1H), 5.06 (br. s., 1H), 4.85-4.80 (m, 1H), 4.65-4.58 (m, 2H), 4.05 (dd, J=12.0, 3.0 Hz, 1H), 3.92 (d, J=11.3 Hz, 1H), 2.73 (dd, J=14.1, 7.0 Hz, 1H), 2.63 (d, J=6.5 Hz, 1H), 2.54-2.49 (m, 1H), 2.48 (d, J=1.3 Hz, 3H), 2.44-2.29 (m, 1H), 1.99-1.86 (m, 2H), 1.77-1.69 (m, 1H), 1.64-1.49 (m, 5H), 1.48 (s, 4H), 1.47-1.19 (m, 5H), 1.16 (s, 6H), 1.12-1.03 (m, 1H), 0.97 (d, J=6.8 Hz, 3H), 0.83 (br. s., 2H), 0.74 (t, J=7.5 Hz, 3H). MS: MS m/z 956.9 (M$^+$+1).

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR(RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, *J. Clin. Microbiol.*, 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, *J. Proc. Natl. Acad. Sci. U.S.A.* 94(16), 8738-8743 (1997); AF054247, see Yanagi, M., St Claire, M., Shapiro, M., Emerson, S. U., Purcell, R. H. and Bukh, J., *Virology* 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. *Biochemistry.* 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in Escherichia. coli strain BL21 (DE3) (Invitrogen) following the protocol described by P. Gallinari et al. (see Gallinari P, Brennan D, Nardi C, Brunetti M, Tomei L, Steinkuhler C, De Francesco R., *J. Virol.* 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-N'-(2-Ethane Sulfonic acid) (HEPES), pH 7.5, 20% glycerol, 500 mM Sodium Chloride (NaCl), 0.5% Triton X-100, 1 microgram/milliliter ("µg/mL") lysozyme, 5 mM Magnesium Chloride ($MgCl_2$), 1 µg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in *Anal. Biochem.* 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y = A + ((B-A)/(1+((C/x)^D)))$.

Compounds of the present disclosure, which were tested against more than one type of NS3/4A complex, were found to have similar inhibitory properties though the compounds uniformly demonstrated greater potency against the 1b strains as compared to the 1a strains.

Generation of HCV Replicon

An HCV replicon whole cell system was established as described by Lohmann V, Korner F, Koch J, Herian U, Theilmann L, Bartenschlager R., Science 285(5424):110-3 (1999) and modified to introduce a luciferase reporter, as first described by Krieger et al (Krieger N, Lohmann V, and Bartenschlager R, *J. Virol.* 75(10):4614-4624 (2001)). cDNA encoding a humanized form of the Renilla luciferase gene and a linker sequence fused directly to the 3'-end of the luciferase gene were introduced into the replicon construct using an AscI restriction site located in core, directly upstream of the neomycin marker gene. The adaptive mutation at position 1179 (serine to isoleucine) was also introduced (Blight K J, Kolykhalov, A A, Rice, C M, *Science* 290(5498):1972-1974). A stable cell line constitutively expressing this HCV replicon construct was generated by first linearizing plasmid DNAs with ScaI. RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

A stable HCV replicon luciferase reporter cell line representing the genotype 1a H77 strain (Yanagi M, Purcell R H, Emerson S U, et al. Transcripts from a single full-length cDNA clone of hepatitis C virus are infectious when directly transfected into the liver of a chimpanzee. Proc Natl Acad Sci USA 1997; 94(16):8738-8743) was generated as described previously for the genotype 1b(Con1) replicon luciferase cell line. The replicon construct was modified by introducing mutations were introduced into the genes encoding the NS3 helicase domain (proline replaced by leucine at position 1496) and NS5A (serine to isoleucine at position 2204) to improve replication in cell culture.

HCV Replicon Luciferase Reporter Assay

HCV replicon luciferase assays were developed to monitor the inhibitory effects of compounds described in the disclosure on HCV genotypes 1a and 1b viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/mL G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 μL of cells at a density of $3.0 \times 10^3$ cells/well in DMEM containing 4% FCS (final DMSO concentration at 0.5%). After 3 days incubation at 37° C., cells were analyzed for Renilla Luciferase activity using the EnduRen as substrate (Promega cat #E6485). The EnduRen substrate was diluted in DMEM and then added to the plates to a final concentration of 7.5 μM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat #G8082). Cell-Titer Blue (3 μL) was added to each well and incubated for 8 hrs at 37° C. The fluorescence signal from each well was read, with an excitation wavelength at 525/10 nm and an emission wavelength of 598/10 nm, using the Viewlux Imager.

The $EC_{50}$ values for compounds were calculated by using a four-parameter logistic equation:

$$y=A+((B-A)/(1+((C/x)^D))),$$

where A and B denotes minimal and maximal % inhibition, respectively, C is the $EC_{50}$, D is the hill slope and x represents compound concentration.

Table 2 shows the EC50 values of representative compounds of the present disclosure. Ranges are as follows: A=0.10 nM-0.50 nM; B=0.51 nM-1.00 nM; C=1.01 nM-5.00 nM; D=5.01 nM-35.00 nM; and E=35.01-145 nM.

TABLE 2

| Cmpd Number | LE_1a (EC50, nM) | LE_1a (EC50, range) | LE_1b (EC50, nM) | LE_1b (EC50, range) |
|---|---|---|---|---|
| 5491 | 5.41 | D | 2.57 | C |
| 5493 |  | E |  | D |
| 5495 |  | C |  | B |
| 5497 |  | D |  | C |
| 5500 |  | D |  | D |
| 6120 |  | E |  | E |
| 6122 | 71.99 | E | 72.46 | E |
| 6125 |  | E |  | E |
| 6127 |  | D |  | D |
| 6129 | 4.21 | C | 0.78 | B |
| 6131 |  | D |  | C |
| 6133 |  | D |  | B |
| 6135 |  | C |  | B |
| 6137 |  | C |  | B |
| 6139 |  | D |  | C |
| 6141 |  | D |  | C |
| 4248 |  | C |  | C |
| 4255 |  | C |  | B |
| 4258 |  | C |  | C |
| 4264 |  | C |  | C |
| 4274 |  | D |  | C |
| 4275 |  | D |  | D |
| 4280 |  | D |  | C |
| 4281 |  | D |  | D |
| 4282 |  | D |  | C |
| 4285 |  | C |  | C |
| 4288 |  | D |  | D |
| 4291 |  | C |  | B |
| 4293 |  | C |  | C |
| 4303 |  | C |  | C |
| 4306 |  | D |  | D |
| 4307 |  | C |  | C |
| 4308 |  | D |  | D |
| 4309 | 3.51 | C | 2.31 | C |
| 4329 |  | E |  | E |
| 4330 |  | D |  | D |
| 4286 |  | C |  | B |
| 4287 |  | C |  | C |
| 4294 | 0.85 | B | 0.89 | B |
| 4299 |  | B |  | B |
| 4301 |  | B |  | B |
| 4358 |  | C |  | C |
| 5507 |  | C |  | B |
| 5509 |  | C |  | B |
| 5511 |  | C |  | C |
| 5513 |  | C |  | B |
| 5515 |  | C |  | B |
| 5517 |  | C |  | C |
| 5519 |  | C |  | B |
| 5521 | 1.23 | C | 0.47 | A |
| 5549 |  | B |  | B |
| 7001 |  | C |  | B |
| 7002 |  | C |  | B |
| 7003 | 3.7 | C | 0.80 | B |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A compound of formula (I)

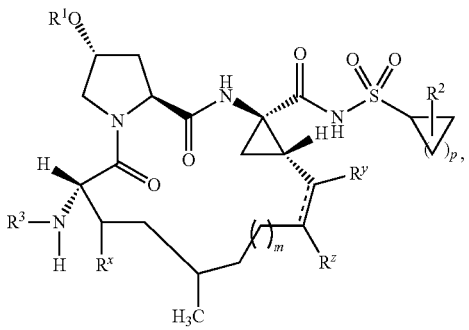

or a pharmaceutically acceptable salt thereof, wherein
p is 1 or 2;
----- is a single or double bond;
R¹ is selected from

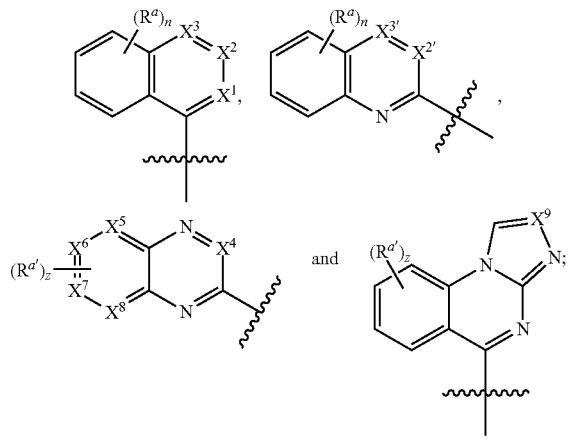

wherein R¹ is attached to the parent molecular moiety through any substitutable carbon atom in the group;
m is 0, 1, or 2;
n is 1, 2, 3, 4, 5, or 6;
z is 0, 1, 2, 3, 4, 5, or 6;
one of $X^1$ and $X^3$ is N and the other is selected from CH and $CR^a$;
$X^2$ is selected from CH and $CR^a$;
$X^{2'}$ is selected from CH and $CR^a$;
$X^{3'}$ is selected from N, CH, and $CR^a$;
$X^4$ is selected from CH and $CR^a$;
one of $X^5$, $X^6$, $X^7$, and $X^8$ is N and the others are selected from CH and $CR^{a'}$;
$X^9$ is selected from $CR^a$, CH, and N;
each $R^a$ and $R^{a'}$ are independently selected from alkoxy, alkoxycarbonyl, alkyl, cycloalkyl, halo, haloalkyl, imidazolyl, oxazolyl, substituted pyrazolyl, thiazolyl, and —$NR^qR^{q'}$, wherein the imidazolyl, the oxazolyl, and the thiazolyl are optionally substituted with one or two groups independently selected from alkoxy, alkyl, halo, and haloalkyl; and wherein the substituted pyrazolyl is substituted with one or two groups independently selected from alkoxy, alkyl, halo, and haloalkyl; and wherein two adjacent $R^a$ groups, together with the carbon atoms to which they are attached, can optionally form a furanyl ring; provided that at least one $R^a$ is other than alkoxy, alkyl, halo, or haloalkyl;
$R^x$ is selected from methyl and ethyl;
$R^y$ and $R^z$ are independently selected from hydrogen and hydroxy; provided that when ----- is a double bond, $R^y$ and $R^z$ are each hydrogen;
$R^2$ is selected from hydrogen, alkyl, halo, haloalkoxy, haloalkyl, and hydroxyalkyl;
$R^3$ is selected from alkoxycarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, haloalkoxycarbonyl, and
one of $R^q$ and $R^{q'}$ is selected from hydrogen and alkyl and the other is selected from alkylcarbonyl and phenylcarbonyl.

2. A compound of claim 1, or a pharmaceutically acceptable salt thereof, wherein m and p are 1.

3. A compound of claim 1, or a pharmaceutically acceptable salt thereof, wherein ----- is a double bond.

4. A compound of claim 1, or a pharmaceutically acceptable salt thereof, wherein $R^y$ and $R^z$ are hydrogen.

5. A compound of claim 1 wherein $R^2$ is selected from hydrogen and alkyl.

6. A compound of claim 1, or a pharmaceutically acceptable salt thereof, wherein
m and p are 1;
----- is a double bond;
$R^y$ and $R^z$ are hydrogen;
and $R^2$ is selected from hydrogen and alkyl.

7. A compound selected from
methyl 1-(((2R,6S,7R,9R,13aS,14aR,16aS,Z)-14a-((cyclopropylsulfonyl)carbamoyl)-7-ethyl-9-methyl-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl)oxy)-6-methoxyisoquinoline-4-carboxylate;
methyl 1-(((2R,6S,7R,9R,13aS,14aR,16aS,Z)-7-ethyl-9-methyl-14a-(((1-methylcyclopropyl)sulfonyl)carbamoyl)-5,16-dioxo-6-((((1,1,1-trifluoro-2-methylpropan-2-yl)oxy)carbonyl)amino)-1,2,3,5,6,7,8,9,10,11,13a,14,14a,15,16,16a-hexadecahydrocyclopropa[e]pyrrolo[1,2-a][1,4]diazacyclopentadecin-2-yl)oxy)-6-methoxyisoquinoline-4-carboxylate;
tert-butyl ((2R,6S,7R,9R,13aS,14aR,16aS,Z)-7-ethyl-2-((2-(3-isopropyl-1H-pyrazol-1-yl)-7-methoxyquinolin-4-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;
1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-((7-methoxy-2-(3-(trifluoromethyl)-1H-pyrazol-1-yl)quinolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;
1,1,1-trifluoro-2-methylpropan-2-yl ((2R,6S,7R,9R,13aS,14aR,16aS,Z)-7-ethyl-2-((7-methoxy-2-(3-(trifluoromethyl)-1H-pyrazol-1-yl)quinolin-4-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a- hexadecahydrocyclopropa[e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-2-((2-(3-isopropyl-1H-pyrazol-1-yl)-7-
methoxyquinolin-4-yl)oxy)-7,9-dimethyl-14a-(((1-
methylcyclopropyl)sulfonyl)carbamoyl)-5,16-dioxo-1,
2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-2-((7-methoxy-2-(3-(trifluoromethyl)-
1H-pyrazol-1-yl)quinolin-4-yl)oxy)-7,9-dimethyl-14a-
(((1-methylcyclopropyl)sulfonyl)carbamoyl)-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-7-ethyl-2-((2-(3-isopropyl-1H-pyrazol-
1-yl)-7-methoxyquinolin-4-yl)oxy)-9-methyl-14a-(((1-
methylcyclopropyl)sulfonyl)carbamoyl)-5,16-dioxo-1,
2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

tert-butyl ((2R,6S,7R,9R,13aS,14aR,16aS,Z)-2-((3-cy-
clopropyl-6-methoxyquinoxalin-2-yl)oxy)-7,9-dim-
ethyl-14a-(((1-methylcyclopropyl)sulfonyl)carbam-
oyl)-5,16-dioxo-1,2,3,5,6,7,8,9,10,11,13a,14,14a,15,
16,16a-hexadecahydrocyclopropa[e]pyrrolo[1,2-a][1,
4]diazacyclopentadecin-6-yl)carbamate;

tert-butyl ((2R,6S,7R,9R,13aS,14aR,16aS,Z)-2-((3-cy-
clopropyl-6-methoxyquinoxalin-2-yl)oxy)-14a-((cy-
clopropylsulfonyl)carbamoyl)-7-ethyl-9-methyl-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

tert-butyl ((2R,6S,7R,9R,13aS,14aR,16aS,Z)-2-((3-cy-
clopropyl-7-methoxyquinoxalin-2-yl)oxy)-14a-((cy-
clopropylsulfonyl)carbamoyl)-7-ethyl-9-methyl-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-2-((3-cyclopropyl-6-methoxyquinoxa-
lin-2-yl)oxy)-14a-((cyclopropylsulfonyl)carbamoyl)-
7-ethyl-9-methyl-5,16-dioxo-1,2,3,5,6,7,8,9,10,11,13a,
14,14a,15,16,16a-hexadecahydrocyclopropa[e]pyrrolo
[1,2-a][1,4]diazacyclopentadecin-6-yl)carbamate;

1,1,1-trifluoro-2-methylpropan-2-yl ((2R,6S,7R,9R,13aS,
14aR,16aS,Z)-2-((3-cyclopropyl-7-methoxyquinoxa-
lin-2-yl)oxy)-14a-((cyclopropylsulfonyl)carbamoyl)-
7-ethyl-9-methyl-5,16-dioxo-1,2,3,5,6,7,8,9,10,11,13a,
14,14a,15,16,16a-hexadecahydrocyclopropa[e]pyrrolo
[1,2-a][1,4]diazacyclopentadecin-6-yl)carbamate;

tert-butyl ((2R,6S,7R,9R,13aS,14aR,16aS,Z)-2-((4-(4-
(tert-butyl)thiazol-2-yl)-6-methoxyisoquinolin-1-yl)
oxy)-14a-((cyclopropylsulfonyl)carbamoyl)-7-ethyl-9-
methyl-5,16-dioxo-1,2,3,5,6,7,8,9,10,11,13a,14,14a,
15,16,16a-hexadecahydrocyclopropa[e]pyrrolo[1,2-a]
[1,4]diazacyclopentadecin-6-yl)carbamate;

1,1,1-trifluoro-2-methylpropan-2-yl ((2R,6S,7R,9R,13aS,
14aR,16aS,Z)-2-((2-(1H-imidazol-1-yl)-7-methoxy-
quinolin-4-yl)oxy)-7-ethyl-9-methyl-14a-(((1-methyl-
cyclopropyl)sulfonyl)carbamoyl)-5,16-dioxo-1,2,3,5,
6,7,8,9,10,11,13a,14,14a,15,16,16a-
hexadecahydrocyclopropa[e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-2-((4-(1H-imidazol-1-yl)-7-methoxy-
quinolin-2-yl)oxy)-7-ethyl-9-methyl-14a-(((1-methyl-
cyclopropyl)sulfonyl)carbamoyl)-5,16-dioxo-1,2,3,5,
6,7,8,9,10,11,13a,14,14a,15,16,16a-
hexadecahydrocyclopropa[e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-7-ethyl-2-((6-methoxy-4-(N-methylben-
zamido)isoquinolin-1-yl)oxy)-9-methyl-14a-(((1-
methylcyclopropyl)sulfonyl)carbamoyl)-5,16-dioxo-1,
2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

tert-butyl ((2R,6S,7R,9R,13aS,14aR,16aS,Z)-7-ethyl-2-
((6-methoxy-4-(thiazol-2-yl)isoquinolin-1-yl)oxy)-9-
methyl-14a-(((1-methylcyclopropyl)sulfonyl)carbam-
oyl)-5,16-dioxo-1,2,3,5,6,7,8,9,10,11,13a,14,14a,15,
16,16a-hexadecahydrocyclopropa[e]pyrrolo[1,2-a][1,
4]diazacyclopentadecin-6-yl)carbamate;

1,1,1-trifluoro-2-methylpropan-2-yl ((2R,6S,7R,9R,13aS,
14aR,16aS,Z)-7-ethyl-2-((6-methoxy-4-(thiazol-2-yl)
isoquinolin-1-yl)oxy)-9-methyl-14a-(((1-methylcyclo-
propyl)sulfonyl)carbamoyl)-5,16-dioxo-1,2,3,5,6,7,8,
9,10,11,13a,14,14a,15,16,16a-
hexadecahydrocyclopropa[e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-7-ethyl-2-((4-(N-ethylbenzamido)-6-
methoxyisoquinolin-1-yl)oxy)-9-methyl-14a-(((1-
methylcyclopropyl)sulfonyl)carbamoyl)-5,16-dioxo-1,
2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

tert-butyl ((2R,6S,7R,9R,13aS,14aR,16aS,Z)-2-((4-(4-
(tert-butyl)thiazol-2-yl)-6-methoxyisoquinolin-1-yl)
oxy)-7-ethyl-9-methyl-14a-(((1-methylcyclopropyl)
sulfonyl)carbamoyl)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-6-yl)
carbamate;

1,1,1-trifluoro-2-methylpropan-2-yl ((2R,6S,7R,9R,13aS,
14aR,16aS,Z)-2-((4-(4-(tert-butyl)thiazol-2-yl)-6-
methoxyisoquinolin-1-yl)oxy)-7-ethyl-9-methyl-14a-
(((1-methylcyclopropyl)sulfonyl)carbamoyl)-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

tert-butyl ((2R,6S,7R,9R,13aS,14aR,16aS,Z)-7-ethyl-2-
((6-methoxy-4-(oxazol-5-yl)isoquinolin-1-yl)oxy)-9-
methyl-14a-(((1-methylcyclopropyl)sulfonyl)carbam-
oyl)-5,16-dioxo-1,2,3,5,6,7,8,9,10,11,13a,14,14a,15,
16,16a-hexadecahydrocyclopropa[e]pyrrolo[1,2-a][1,
4]diazacyclopentadecin-6-yl)carbamate;

1,1,1-trifluoro-2-methylpropan-2-yl ((2R,6S,7R,9R,13aS,
14aR,16aS,Z)-7-ethyl-2-((6-methoxy-4-(oxazol-5-yl)
isoquinolin-1-yl)oxy)-9-methyl-14a-(((1-methylcyclo-
propyl)sulfonyl)carbamoyl)-5,16-dioxo-1,2,3,5,6,7,8,
9,10,11,13a,14,14a,15,16,16a-
hexadecahydrocyclopropa[e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-14a-((cyclopropylsulfonyl)carbamoyl)-
7-ethyl-2-((6-methoxy-4-(oxazol-5-yl)isoquinolin-1-
yl)oxy)-9-methyl-5,16-dioxo-1,2,3,5,6,7,8,9,10,11, 13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-14a-((cyclopropylsulfonyl)carbamoyl)-7-ethyl-9-methyl-5,16-dioxo-2-((3-(trifluoromethyl)pyrido[2,3-b]pyrazin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-14a-((cyclopropylsulfonyl)carbamoyl)-7-ethyl-9-methyl-5,16-dioxo-2-((2-(trifluoromethyl)pyrido[2,3-b]pyrazin-3-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-14a-((cyclopropylsulfonyl)carbamoyl)-7-ethyl-2-((7-methoxy-3-(trifluoromethyl)pyrido[3,4-b]pyrazin-2-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((4-(4-(tert-butyl)thiazol-2-yl)-6-methoxyisoquinolin-1-yl)oxy)-14a-((cyclopropylsulfonyl)carbamoyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((2-ethoxy-7-methoxypyrido[3,4-b]pyrazin-3-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-7-ethyl-2-((7-methoxy-2-(trifluoromethyl)pyrido[3,4-b]pyrazin-3-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((2,3-dihydrofuro[2,3-f]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-((2,3-dihydrofuro[2,3-f]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9S,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9R,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((2,3-dihydrofuro[2,3-f]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((2,3-dihydrofuro[2,3-f]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((2,3-dihydrofuro[2,3-f]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-(imidazo[1,2-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-(imidazo[1,2-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13 aS,14aR,16aS,Z)-2-([1,2,4]triazolo[4,3-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13 aS,14aR,16aS,Z)-2-([1,2,4]triazolo[4,3-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((7-chloroimidazo[1,2-a]quinazolin-5-yl)oxy)-7,9-dimethyl-14a-(((1-methylcyclopropyl)sulfonyl)carbamoyl)-5, 16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-(imidazo[1,2-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-(imidazo[1,2-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-([1,2,4]triazolo[4,3-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-([1,2,4]triazolo[4,3-a]quinazolin-5-yloxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl((2R,6S,7R,9S,13aS,14aR,16aS,Z)-2-((7-chloroimidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl((2R,6S,7R,9R,13aS,14aR,16aS,Z)-2-((7-chloroimidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((7-chloroimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((7-chloroimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((7-chloroimidazo[1,2-a]quinazolin-5-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((7-chloroimidazo[1,2-a]quinazolin-5-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((7-chloro-2-methylimidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((7-chloro-2-methylimidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9S,13aS,14aR,16aS,Z)-2-((7-chloro-2-methylimidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9R,13aS,14aR,16aS,Z)-2-((7-chloro-2-methylimidazo[1,2-a]quinazolin-5-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((7-chloro-2-methylimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((7-chloro-2-methylimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9S,13aS,14aR,16aS,Z)-2-((7-chloro-2-methylimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; and 3,3-difluoro-2-methylbutan-2-yl ((2R,6S,7R,9R,13aS,14aR,16aS,Z)-2-((7-chloro-2-methylimidazo[1,2-a]quinazolin-5-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

or a pharmaceutically acceptable salt thereof.

8. A compound selected from
Compound 5506
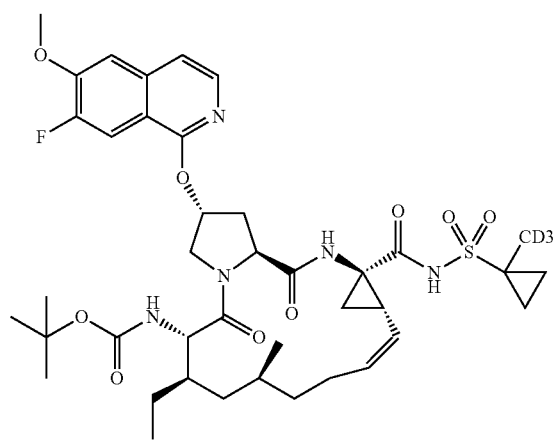
Compound 5507
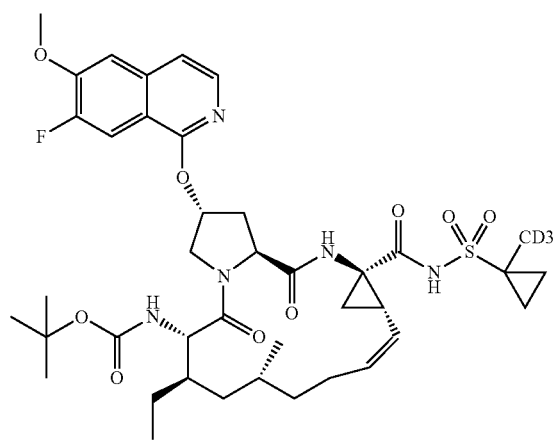
Compound 5508
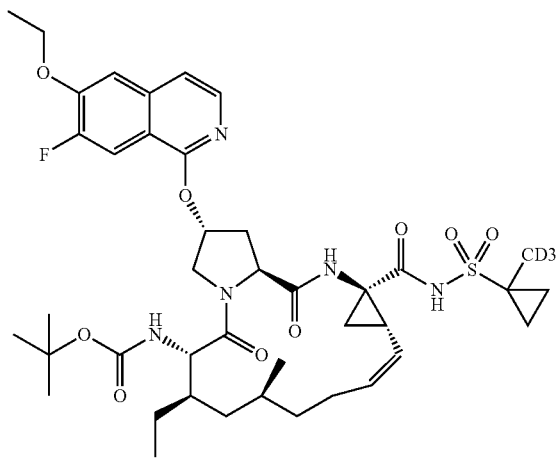
-continued
Compound 5509
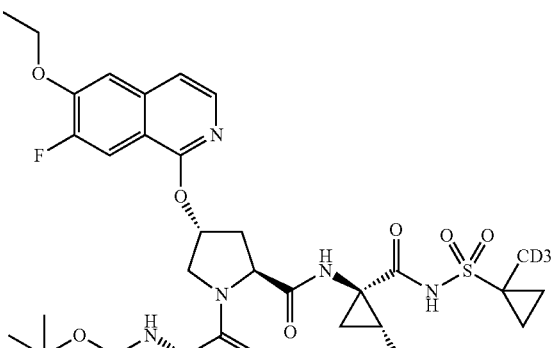
Compound 5510
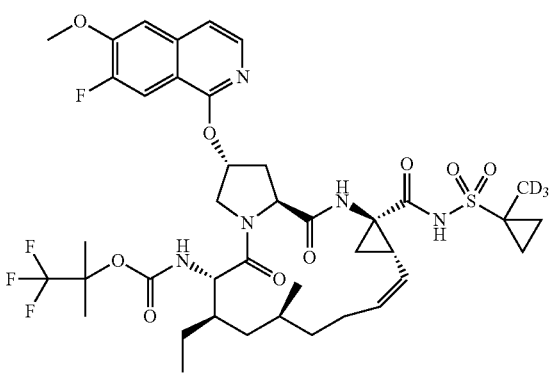
Compound 5511
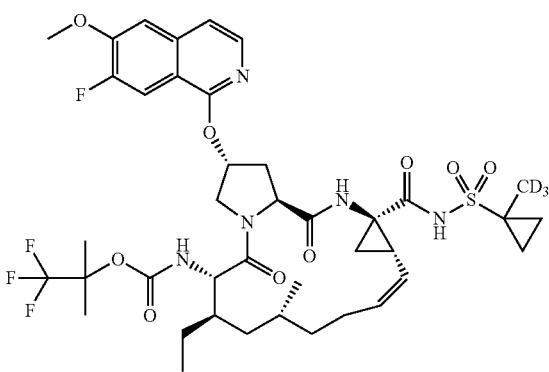
Compound 5512
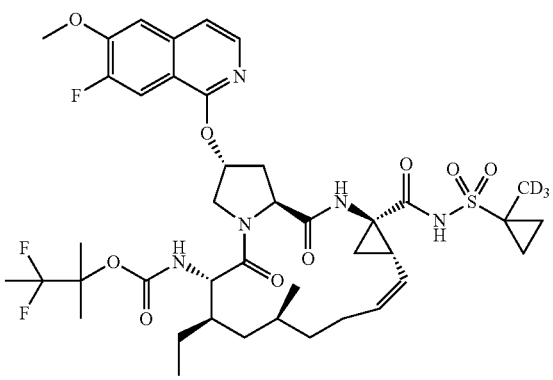

-continued
Compound 5513
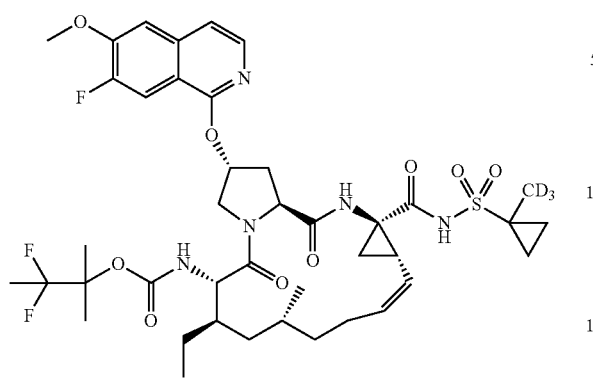
Compound 5517
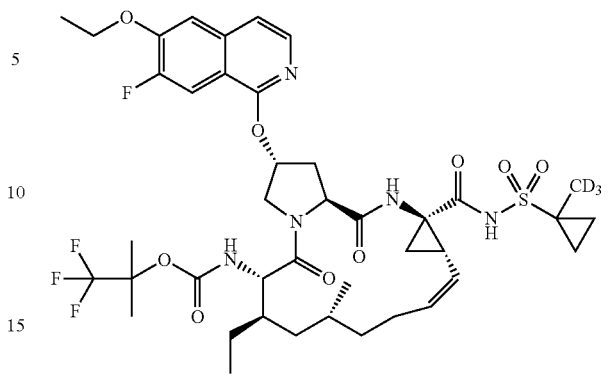
Compound 5514
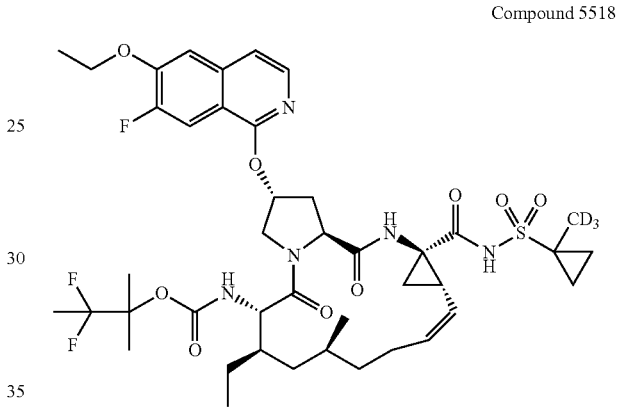
Compound 5518
Compound 5515
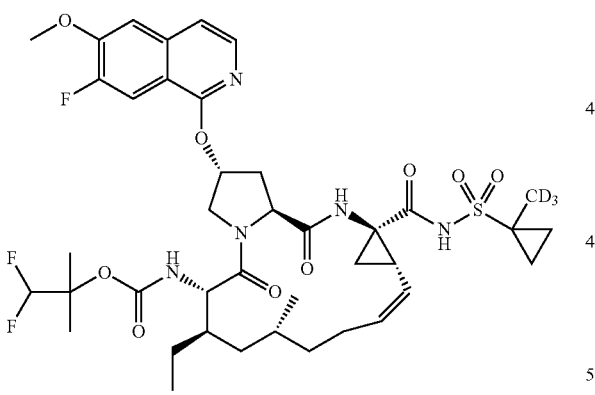
Compound 5519
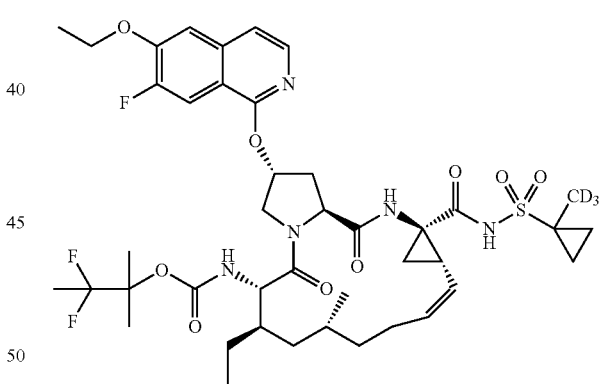
Compound 5516
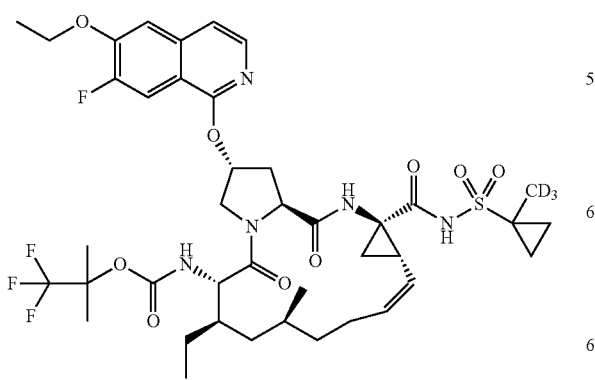
Compound 5520
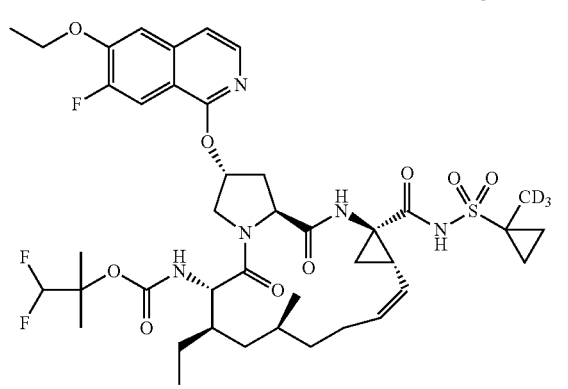

Compound 5521
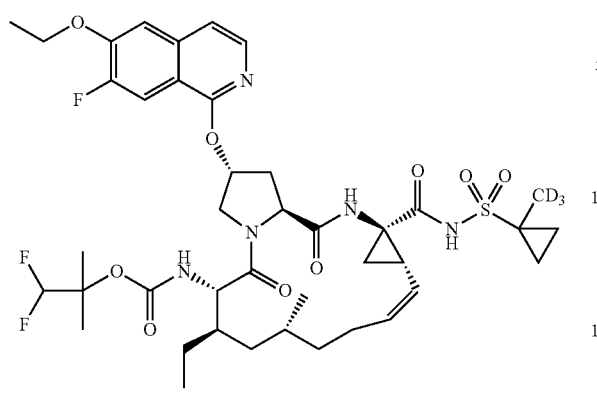
Compound 5538
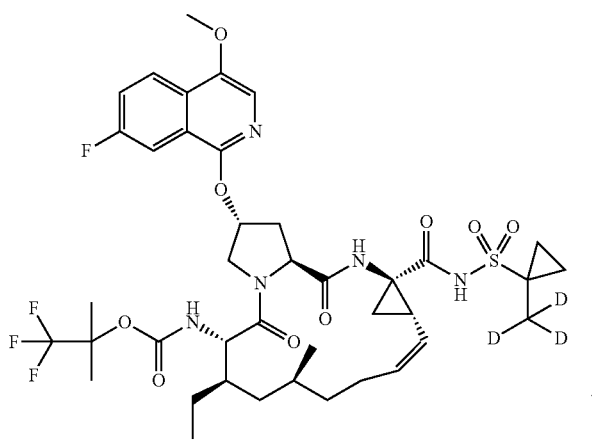
Compound 5539
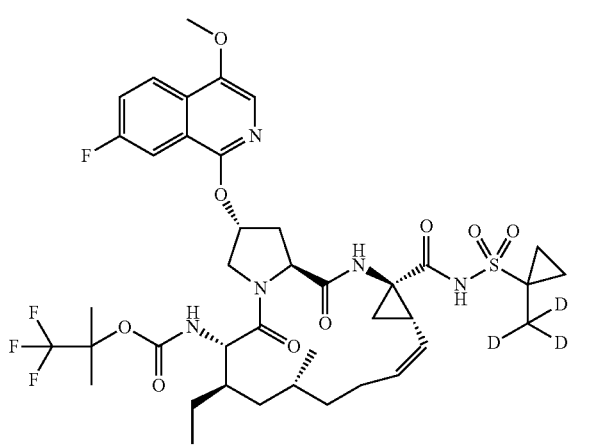
Compound 5540
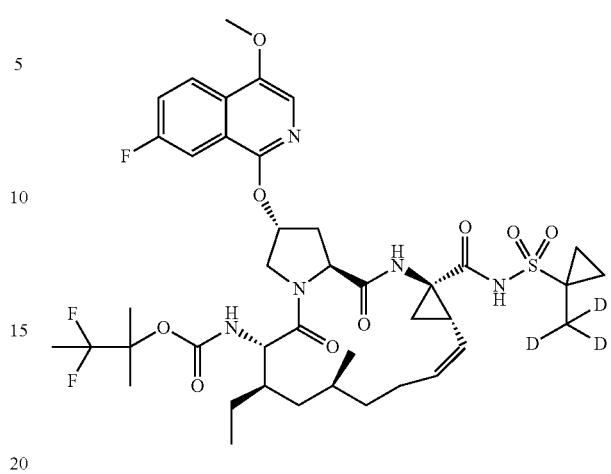
Compound 5541
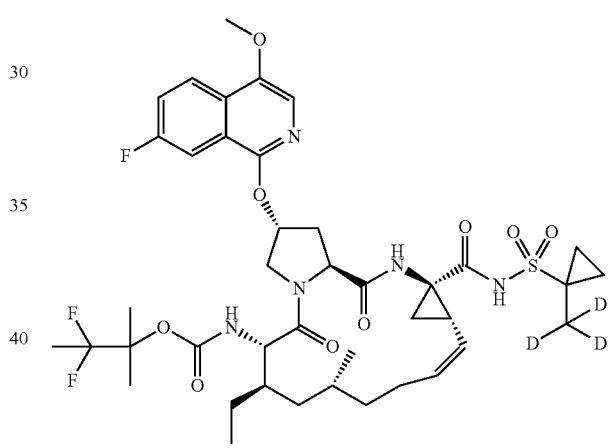
Compound 5542
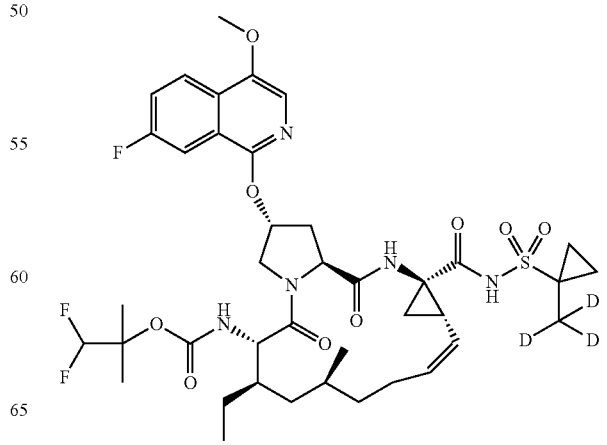

Compound 5543
Compound 5546
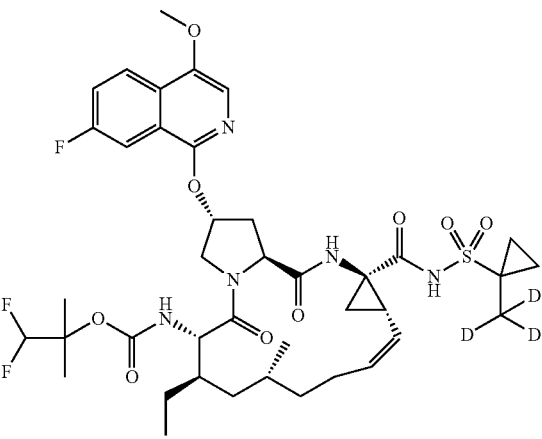
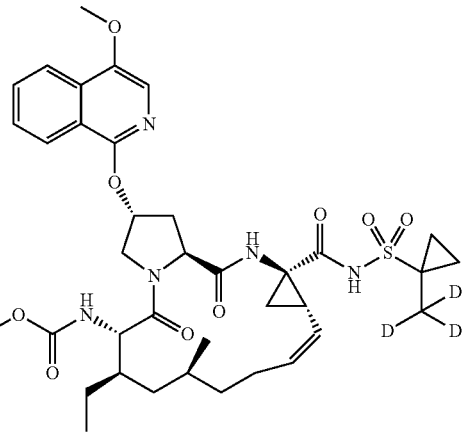
Compound 5544
Compound 5547
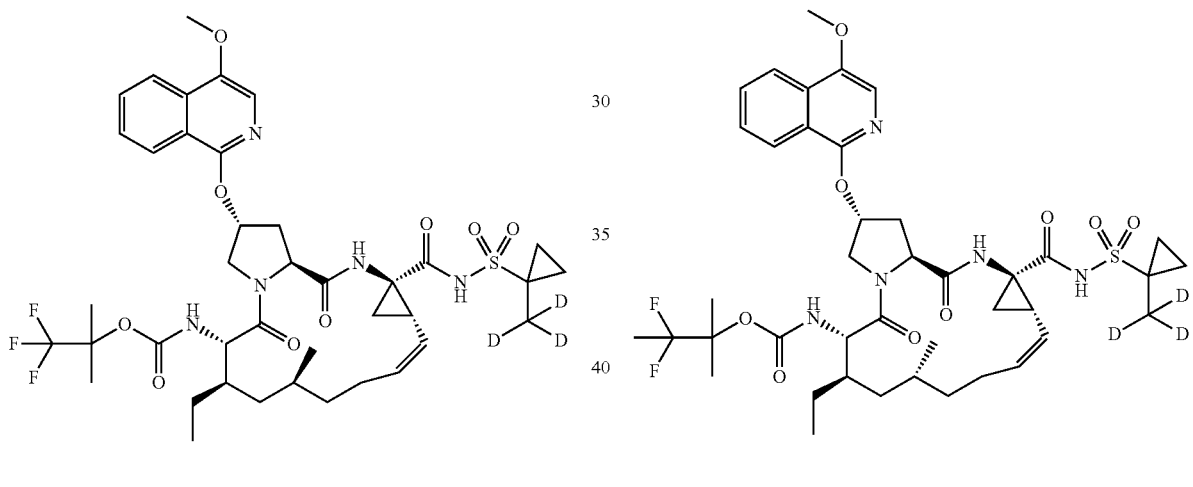
Compound 5545
Compound 5548
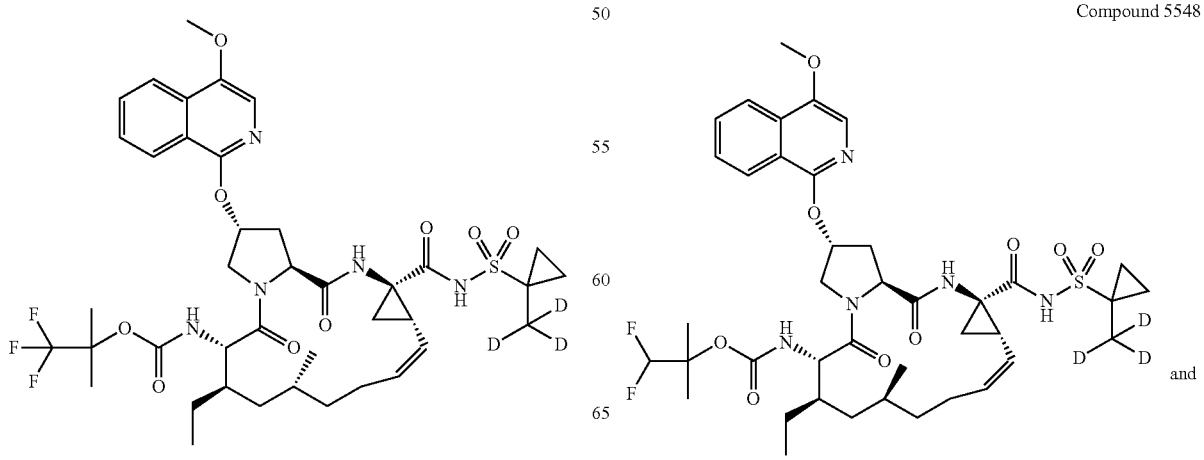
and -continued Compound 5549

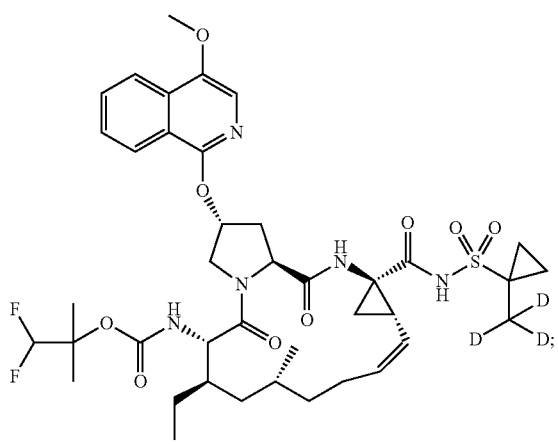

or a pharmaceutically acceptable salt thereof.

9. A compound selected from

Compound 7001

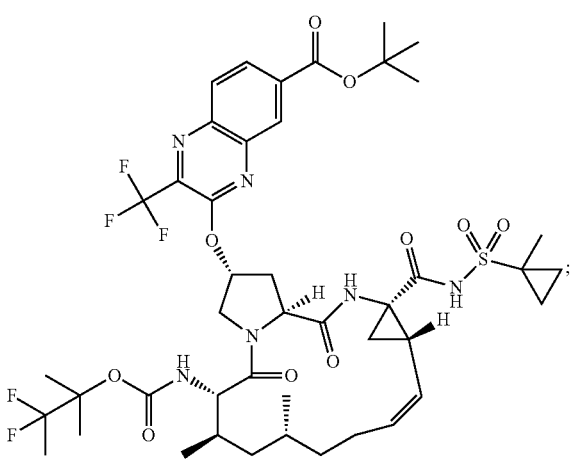

Compound 7002

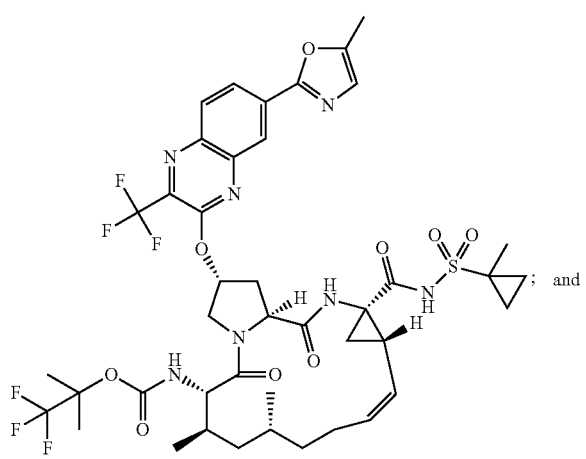

; and

-continued

Compound 7003

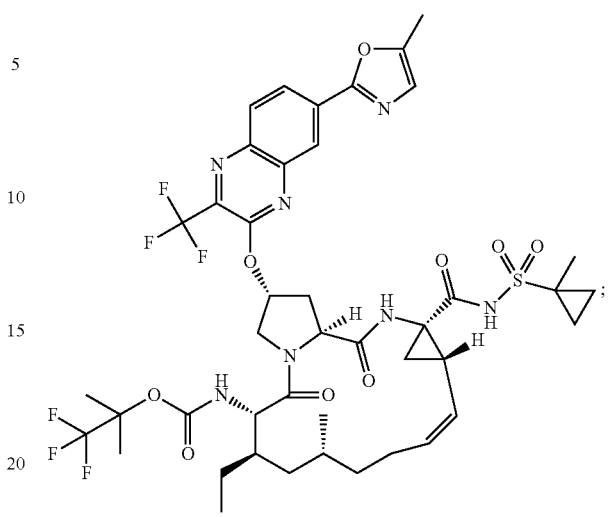

or a pharmaceutically acceptable salt thereof.

10. A composition comprising a compound of claim 1, or a pharmaceutically acceptable salt thereof, and a pharmaceutically acceptable carrier.

11. A method of treating an HCV infection in a patient, comprising administering to the patient a therapeutically effective amount of a compound of claim 1, or a pharmaceutically acceptable salt thereof.

12. The method of claim 11 further comprising administering at least one additional compound having anti-HCV activity prior to, after, or simultaneously with the compound of formula (I), or a pharmaceutically acceptable salt thereof.

13. The method of claim 12 wherein at least one of the additional compounds is an interferon or a ribavirin.

14. The method of claim 13 wherein the interferon is selected from interferon alpha 2B, pegylated interferon alpha, consensus interferon, interferon alpha 2A, and lymphoblastoid interferon tau.

15. The method of claim 12 wherein at least one of the additional compounds is selected from interleukin 2, interleukin 6, interleukin 12, Imiquimod, ribavirin, an inosine 5'-monophosphate dehydrogenase inhibitor, amantadine, and rimantadine.

16. The method of claim 12 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

PATENT NO.          : 9,643,999 B2
APPLICATION NO.     : 14/064619
DATED               : May 9, 2017
INVENTOR(S)         : Sun et al.

It is certified that error appears in the above-identified patent and that said Letters Patent is hereby corrected as shown below:

On the Title Page

Item (56) References Cited, under OTHER PUBLICATIONS:
Column 2, Llinas-Brunet, M. et al., reference, change "N53" to -- NS3 --.

In the Claims

Claim 7, Column 144, Lines 27-28:
Delete "13 aS," and insert -- 13aS, --.

Claim 7, Column 144, Line 42:
Delete "-yloxy)-" and insert -- -yl)oxy)- --.

Claim 7, Column 144, Line 48:
Delete "-yloxy)-" and insert -- -yl)oxy)- --.

Claim 7, Column 144, Line 53:
Delete "13 aS," and insert -- 13aS, --.

Claim 7, Column 144, Line 54:
Delete "-yloxy)-" and insert -- -yl)oxy)- --.

Claim 7, Column 144, Line 59:
Delete "13 aS," and insert -- 13aS, --.

Claim 7, Column 144, Line 60:
Delete "-yloxy)-" and insert -- -yl)oxy)- --.

Claim 7, Column 145, Line 5:
Delete "-yloxy)-" and insert -- -yl)oxy)- --.

Signed and Sealed this
Twentieth Day of November, 2018

Andrei Iancu
*Director of the United States Patent and Trademark Office*

Claim 7, Column 145, Line 11:
Delete "-yloxy)-" and insert -- -yl)oxy)- --.

Claim 7, Column 145, Line 18:
Delete "yloxy)-" and insert -- yl)oxy)- --.

Claim 7, Column 145, Line 25:
Delete "yloxy)-" and insert -- yl)oxy)- --.

Claim 7, Column 145, Line 30:
Delete "-yl((" and insert -- -yl ((  --.

Claim 7, Column 145, Line 37:
Delete "-yl((" and insert -- -yl ((  --.